(12) United States Patent
Hirotsuka et al.

(10) Patent No.: US 10,582,919 B2
(45) Date of Patent: *Mar. 10, 2020

(54) SUTURE ANCHORS WITH ONE-WAY CINCHING MECHANISMS

(71) Applicant: The Foundry, LLC

(72) Inventors: Mark Hirotsuka, San Jose, CA (US); Michael Hendricksen, Redwood City, CA (US); Darin Gittings, Sunnyvale, CA (US); John Morriss, San Francisco, CA (US)

(73) Assignee: The Foundry, LLC, Menlo Park, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 14/585,654

(22) Filed: Dec. 30, 2014

(65) Prior Publication Data
US 2015/0112384 A1 Apr. 23, 2015

Related U.S. Application Data

(63) Continuation of application No. 14/015,934, filed on Aug. 30, 2013, now abandoned, which is a
(Continued)

(51) Int. Cl.
*A61B 17/04* (2006.01)
*A61B 17/06* (2006.01)
(Continued)

(52) U.S. Cl.
CPC .... *A61B 17/0401* (2013.01); *A61B 17/06166* (2013.01); *A61B 90/92* (2016.02);
(Continued)

(58) Field of Classification Search
CPC ............ A61B 17/0401; A61B 17/0487; A61B 2017/0414; A61B 2017/0446–0462
See application file for complete search history.

(56) References Cited

U.S. PATENT DOCUMENTS 3,939,969 A 2/1976 Miller et al.
3,981,307 A 9/1976 Borysko
(Continued)

FOREIGN PATENT DOCUMENTS

EP 1013229 A2 6/2000
EP 1588666 A2 10/2005
(Continued)

OTHER PUBLICATIONS

US 6,238,418 B1, 05/2001, Schwartz et al. (withdrawn)
(Continued)

*Primary Examiner* — Shaun L David
(74) *Attorney, Agent, or Firm* — Wilson Sonsini Goodrich & Rosati

(57) ABSTRACT

Various devices, systems and methods for knotless anchoring of sutures to repair bodily tissue are disclosed. These devices allow sutures to be anchored to bone or other tissues, and more specifically provide a suture anchor which eliminates the need for the operator to knot the suture to secure the suture under tension. Thus, damaged tissue may be re-attached to a substrate tissue. The anchors have a minimum of moving parts and find particular utility in hip and shoulder arthroscopy, e.g. labral reattachment, rotator cuff repair, and similar procedures.

50 Claims, 83 Drawing Sheets

Related U.S. Application Data continuation of application No. 12/776,208, filed on May 7, 2010, now Pat. No. 8,545,535.

(60) Provisional application No. 61/177,602, filed on May 12, 2009, provisional application No. 61/219,290, filed on Jun. 22, 2009, provisional application No. 61/263,728, filed on Nov. 23, 2009, provisional application No. 61/263,751, filed on Nov. 23, 2009, provisional application No. 61/298,780, filed on Jan. 27, 2010, provisional application No. 61/304,352, filed on Feb. 12, 2010.

(51) Int. Cl.
*A61B 90/92* (2016.01)
*B29C 45/00* (2006.01)
*A61B 90/00* (2016.01)

(52) U.S. Cl.
CPC .......... *B29C 45/00* (2013.01); *A61B 17/0482* (2013.01); *A61B 2017/044* (2013.01); *A61B 2017/045* (2013.01); *A61B 2017/0409* (2013.01); *A61B 2017/0412* (2013.01); *A61B 2017/0414* (2013.01); *A61B 2017/0416* (2013.01); *A61B 2017/0432* (2013.01); *A61B 2017/0433* (2013.01); *A61B 2017/0438* (2013.01); *A61B 2017/0441* (2013.01); *A61B 2017/0445* (2013.01); *A61B 2017/0448* (2013.01); *A61B 2017/0451* (2013.01); *A61B 2017/0453* (2013.01); *A61B 2017/0454* (2013.01); *A61B 2017/0461* (2013.01); *A61B 2017/0496* (2013.01); *A61B 2017/06142* (2013.01); *A61B 2090/0807* (2016.02)

(56) References Cited

U.S. PATENT DOCUMENTS

| | | |
|---|---|---|
| 4,249,656 A | 2/1981 | Cerwin et al. |
| 4,253,563 A | 3/1981 | Komarnycky |
| 4,406,363 A | 9/1983 | Aday |
| 4,412,614 A | 11/1983 | Ivanov |
| 4,413,727 A | 11/1983 | Cerwin et al. |
| 4,427,109 A | 1/1984 | Roshdy |
| 4,483,437 A | 11/1984 | Cerwin et al. |
| 4,491,218 A | 1/1985 | Aday |
| 4,533,041 A | 8/1985 | Aday et al. |
| 4,555,016 A | 11/1985 | Aday et al. |
| 4,572,363 A | 2/1986 | Alpern |
| 4,608,019 A | 8/1986 | Kumabe et al. |
| 4,615,435 A | 10/1986 | Alpern et al. |
| 4,750,492 A | 6/1988 | Jacobs |
| 4,884,681 A | 12/1989 | Roshdy et al. |
| 4,887,710 A | 12/1989 | Roshdy et al. |
| 4,898,156 A | 2/1990 | Gatturna et al. |
| 4,899,743 A | 2/1990 | Nicholson et al. |
| 4,904,272 A | 2/1990 | Middleton et al. |
| 4,946,043 A | 8/1990 | Roshdy et al. |
| 4,946,468 A | 8/1990 | Li |
| 4,968,315 A | 11/1990 | Gatturna |
| 4,969,892 A | 11/1990 | Burton et al. |
| 4,979,956 A | 12/1990 | Silvestrini |
| 5,002,550 A | 3/1991 | Li |
| 5,013,316 A | 5/1991 | Goble et al. |
| 5,019,083 A | 5/1991 | Klapper et al. |
| 5,046,513 A | 9/1991 | Gatturna et al. |
| 5,057,112 A | 10/1991 | Sherman et al. |
| 5,061,283 A | 10/1991 | Silvestrini |
| 5,078,730 A | 1/1992 | Li et al. |
| 5,108,400 A | 4/1992 | Appel et al. |
| 5,152,790 A | 10/1992 | Rosenberg et al. |
| 5,171,251 A | 12/1992 | Bregen et al. |
| 5,174,087 A | 12/1992 | Bruno |
| 5,178,629 A | 1/1993 | Kammerer |
| 5,188,636 A | 2/1993 | Fedotov |
| 5,192,303 A | 3/1993 | Gatturna et al. |
| 5,201,656 A | 4/1993 | Sicurelli, Jr. |
| 5,203,864 A | 4/1993 | Phillips |
| 5,207,679 A | 5/1993 | Li |
| 5,217,092 A | 6/1993 | Potter |
| 5,217,486 A | 6/1993 | Rice et al. |
| 5,242,457 A | 9/1993 | Akopov et al. |
| 5,258,016 A | 11/1993 | DiPoto et al. |
| 5,259,398 A | 11/1993 | Vrespa |
| 5,268,001 A | 12/1993 | Nicholson et al. |
| 5,282,809 A | 2/1994 | Kammerer et al. |
| 5,318,570 A | 6/1994 | Hood et al. |
| 5,336,240 A | 8/1994 | Metzler et al. |
| 5,352,230 A | 10/1994 | Hood |
| 5,358,511 A | 10/1994 | Gatturna et al. |
| 5,370,662 A | 12/1994 | Stone et al. |
| 5,380,334 A | 1/1995 | Torrie et al. |
| 5,383,905 A | 1/1995 | Golds et al. |
| 5,397,357 A | 3/1995 | Schmieding et al. |
| 5,407,420 A | 4/1995 | Bastyr et al. |
| 5,411,506 A | 5/1995 | Goble et al. |
| 5,411,523 A | 5/1995 | Goble |
| 5,415,651 A | 5/1995 | Schmieding |
| 5,417,691 A | 5/1995 | Hayhurst |
| 5,441,502 A | 8/1995 | Bartlett |
| 5,443,482 A | 8/1995 | Stone et al. |
| 5,454,815 A | 10/1995 | Geisser et al. |
| 5,464,425 A | 11/1995 | Skiba |
| 5,464,427 A | 11/1995 | Curtis et al. |
| 5,466,243 A | 11/1995 | Schmieding et al. |
| 5,480,403 A | 1/1996 | Lee et al. |
| 5,484,451 A | 1/1996 | Akopov et al. |
| 5,486,197 A | 1/1996 | Le et al. |
| 5,520,700 A | 5/1996 | Beyer et al. |
| 5,522,817 A | 6/1996 | Sander et al. |
| 5,522,843 A | 6/1996 | Zang |
| 5,522,844 A | 6/1996 | Johnson et al. |
| 5,527,342 A | 6/1996 | Pietrzak et al. |
| 5,540,718 A | 7/1996 | Barlett |
| 5,545,180 A | 8/1996 | Le et al. |
| 5,554,171 A | 9/1996 | Gatturna et al. |
| 5,569,306 A | 10/1996 | Thal |
| 5,571,139 A | 11/1996 | Jenkins, Jr. |
| 5,573,543 A | 11/1996 | Akopov et al. |
| 5,573,548 A | 11/1996 | Nazre et al. |
| 5,575,801 A | 11/1996 | Habermeyer et al. |
| 5,578,057 A | 11/1996 | Wenstrom, Jr. |
| 5,584,835 A | 12/1996 | Greenfield |
| 5,584,836 A | 12/1996 | Ballintyn et al. |
| 5,584,860 A | 12/1996 | Goble et al. |
| 5,591,207 A | 1/1997 | Coleman |
| 5,601,557 A | 2/1997 | Hayhurst |
| 5,601,558 A | 2/1997 | Torrie et al. |
| 5,618,314 A | 4/1997 | Harwin et al. |
| 5,626,587 A | 5/1997 | Bishop et al. |
| 5,626,612 A | 5/1997 | Barlett |
| 5,626,613 A | 5/1997 | Schmieding |
| 5,630,824 A | 5/1997 | Hart |
| 5,643,320 A | 7/1997 | Lower et al. |
| 5,643,321 A | 7/1997 | McDevitt |
| 5,647,874 A | 7/1997 | Hayhurst |
| 5,649,963 A | 7/1997 | McDevitt |
| 5,658,313 A | 8/1997 | Thal |
| 5,662,662 A | 9/1997 | Bishop et al. |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,702,397 A | 12/1997 | Goble et al. |
| 5,713,903 A | 2/1998 | Sander et al. |
| 5,720,753 A | 2/1998 | Sander et al. |
| 5,720,766 A | 2/1998 | Zang et al. |
| 5,725,529 A | 3/1998 | Nicholson et al. |
| 5,725,541 A | 3/1998 | Anspach, III et al. |
| 5,725,557 A | 3/1998 | Gatturna et al. |

(56) References Cited

U.S. PATENT DOCUMENTS

| | | |
|---|---|---|
| 5,728,100 A | 3/1998 | Skiba |
| 5,728,135 A | 3/1998 | Bregen et al. |
| 5,728,136 A | 3/1998 | Thal |
| 5,733,307 A | 3/1998 | Dinsdale |
| 5,741,282 A | 4/1998 | Anspach, III et al. |
| 5,769,894 A | 6/1998 | Ferragamo |
| 5,782,863 A | 7/1998 | Barlett |
| 5,782,864 A | 7/1998 | Lizardi |
| 5,782,865 A | 7/1998 | Grotz |
| 5,782,866 A | 7/1998 | Wenstrom, Jr. |
| 5,788,063 A | 8/1998 | Van Ness |
| 5,792,142 A | 8/1998 | Galitzer |
| 5,797,963 A | 8/1998 | McDevitt |
| 5,800,447 A | 9/1998 | Wenstrom, Jr. |
| 5,807,403 A | 9/1998 | Beyar et al. |
| 5,810,848 A | 9/1998 | Hayhurst |
| 5,814,051 A | 9/1998 | Wenstrom, Jr. |
| 5,814,070 A | 9/1998 | Borzone et al. |
| 5,814,071 A | 9/1998 | McDevitt et al. |
| 5,817,095 A | 10/1998 | Smith |
| 5,824,011 A | 10/1998 | Stone et al. |
| 5,842,478 A | 12/1998 | Benderev et al. |
| 5,843,087 A | 12/1998 | Jensen et al. |
| 5,851,219 A | 12/1998 | Goble et al. |
| 5,885,294 A | 3/1999 | Pedlick et al. |
| 5,894,921 A | 4/1999 | Le et al. |
| 5,899,920 A | 5/1999 | DeSatnick et al. |
| 5,904,704 A | 5/1999 | Goble et al. |
| 5,906,624 A | 5/1999 | Wenstrom, Jr. |
| RE36,289 E | 8/1999 | Le et al. |
| 5,935,129 A | 8/1999 | McDevitt et al. |
| 5,935,134 A | 8/1999 | Pedlick et al. |
| 5,938,686 A | 8/1999 | Benderev et al. |
| 5,941,882 A | 8/1999 | Jammet et al. |
| 5,944,724 A | 8/1999 | Lizardi |
| 5,944,739 A | 8/1999 | Zlock et al. |
| 5,948,000 A | 9/1999 | Larsen et al. |
| 5,948,001 A | 9/1999 | Larsen |
| 5,950,633 A | 9/1999 | Lynch et al. |
| 5,951,559 A | 9/1999 | Burkhart |
| 5,957,924 A | 9/1999 | Tormala et al. |
| 5,957,953 A | 9/1999 | DiPoto et al. |
| 5,961,538 A | 10/1999 | Pedlick et al. |
| 5,964,783 A | 10/1999 | Grafton et al. |
| 5,972,000 A | 10/1999 | Beyar et al. |
| 5,980,558 A | 11/1999 | Wiley |
| 5,993,451 A | 11/1999 | Burkhart |
| 5,993,458 A | 11/1999 | Vaitekunas et al. |
| 5,993,477 A | 11/1999 | Vaitekunas et al. |
| 6,007,566 A | 12/1999 | Wenstrom, Jr. |
| 6,019,768 A | 2/2000 | Wenstrom, Jr. et al. |
| 6,027,523 A | 2/2000 | Schmieding |
| 6,029,805 A | 2/2000 | Alpern et al. |
| 6,045,573 A | 4/2000 | Wenstrom, Jr. et al. |
| 6,045,574 A | 4/2000 | Thal |
| 6,056,751 A | 5/2000 | Fenton, Jr. |
| 6,066,160 A | 5/2000 | Colvin et al. |
| 6,080,154 A | 6/2000 | Reay-Young et al. |
| 6,086,608 A | 7/2000 | Ek et al. |
| 6,093,201 A | 7/2000 | Cooper et al. |
| 6,117,162 A | 9/2000 | Schmieding et al. |
| 6,146,406 A | 11/2000 | Shluzas et al. |
| 6,149,669 A | 11/2000 | Li |
| 6,179,840 B1 | 1/2001 | Bowman |
| 6,183,479 B1 | 2/2001 | Tormala et al. |
| 6,190,401 B1 | 2/2001 | Green et al. |
| 6,214,031 B1 | 4/2001 | Schmieding et al. |
| 6,241,736 B1 | 6/2001 | Sater et al. |
| 6,264,676 B1 | 7/2001 | Gellman et al. |
| 6,267,718 B1 | 7/2001 | Vitali et al. |
| 6,270,518 B1 | 8/2001 | Pedlick et al. |
| 6,287,324 B1 | 9/2001 | Yarnitsky et al. |
| 6,293,961 B2 | 9/2001 | Schwartz et al. |
| 6,306,159 B1 | 10/2001 | Schwartz et al. |
| 6,319,252 B1 | 11/2001 | McDevitt et al. |
| 6,319,270 B1 | 11/2001 | Grafton et al. |
| 6,319,271 B1 | 11/2001 | Schwartz et al. |
| 6,319,272 B1 | 11/2001 | Brenneman et al. |
| 6,334,446 B1 | 1/2002 | Beyar |
| 6,338,765 B1 | 1/2002 | Statnikov |
| 6,368,350 B1 | 4/2002 | Erickson et al. |
| 6,387,113 B1 | 5/2002 | Hawkins et al. |
| 6,406,480 B1 | 6/2002 | Beyar et al. |
| 6,423,072 B1 | 7/2002 | Zappala |
| 6,461,373 B2 | 10/2002 | Wyman et al. |
| 6,500,169 B1 | 12/2002 | Deng |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,520,980 B1 | 2/2003 | Foerster |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,533,795 B1 | 3/2003 | Tran et al. |
| 6,544,281 B2 | 4/2003 | ElAttrache et al. |
| 6,551,330 B1 | 4/2003 | Bain et al. |
| 6,554,852 B1 | 4/2003 | Oberlander |
| 6,569,186 B1 | 5/2003 | Winters et al. |
| 6,569,188 B2 | 5/2003 | Grafton et al. |
| 6,575,984 B2 | 6/2003 | Beyar |
| 6,582,453 B1 | 6/2003 | Tran et al. |
| 6,585,730 B1 | 7/2003 | Foerster |
| 6,616,674 B2 | 9/2003 | Schmieding |
| 6,616,694 B1 | 9/2003 | Hart |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,561 B1 | 11/2003 | Tran |
| 6,652,562 B2 | 11/2003 | Collier et al. |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,660,023 B2 | 12/2003 | McDevit et al. |
| 6,673,094 B1 | 1/2004 | McDevitt et al. |
| 6,685,728 B2 | 2/2004 | Sinnott et al. |
| 6,689,153 B1 | 2/2004 | Skiba |
| 6,692,516 B2 | 2/2004 | West, Jr. et al. |
| 6,716,234 B2 | 4/2004 | Grafton et al. |
| 6,726,707 B2 | 4/2004 | Pedlick et al. |
| 6,743,233 B1 | 6/2004 | Baldwin et al. |
| 6,746,483 B1 | 6/2004 | Bojarski et al. |
| 6,767,037 B2 | 7/2004 | Wenstrom, Jr. |
| 6,770,073 B2 | 8/2004 | McDevitt et al. |
| 6,770,076 B2 | 8/2004 | Foerster |
| 6,773,436 B2 | 8/2004 | Donnelly et al. |
| 6,780,198 B1 | 8/2004 | Gregoire et al. |
| 6,830,572 B2 | 12/2004 | McDevitt et al. |
| 6,855,157 B2 | 2/2005 | Foerster et al. |
| 6,887,259 B2 | 5/2005 | Lizardi |
| 6,916,333 B2 | 7/2005 | Schmieding et al. |
| 6,932,834 B2 | 8/2005 | Lizardi et al. |
| 6,942,666 B2 | 9/2005 | Overaker et al. |
| 6,972,027 B2 | 12/2005 | Fallin et al. |
| 6,984,237 B2 | 1/2006 | Hatch et al. |
| 6,986,781 B2 | 1/2006 | Smith |
| 6,989,034 B2 | 1/2006 | Hamme et al. |
| 6,991,636 B2 | 1/2006 | Rose |
| 6,994,719 B2 | 2/2006 | Grafton |
| 7,022,129 B2 | 4/2006 | Overaker et al. |
| 7,029,490 B2 | 4/2006 | Grafton et al. |
| 7,033,380 B2 | 4/2006 | Schwartz et al. |
| 7,037,324 B2 | 5/2006 | Martinek |
| 7,052,499 B2 | 5/2006 | Steger et al. |
| 7,063,717 B2 | 6/2006 | St. Pierre et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,104,999 B2 | 9/2006 | Overaker |
| 7,131,973 B2 | 11/2006 | Hoffman |
| 7,144,414 B2 | 12/2006 | Harvie et al. |
| 7,144,415 B2 | 12/2006 | Del Rio et al. |
| 7,150,757 B2 | 12/2006 | Fallin et al. |
| 7,153,312 B1 | 12/2006 | Torrie et al. |
| 7,163,563 B2 | 1/2007 | Schwartz et al. |

(56) References Cited

U.S. PATENT DOCUMENTS

| | | |
|---|---|---|
| 7,195,634 B2 | 3/2007 | Schmieding et al. |
| 7,204,839 B2 | 4/2007 | Dreyfuss et al. |
| 7,217,279 B2 | 5/2007 | Reese |
| 7,226,469 B2 | 6/2007 | Benavitz et al. |
| 7,232,455 B2 | 6/2007 | Pedlick et al. |
| 7,235,100 B2 | 6/2007 | Martinek |
| 7,247,164 B1 | 7/2007 | Ritchart et al. |
| 7,250,057 B2 | 7/2007 | Forsberg et al. |
| 7,279,008 B2 | 10/2007 | Brown et al. |
| 7,300,451 B2 | 11/2007 | Crombie et al. |
| 7,309,337 B2 | 12/2007 | Colleran et al. |
| 7,309,346 B2 | 12/2007 | Martinek |
| 7,320,701 B2 | 1/2008 | Haut et al. |
| 7,329,272 B2 | 2/2008 | Burkhart et al. |
| 7,331,982 B1 | 2/2008 | Kaiser et al. |
| 7,335,221 B2 | 2/2008 | Collier et al. |
| RE40,237 E | 4/2008 | Bilotti et al. |
| 7,357,810 B2 | 4/2008 | Koyfman et al. |
| 7,361,195 B2 | 4/2008 | Schwartz et al. |
| 7,371,244 B2 | 5/2008 | Chatlynne et al. |
| 7,381,213 B2 | 6/2008 | Lizardi |
| 7,390,329 B2 | 6/2008 | Westra et al. |
| 7,390,332 B2 | 6/2008 | Selvitelli et al. |
| 7,407,512 B2 | 8/2008 | Bojarski et al. |
| 7,442,202 B2 | 10/2008 | Dreyfuss |
| 7,455,674 B2 | 11/2008 | Rose |
| 7,455,683 B2 | 11/2008 | Geissler et al. |
| 7,468,074 B2 | 12/2008 | Caborn et al. |
| 7,485,124 B2 | 2/2009 | Kuhns et al. |
| 7,556,638 B2 | 7/2009 | Morgan et al. |
| 7,556,640 B2 | 7/2009 | Foerster |
| 7,566,339 B2 | 7/2009 | Fallin et al. |
| 7,572,275 B2 | 8/2009 | Fallin et al. |
| 7,572,283 B1 | 8/2009 | Meridew |
| 7,585,311 B2 | 9/2009 | Green et al. |
| 7,591,850 B2 | 9/2009 | Cavazzoni |
| 7,601,165 B2 | 10/2009 | Stone |
| 7,780,701 B1 | 8/2010 | Meridew et al. |
| 7,874,839 B2 | 1/2011 | Bouneff |
| 8,545,535 B2 | 10/2013 | Hirotsuka et al. |
| 2001/0027321 A1 | 10/2001 | Gellman et al. |
| 2002/0026187 A1 | 2/2002 | Swanson |
| 2002/0111653 A1 | 8/2002 | Foerster |
| 2002/0183762 A1 | 12/2002 | Anderson et al. |
| 2003/0060835 A1 | 3/2003 | Wenstrom, Jr. |
| 2003/0088272 A1 | 5/2003 | Smith |
| 2003/0105474 A1 | 6/2003 | Bonutti |
| 2003/0120309 A1 | 6/2003 | Colleran et al. |
| 2003/0130694 A1 | 7/2003 | Bojarski et al. |
| 2003/0135151 A1 | 7/2003 | Deng |
| 2003/0195563 A1 | 10/2003 | Foerster et al. |
| 2004/0002734 A1 | 1/2004 | Fallin et al. |
| 2004/0030341 A1 | 2/2004 | Aeschlimann et al. |
| 2004/0138706 A1 | 7/2004 | Abrams et al. |
| 2004/0236373 A1 | 11/2004 | Anspach, III et al. |
| 2005/0149122 A1 | 7/2005 | McDevitt et al. |
| 2005/0240199 A1 | 10/2005 | Martinek et al. |
| 2005/0245932 A1 | 11/2005 | Fanton et al. |
| 2005/0251208 A1 | 11/2005 | Elmer et al. |
| 2005/0283192 A1 | 12/2005 | Torrie et al. |
| 2006/0100630 A1 | 5/2006 | West, Jr. |
| 2006/0106422 A1 | 5/2006 | Del Rio et al. |
| 2006/0106423 A1 | 5/2006 | Weisel et al. |
| 2006/0149286 A1 | 7/2006 | Hoffman |
| 2006/0282083 A1 | 12/2006 | Fanton et al. |
| 2006/0293710 A1 | 12/2006 | Foerster et al. |
| 2007/0005071 A1 | 1/2007 | Kucklick |
| 2007/0088391 A1 | 4/2007 | McAlexander et al. |
| 2007/0088412 A1 | 4/2007 | Ashman et al. |
| 2007/0162022 A1 | 7/2007 | Zhang et al. |
| 2007/0219557 A1 | 9/2007 | Bourque et al. |
| 2007/0226719 A1 | 9/2007 | Stone et al. |
| 2007/0255317 A1 | 11/2007 | Fanton et al. |
| 2007/0260259 A1 | 11/2007 | Fanton et al. |
| 2008/0009904 A1 | 1/2008 | Bourque et al. |
| 2008/0021474 A1 | 1/2008 | Bonutti et al. |
| 2008/0027444 A1 | 1/2008 | Malek |
| 2008/0054814 A1 | 3/2008 | Deppe et al. |
| 2008/0058816 A1 | 3/2008 | Philippon et al. |
| 2008/0086072 A1 | 4/2008 | Bonutti et al. |
| 2008/0103528 A1 | 5/2008 | Zirps et al. |
| 2008/0109080 A1 | 5/2008 | Aeschlimann et al. |
| 2008/0147119 A1 | 6/2008 | Cauldwell et al. |
| 2008/0188854 A1 | 8/2008 | Moser |
| 2008/0275469 A1 | 11/2008 | Fanton et al. |
| 2008/0281325 A1 | 11/2008 | Stone et al. |
| 2008/0306510 A1 | 12/2008 | Stchur |
| 2009/0012617 A1 | 1/2009 | White et al. |
| 2009/0069845 A1 | 3/2009 | Frushell et al. |
| 2009/0088798 A1 | 4/2009 | Snyder et al. |
| 2009/0099598 A1 | 4/2009 | McDevitt et al. |
| 2010/0016892 A1 | 1/2010 | Kaiser et al. |
| 2010/0121355 A1 | 5/2010 | Gittings et al. |
| 2010/0292731 A1 | 11/2010 | Gittings et al. |
| 2010/0292732 A1 | 11/2010 | Hirotsuka et al. |
| 2010/0292733 A1 | 11/2010 | Hendricksen et al. |
| 2011/0313453 A1 | 12/2011 | Krumme et al. |
| 2013/0345746 A1 | 12/2013 | Gittings et al. |
| 2014/0005720 A1 | 1/2014 | Hirotsuka et al. |
| 2014/0031863 A1 | 1/2014 | Gittings et al. |
| 2014/0142627 A1 | 5/2014 | Hendricksen et al. |
| 2015/0320413 A1 | 11/2015 | Gittings et al. |
| 2017/0020505 A1 | 1/2017 | Gittings et al. |
| 2017/0071594 A1 | 3/2017 | Hendricksen et al. |

FOREIGN PATENT DOCUMENTS

| | | |
|---|---|---|
| GB | 2084468 A | 4/1982 |
| WO | WO95/29637 A1 | 11/1995 |
| WO | WO97/30649 A1 | 8/1997 |
| WO | WO 2003/096908 A2 | 11/2003 |
| WO | WO 2003/096908 A3 | 4/2004 |
| WO | WO2006/037131 A2 | 4/2006 |
| WO | WO2006/039296 A2 | 4/2006 |
| WO | WO-2007078281 A2 | 7/2007 |
| WO | WO 2008/054814 A2 | 5/2008 |
| WO | WO 2008/054814 A3 | 6/2008 |
| WO | WO2008/109087 A1 | 9/2008 |
| WO | WO 2008/124206 A2 | 10/2008 |
| WO | WO 2008/124463 A2 | 10/2008 |
| WO | WO 2008/124206 A3 | 12/2008 |
| WO | WO 2009/023034 A1 | 2/2009 |
| WO | WO 2009/039513 A1 | 3/2009 |

OTHER PUBLICATIONS

Co-pending U.S. Appl. No. 14/804,178, filed Jul. 20, 2015.
Office action dated Sep. 11, 2015 for U.S. Appl. No. 13/749,038.
Office action dated Dec. 4, 2015 for U.S. Appl. No. 13/855,445.
Notice of allowance dated Mar. 31, 2016 for U.S. Appl. No. 13/749,038.
European search report and search opinion dated Apr. 15, 2016 for EP Application No. 10775301.4.
European search report and search opinion dated Apr. 2, 2015 for EP Application No. 10775303.0.
European search report and search opinion dated Apr. 20, 2015 for EP Application No. 10775304.8.
Office action dated Apr. 20, 2015 for U.S. Appl. No. 13/692,596.
Ambrose et al., "Bioabsorbable Implants: Review of Clinical Experience in Orthopedic Surgery," Annals of Biomedical Engineering, Jan. 2004; 32(1):171-177.
Arthrex, Inc., 2.5 mm PushLock® Knotless Suture Anchor [brochure], 2007, 2 pages total.
Arthrex, Inc., "4.5 mm/6.7 mm Low Profile Screw System Surgical Technique" [brochure], 2009, 6 pages total.
Arthrex, Inc., "Acetabular Labral Repair Using the Bio-SutureTak® Suture Anchor System Surgical Technique" [brochure], 2007, 6 pages total.
Arthrex, Inc., "Achilles SutureBridge™ Surgical Technique" [brochure], 2009, 6 pages total.

(56) References Cited

OTHER PUBLICATIONS

Arthrex, Inc., "ACL Graft Tensioning using the Suture Tensioner with Tensionmeter Surgical Technique" [brochure], 2009, 6 pages total.
Arthrex, Inc., "AdapteurTM Power System II" [brochure], 2008, 12 pages total.
Arthrex, Inc., "Advanced Technology" [brochure], 2008, 15 pages total.
Arthrex, Inc., "All-Inside BTB ACL RetroConstructionTM with Bone-Tendon-Bone Grafts Surgical Technique" [brochure], 2007, 8 pages total.
Arthrex, Inc., "Arthrex 300 Power System—Small Bone" [brochure], undated, 2 pages total.
Arthrex, Inc., "Arthrex 600 Power System—Small Bone" [brochure], undated, 2 pages total.
Arthrex, Inc., "Arthrex ACPTM Double Syringe System" [brochure], 2009, 6 pages total.
Arthrex, Inc., "Arthrex Bio-Composite Suture Anchors", p. 9 of 510(k) Summary, FDA Approval Letter and Indications of Use for 510(k) No. K082810, Jan. 2009, 6 pages total.
Arthrex, Inc., "Arthrex Flatfoot Solutions"[brochure], 2008, 2 pages total.
Arthrex, Inc., "Arthrex Hallux Valgus Solutions"[brochure], 2008, 2 pages total.
Arthrex, Inc., "Arthrex PushLock, Tak, and Corkscrew Products", p. 12 of 510(k) Summary, FDA Approval Letter and Indications of Use for 510(k) No. K061863, Oct. 2006, 6 pages total.
Arthrex, Inc., "Arthroscopic Meniscal Repair: Arthroscopic All-Inside Meniscal Repair with the Mensical ViperTM and DarkstickTM Surgical Technique" [brochure], 2006, 6 pages total.
Arthrex, Inc., "Arthroscopic Rotator Cuff Repair: Bio-Corkscrew® Suture Anchor Rotator Cuff Repair Surgical Technique" [brochure], 2007, 6 pages total.
Arthrex, Inc., "Arthroscopy Instruments" [brochure], 2008, 12 pages total.
Arthrex, Inc., "Beach Chair Lateral Traction Device Assembly Instructions" [instructions for use], 2006, 2 pages total.
Arthrex, Inc., "BioComposite SutureTak, BioComposite Corkscrew FT and BioComposite PushLock: An In Vitro Degradation Study" [white paper], Arthrex Research and Development, 2009, 1 page.
Arthrex, Inc., "BioCompositeTM Interference Screws for ACL and PCL Reconstruction," Arthrex Research and Development, 2008, 5 pages total.
Arthrex, Inc., "BioCompositeTM Interference Screws: a Stronger Turn in ACL/PCL Reconstruction," 2008, 56 pages total.
Arthrex, Inc., "Bio-Compression Screw System" [brochure], 2008, 6 pages total.
Arthrex, Inc., "Bio-FASTak® Bankart Repair Surgical Technique" [brochure], 2007, 6 pages total.
Arthrex, Inc., "Biomechanical Testing Comparison of Cayenne Medical and Arthrex, Inc. Repair Products" [white paper], Arthrex Research and Development, 2009, 1 page total.
Arthrex, Inc., "Bio-PostTM and Washer System" [brochure], 2001, 2 pages total.
Arthrex, Inc., "Bio-SutureTak Suture Anchor" [brochure], 2006, 2 pages total.
Arthrex, Inc., "Bio-TenodesisTM Screw System" [brochure], 2008, 6 pages total.
Arthrex, Inc., "Bone, Tendon or Ligament Repair?" [brochure], 2004, 1 page total.
Arthrex, Inc., "ClearCut Burrs" [brochure], 2006, 2 pages total.
Arthrex, Inc., "Comprehensive Solutions for Forefoot and Midfoot Surgery using the Mini TightRope® System—Five Surgical Techniques" [brochure], 2008, 13 pages total.
Arthrex, Inc., "CoolCut Series: Shaver Blades and Burrs" [brochure], 2009, 4 pages total.
Arthrex, Inc., "Double Row Rotator Cuff Repair using the Bio-Corkscrew® FT Surgical Technique" [brochure], 2007, 6 pages total.
Arthrex, Inc., "Elbow/Ankle Arthroscopy Instrument Set" [brochure], 2007, 8 pages total.
Arthrex, Inc., "Endoscopic Carpal Tunnel Release System" [brochure], 2000 ,2 pages total.
Arthrex, Inc., "FiberWire® Braided Composite Suture" [brochure], 2008, 8 pages total.
Arthrex, Inc., "FiberWire® Collective Summary of Strength and Biocompatibility Testing Data Comparisons of Polyester and Polyblend Sutures" [white paper], 2006, 4 pages total.
Arthrex, Inc., "FiberWire® Confidence After Closure" [brochure], 2008, 6 pages total.
Arthrex, Inc., "FiberWire® Orthopaedic Composite Suture" [sell sheet], 2007, 2 pages total.
Arthrex, Inc., "FlipCutter ACL Reconstruction™: ACL Reconstruction using the FlipCutterTM and the Constant Femoral Guide Surgical Technique" [brochure], 2008, 6 pages total.
Arthrex, Inc., "FlipCutterTM" [brochure], 2009, 2 pages total.
Arthrex, Inc., "Freedom in Anatomic Femoral Socket Placement" [brochure], 2009, 2 pages total.
Arthrex, Inc., "Fulfilling the Need for Precision and Speed Rotator Cuff Repair" [brochure], 2009, 12 pages total.
Arthrex, Inc., "Innovative Solutions for Hip Arthroscopy" [brochure], 2008, 16 pages total.
Arthrex, Inc., "Knotless Rotator Cuff Repair: SpeedBridgeTM and SpeedFixTM Knotless Rotator Cuff Repair using the SwiveLockTM C and FiberTape® Surgical Technique" [brochure], 2008, 8 pages total.
Arthrex, Inc., "Knotless SingleRow Rotator Cuff Repair using the PushLockTM and FiberTape® Surgical Technique" [brochure], 2007, 4 pages total.
Arthrex, Inc., "MultiFire Scorpion ™ Independently Pass Two FiberWire® Suture Tails Through Tissue Without Scorpion Removal" [brochure], 2009, 4 pages total.
Arthrex, Inc., "Next Generation in Knee Ligament Reconstruction & Repair Technology" [brochure], 2009, 42 pages total.
Arthrex, Inc., "Orthopaedic Procedure Electrosurgical System (ORES®)" [brochure], 2008, 11 pages total.
Arthrex, Inc., "OSferion: Porous Trapezoid 6-TCP Synthetic Grafting of BTB Autograft Harvest Sites" [brochure], 2008, 18 pages total.
Arthrex, Inc., "OSferion: Porous Trapezoid 6-TCP Synthetic Wedge Grafting of Tibial and Femoral Opening Wedge Osteotomy Sites" [brochure], 2009, 6 pages total.
Arthrex, Inc., "Percutaneous Glenohumeral Repair with SutureTak® Implants" [brochure], 2009, 2 pages total.
Arthrex, Inc., "ProStop® and ProStop® Plus for Correction of Posterior Tibial Tendon Dysfunction," [brochure], 2009, 6 pages total.
Arthrex, Inc., "ProWickTM Knee Postoperative and Cold Therapy Dressing System" [brochure], 2009, 4 pages total.
Arthrex, Inc., "ProWickTM Shoulder Postoperative and Cold Therapy Dressing System" [brochure], 2009, 4 pages total.
Arthrex, Inc., "Pull Out Strength of a 3.5 mm Bio-PushLock (AR-1926B)" [white paper], Arthrex Research and Development Nov. 10, 2005, 1 page total.
Arthrex, Inc., "PushLock® Bankart & SLAP Repair: PushLock® Knotless Anchor for Bankart & SLAP Repair Surgical Technique" [brochure], 2009, 8 pages total.
Arthrex, Inc., "PushLock® Knotless Instability Repair" [brochure], 2009, 12 pages total.
Arthrex, Inc., "PushLock®" [advertisement], 2008, 1 page total.
Arthrex, Inc., PushLockTM [directions for use], DFU-0099, Revision 8, 2 page total.
Arthrex, Inc., "Raising the Bar in Arthroscopic Imaging and Resection Technology" [brochure], 2009, 8 pages total.
Arthrex, Inc., "RetroConstruction™ Minimally Invasive Options for Anatomic ACL/PCL Reconstruction" [brochure], 2009, 11 pages total.
Arthrex, Inc., "Scorpion—Fulfilling the Need for Precision and Speed in Arthroscopic Rotator Cuff Repair" [brochure], 2008, 6 pages total.
Arthrex, Inc., "Shaver Blades and Burrs" [brochure], 2005, 1 page total.

(56) References Cited

OTHER PUBLICATIONS

Arthrex, Inc., "Single Use Disposable Shaver Blades and Burrs" [brochure], 2008, 2 pages total.
Arthrex, Inc., "Small Joint: Fracture—Fusion—Osteotomy Fixation Options" [brochure], 2007, 2 pages total.
Arthrex, Inc., "SutureLasso™ SD Products Reference Guide" [brochure], 2007, 1 page total.
Arthrex, Inc., "SutureTakTm Suture Anchors" [directions for use], DFU-0069, Revision 10, 2 page total.
Arthrex, Inc., "SwiveLockTM & FiberChain™ Knotless Rotator Cuff Repair Surgical Technique" [brochure], 2007, 8 pages total.
Arthrex, Inc., "Thumb UCL Repair/Reconstruction: 2.5 mm PushLock®/3 mm × 8 mm BioTenodesisTM Thumb Collateral Ligament Repair/Reconstruction" [brochure], 2008, 8 pagest total.
Arthrex, Inc., "Transtibial ACL Reconstruction with Soft Tissue Grafts Surgical Technique" [brochure], 2007, 5 pages total.
Arthrex, Inc., "Trim-It Drill Pin™ The Need to Remove Hardware is Disappearing" [brochure], 2009, 2 pages total.
Arthrex, Inc., "Trim-It Drill Pin® Osteotomy Fixation Kit" [brochure], 2009, 6 pages total.
Arthrex, Inc., "Trim-ItTm Screw System" [brochure], 2006, 6 pages total.
Arthrex, Inc., "V-TakTm Soft Tissue Anchor" [brochure], 2006, 6 pages total.
Arthrex, Inc., "Wishbone™ Series Arthroscopy Instruments" [brochure], 2008, 8 pages total.
Arthrex, Inc., In Arthroscopic Surgery, You Can't Treat It If You Can't Reach It[brochure], 2007, 12 pages total.
Arthrex, Inc., New Materials in Sports Medicine [white paper], 2006, 7 pages total.
Arthrex, Inc., The Arthrex Chondral DartTM [brochure], 2006, 4 pages total.
Arthrex, Inc., The Continuous Wave III Arthroscopy Pump: Clear Vision in Arthroscopic Fluid Management [brochure], 2006, 12 pages total.
Arthrex, Inc., The Fully Threaded Family of Soft Tissue Repair Anchors: Cortical Cancellous Fixation with Fiberwire® Composite Suture for Superior Repair Strength [brochure], 2008, 6 pages total.
Arthrex, Inc., The Next Generation in Foot and Ankle Repair Technology [brochure], 2009, 44 pages total.
Arthrex, Inc., The Next Generation in Hand, Wrist and Elbow Repair Technology [brochure], 2009, 28 pages total.
Arthrex, Inc., The Next Generation in Shoulder Repair Technology [brochure], 2008, 24 pages total.
Arthrex, Inc., The Next Generation in Shoulder Repair Technology [brochure], 2009, 26 pages total.
Arthrex, Inc., The OATS® Sterile, Single Use Kit [brochure], 2007, 2 pages total.
Arthrex. Acetabular Labral Repair [brochure], Arthrex, Inc., 2007, 6 pages total; retrieved from the Internet: <http://arthromed.org/pdf/hip/Surgical%20Techniques/Acetabular%20Labral%20Repair%20Ou sing%20the%20PushLock%20Knotless%20Anchor%20System.pdf>.
Arthrex. Bio-Corkscrew Anchor FT and Corkscrew FT II Suture Anchors [brochure], Arthrex, Inc., 2005, 6 pages total; retrieved from the Internet: <http://www.rcsed.ac.uk/fellows/Ivanrensburg/classification/surgtech/arthrex/arthrex%20man uals/biocorkscrew. pdf>.
Arthrex. Bio-SutureTak Bankart & SLAP Repair [brochure], Arthrex, Inc., 2007, 6 pages total; retrieved from the Internet: <http://depts.washington.edu/shoulder/Surgery/ArthroscopicTechniques/Arthrex/Bio-SutureTak-SLAP-Bankart-Repair.pdf>.
Arthrocare Corporation, "LabraLock P Knotless Implant w/Inserter Handle" [website], 1 page; retrieved: <http://www.arthrocaresportsmedicine.com/products/view/430>.
Arthrocare Corporation, "Magnum® MP Suture Implant" [brochure], 2009, 2 pages total.
Arthrocare Corporation, "Mini Magnum Knotless Implant w/Inserter Handle" [website], 1 page; retrieved: <http://www.arthrocaresportsmedicine.com/products/view/429>.
Arthrocare Corporation, "Mini Magnum® Knotless Fixation Implant" [brochure], 2009, 2 pages total.
Arthrocare Corporation, "SpeedScrewTM Fully Threaded OPUS® Knotless Fixation Implant" [brochure], 2009, 2 pages total.
Arthrocare Corporation, The OPUS® AutoCuff System Featuring SpeedScrew for Rotator Cuff Repair Technical Guide [brochure], 2009, 8 pages total.
Arthrocare Corporation, The OPUS® AutoCuff System for Rotator Cuff Repair Technical Guide [brochure], 2008, 8 pages total.
Arthrocare. OPUS LabraFix Knotless System [brochure], ArthroCare Corporation, 2008, A1027 Rev D, 6 pages total; retrieved: <http://www.arthrocaresportsmedicine.com/files/datasheets/A1027D.pdf>.
Arthrotek®. Charlotte™ Shoulder System: Arthroscopic Bankart Lesion Repair Using the 3.5 mm LactoScrew Suture Anchor [brochure], a Biomet Company. 2006, 4 pages total.
Arthrotek®. MicroMax-fly' Resorbable Suture Anchor [brochure], a Biomet Company. 2006, 8 pages total.
Arthrotek®. Charlotte™ Shoulder System [brochure], a Biomet Company. 2006, 16 pages total.
Arthrotek®. CharlotteTM Shoulder System: SLAP Lesion Repair Using the 3.5 mm LactoScrew Suture Anchor [brochure], a Biomet Company. 2002, 4 pages total.
Arthrotek®. MaxBraidTM PE Suture [brochure], a Biomet Company. 2004, 2 pages total.
Barber et al., "Suture Anchors—Update 1999," Arthroscopy, Oct. 1999; 15(7):719-725.
Bardana et al, The Effect of Suture Anchor Design and Orientation on Suture Abrasion: An In Vitro Study, Arthroscopy, Mar. 2003; 19(3,):274-281.
Benthien et al., "Cyclic Loading Achilles Tendon Repairs: A Comparison of Polyester and Polyblend Suture," Foot Ankle Int. Jul. 2006;27(7):512-518.
Biomet Sports Medicine, Hitch Suture Anchor [brochure], 2008, 2 pages total.
Biomet Sports Medicine, MicroMax™ Flex Suture Anchor MicroMaxTM Resorbable Suture Anchor [brochure], 2009, 20 pages total.
Biomet Sports Medicine, MicroMaxTm Flex Suture Anchor [advertisement], 2009, 2 pages total.
Biomet Sports Medicine, The Material Difference: Options for Rotator Cuff Repair, Labral Repair and Suture Management [brochure], 2008, 12 pages total.
Biomet, Inc., MicroMax-rm Resorbable Suture Anchor [website], 1 page; retrieved from the Internet: <http://www.biomet.com/sportsMedicine/productDetail.cfm?category=23&subCategory=33& product=108.
Blokhuis et al., "Properties of Calcium Phosphate Ceramics in Relation to Their In Vivo Behavior," J Trauma. Jan. 2000;48(1):179-86.
Brady et al., "Arthroscopic Rotator Cuff Repair: Establishing the Footprint," Techniques in Shoulder & Elbow Surgery, Dec. 2005; 6(4):242-251.
Burkhart et al., "Loop Security as a Determinant of Tissue Fixation Security," Arthroscopy, Oct. 1998;14(7):773-776.
Burkhart et al., "SLAP Lesions in the Overhead Athlete," Operative Techniques in Sports Medicine, Jul. 2000; 8(3):213-220.
Burkhart, "Arthroscopic Repair of Retracted Adhesed Rotator Cuff Tears and Subscapularis Tears: The Effective Use of Interval Slide Releases," Int J Shoulder Surg 2007; 1(1):39-44; retrieved from the internet: <http://www.internationalshoulderjournal.org/text.asp?2007/1/1/39/30677>.
Burkhart, "Arthroscopic Rotator Cuff Repair: Indications and Technique," Operative Techniques in Sports Medicine, Oct. 1997; 5(4):204-214.
Burkhart, "Knotless Self-Reinforcing Rotator Coff Repair with FiberChain-SwiveLock System" [video recording], ArthroCologne, 2nd International Symposium on Operative and Biologic Treatments in Sports Medicine, Cologne, Germany, Jun. 15-16, 2007; retrieved from thet Internet: <http://www.arthrocologne.com/SwiveLock-Rotator-Cuff-Repair.16361.html.
Burkhart, New Thoughts on SLAP Lesions, Arthroscopy and Arthroplasty of the Shoulder 15th Annual San Diego, 1998; pp. 351-355.

(56) References Cited

OTHER PUBLICATIONS

Bynum et al., "Failure Mode of Suture Anchors as a Function of Insertion Depth," Am J Sports Med Jul. 2005; 33(7):1030-1034.
C2M Medical, Inc., "Cinch™ Knotless Fixation Implant System", pp. 63-65 of 510(k) Summary, FDA Approval Letter and Indications of Use for 510(k) No. K073226, Dec. 2007, 5 pages total.
Caborn et al., "A Biomechanical Comparison of Initial Soft Tissue Tibial Fixation Devices: The Intrafix Versus a Tapered 35-mm Bioabsorbable Interference Screw," Am J Sports Med, Jun. 2004; 32(4):956-961.
Chang et al., "Biomechanical Evaluation of Meniscal Repair Systems: A Comparison of the Meniscal Viper Repair System, the Vertical Mattress FasT-Fix Device, and Vertical Mattress Ethibond Sutures," Am J Sports Med, Dec. 2005; 33(12):1846-1852.
Chokshi et al., The effect of arthroscopic suture passing instruments on rotator cuff damage and repair strength, Bulletin of the NYU Hospital for Joint Diseases, Winter-Spring, 2006; 63(3/4):123-125; retrieved from the Internet: <http://www.nyuhjdbulletin.org/Mod/BulletinA/63N3-4/DocsA/63N3-4_11.pdf>.
Conmed Corporation, "Bio Mini-Revo® Anchor" [website], 1 page; retrieved from the Internet: <http://www.conmed.com/products_shoulder_biominirevo.php>.
Conmed Corporation "Bio Mini-Revo Suture Anchor", 510(k) Summary, FDA Approval Letter, FDA Approval Letter, and Indications of Use for 510(k) No. K073226, Jul. 2008, 5 pages total.
Conmed Linvatec, "Arthroscopy Product Catalog" [catalog], 2009, 194 pages total.
Conmed Linvatec, "Bio Mini-Revo™ Surgical Technique" [brochure] 2006, 12 pages total.
Conmed Linvatec, "Bio-Anchor® Shoulder Instability Repair System" [website], 2006, 1 page; retrieved from the Internet: <http://www.conmed.com/products_shoulder_bioanch.php>.
Conmed Linvatec, "Course: Bio Mini-Revo TM Surgical Technique—Designed in conjunction with Stephen J. Snyder, MD" [Slideshow] 2006, 26 pages; retrieved from the Internet: <http://www.conmed.com/SurgicalTechniques/BioMiniRevo.swf>.
Conmed Linvatec, "Duet™ Suture Anchor" [brochure], 2008, 4 pages total.
Conmed Linvatec, "Linvatec SRS Shoulder Restoration System: Simple Solutions for Complex Procedures" [website], 2009, 2 pages; retrieved from the Internet: <http://www.conmed.com/products_shoulder_srs_system.php?SelectCountry=0THER+COUNTRY.>.
Conmed Linvatec, "Paladin $^{TM}$ Rotator Cuff Anchor" [brochure], 2009, 2 pages total.
Conmed Linvatec, "Shoulder Restoration System" [brochure], 2009, 4 pages total.
Conmed Linvatec, "Shoulder Restoration System" [website], 2009, 1 page; retrieved from the Internet: <http://srs.linvatec.com/>.
Conmed Linvatec, "Shoulder Restoration System: PopLok™ Deployment Stages" [brochure], 2009, 2 pages total.
Conmed Linvatec, "Spectrum® II Soft Tissue Repair System" [brochure], 2006, 4 pages total.
Conmed Linvatec, "Spectrum® MVP™" [brochure], 2008, 4 pages total.
Conmed Linvatec, "Super Shuttle™" [brochure], 2009, 2 pages total.
Covidien AG, "Herculon™ Soft Tissue Fixation System—Bringing greater pullout strength to rotator cuff repair" [brochure], 2008, 4 pages total.
Daculsi et al., "Current State of the Art of Biphasic Calcium Phosphate Bioceramics," Journal of Materials Science, Mar. 2003; 14(3):195-200.
Depuy Mitek, Inc, a Johnson & Johnson Company, "Biocryl Rapide—TCP/PLGA Composite" [brochure], 2007, 4 pages total.
Depuy Mitek, Inc, a Johnson & Johnson Company, "BioKnotless™ RC Suture Anchor: Rotator Cuff Repair Surgical Technique" [brochure], 2006, 6 pages total.
Depuy Mitek, Inc, a Johnson & Johnson Company, "Dual Threaded Suture Anchor Healix PEEK™" [brochure], 2009, 2 pages total.
Depuy Mitek, Inc, a Johnson & Johnson Company, "ExpresSew™ Flexible Suture Passer" [instructions for use], Aug. 2007, 124 pages total.
Depuy Mitek, Inc, a Johnson & Johnson Company, "ExpresSew™ II Flexible Suture Passer" [instructions for use], Oct. 2006, 105 pages total.
Depuy Mitek, Inc, a Johnson & Johnson Company, "ExpresSew™ II: Surgical Technique" [brochure], 2007, 8 pages total.
Depuy Mitek, Inc, a Johnson & Johnson Company, "ExpresSew™ Surgical Technique" [brochure], 2005, 2 pages total.
Depuy Mitek, Inc, a Johnson & Johnson Company, "ExpresSew™: A Single-Step Passer Under 5 mm" [brochure], 2005, 2 pages total.
Depuy Mitek, Inc, a Johnson & Johnson Company, "Healix BR™" [brochure], 2009, 2 pages total.
Depuy Mitek, Inc, a Johnson & Johnson Company, "Healix PEEK™—Dual Threaded Suture Anchor" [brochure], 2009, 2 pages total.
Depuy Mitek, Inc, a Johnson & Johnson Company, Lupine $^T$ BR & Bioknotless™ BR Anchors . . . Now with Biocryl Rapide—BIOCRYL Rapide has refined our Suture Anchors as "Bio-Replaceable" [brochure], 2007, 4 pages total.
Depuy Mitek, Inc, a Johnson & Johnson Company, "Mitek Suture Grasper" [instructions for use], 2007, 60 pages total.
Depuy Mitek, Inc, a Johnson & Johnson Company, "Palenlok® RC—Quick Anchor Plus® Absorbable" [brochure] 2006, 2 pages total.
Depuy Mitek, Inc, a Johnson & Johnson Company, PathSeeker™ Flexible Suture Grasper [brochure], 2005, 2 pages total.
Depuy Mitek, Inc, a Johnson & Johnson Company, "PathSeeker™ Suture Passer" [instructions for use], 2007, 174 pages total.
Depuy Mitek, Inc, a Johnson & Johnson Company, Procedural Solutions in Shoulder Repair [advertorial and detail],2005; retrieved from the Internet: <http://issuu.com/valmaass/docs/mitek_advertorial?mode=a_p.
Depuy Mitek, Inc, a Johnson & Johnson Company, "Quick Anchor® Plus Family" [brochure], 2005, 2 pages total.
Depuy Mitek, Inc, a Johnson & Johnson Company, SpiraLok™ Absorbably Dual-Eyelet Theaded Suture Anchor [brochure], 2005, 2 pages total.
Depuy Mitek, Inc, a Johnson & Johnson Company, Versalok™ Anchor [instructions for use], Aug. 2007, 92 pages total.
Dines et al., "Horizontal Mattress With a Knotless Anchor to Better Recreate the Normal Superior Labrum Anatomy," Arthroscopy, Dec. 2008;24(12):1422-1425.
Esch, "Arthroscopic Rotator Cuff Repair with the Elite™ Shoulder System," A Smith & Nephew Techique Plus $^T$ Illustrated Guide, 2001, 16 pages total.
Ethicon, Inc., a Johnson & Johnson Company, Mitek® Products Bioknotless™ Anchors: The First Absorbable Knotless Suture Anchor [brochure], 2007, 2 pages total.
Ethicon, Inc., a Johnson & Johnson Company, Mitek® Products, "Absorbable Soft Anchor PANALOK®" [brochure] 2001, 2 pages; can be retrieved from the Internet: <www.shoulderdoc.co.uk/documents/mitek_panalok.pdf >.
Fox et al., "Update on Articular Cartilage Restoration," Techniques in Knee Surgery, Mar. 2003; 2(1):2-17.
Gartsman et al., "Arthroscopic Rotator Cuff Repair," Techniques in Shoulder and Elbow Surgery, 1999, pp. 1-7.
Gartsman, "Arthroscopic Repair of Full-Thickness Tears of the Rotator Cuff," The Journal of Bone and Joint Surgery, 1998; 80:832-840.
Gartsman, Shoulder Series Technique Guide: Bankart Repair Using the Smith & Nephew Bioraptor 2.9 Suture Anchor [brochure], Smith & Nephew, Inc., Sep. 2004, Rev. A, 7 pages total; retrieved from the Internet: <http://global.smith-nephew.com/cps/rde/xbcr/smithnephewls/V1-1061563A_bioraptorpdf.
Gill, The Treatment of Articular Cartilage Defects Using Microfracture and Debridement, Am J Knee Surg 2000;13(1):33-40.
Green et al., "Arthroscopic versus open Bankart procedures: a comparison of early morbidity and complications," Arthroscopy, 1993; 9(4):371-374.
Guanche et al., "Labral Repair" [video recording], A young track athlete with a pincer lesion in her hip undergoes an arthroscopic labral takedown and repair by Carlos Guanche, MD at Southern

(56) References Cited

OTHER PUBLICATIONS

California Orthopedic institute in Van Nuys, CA. Dr. Guanche performs complex hip arthroscopic procedures including resection of cam lesions, labral repairs, psoas releases and abductor repairs, posted on the Internet: <http://www.youtube.com/watch?v=onCIESDRVZM&feature=channel_page> on Jun. 18, 2008.

Guanche, "Large Hip Labral Repair Using PushLockTM Anchor" [video recording], Arthroscopic surgery of a hip labral repair with a knotless anchor performed by Dr. Carlos Guanche in Van Nuys, CA, posted on the Internet: <http://www.youtube.com/watch?v=t04fj2TcXv0>on Mar. 25, 2008.

Halbrecht, "Versalok: A New technique for Arthroscopic Knotless Rotator Cuff Repair" [presentation], Mitek Sponsored Dinner Meeting. Tuscon AZ. Jun. 5, 2007; retrieved from the Internet: <http://www.iasm.com/pdfs/KnotlessArthroscopicRotatorCuffRepairUsingVersalok.pdf >, 44 pages total.

Hughes, The Kinematics and Kinetics of Slipknots for Arthroscopic Bankart Repair, Am J Sports Med, Nov. 2001; 29( 6):738-745.

International search report and written opinion dated Jul. 2, 2010 for PCT/US2010/034118.

International search report and written opinion dated Jul. 2, 2010 for PCT/US2010/034104.

International search report and written opinion dated Jul. 9, 2010 for PCT/US2010/034115.

Jeys et al., "Bone Anchors or Interference Screws? A Biomechanical Evaluation for Autograft Ankle Stabilization," Am J Sports Med, Oct. 2004; 32( 7):1651-1659.

KFX® Medical, Arthroscopic Double Row Rotator Cuff Repair [procedural Video], Performed by Joe Tauro, M.D., Toms River, NJ; can be view at: <http://www.kfxmedical.com/technology_procedure.htm>.

KFX® Medical, "Arthroscopic PASTA lesion repair using the SutureCross® System" [procedural Video] Performed by Joe Tauro, M.D., Toms River, NJ; can be view at: <http://www.kfxmedical.com/technology_procedure_pasta_video.htm.

KFX® Medical, "SutureCross® Knotless Anatomic Fixation System: Double Row Fixation for Rotator Cuff Repair Animation" [video screenshots] 2008, 52 pages total.; video available online at <http://www.kfxmedical.com/video/SURGTECH9-23.wmv>.

KFX® Medical, "SutureCross® Knotless Anatomic Fixation System: Double Row Fixation Rotator Cuff Repair Surgical Technique" [brochure], 2008, 12 pages total.

KFX® Medical, "SutureCross® Knotless Anatomic Fixation System: Double Row Rotator Cuff Fixation" [website]; retrieved from the Internet: <http://www.kfxmedical.com/product_suturecross.htm>, 1 page.

KFX® Medical, "SutureCross® Knotless Anatomic Fixation System: Rotator Cuff Repair" [datasheet], 2008, 2 pages total.

KFX® Medical, The PASTAFxTM System Surgical Technique: Simplified PASTA Rotator Cuff Repair [technique guide], 2008, 8 pages total.

KFX® Medical, The PASTAFxTM System: No need to Tear to Repair [website]; retrieved from the internet: <http://www.kfxmedical.com/product_pastafx.htm>, 2 pages total.

KFX® Medical, The PASTAFxTM System: Simplified PASTA Repair [datasheet] 2008, 2 pages total.

Khabie et al., "Fixation Strength of Suture Anchors After Intraoperative Failure of the First Anchor," 45th Annual Meeting of Orthopaedic Research Society, Feb. 1-4, 1999, Anaheim, p. 1074 ; retrieved from the Internet: <http://www.ors.org/web/Transactions/45/1074.PDF>.

Langdown et al., In Vivo Evaluation of 6-TCP Bone Graft Substitutes in a Bilateral Tabial Defect Model, Paper No. 1712, 52nd Annual Meeting of the Orthopaedic Research Society, The Lakeside Center, McCormick Place, Chicago, IL, Mar. 19-22, 2006, 1 page total.

Larson et al., "Arthroscopic Management of Femoroacetabular Impingement: Early Outcomes Measures," Arthroscopy. May 2008;24(5):540-546.

Linvatec, "Course: Bio-Anchor® Surgical Technique" [Slideshow], 2004, 13 pages; retrieved from the Internet: <http://www.conmed.com/SurgicalTechniques/BioAnchor.swf>.

Linvatec, a Conmed® Company, "Bio-Anchor® Surgical Technique: Shoulder Instability System" [brochure], 2004, 2 pages; retrieved from the Internet: <http://www. con med. com/PDF%20files/CST%203021%20Rev%201%20BioAnchorST.pdf.

Linvatec, a Conmed® Company, "ImpactTM Suture Anchor Surgical Technique" [brochure], 2004, 4 pages total.

Lo et al., "Abrasion Resistance of Two Types of Nonabsorbable Braided Suture," Arthroscopy, Apr. 2008; 20(4):407-413.

Lo et al., "Arthroscopic Knots: Determining the Optimal Balance of Loop Security and Knot Security," Arthroscopy. May 2004;20(5):489-502.

Louden et al., "Tendon Transfer Fixation in the Foot and Ankle: A Biomechnanical Study Evaluating Two Sizes of Pilot Holes for Bioabsorbable Screws," Foot & Ankle International, Jan. 2003; 24(1):67-72.

Ma et al., "Biomechanical Evaluation of Arthroscopic Rotator Cuff Stitches," The Journal of Bone and Joint Surgery, 2004; 86:1211-1216.

McGuire et al., "Bioabsorbable Interference Screws for Graft Fixation in Anterior Cruciate Ligament Reconstruction," Arthroscopy, Jul. 1999; 15(5):463-473.

Menche et al., "Inflammatory Foreign-Body Reaction to an Arthroscopic Bioabsorbable Meniscal Arrow Repair," Arthroscopy. Oct. 1999;15(7):770-772.

Meyer et al., "Mechanical Testing of Absorbable Suture Anchors," Arthroscopy, Feb. 2003; 19(2):188-193.

Middleton et al., "Synthetic Biodegradable Polymers as Orthopedic Devices," Biomaterials, Dec. 2000, 21(23):2335-2346.

Millett et al., "Mattress Double Anchor Footprint Repair: A Novel, Arthroscopic Rotator Cuff Repair Technique," Arthroscopy Oct. 2004; 20(8):875-879.

Morgan, "Arthroscopic Management of Rotator Cuff Tears" [Presentation Outline], The Morgan Kalman Clinic, Wilmington, Delaware, undated, 2 pages.

Murray, Jr., "Arthroscopic Rotator Cuff Repair with a Bioabsorbable Suture Anchor: Preliminary Results," [Abstract] Orthopaedic Associates of Portland, Portland, ME, 1 page.

Office action dated Jun. 5, 2012 for U.S. Appl. No. 12/605,065.

Office action dated Oct. 4, 2012 for U.S. Appl. No. 12/776,225.

Ogose et al., "Histological Assessment in Graft of Highly Purified Beta-Tricalcium Phosphate (Osferion) in Human Bones," Biomaterials. Mar. 2006;27(8):1542-1549.

Ogose et al., "Histological Examination of 6-Tricalcium Phosphate Graft in Human Femur," J Biomed Mater Res, 2002;63(5):601-604.

Parcus Medical, LLC, "Parcus V-LoxTM PEEK CF Suture Anchor", pp. 15, 16 of 510(k) Summary, FDA Approval Letter and Indications of Use for 510(k) No. K091094, Sep. 2009, 5 pages total.

Parcus Medical, LLC, "PEEK CF V-LoxTM Suture Anchor Demo" [video]; can be view at: <http://www.parcusmedical.com/techniques/animations/peek-vlox-anchor-demo.html>.

Parcus Medical, LLC, "V-LoxTM PEEK CF Suture Anchor [Production Information and Directions for use", undated, 2 pages total.

Parcus Medical, LLC, "V-LoxTM PEEK CF Suture Anchors Product Information Sheet" [brochure] undated, 1 page total.

Parcus Medical, LLC, "V-LoxTM PEEK CF Suture Anchors" [website]; retrieved from the Internet: <http://www.parcusmedical.com/products/peek-anchor.html>, 2 pages total.

Park et al., "Transosseous-Equivalent" Rotator Cuff Repair Technique, Arthroscopy, Dec. 2006; 22(12):1360.e1-1360.e5.

Romeo et al., "Arthroscopic Repair of Full-Thickness Rotator Cuff Tears: Surgical Technique and Instrumentation" Orthopedic Special Edition, 2001; 7(1 of 2):25-30; retrieved from the Internet: <http://www.cartilagedoc.org/downloads/shoulder/Rotat.pdf>.

Schamblin, Conexa® Case Series Report: Arthroscopic Reinforcement of Revision Rotator Cuff Repair Tornier, Inc., 2009, 2 pages; retrieved from the Internet: <www.bhportho.com/docs/Conexa_RCR_Repair_Schamblin.pdf>.

Smith & Nephew, Inc., "2008 Product Catalog" [catalog], 2009, 311 pages total.

(56) References Cited

OTHER PUBLICATIONS

Smith & Nephew, Inc., "2009 Product Catalog" [catalog], 2008, 373 pages total.
Smith & Nephew, Inc., "ACCU-PASS Suture Shuttle" [video animation] 2005, 59 image screen shots; can be view at : <http://endo.smith-nephew.com/fr/View.asp?guid={6F27C42E-1632-4974-84E9-F18922FC19AA} &b=2->.
Smith & Nephew, Inc., Bioraptor 2.9 Suture Anchor [video animation], 2004; can be viewed at: <http://endo.smith-nephew.com/fr/View.asp?guid={98BCCE86-B5C2-413F-80AE¬CF7260A38C17} &b=2-BIORAPTOR%20animation.wmv>.
Smith & Nephew, Inc., "Bioraptor 2.9" [website], 3 pages total; retrieved from the Internet: <http://endo.smith-nephew.com/fr/node.asp?NodeId=3608>.
Smith & Nephew, Inc., "Bioraptor PK suture Anchor", 510(k) Summary, FDA Approval Letter, and Indications of Use for 510(k) No. K071586, Aug. 2007, 5 pages total.
Smith & Nephew, Inc., "ELITE PASS Premium Arthroscopic Suture Shuttle" [video animation], Mar. 2005, 44 image screen shots; video can be viewed at: <http://global.smith-nephew.com/us/showfile.xml?doc=V1-ELITE_PASS_Animation(26)_.wmv>.
Smith & Nephew, Inc., "Footprint PK Suture Anchor: Arthroscopic Shoulder Repair Using the Smith & Nephew Footprint PK Suture Anchor" [brochure], 2008, 12 pages total.
Smith & Nephew, Inc., "KINSA* Suture Achnor" [website], 2 pages; retrieved from the Internet: <http://www.endo.smith-nephew.com/fr/node.asp?NodeId=3739>.
Smith & Nephew, Inc., "OsteoraptorTM Suture Anchor", pp. 10-11 of 510(k) Summary, FDA Approval Letter, and Indications of Use for 510(k) No. K082215, Nov. 2008, 5 pages total.
Smith & Nephew, Inc., "TWINFIX Suture Anchors with ULTRABRAID Suture—Unparalleled strength, superior handling" [brochure], 2005, 12 pages total.
Smithnephew. Shoulder Series Technique Guide: Arthroscopic Shoulder Repair Using the Smith & Nephew Kinsa Suture Anchor [brochure], Smith & Nephew, Inc., Sep. 2006, Rev. B, 12 pages total; retrieved from the Internet: <http://global.smith-nephew.com/cps/rde/xbcr/smithnephewls/V1-10600180b%2829%29.pdf.
Spiralok and-Bio-Corkscrew FT Cadaver Study [white paper], no publication information, 2 pages total.
Stryker Corporation, "PEEK TwinLoop" [website], 1 page; retrieved from the Internet: <http://www.strykercom/enus/products/Orthopaedics/SportsMedicine/ShoulderInstrumentation/Anchors/Peek/056652.
Stryker Corporation, "Point to the Solution: BioZip Absorbable Suture Anchor" [brochure,] 2008, 4 pages total.
Stryker Corporation, "Shoulder Repair Made Simpler: Champion Shoulder Instrumentation" [brochure], 2008, 4 pages total.
Stryker Corporation, Strength & Flexibility in Soft-Tissue Repair [brochure], 2008, 4 pages total.
Stryker Corporation, Stronger Than Ever: PEEK Zip Anchor [brochure] 2008, 4 pages total.
Stryker Corporation, "Suture Sliding Made Simple" [brochure], 2005, 4 pages total.
Stryker Corporation, One Shot for Success—Titanium Wedge Anchor [brochure], 2008, 4 pages total.
Stryker. Stability, Precision, Flexibility—PEEK Twinloop Anchor [brochure], Stryker Corporation, Jun. 2008, Rev 1, 4 pages total; retrieved from the Internet: <http://www.strykercom/stellent/groups/public/documents/web_prod/056750.pdf>.
Tetik et al., "Bioabsorbable Interference Screw Fixation in a Bone Tunnel: Comparison of 28mm; 35 \mm Single Screw Fixation and Bi-Cortical Fixation with a 20mm and 17mm Screws," Lexington, Kentucky, undated, 3 pages total.
Tornier, Inc., "CINCHTM Knotless Fixation Implant System", pp. 38-40 of 510(k) Summary, FDA Approval Letter and Indications of Use for 510(k) No. K080335 , Feb. 2008, 6 pages total.
Tornier, Inc., "InsiteTM Suture Anchors", pp. 66-67 of 510(k) Summary, FDA Approval Letter and Indications of Use for 510(k) No. K080368, Feb. 2009, 5 pages total.
Tornier. Piton Knotless Fixation System, Tornier, Inc., 2009, 3 pages total; retrieved from the Internet: <http://www.tornier-us.com/sportsmed/smd003/index.php?pop=1> on Oct. 14, 2009.
Vogt et al., "Injuries to the Articular Cartilage," European Journal of Trauma, Aug. 2006; 32(4):325-331.
Walsh et al., "Healing of a Critical Size Defect in Sheep Using Bone Graft Substitutes in Block Form," Poster No. 1433, 53rd Annual Meeting of the Orthopaedic Research Society, San Diego Convention Center, San Diego, California, Feb. 11-14, 2007, 1 page total.
Warden et al., "Magnetic Resonance Imaging of Bioabsorbably Polylactic Acid Interference Screws During the First 2 Years After Anterior Cruciate Ligament Reconstruction," Arthroscopy, Jul.-Aug., 15(5):474-480.
Weiler et al., "Biodegradable Implants in Sports Medicine: The Biological Base," Arthroscopy, Apr. 2000;16(3):305-321.
Yanke et al., 'Arthroscopic Double-Row and "Transosseous-Equivalent" Rotator Cuff Repair,' Am J Orthop (Belle Mead NJ). Jun. 2007;36(6):294-297.
Zimmer, Inc., "Labral Repair with Statak Suture Anchors—Surgical Techniques: Arthroscopic & Open" [brochure], 1996, 6 pages total.
Zimmer, Inc., "Rotator Cuff Repair with Statak Suture Anchors—Surgical Techniques: Arthroscopic & Open" [brochure], 1996, 6 pages total.
Notice of allowance dated Aug. 2, 2013 for U.S. Appl. No. 12/776,208.
Office action dated Jun. 18, 2013 for U.S. Appl. No. 12/776,208.
Office action dated Oct. 23, 2014 for U.S. Appl. No. 14/015,934.
Office action dated Dec. 5, 2014 for U.S. Appl. No. 13/692,596.
Notice of allowance dated Aug. 26, 2016 for U.S. Appl. No. 13/855,445.
Office Action dated Jan. 5, 2018 from U.S. Appl. No. 14/804,178.
"Office action dated Aug. 7, 2018 for U.S. Appl. No. 14/804,178".
Office action dated Nov. 1, 2019 for U.S. Appl. No. 15/361,850.

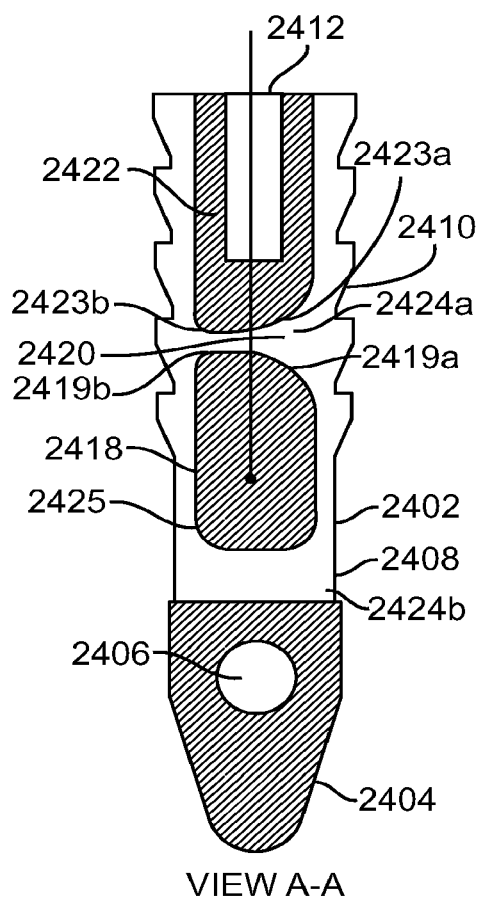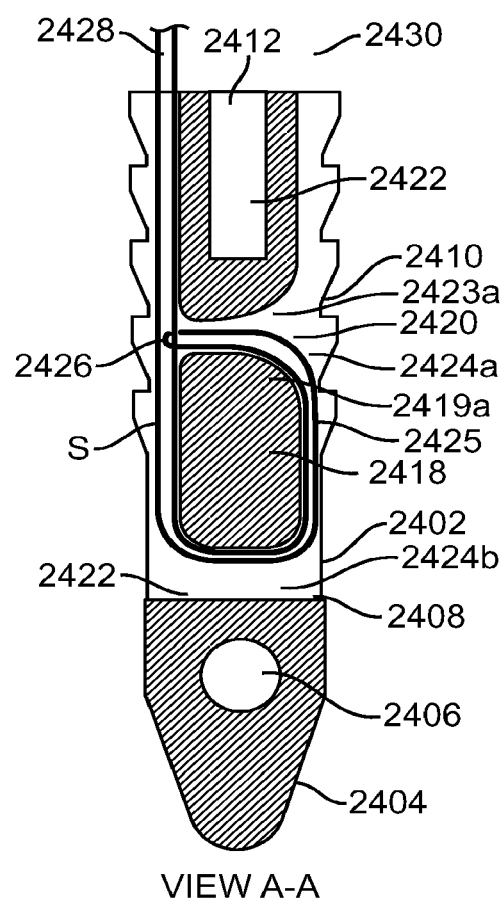
FIG. 24E
FIG. 24F

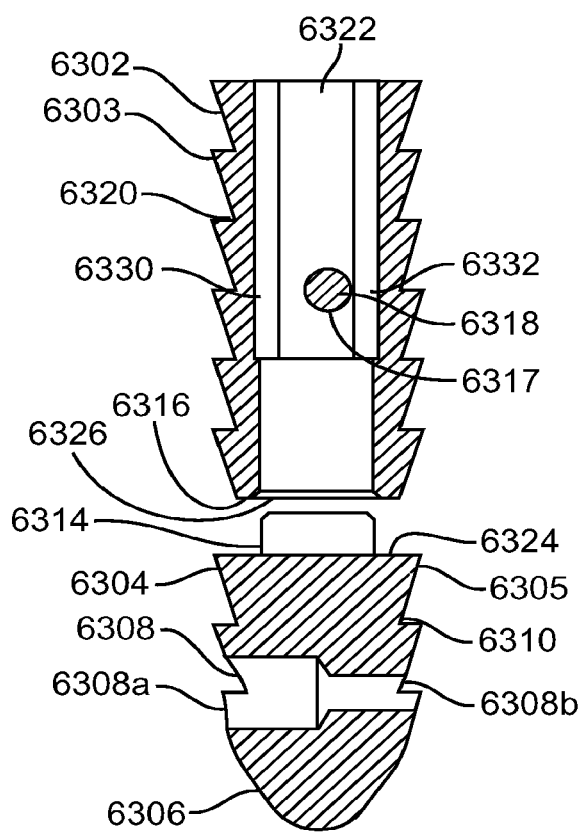
FIG. 25D
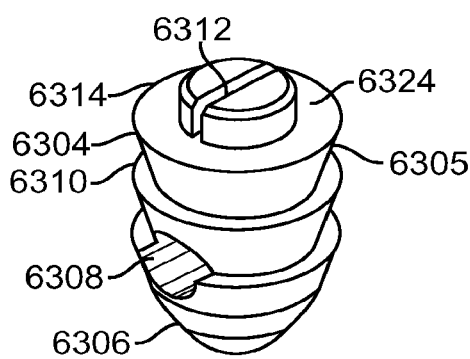 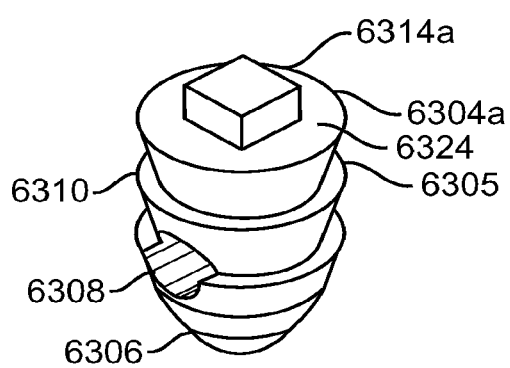
FIG. 25E  FIG. 25F

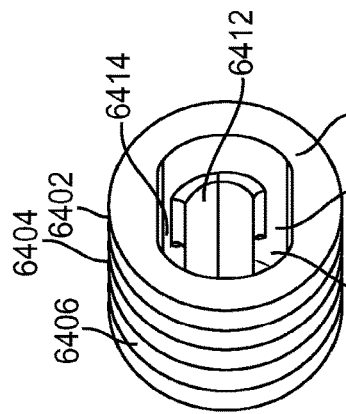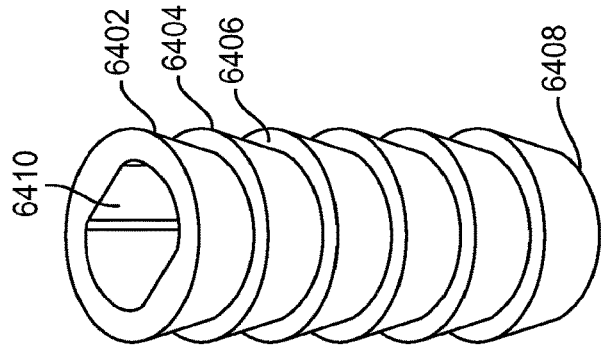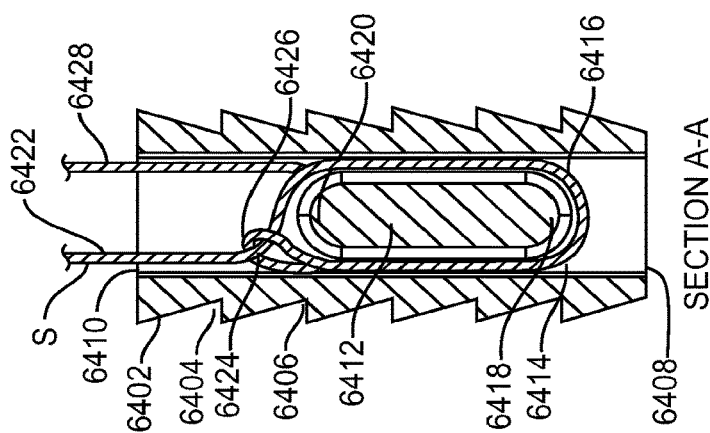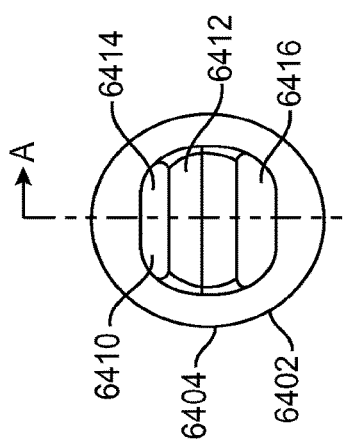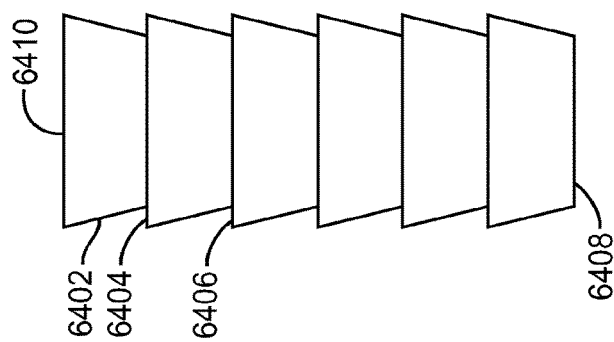

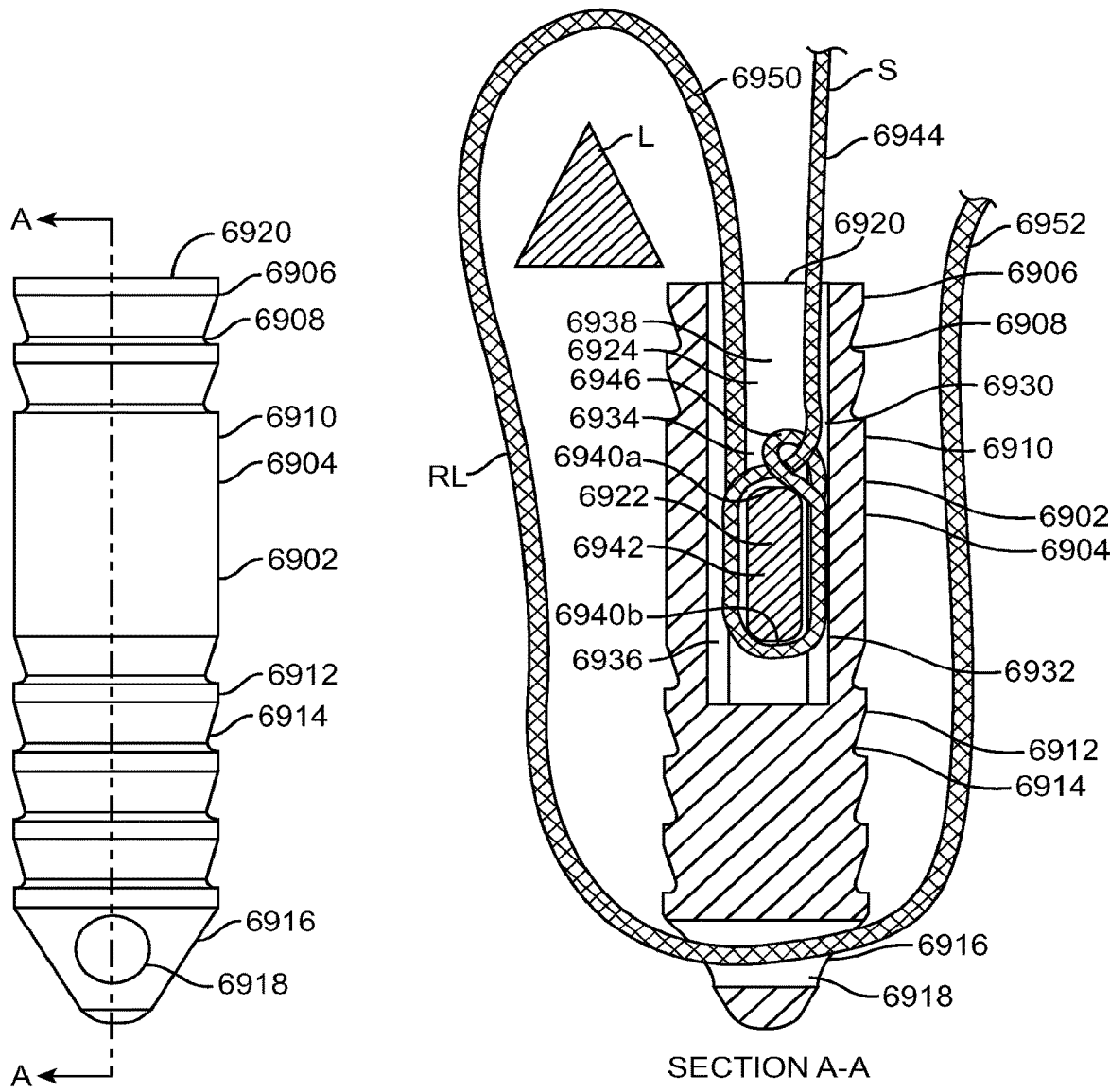
FIG. 27A
FIG. 27C
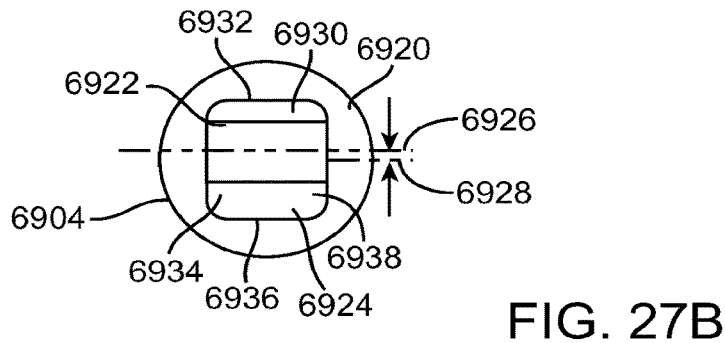
FIG. 27B

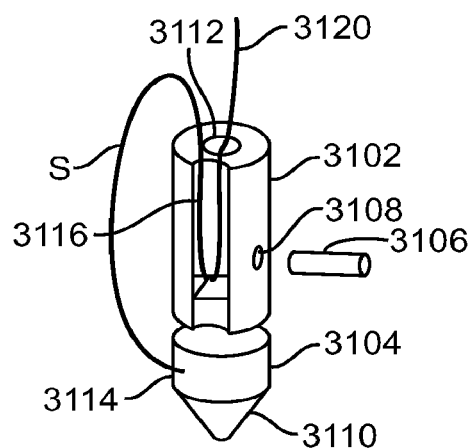 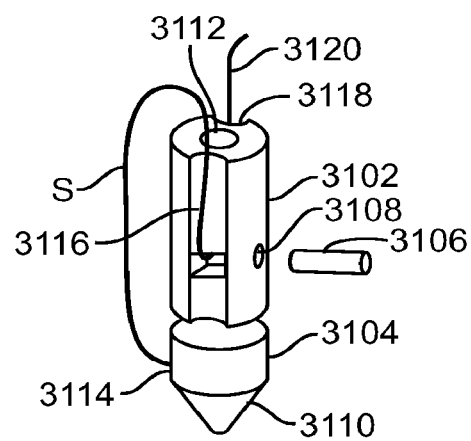
FIG. 28A　　　　　　　　　FIG. 28B
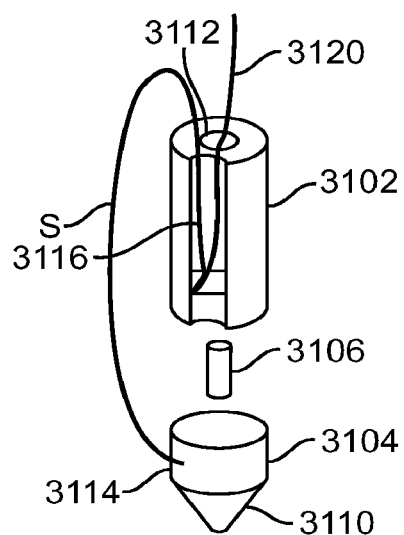 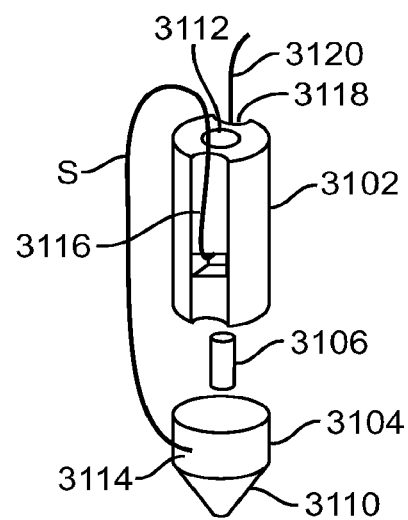
FIG. 29A　　　　　　　　　FIG. 29B

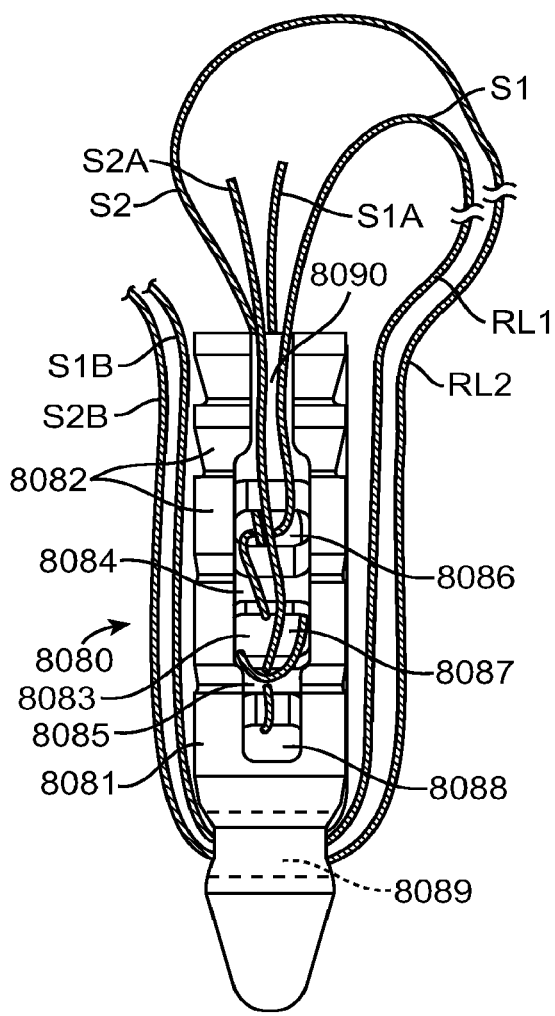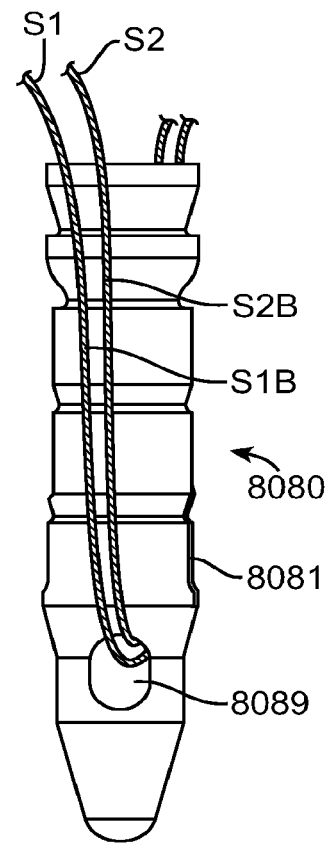
FIG. 32C
FIG. 32D
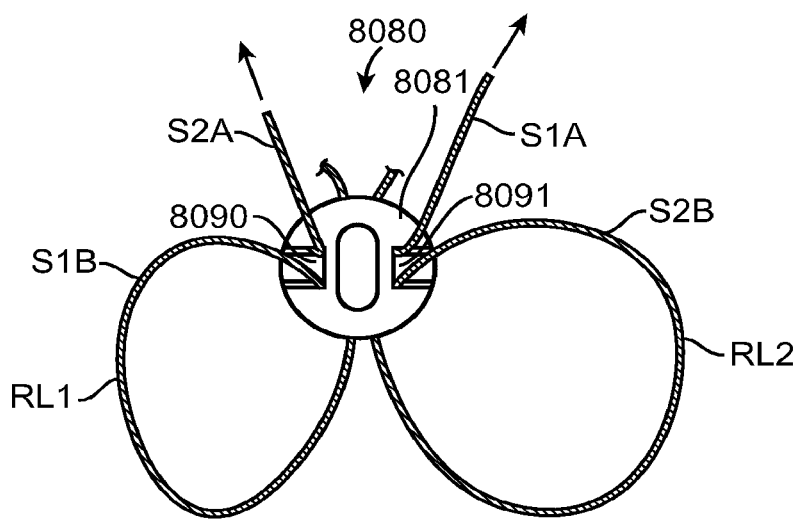
FIG. 32E

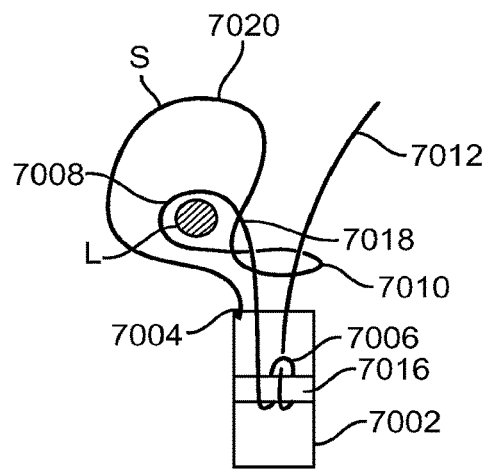
FIG. 33
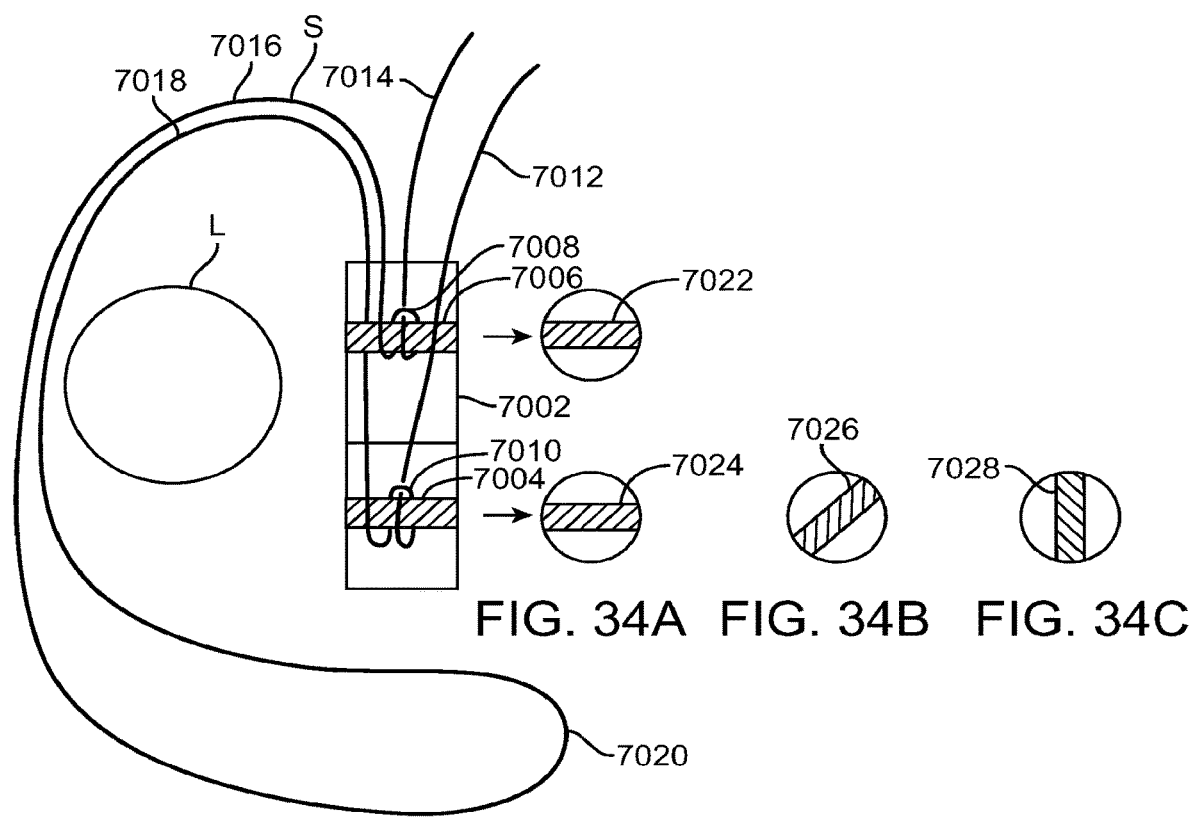
FIG. 34A    FIG. 34B    FIG. 34C
FIG. 34

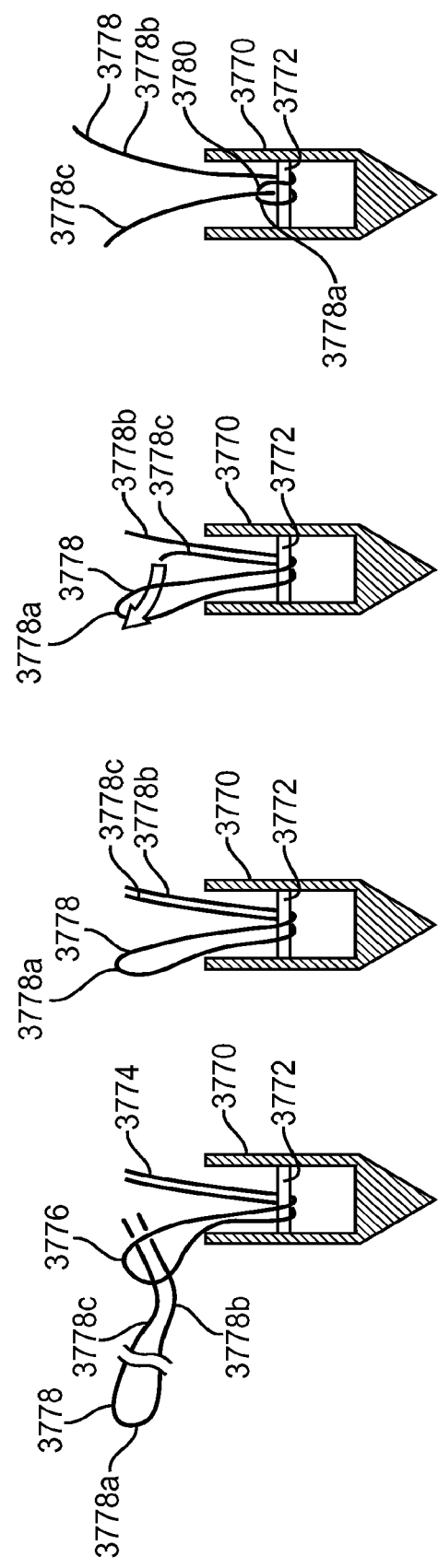

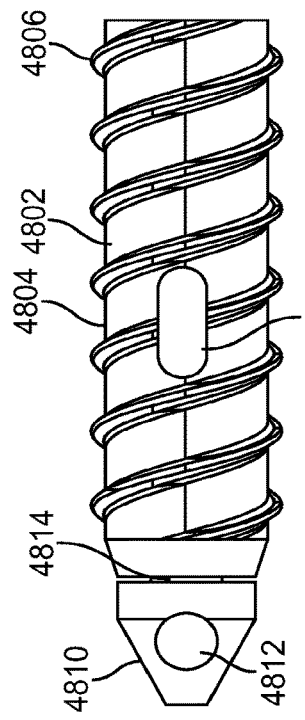
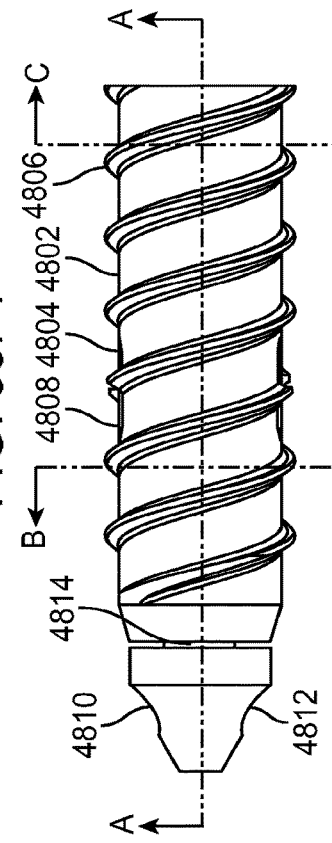
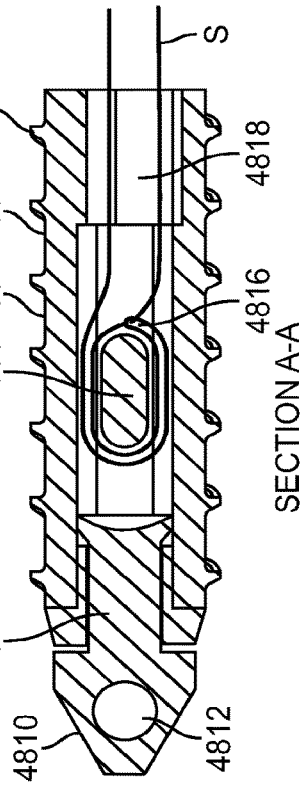
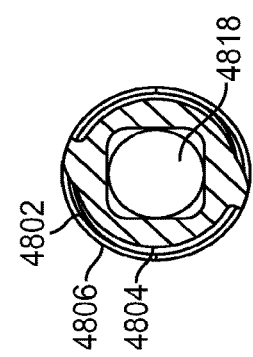
FIG. 38F4 SECTION C-C
FIG. 38F1
FIG. 38F3
FIG. 38F5 SECTION A-A
FIG. 38F2 SECTION B-B

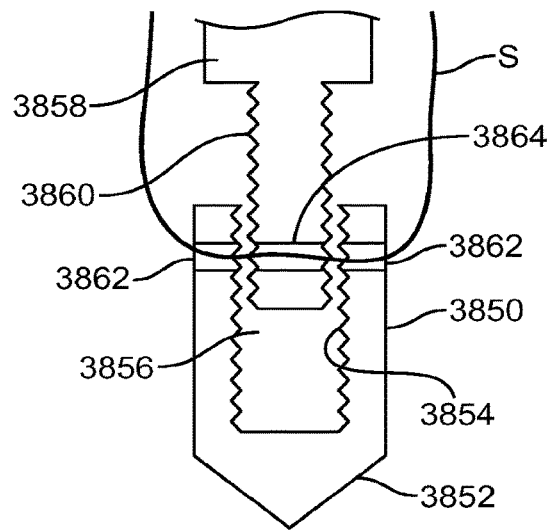
FIG. 38H1
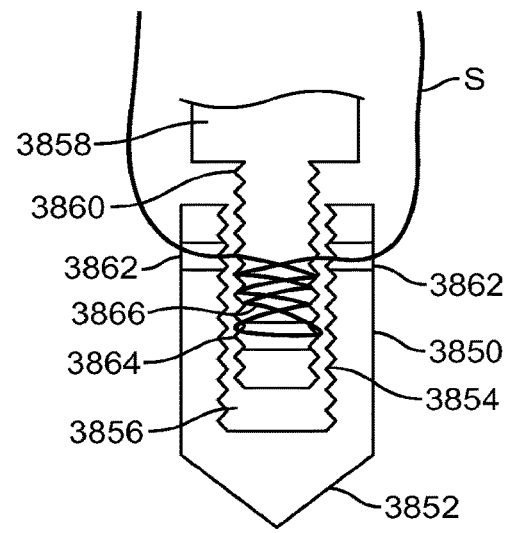
FIG. 38H2
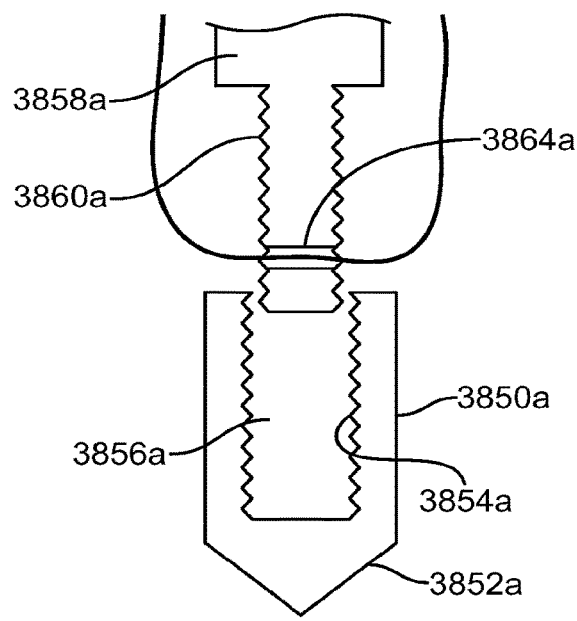
FIG. 38I1
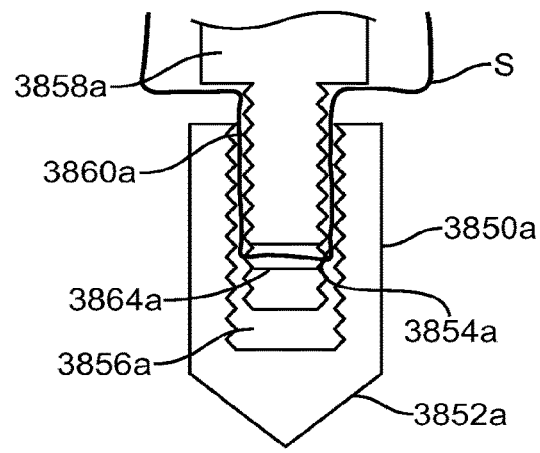
FIG. 38I2

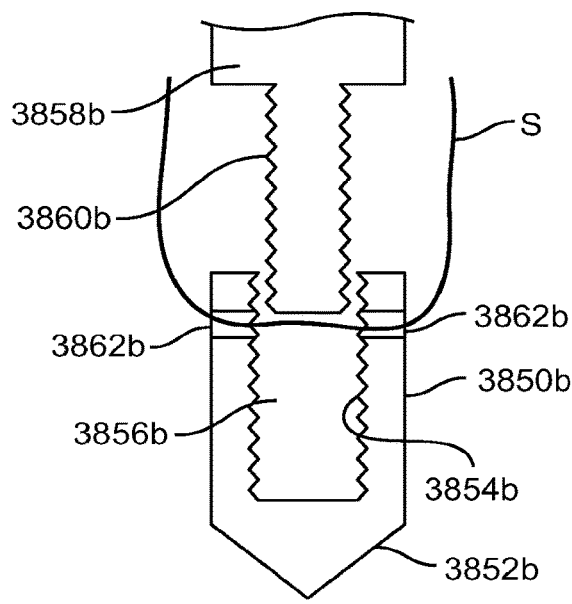
FIG. 38J1
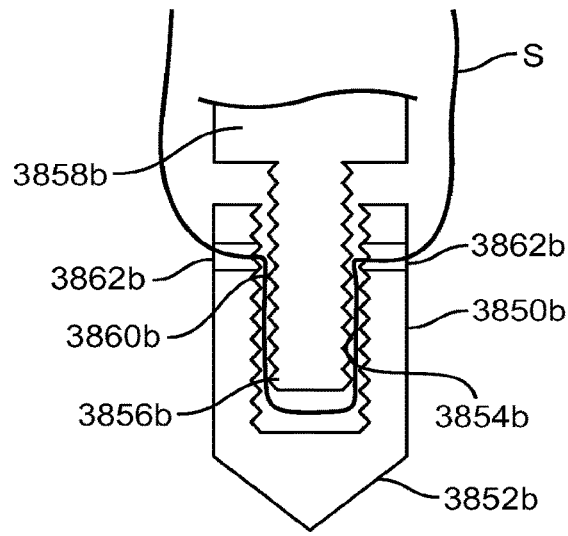
FIG. 38J2
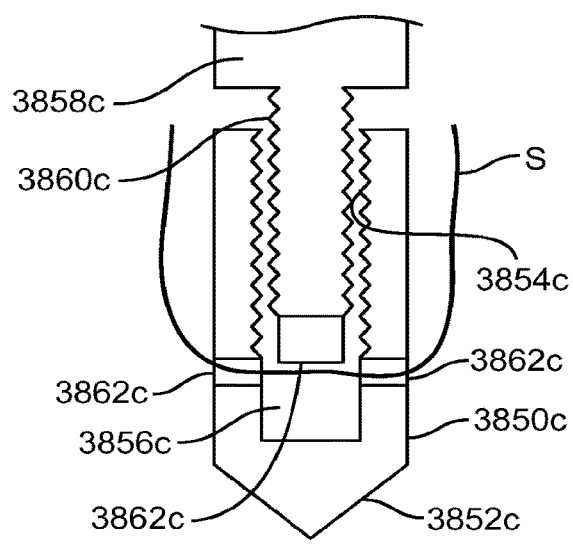
FIG. 38K1
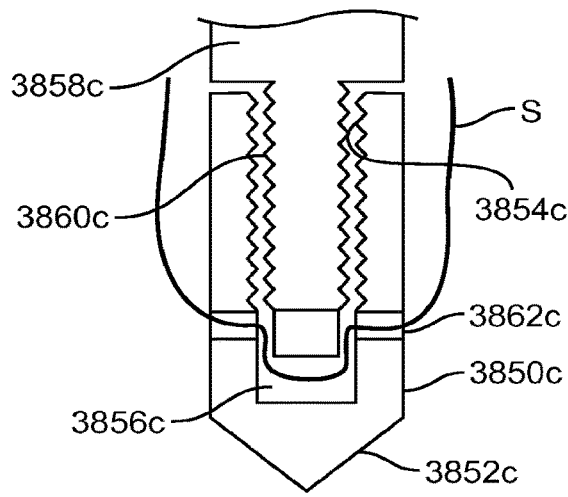
FIG. 38K2

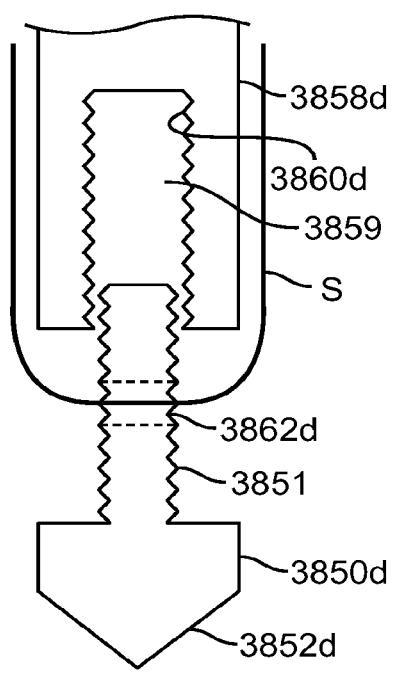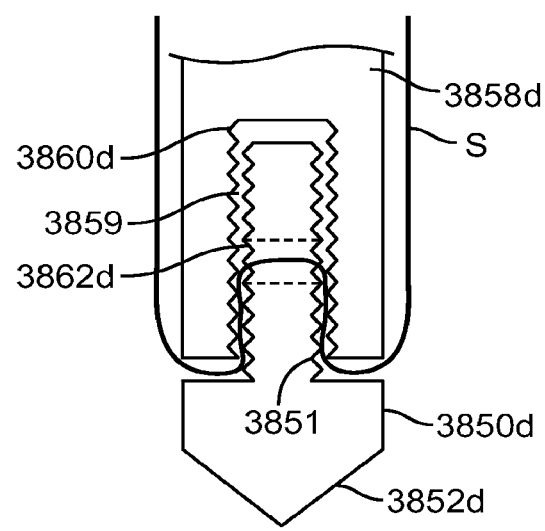
FIG. 38L1
FIG. 38L2

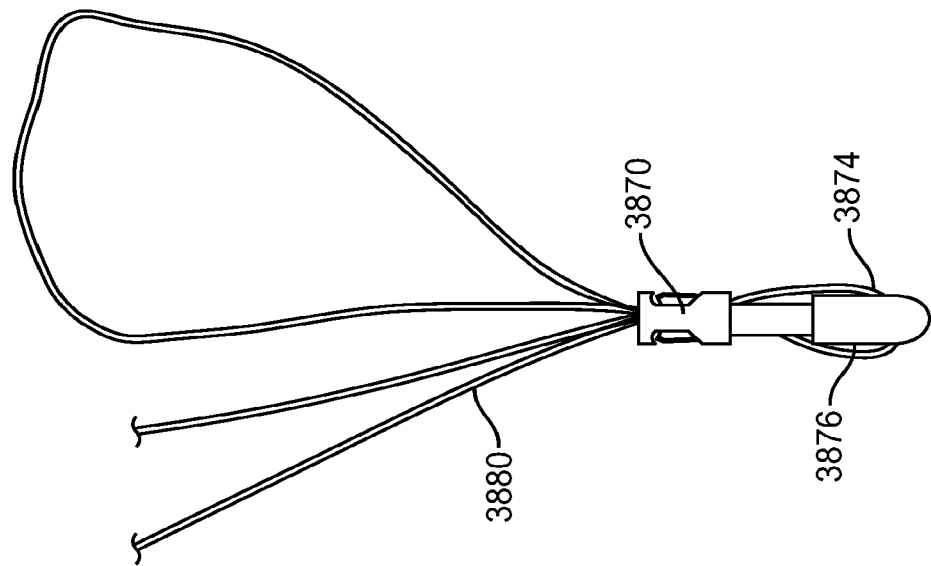
FIG. 38M2
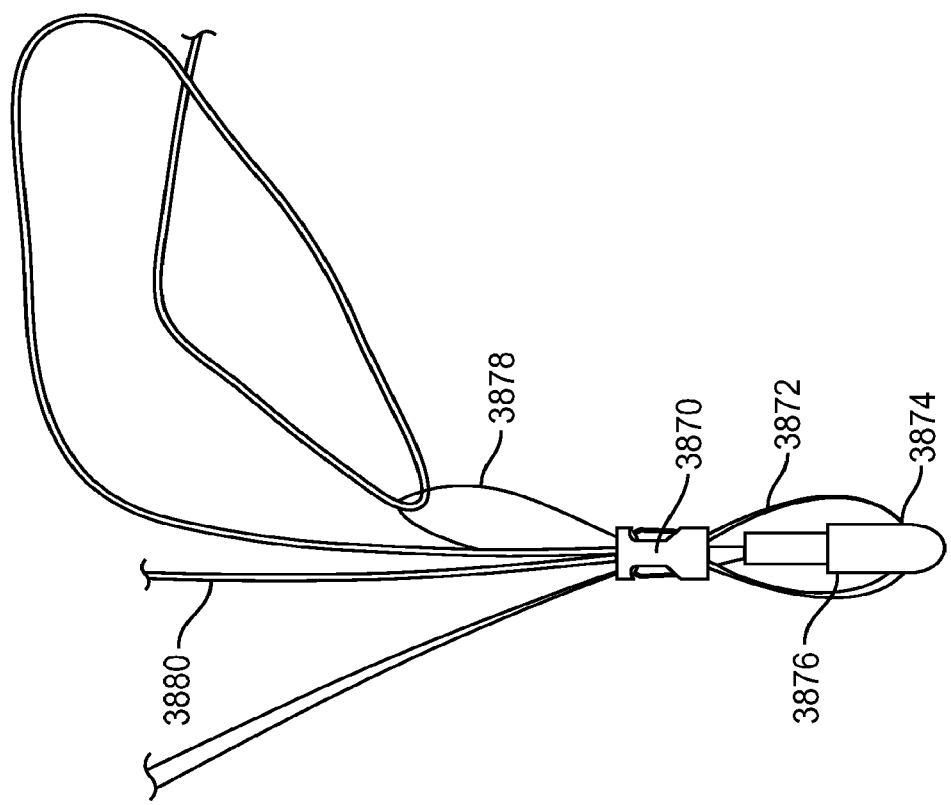
FIG. 38M1

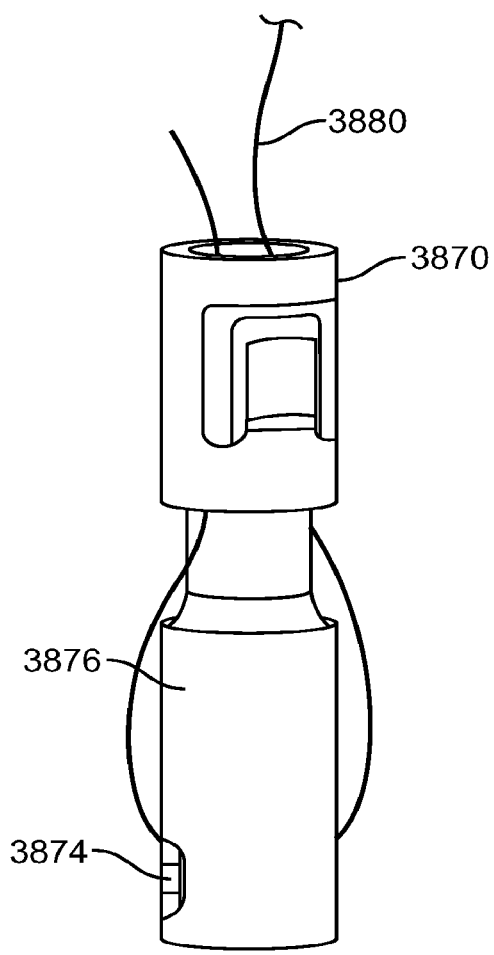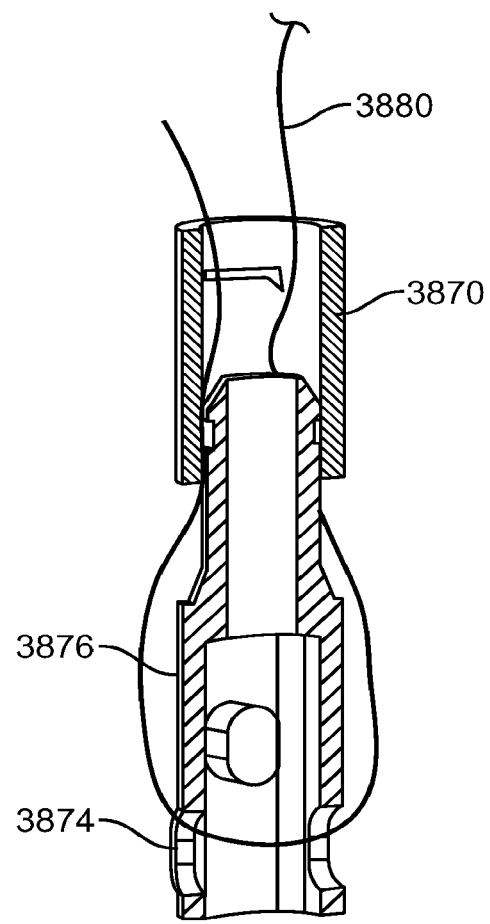
FIG. 38M2A  FIG. 38M2B

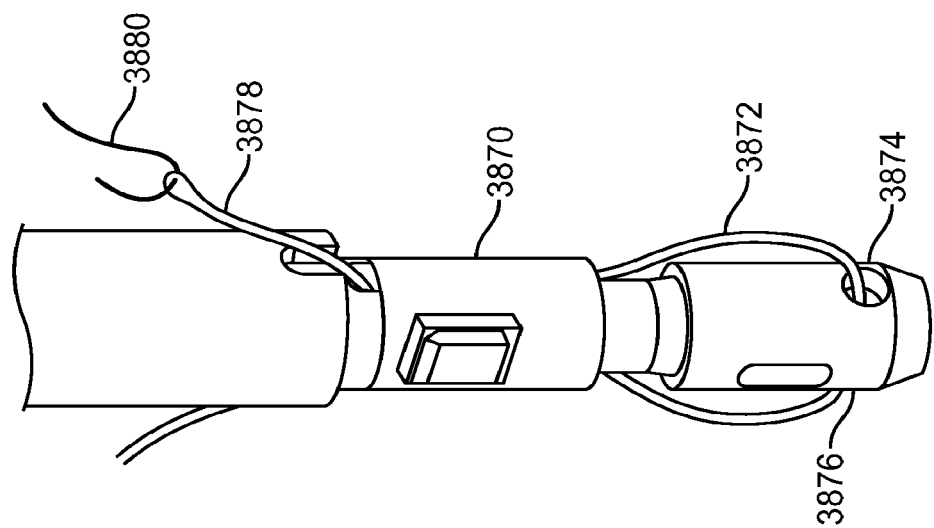
FIG. 38M5
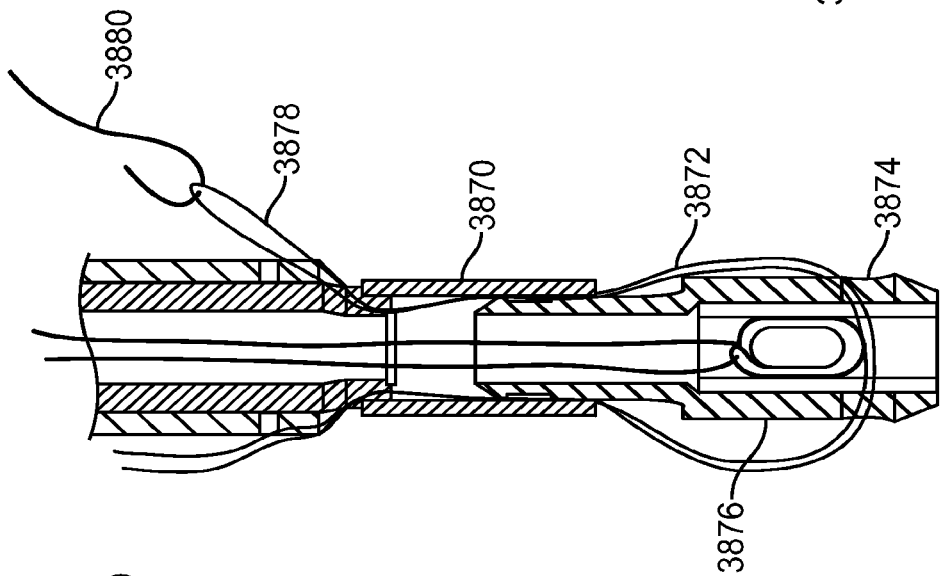
FIG. 38M4
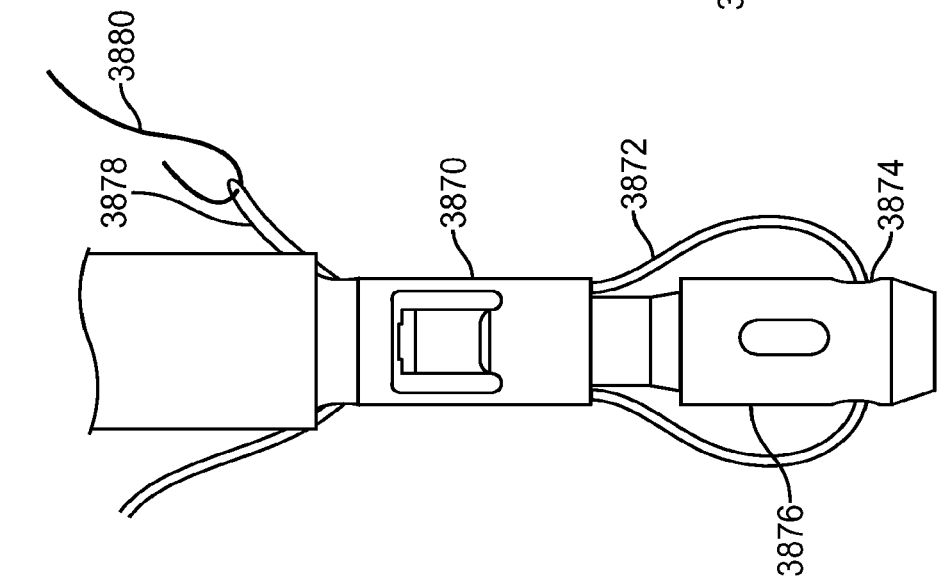
FIG. 38M3

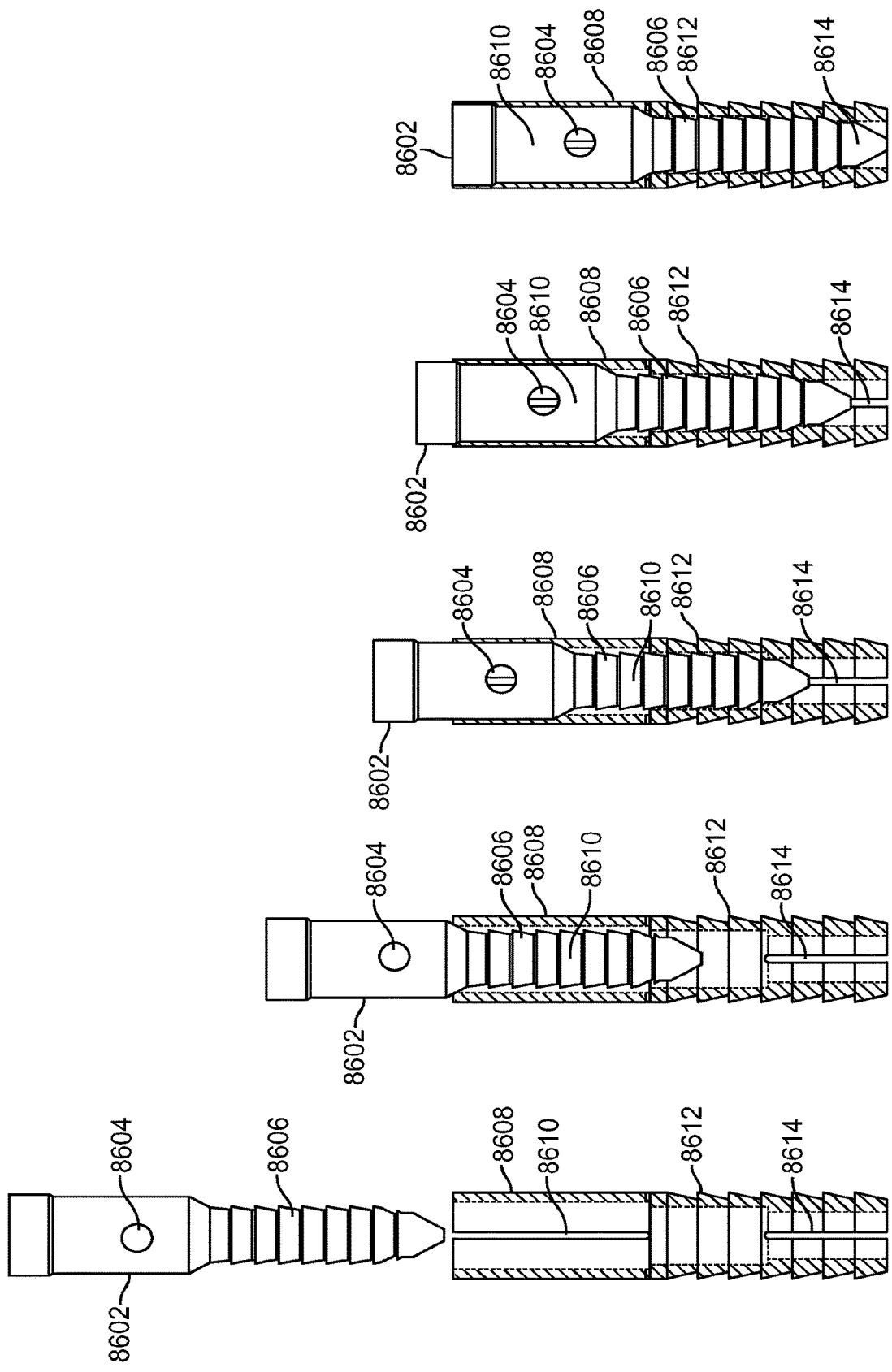

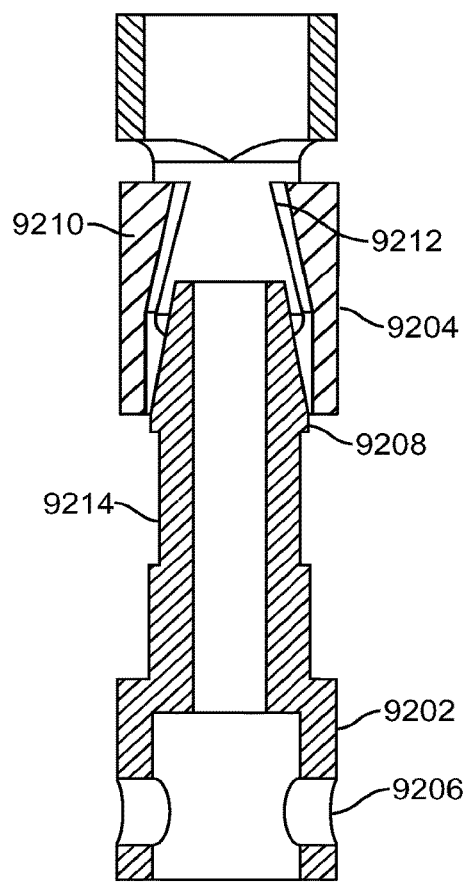
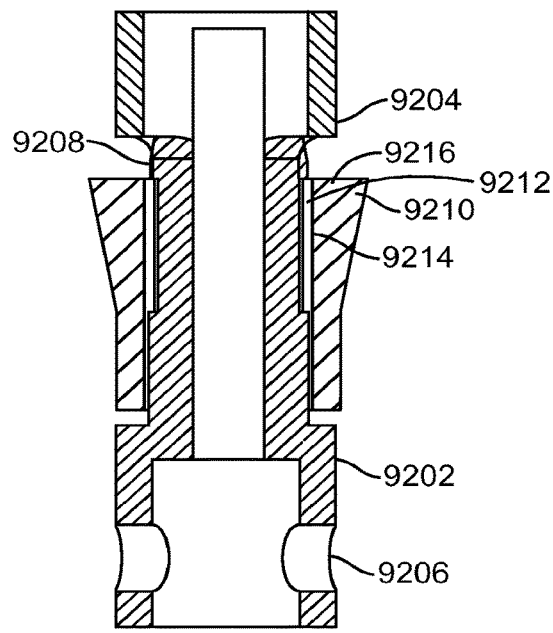
FIG. 47A
FIG. 47B
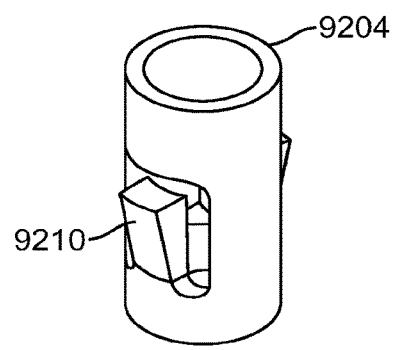
FIG. 47C

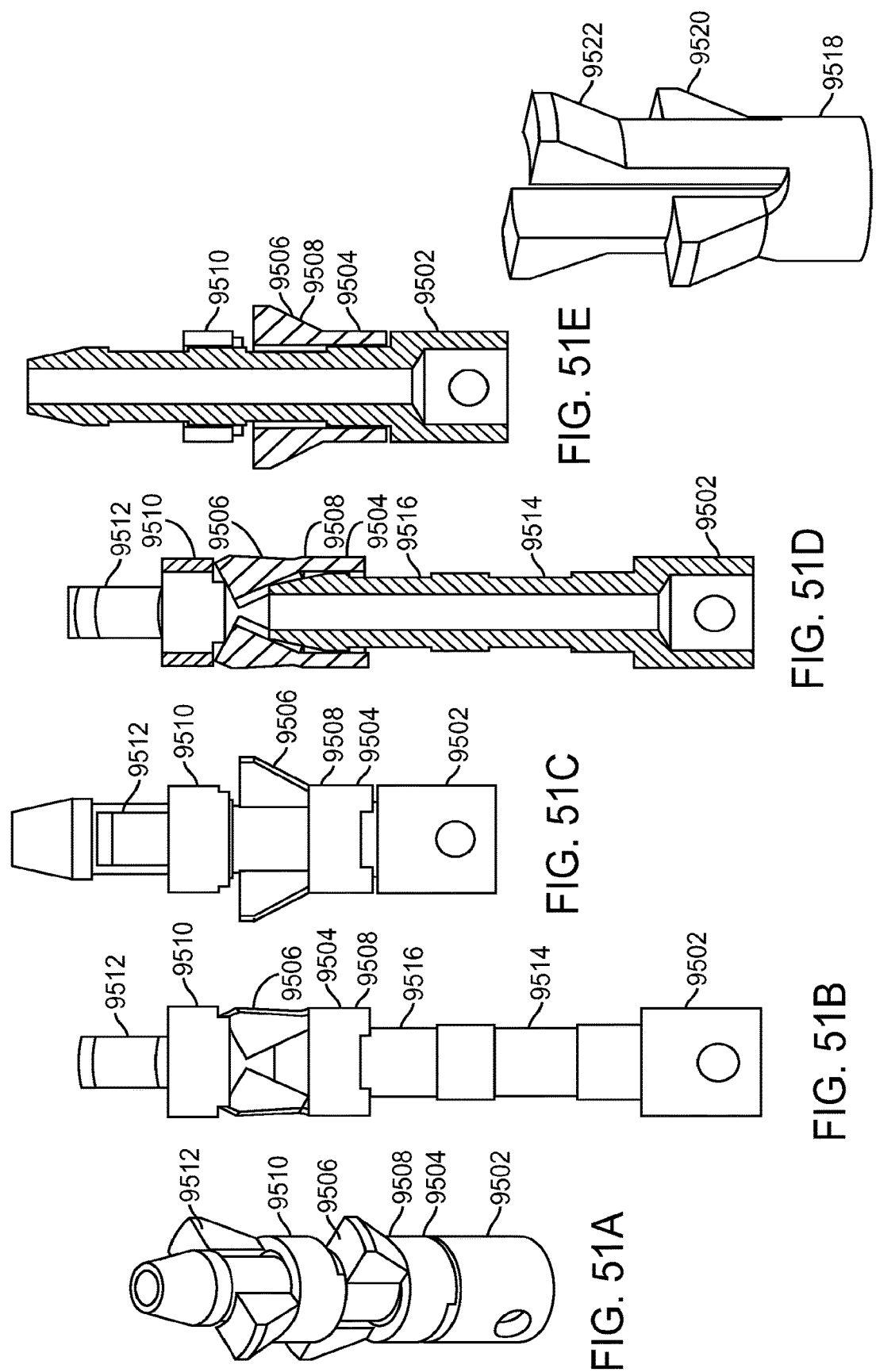

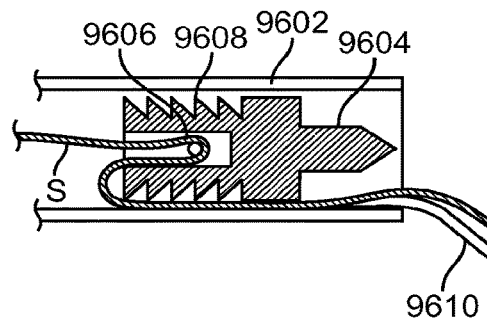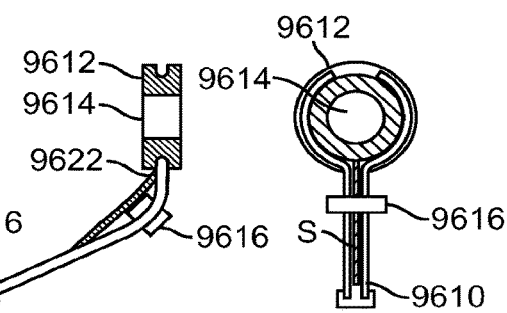
FIG. 54A  FIG. 54B
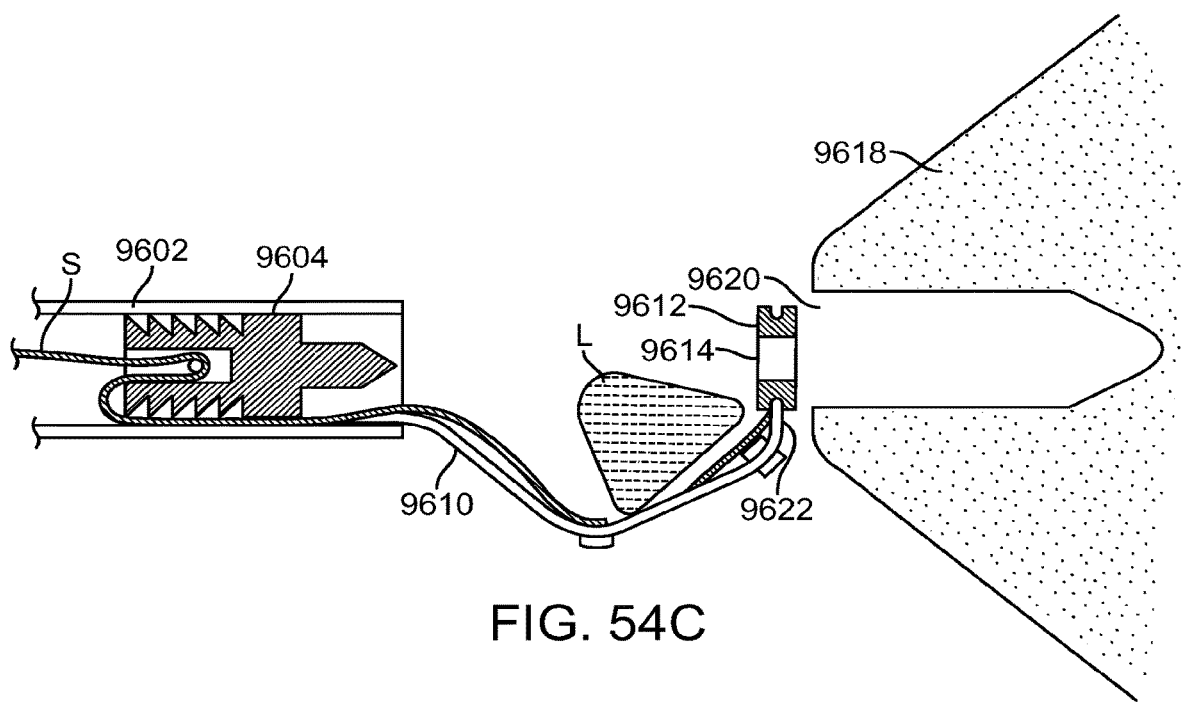
FIG. 54C

SUTURE ANCHORS WITH ONE-WAY CINCHING MECHANISMS

CROSS-REFERENCES TO RELATED APPLICATIONS

The present application is a continuation of U.S. patent application Ser. No. 14/015,934 filed Aug. 30, 2013, which is a continuation of U.S. patent application Ser. No. 12/776, 208 now U.S. Pat. No. 8,545,535, filed May 7, 2010, which is a non-provisional of, and claims the benefit of U.S. Provisional Patent Application Nos. 61/177,602, filed May 12, 2009; 61/219,290 filed Jun. 22, 2009; 61/263,728 filed Nov. 23, 2009; 61/263,751 filed Nov. 23, 2009; 61/298,780 filed Jan. 27, 2010; and 61/304,352 filed Feb. 12, 2010; the entire contents of which are incorporated herein by reference.

The present application is also related to U.S. patent application Ser. No. 12/605,065 filed Oct. 23, 2009; Ser. No. 12/776,177 filed May 7, 2010; and Ser. No. 12/776,225 also filed May 7, 2010; each of which, the entire contents are incorporated herein by reference.

BACKGROUND OF THE INVENTION

1. Field of the Invention

The present disclosure relates to medical devices, systems and methods, and more specifically to methods, systems and devices used for knotless suturing of tissue.

Soft tissue such as tendons, ligaments and cartilage are generally attached to bone by small collagenous fibers which are strong, but which nevertheless still can tear due to wear or disease. Examples of musculoskeletal disease include a torn rotator cuff as well as a torn labrum in the acetabular rim of a hip joint or the glenoid rim in a shoulder joint.

Thus, treatment of musculoskeletal disease may involve reattachment of torn ligaments, tendons or other tissue to bone. This may require the placement of devices such as suture anchors within bone. A suture anchor is a device which allows a suture to be attached to tissue such as bone. Suture anchors may include screws or other tubular fasteners which are inserted into the bone and anchored in place. After insertion of the anchor, the tissue to be repaired is captured by a suture, the suture is attached to the anchor (if not already pre-attached), tension is adjusted, and then the suture is often knotted so that the tissue is secured in a desired position.

Most conventional suture anchors require the surgeon to tie knots in the suture to secure the target tissue to the bone after the anchor is placed. Knot tying can be difficult during surgery, particularly if working in a confined space through cannulas or other surgical ports as in arthroscopic surgery. Therefore, it would be desirable to provide knotless suture anchor systems.

Additionally, many surgeons prefer to use polymeric anchors rather than metal ones so that the anchors are compatible with the use of MRI. While polymeric anchors are available, they do not have the knotless suture securing capabilities described above. This may be in part due to challenges of fabricating polymer anchors that provide a reliable cinching mechanism for a knotless anchor at the small scale required for orthopedic procedures. Further, while it is frequently advantageous to fabricate polymeric devices by molding, known knotless anchor designs require multiple moving parts and geometries which are not suitable for molding. Therefore it would be advantageous to provide a knotless anchor with the characteristics described above and which is also suitable to being molded with a polymer as a single integral part or as series of molded components that can be easily assembled together. By single integral part, it is meant that the entire part is formed from a single piece of material or molded as a single piece, without need for fastening, bonding, welding or otherwise interconnecting multiple components together. Examples of this include, but are not limited to, single-piece components that are injection molded, cast, or machined from a single block of material. The word "molded" is intended to encompass materials which are injection molded, blow molded, compression molded, thermoformed, or made using other molding processes known to those of skill in the art, useful for shaping polymers, ceramics, or other formable materials.

Frequently two or more anchors and multiple lengths of suture are required. Using such devices can be time consuming and difficult to undertake in the tight space encountered during endoscopic surgery and sometimes even in conventional open surgery. Recently, knotless suture anchors having suture clamping mechanisms have been developed to eliminate the need to tie knots but they still can be difficult or awkward to use.

Some knotless suture anchors have been devised which allow the suture to be cinched and secured without tying a knot, however these typically rely upon trapping the suture between the anchor and the bone to secure the suture, which means the anchor cannot be fully inserted into the bone until the tissue has been captured and secured tightly. The process of maintaining tension on the suture, keeping the tissue at the desired location and simultaneously inserting the anchor into the bone is difficult. Other knotless anchors rely on the manual actuation of some type of moving part on the anchor to clamp or trap the suture within the anchor, requiring an extra hand that the surgeon may not have available. It would be desirable to allow the anchor to be fully inserted in the bone prior to securing the tissue and to avoid the requirement of extra manipulations to secure the suture.

Thus, it would be desirable to provide improved knotless suture anchors that are easier to use and also that may take up less space during deployment and that are easier to deploy.

In particular, treating musculoskeletal disease in a hip joint can be especially challenging. The hip joint is a deep joint surrounded by a blanket of ligaments and tendons that cover the joint, forming a sealed capsule. The capsule is very tight thereby making it difficult to advance surgical instruments past the capsule into the joint space. Also, because the hip joint is a deep joint, delivery of surgical instruments far into the joint space while still allowing control of the working portions of the instrument from outside the body can be challenging. Additionally, the working space in the joint itself is very small and thus there is little room for repairing the joint, such as when reattaching a torn labrum to the acetabular rim. Moreover, when treating a torn labrum, the suture anchor must be small enough to be inserted into the healthy rim of bone with adequate purchase, and the anchor also must be short enough so that it does not protrude through the bone into the articular surface of the joint (e.g. the acetabulum). Existing anchors may be used to repair the labrum, but are not well-suited to labral repair especially in the hip. First, the reattachment of the labrum to the acetabular rim is most effective if both ends of the suture are attached to the same point in the bone. This provides the most precise and secure apposition of the labrum to the rim. The space available on the acetabular rim is very limited, typically requiring an anchor with a transverse dimension (e.g. diameter) preferably less than 4 mm and no more than about 3.5 mm and therefore many commercially available anchors are too large. Thus, it would be desirable to provide suture anchors that have a small diameter and length.

Additionally, existing knotless anchors are typically designed for use in rotator cuff repair in the shoulder and they are intended for placement in separate holes in the bone. These devices have no mechanism for coupling one anchor to the other within the same hole, cannot be implanted concentrically within the hole, and are too long for stacking within the same hole. Further, many existing knotless anchors are too large for placement on the acetabular rim for labral repair of the hip.

In addition, existing knotless anchors and interconnecting anchors have suture locking mechanisms which have moving parts and other complex designs that are not reliably manufacturable at the small scale required for labral repair anchors. While various types of anchors with suture locking mechanisms have been disclosed, many of these cannot be made in an anchor less than 4 mm, and no more than 3.5 mm in diameter.

Moreover, because of the difficulty of performing labral repairs arthroscopically, it is highly desirable to minimize the manipulations of the suture and anchor that are required intraoperatively. Many existing knotless anchors require the surgeon, after initial anchor placement and capture of the labrum, to thread the free end of the suture through the anchor or a component of the anchor, which is difficult and takes an excessive amount of time. Some anchors further require the surgeon to push the anchor further into bone, or push a locking mechanism on the anchor, or perform some other manipulation of the anchor in order to lock the suture. These manipulations add difficulty and time to arthroscopic labral repair that would be desirably avoided.

Therefore, it would be desirable to provide improved knotless suture anchors that are ideally suited to arthroscopic procedures, and in particular labral repair in the hip. The anchors would preferably be adapted for placement in a single hole in the bone, extremely simple in design with few or no moving parts, manufacturable at very small scale (e.g. diameter less than 4 mm, and preferably no more than 3.5 mm), and ideally be moldable as a single part or a few easily assembled parts. Further, once the suture has been tightened as desired, the anchor should automatically lock the suture in place without requiring tying or manipulation of the suture or any mechanisms on the anchor itself. The anchors should further require no intraoperative threading or tying of the suture ends before or after initial anchor placement.

Thus, there is a need for improved devices, systems and methods which overcome some of the aforementioned challenges. At least some of these objectives will be met by the inventions described hereinbelow.

2. Description of the Background Art

Patents disclosing suture anchoring devices and related technologies include U.S. Pat. Nos. 7,566,339; 7,390,329; 7,309,337; 7,144,415; 7,083,638; 6,986,781; 6,855,157; 6,770,076; 6,767,037; 6,656,183; 6,652,561; 6,066,160; 6,045,574; 5,810,848; 5,728,136; 5,702,397; 5,683,419; 5,647,874; 5,630,824; 5,601,557; 5,584,835; 5,569,306; 5,520,700; 5,486,197; 5,464,427; 5,417,691; and 5,383,905. Patent publications disclosing such devices include U.S. Patent Publication Nos. 2009/0069845 and 2008/0188854 and PCT Publication No. 2008/054814.

SUMMARY OF THE INVENTION

The present invention provides devices, systems and method for knotless suturing of tissue. Exemplary procedures where knotless suturing may be advantageous include repair of torn rotator cuffs, as well as a torn labrum in the acetabular rim of a hip joint or the glenoid rim in a shoulder joint, and also in urinary incontinence repair. The invention relates to suture anchors for anchoring sutures to bone, and more specifically provides a suture anchor which eliminates the need for knotting the suture and which is suited to being a molded polymer construction. The anchors will find particular utility in hip and shoulder arthroscopy, e.g. labral reattachment and similar procedures.

In a first aspect of the present invention a suture anchor system for securing target tissue to base tissue comprises a first anchor having a proximal end, a distal end, and a longitudinal axis therebetween. The first anchor is configured for insertion in the base tissue with an exterior thereof in engagement with the base tissue so as to resist removal of the first anchor from the base tissue. A bar is coupled to the first anchor and a suture is tied around the bar so as to form a one-way sliding knot with first and second extremities of the suture extending therefrom. The one-way sliding knot is configured to allow the suture to slide around the bar in a first direction when the first extremity is tensioned and to substantially prevent the suture from sliding around the bar in a second direction opposite the first direction when the second extremity is tensioned.

The one-way sliding knot preferably comprises a hitch having a pole portion and a loop portion wrapped around the pole portion, whereby tension on the loop portion pulls the pole portion in a direction transverse to the pole portion, increasing friction between the pole portion and the bar. Preferably the loop portion when tensioned pulls the pole portion in a direction tangential to an outer surface of the bar. In some embodiments, the loop portion pulls the pole portion into a gap disposed between the bar and a wall of the first anchor whereby the pole and loop portions are wedged between the bar and the wall. In preferred embodiments, the hitch is a munter hitch.

In a particular embodiment, the bar is coupled with the first anchor in a position spaced apart from the exterior surfaces of the first anchor which engage the base tissue to allow a suture to slide around the bar when the exterior is engaging the base tissue. The bar has an outer surface which is separated from a wall of the first anchor by a gap. The length of suture has a first extremity extending from a first side of the bar and a second extremity wrapped around the bar and looped around the first extremity to form a U-loop having first and second segments. Each of the first and second segments extend slidably through the gap, such that upon tensioning the second extremity the U-loop pulls the first extremity toward the gap. The suture is longitudinally movable in a first direction when the first extremity is tensioned and the suture is inhibited from moving in a second direction opposite the first direction when the second extremity is tensioned.

The second extremity may be wrapped back around the bar from the U-loop such that the first and second extremities extend out of the cavity from a same side of the bar. The first anchor may have a cavity with at least one opening in the proximal end, and the bar may be disposed in the cavity. The U-loop may pull the first extremity in a direction generally tangential to the outer surface of the bar. The gap may have a width which is smaller than the combined uncompressed thickness of the first and second extremities. A space may be disposed between the bar and the distal end and may be configured to allow a suture to slide through the space when the distal end is engaging tissue.

The second extremity may have a free end adapted to be coupled to the first anchor so as to form a repair loop configured to be placed around or through tissue to be secured. The system may further comprise a suture retaining structure on the first anchor for retaining the free end of the second extremity. The suture retaining structure is preferably configured to receive a free end of the second extremity such that the second extremity forms a repair loop between the hitch and the retaining structure in which to capture the target tissue. The retaining structure preferably retains the second extremity such that the free end is movable relative to the retaining structure to allow adjustment of the size of the repair loop. In preferred embodiments, with the anchor fully assembled and ready for implantation, the retaining structure is accessible from the exterior of the anchor so that the user can couple the free end with the retaining structure intraoperatively and adjust the size of the repair loop by pulling the free end relative to the anchor after the target tissue has been captured in the repair loop. This allows gross adjustment of the repair loop size and tension before or during insertion of the anchor in the base tissue. Final adjustment of the repair loop can then be performed by tensioning the first extremity when the anchor has been fully implanted in its final position.

The suture retaining structure may comprise a transverse passage through the first anchor, preferably having an opening exposed on and exterior wall of the anchor to receive the free end of the second extremity intraoperatively with the anchor in its fully assembled condition. The suture retaining structure may comprise a clamping mechanism coupled to the first anchor. The clamping mechanism may comprise a clamping member movably coupled to the first anchor. The clamping member may be movable from a first position in which the second extremity is longitudinally movable relative to the first anchor to a second position in which the clamping member engages the second extremity to inhibit its movement relative to the first anchor. The clamping member may compress the second extremity against a clamping surface on the first anchor.

The suture retaining structure may comprise a movable element coupled to the first anchor. The movable element may be movable so as to move the second extremity from a less tortuous path through the first anchor to a more tortuous path through the first anchor. The movable element may have a transverse passage through which the second extremity extends. The movable element may be disposed within an inner channel in the first anchor. The movable element may be concentrically disposed around the exterior of the first anchor. The movable element may be rotatably coupled to the first anchor or it may be threadably coupled thereto. The movable element may extend distally from a distal end of the first anchor or it may be configured to remain stationary relative to the first anchor as the first anchor is rotated.

The first anchor may have threads on an exterior thereof configured to allow the first anchor to be screwed into bone or tissue. The second extremity may form at least a first loop around the bar. The free end may be positionable between the first loop and the bar so as to be clamped therebetween. The system may further comprise a blocking structure on the first anchor adapted to prevent the U-loop from moving around the bar when the first extremity is tensioned. The first anchor may further comprise a cavity. The bar may be disposed in the cavity, and the wall may be a first wall of the cavity. The blocking structure may comprise at least a portion of the first wall disposed in a position relative to the bar which prohibits the U-loop from passing between the wall and the bar. The bar may be disposed asymmetrically within the cavity such that a second wall of the cavity is further from the bar than the first wall. The blocking structure may comprise an extension extending laterally outward from a first side of the bar. The first anchor may further comprise a cavity. The bar may be disposed in the cavity, and the blocking structure may comprise an extension extending inward from a first wall of the cavity. The anchor may further comprise a cavity having at least one opening in the proximal end and the bar is recessed within the cavity distally from the at least one opening. The bar may be spaced proximally from the distal end of the first anchor. The bar may further comprise a cavity having a distal floor. The bar may be disposed within the cavity and spaced proximally from the distal floor. The first anchor and the bar may be a unitary molded construct.

The system may further comprise a tissue retention structure on the exterior of the first anchor for retaining the first anchor in tissue or bone. The tissue retention structure may comprise a plurality of ribs, barbs, or concentric scallops. The first anchor may be configured to be hammered into bone without a pre-drilled hole. The first anchor may comprise threads on an exterior thereof for screwing the first anchor into bone. The distal end of the first anchor may comprise a pointed tissue piercing tip. The system may further comprise a second anchor member separable from the first anchor and having means for coupling to the first anchor. The first anchor and the second anchor member may be concentrically coupled together. The first anchor and the second anchor member may be coupled together end to end.

The first anchor may have a cavity having a sidewall and the bar may be asymmetrically positioned in the cavity such that the space between the bar and the sidewall is larger on a first side of the bar than on a second side of the bar. The space on the first side of the bar may be substantially larger than a cross-sectional thickness of the suture. The space on the second side of the bar may be less than the cross-sectional thickness of the suture. The space on the second side of the bar may be configured to prevent the U-loop from rotating about the bar in response to tension on the second extremity. The first anchor may further comprise a cavity and the bar may divide the cavity into first and second longitudinal channels. The first and second longitudinal channels may be interconnected by a transverse passage within the first anchor distal to the bar. The cavity may have a distal floor opposite the at least one opening. The transverse passage may comprise a space between the bar and the distal floor.

The first anchor may comprise at least one deployable retention member coupled thereto. The retention member may be movable from a first configuration in which it has a low radial profile suitable for introduction into tissue, to a second configuration in which it has a higher radial profile for engagement with tissue adjacent the first anchor. The first anchor may comprise an actuation member movable relative to the retention member from a first position in which the retention member is in the first configuration to a second position in which it engages the retention member to move it into the second configuration. The retention member may be coupled to a tubular retainer body disposed concentrically over the actuation member. The actuation member may comprise a camming element configured to engage an inner surface of the retention member to move it from the first configuration to the second configuration. The inner surface of the retention member may be sloped inwardly in the first configuration. When the anchor system has been implanted in tissue the retainer body may be configured to remain stationary in the tissue and the actuation member may be movable relative to the retainer body to move the retention member from the first to the second configuration. The actuation member may be retractable proximally relative to the retainer body. The actuation member may be fixed to the first anchor such that the first anchor is movable together with the actuation member relative to the retention member.

The system may further comprise a suture retaining structure in the first anchor for applying a retention force to a free end portion of the suture. Moving the retention member from the first configuration to the second configuration causes the suture retaining structure to increase a retention force applied to the free end portion. Movement of the retention member from the first configuration to the second configuration may move the free end portion from a less tortuous configuration to a more tortuous configuration.

The hitch may be formed around an axial axis of the bar, the axial axis being transverse to the longitudinal axis of the first anchor. Alternatively, the hitch may be formed around an axial axis of the bar, the axial axis being generally parallel to the longitudinal axis of the first anchor. The bar may be disposed within a cavity in a middle portion of the first anchor having a lateral opening on a sidewall of the first anchor. The first anchor may further include least one longitudinal channel on the sidewall of the first anchor extending from the proximal end to the lateral opening. The bar may also be coupled to a proximal end of the first anchor and spaced proximally therefrom in a handle-like or cleat-like configuration.

In another aspect of the present invention, a method of securing target tissue to base tissue comprises providing a first anchor having a bar, a suture tied around the bar to form a hitch which allows the suture to slide around the bar in a first direction and substantially prevents the suture from sliding around the bar in a second opposite direction, the suture having first and second extremities extending from the bar. The second extremity is coupled to the target tissue, and the first anchor is inserted into the base tissue. The first extremity is tensioned to slide the suture relative to the bar in a first direction whereby the target tissue is drawn toward the base tissue by the second extremity with the first extremity remaining uncoupled to the target tissue.

In preferred embodiments the hitch comprises a pole portion and a loop portion wrapped around the pole portion, whereby tension on the loop portion pulls the pole portion in a direction transverse to the pole portion, increasing friction between the pole portion and the bar. Tension on the loop portion preferably pulls the pole portion in a direction tangential to an outer surface of the bar. In some embodiments the loop portion pulls the pole portion into a gap disposed between the bar and a wall of the first anchor whereby the pole and loop portions are wedged between the bar and the wall.

The second extremity may form a U-loop around the first extremity such that tension in the second extremity causes the U-loop to pull on the first extremity in a direction generally tangential to an exterior surface of the bar so as to inhibit movement of the suture. The wrapping of the suture may comprise wrapping the suture around the bar so that the first and second extremities extend from opposite sides of the bar, and looping the second extremity around the first extremity to form the U-loop. The second extremity may be wrapped back around the bar so that both the first and second extremities extend from the same side of the bar. The first anchor may comprise a cavity having a sidewall, the bar being disposed within the cavity. A gap may lie between the bar and sidewall. The U-loop may pull the first extremity into the first gap when the second extremity is tensioned.

The first gap may have a first width which is less than the combined thickness of the first and second extremities. A second gap may lie between the bar and a second wall of the cavity. The second gap may have a second width substantially larger than the first width. The inserting step may comprise screwing the first anchor into the base tissue. The inserting may also comprise coupling an insertion tool to the first anchor, and rotating the insertion tool to screw in the anchor. The method may further comprise preventing the second extremity from wrapping around the insertion tool as it is rotated. The second extremity may be pre-wound around the insertion tool a predetermined number of winds, and the preventing step may comprise unwrapping the predetermined number of winds from the insertion tool as it is rotated.

The coupling step may comprise passing the second extremity around or through the target tissue to form a loop, further comprising retaining a free end portion of the second extremity in the suture anchor. The free end portion may be retained in the suture anchor such that it remains in a stationary position relative to the base tissue as the anchor is screwed into the base tissue. The free end portion may be retained by a retaining structure rotatably coupled to the first anchor. The method may further comprise deploying a retention element from the first anchor after the step of inserting. The first anchor may have an actuation element coupled thereto, and the deploying step may comprise moving the actuation element relative to the retention structure. The retention element may be coupled to a retainer body, and the actuation element may be moved relative to the retainer body to deploy the retention element. During the deploying step the retainer body may remain stationary relative to the base tissue and the actuation element may be refracted proximally relative to the retainer body. The actuation element may be fixed to the first anchor.

The method may further comprise creating a loop with the second extremity, passing at least a portion of the loop around or through the target tissue, and coupling the loop to the first anchor. The loop may be coupled to the first anchor by retaining a free end portion of the second extremity on the first anchor. The free end portion may be retained by passing it through a transverse passage in the first anchor. Retaining the free end portion may comprise clamping the fee end portion between two opposing surfaces of the first anchor. Retaining the free end portion may also comprise passing the free end portion through a loop formed by the second extremity around the bar. The second extremity may form two loops around the bar, and the free end portion is passed through both loops. The free end portion may be retained on the first anchor without tying a knot.

In another aspect of the present invention, a method of securing target tissue to base tissue comprises providing an anchor having a one-way cinching mechanism and a suture pre-threaded through the one-way cinching mechanism. The suture has first and second extremities extending from the anchor. A second extremity is passed through or around the target tissue, and a free end portion of the second extremity is coupled to the anchor to form a repair loop. The anchor is inserted into the base tissue, and the first extremity is tensioned to shorten the loop. The first extremity may be tensioned to shorten the repair loop to a final size without moving the anchor relative to the base tissue. Preferably the step of tensioning the first extremity is performed after the anchor is fully inserted in the base tissue. The one-way cinching mechanism allows the suture to move longitudinally in a first direction when the second extremity is tensioned and inhibits movement thereof in an opposite direction. The suture is locked with the desired degree of tension in the repair loop without requiring the operator to form a knot.

The one-way cinching mechanism preferably comprises a bar coupled to the anchor, the suture being tied around the bar to form a one-way sliding knot or hitch, such as a munter hitch. The hitch may comprise a pole portion and a loop portion formed around the pole portion, wherein tension in the repair loop causes the loop portion to pull transversely on the pole portion to inhibit movement of the suture.

Preferably the anchor is inserted using an insertion tool to which the anchor is releasably coupled, and the method further comprises releasing the anchor from the insertion tool after the step of inserting. The first extremity may be tensioned to increase tension in the repair loop after the step of releasing.

The free end portion of the second extremity is preferably slidably coupled to the anchor to allow adjustment of the size and tension in the repair loop. After the free end portion of the second extremity is coupled to the anchor, the method may further include the steps of tensioning the second extremity to shorten the repair loop to an initial size, and locking the second extremity in position relative to the anchor. The second extremity is preferably locked without forming a knot in the second extremity. The free end portion of the second extremity may be coupled to the anchor in various ways, such as being passed through a transverse channel in the anchor. The second extremity may be locked by means of a clamping or other securing mechanism in the anchor, or by being trapped or compressed between the exterior of the anchor and the surrounding base tissue. Preferably, step of tensioning the first extremity is performed after the step of locking the second extremity.

Usually the final size of the repair loop will be smaller than the initial size. The method may further include a step of holding a predetermined portion of the repair loop as the second extremity is tensioned such that the repair loop may not be shortened beyond the initial size. The predetermined portion may be held within a delivery instrument for the anchor and released after the anchor has been inserted in the base tissue.

In another aspect of the present invention, an anchor for securing target tissue to base tissue comprises an anchor body, and a suture loop coupled to the anchor body. A first suture extremity extends from the anchor body and has a free end portion. The free end portion is passed through the suture loop thereby forming a repair loop outside the anchor body. The suture loop is tightenable to secure the free end portion to the anchor body.

The first suture extremity and the suture loop may be a part of the same continuous suture. The suture loop may comprise a one-way cinching knot allowing the suture to move longitudinally in a first direction and preventing the suture from moving in an opposite direction. The suture may comprise a second suture extremity extending from the one-way cinching knot. The suture may be movable in the first direction when the second suture extremity is tensioned. The anchor may further comprise a bar coupled to the anchor body. The suture loop may be formed around the bar such that the free end portion is passed between the suture loop and the bar and clamped therebetween.

In yet another aspect of the present invention, an anchor for securing target tissue to base tissue comprises an anchor body having a threaded exterior adapted to be screwed into the base tissue, and a suture coupled to the anchor body and having a first extremity with a free end portion. A tip member is rotatably coupled to the anchor body. The tip member has a suture retention structure configured to retain the free end portion such that the first extremity forms a repair loop outside the anchor. The tip member is configured to remain rotationally stationary relative to the base tissue as the anchor body is screwed in.

The tip member may be threadably coupled to the anchor body. The anchor body may have a distal surface configured to engage the free end portion as the anchor body is screwed in. The tip member may be movable relative to the anchor body so as to move the free end portion from a less tortuous configuration to a more tortuous configuration as the anchor is screwed in. The tip member may have a transverse passage through which the free end portion is passed. The suture retention structure may retain the free end portion without a knot therein. The suture retention structure may allow the free end portion to be tensioned to tighten the repair loop. The suture retention structure may allow the suture to be locked relative to the anchor body at any of a plurality of longitudinal positions along the free end portion.

The suture may comprise a second extremity, and the suture may be coupled to the anchor body so as to be longitudinally movable in a first direction when the second extremity is tensioned and to be immovable in a second direction opposite the first direction when the first extremity is tensioned. The anchor may further comprise a one-way cinching mechanism to which the suture is coupled. The one-way cinching mechanism comprises a bar around which the suture is wrapped. The first extremity may be wrapped around the bar and looped around the second extremity to form a U-loop such that tensioning the first extremity causes the U-loop to pull the second extremity in a direction generally tangential to the outer surface of the bar.

In another aspect of the present invention, an anchor for securing target tissue to base tissue comprises an anchor body having proximal and distal ends and threads on an exterior thereof so as to be screwed in to the target tissue. A spool is coupled to the anchor body and is rotatable with the anchor body as it is screwed in. A suture is coupled to the anchor body and has a first extremity with a free end portion, and a suture retention structure is coupled to the anchor body adjacent to the spool and configured to retain the free end portion such that the first extremity is wound around the spool as the anchor is screwed in to the base tissue.

The anchor body may comprise a cylindrical shaft having a first diameter and the spool may comprise a hub having a second diameter substantially smaller than the first diameter. The hub may be disposed between a proximal portion of the shaft and a distal portion of the shaft. The suture retention structure may comprise a transverse passage through the hub. The suture may comprises a second extremity. The suture may be coupled to the anchor body so as to be longitudinally movable in a first direction if the second extremity is tensioned, and inhibited from movement in a second direction opposite the first direction if the first extremity is tensioned. The suture may be coupled to a one-way cinching mechanism in the anchor body. The one-way cinching mechanism may comprise a bar around which the suture is wrapped. The first extremity may wrap around the bar and loop around the second extremity to form a U-loop. The U-loop may pull on the second extremity in a direction generally tangential to an exterior surface of the bar if the first extremity is tensioned.

In still another aspect of the present invention, an anchor for securing target tissue to base tissue comprises an anchor body configured for insertion in the base tissue, and a suture coupled to the anchor body and adapted for coupling to the target tissue. A first retention element is movably coupled to the anchor body, and a second retention element is movably coupled to the anchor body axially spaced from the first retention element. The first and second retention elements are movable from a first configuration having a lower profile suitable for insertion in the base tissue to a second configuration laterally extended from the anchor body to retain the anchor body in the base tissue.

The anchor may further comprise an actuation element coupled to the anchor body and that is movable relative to the first and second retention elements from a first position in which the first and second retention elements are in the first configuration, to a second position in which the first and second retention elements are in the second configuration. The actuation element may comprise at least one camming surface which engages inner surfaces of the first and second retention elements to urge them laterally outward. The retention elements may be coupled to a retainer body. The actuation element may be axially movable relative to the retainer body. The actuation element may be retractable proximally relative to the retainer body. The anchor body may be fixed to the actuation element to move therewith.

The suture may be coupled to a one-way cinching mechanism in the anchor body. The one-way cinching mechanism may allow the suture to move longitudinally in a first direction and inhibit the suture from moving in an opposite direction. The anchor may further comprise a suture retaining structure coupled to the anchor body that is configured to retain a free end portion of the suture. The suture retaining structure may comprise a transverse passage through the anchor body. The suture retaining structure may be movable from a first position in which the free end portion is movable relative to the anchor body to a second position in which the free end portion is fixed relative to the anchor body. The suture retaining structure may move the free end portion from a less tortuous configuration to more tortuous configuration. The anchor may further comprise an actuation element coupled to the anchor body and configured to move the first and second retention elements from the first to the second configuration, wherein moving the actuation element also moves the suture retaining structure. The suture retaining structure may be fixed to the actuation element. The first retention element may be radially offset from the second retention element. The anchor may also comprise a third retention element and a fourth retention element axially spaced apart from the third retention element. The third and fourth retention elements each may be movable from a first configuration having a lower profile suitable for insertion in the base tissue to a second configuration laterally extended from the anchor body to retain the anchor body in the base tissue.

In another aspect of the present invention, an anchor system for securing target tissue to base tissue comprises an anchor for insertion in the base tissue. The anchor has a threaded exterior suitable to allow the anchor to be fully inserted into the base tissue by turning through a first number of rotations. A suture is coupled to the anchor and has at least a first extremity extending therefrom. An insertion tool has a shaft with a distal end. The anchor is removably coupled to the distal end, and the shaft further has a suture winding portion. The first extremity is wound around the suture winding portion a predetermined number of turns correlated with the first number of rotations such that the first extremity is fully unwound from the suture winding portion when the anchor is fully inserted in the base tissue.

The suture may comprise a second extremity that extends from the anchor. The second extremity may not be wound around the suture winding portion of the shaft. The anchor may comprise a suture retaining structure for knotlessly retaining a free end portion of the first extremity. The anchor may further comprise a knotless cinching mechanism through which the suture is threaded. The knotless cinching mechanism may allow the suture to move longitudinally in a first direction and may inhibit the suture from moving in an opposite direction. The shaft may have an inner lumen and the suture winding portion may be on an exterior of the shaft. The shaft may further have an aperture in a side wall thereof through which the first extremity extends from the inner lumen to the suture winding portion. The suture may comprises a second extremity and the second extremity may not extend through the aperture. The second extremity may extend through an inner lumen of the shaft to a proximal end of the shaft. The suture may be longitudinally movable in a first direction when the second extremity is tensioned, but may be inhibited from moving in an opposite direction when the first extremity is tensioned.

In still another aspect of the present invention, an anchor for securing target tissue to base tissue comprises an anchor body, and a first one-way cinching mechanism coupled to the anchor body. The first one-way cinching mechanism is threaded with a suture and allows the suture to move longitudinally in a first direction and prevents the suture from moving in an opposite direction. A suture retention structure is coupled to the anchor body and configured to receive a free end portion of the suture such that the free end portion is longitudinally movable relative to the anchor body and configured to allow the free end portion to be locked relative to the anchor body at any of a plurality of longitudinal positions.

The suture retention structure may comprise a second one-way cinching mechanism configured to allow the free end portion to move longitudinally in one direction and to inhibit movement thereof in an opposite direction. At least one of the first and second one-way cinching mechanisms may comprise a bar coupled to the anchor body, the suture being wrapped around the bar. The suture may comprise first and second extremities. The second extremity may be wrapped around the bar and looped around the first extremity to form a U-loop such that tension on the second extremity causes the U-loop to pull the first extremity in a direction generally tangential to an exterior surface of the bar. The free end portion may be on the second extremity. The suture retention structure may comprise a transverse passage through at least a portion of the anchor body. The suture retention structure may clamp the suture between two opposing surfaces movable relative to each other. The anchor may further comprise a suture retention member movably coupled to the anchor body. The suture retention member may move the suture from a less tortuous configuration to a more tortuous configuration. The suture retention member may be concentrically coupled to the anchor body. The suture retention member may be axially movable relative to the anchor body. The suture retention member may be rotationally coupled to the anchor body. The anchor body may have a threaded exterior configured to be screwed into tissue. The suture retention member may be threadably coupled to the anchor body.

In another aspect of the present invention, an anchor for securing target tissue to base tissue comprises an anchor body, and a first one-way cinching mechanism coupled to the anchor body. The first one-way cinching mechanism is threaded with a first length suture and allows the first length of suture to move longitudinally in a first direction and prevents the first length of suture from moving in a direction opposite the first direction. A second one-way cinching mechanism is coupled to the anchor body. The second one-way cinching mechanism is threaded with a second length of suture and allows the second length of suture to move longitudinally in a second direction and prevents the second length of suture from moving in a direction opposite the second direction.

The first and second lengths may form a single continuous length of suture. The continuous length of suture may form a repair loop between the first one-way cinching mechanism and the second one-way cinching mechanism. The repair loop may be tightened by either moving the first length in the first direction or moving the second length in the second direction.

The first one-way cinching mechanism may comprise a first bar coupled to the anchor body, the first length of suture being tied around the first bar to form a first hitch. The first hitch may include a pole portion and a loop portion looped around the pole portion, wherein when the loop portion is tensioned the loop portion pulls the pole portion transversely to inhibit the first length of suture from moving. The second one-way cinching mechanism may also comprise a second bar coupled to the anchor body, the second length of suture being tied around the second bar to form a second hitch.

The first length of suture may have first and second free ends, and the second length of suture may have third and fourth free ends. A first suture retaining structure may be provided on the anchor body for retaining at least the first free end so as to form a first repair loop in the first length of suture, wherein the second free end is tensionable to tighten the first repair loop. The anchor may further include a second suture retaining structure on the anchor body for retaining the third free end so as to form a second repair loop in the second length of suture, wherein the fourth free end is tensionable to tighten the second repair loop.

The first one-way cinching mechanism may be disposed proximally on the anchor body from the second one-way cinching mechanism. In addition, the first and second one-way cinching mechanisms may be integrally formed with the anchor body.

These and other embodiments are described in further detail in the following description taken together with the appended drawing figures.

BRIEF DESCRIPTION OF THE DRAWINGS

FIGS. 24E-24F are partial side cross-sections of a suture anchor.
FIG. 25D is a side cross-sectional view of a suture anchor.
FIGS. 25E-25F are perspective views of a suture anchor.
FIGS. 26A-26B are perspective views of a suture anchor.
FIG. 26C is a side view of the anchor in FIG. 26A.
FIG. 26D is a top view of the anchor in FIG. 26A.
FIG. 26E is a side cross-section of the anchor in FIG. 26A.
FIGS. 27A-27C are side, top, and side cross-sectional views of a suture anchor.
FIGS. 28AA-28BB, and 29AA-29BB are side cross-sectional views of suture anchor systems.
FIGS. 32C-32E are front, side and top elevational views of a further embodiment of a suture anchor system having multiple cinching mechanisms according to the invention.
FIG. 33 is a side-view of a suture anchor system.
FIGS. 34 and 34A-34C are partial side cross-sectional views of a suture anchor system.
FIGS. 37E-37H are partial side cross-sectional views of a suture anchor systems.
FIG. 38F1 is a side-view of a suture anchor.
FIG. 38F2 is a cross-sectional view of the suture anchor in FIG. 38F1.
FIG. 38F3 is a side-view of the suture anchor in FIG. 38F1.
FIG. 38F4 is a cross-sectional view of the suture anchor in FIG. 38F1.
FIG. 38F5 is a side cross-sectional of the suture anchor in FIG. 38F1.

FIGS. 38H1-38H2 are side-views of a suture anchor.

FIGS. 38I1-38I2 are side-views of a suture anchor.

FIGS. 38J1-38J2 are side-views of a suture anchor.

FIGS. 38K1-38K2 are side-views of a suture anchor.

FIGS. 38L1-38L2 are side-views of a suture anchor.

FIGS. 38M1-38M2 are side-views illustrating the use of a suture passer loop to load a repair suture into a suture anchor system.

FIGS. 38M2A-38M2B are perspective and cross-sectional views illustrating the use of a suture passer loop to load a repair suture into a suture anchor system.

FIGS. 38M3-38M5 are side, cross-sectional, and perspective views illustrating the use of a suture passer loop to load a repair suture into a suture anchor system.

FIGS. 41A-41E are side-views illustrating a suture anchor system having features for lodging the anchor in tissue.

FIGS. 47A-47B are side cross-sections illustrating anchor lodging features.

FIG. 47C is a perspective view of the anchor lodging features in FIG. 47A.

FIG. 51A is a perspective view of an anchor with lodging features.

FIGS. 51B-51C are side-views of the lodging features in FIG. 51A.

FIGS. 51D-51E are side cross-sectional views of the lodging features in FIG. 51A.

FIG. 51F is a perspective view of anchor lodging features.

FIG. 54A is a side cross-sectional view illustrating an anchor delivery instrument.

FIG. 54B is a bottom view of the instrument illustrated in FIG. 54A.

FIG. 54C-54D are side cross-sectional views illustrating the anchor delivery instrument of FIG. 54A.

DETAILED DESCRIPTION OF THE INVENTION

Several exemplary embodiments of knotless suture anchors, methods of use and delivery instruments for such anchors are illustrated and described in the attached figures.

When the anchors of the invention are described herein as being "knotless," this is intended to mean that the anchors allow the operator to cinch the suture to a desired degree of tension and the anchor holds the suture in this position without requiring the operator to tie a knot in the suture. It will be understood that, in some embodiments described herein, specialized one-way sliding knots may be utilized in the anchor to secure the suture to the anchor, but advantageously, these may be pre-tied to the anchors when supplied to the surgeon and need not be tied by the surgeon during the procedure. In some embodiments, specialized anchor threading devices are provided which allow a suture to be tied in such a one-way sliding knot during a procedure, but even in these embodiments, after the suture has been coupled to the target tissue, the surgeon need not tie a knot in the suture to lock it with the desired tension.

Figure 1:
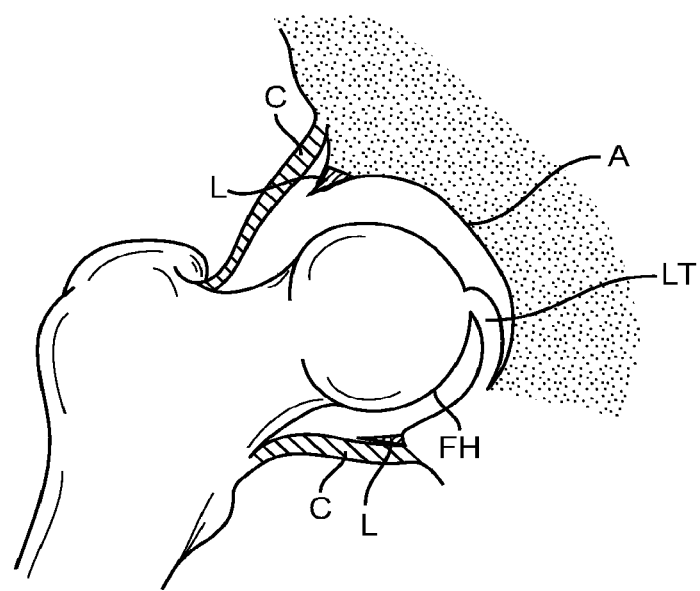
FIG. 1 is a side-view illustrating basic anatomy of the hip.
Figure 2:
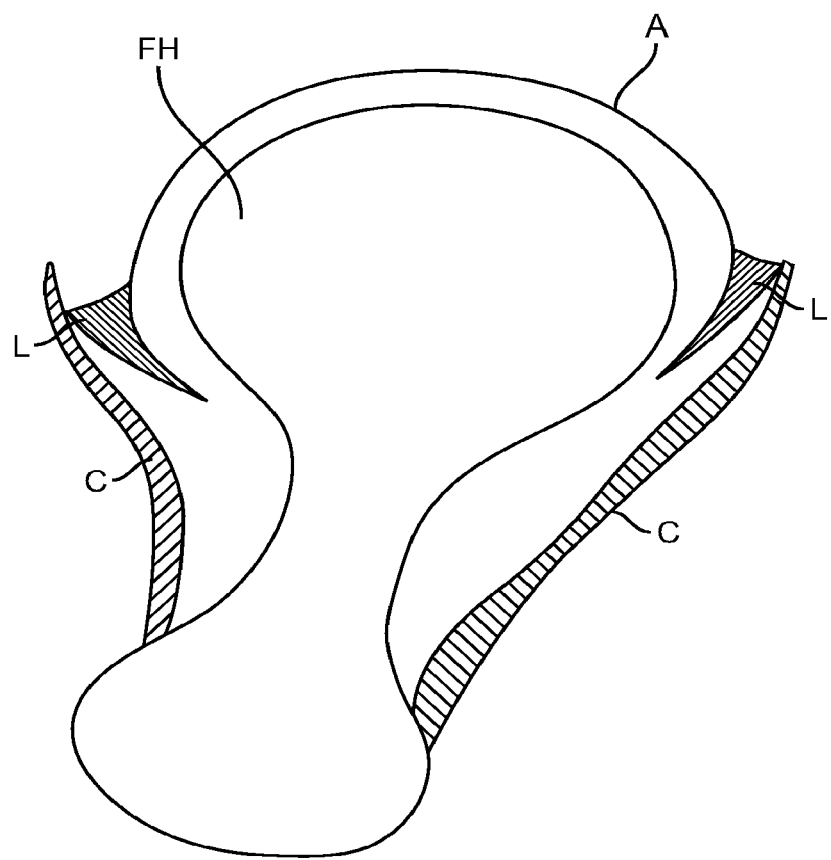
FIG. 2 is a top-view illustrating basic anatomy of the hip.

Anatomy:

Exemplary use of the devices, systems and methods of the present invention will be discussed primarily in terms of treatment of a hip joint. However, one of skill in the art will appreciate that other tissues may be re-attached to a base tissue or another substrate in other areas of the body including joints such as the shoulder joint, the ankle, wrist and other joints. Other areas may also be treated with the devices, systems and methods disclosed herein. Thus, the exemplary usage described herein is not intended to be limiting. FIG. 1 illustrates the basic anatomy of a hip joint. In FIG. 1 the hip joint is formed between the head of the femur FH and the acetabulum A, a concave surface of the pelvis. A blanket of ligaments cover the joint forming a capsule C. Additionally the acetabular labrum L, a fibrocartilaginous lip, surrounds the head of the femur, deepens the joint pocket and increases the surface area of contact. The ligamentum teres LT is a ligament attached to a depression in the acetabulum (the acetabular notch or fossa) and a depression on the femoral head (the fovea of the head). FIG. 2 is a top view of a hip joint highlighting the labrum L.

Figure 3:
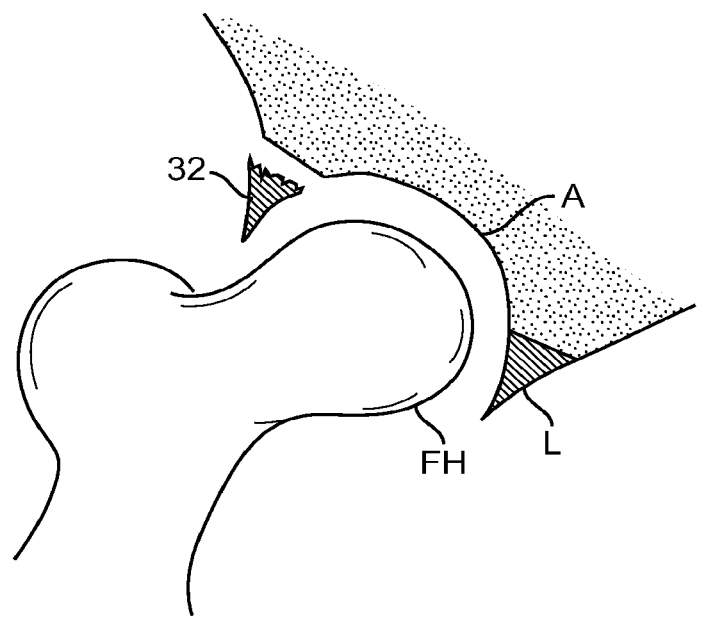
FIGS. 3-4 are side-views illustrating an exemplary method of reattaching a torn labrum to the acetabular rim.
Figure 4:
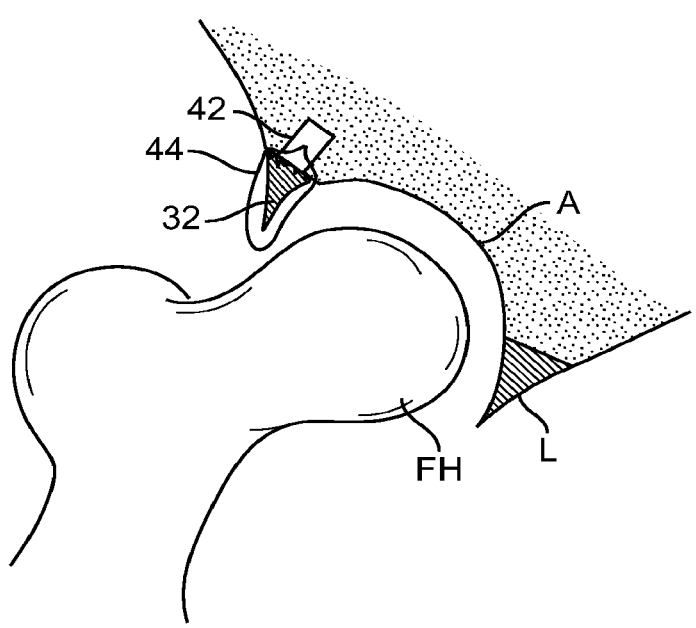

The labrum L can tear or separate from the acetabular rim due to wear or disease and this can result in pain as well as loss of joint mobility. FIG. 3 illustrates a torn labrum 32. Surgeons typically use suture and suture anchors to reattach the labrum to the acetabular rim. The surgeon often wraps a free end of the suture around the torn labrum and then the free end is threaded through a suture anchor. The anchor is inserted into bone and the suture length and/or tension is adjusted. FIG. 4 illustrates a torn labrum after it has been reattached to the substrate acetabulum. A suture anchor 42 with a suture 44 coupled thereto has been inserted into the acetabulum A thereby fixing one end of the suture 44 to the bone. The suture 44 is looped around the torn labrum 32 in order to capture the damaged tissue. The other end of the suture is also attached to the anchor and suture length has been adjusted in order to draw the labrum toward the acetabulum, where it is held until it heals and re-attaches. Suture anchors are typically used instead of screws, pins, rivets or other fasteners due to the limited working space within the joint.

Figure 5A:
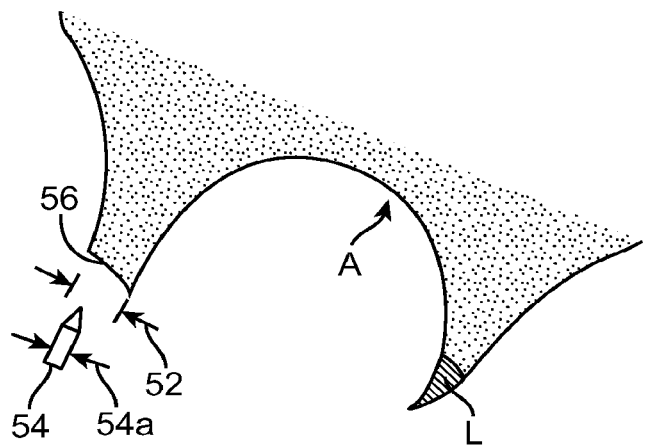
FIGS. 5A-5C are partial side cross-sections of a hip joint illustrating dimensional constraints of a suture anchor.
Figure 5B:
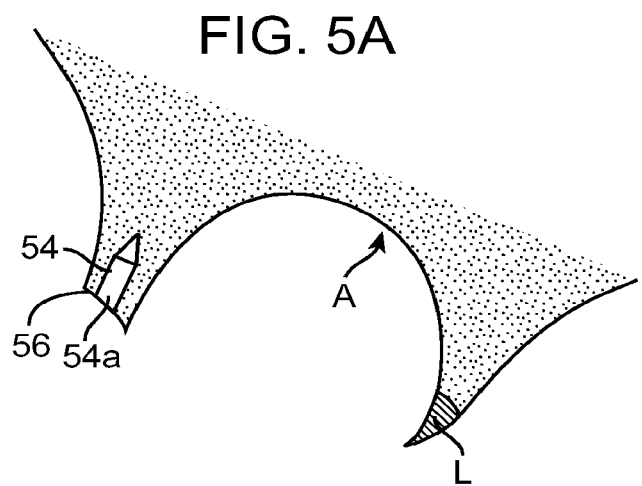
Figure 5C:
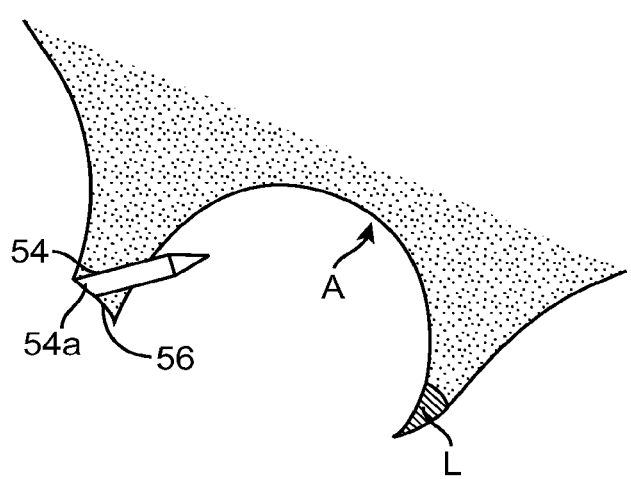

Referring now to FIGS. 5A-5C, the size of the suture anchor can be very important depending on the treatment zone. For example, when placing a suture anchor 54 into the acetabular rim 56 to repair the labrum L, the anchor width or diameter 54a cannot exceed the width 52 of the acetabular rim 56. Moreover, as shown in FIGS. 5A-5B, the anchor width 54a must be small enough relative to the width of the acetabular rim 56 so that adequate purchase is obtained without compromising strength of the rim 56. Thus, in most anchor embodiments described below, the suture anchor width (transverse to the anchor's longitudinal axis), or outer diameter if the anchor has a round profile, is preferably less than about 4 mm and no more than about 3.5 mm. Additionally, length of the anchor can also be critical. In FIG. 5B, the anchor 54 is placed substantially orthogonally into the acetabular rim and thus the anchor may be as long as necessary to obtain adequate purchase in the bone without risk of extending into the joint socket. However, it may be difficult to insert the anchor orthogonally into the acetabular rim due to the angle of approach, the narrow width of the rim, or for other reasons. In such cases, the anchor may be placed at a non-perpendicular angle relative to the rim surface, or it may be placed into a lateral facet of the acetabulum. In such cases, if the anchor is either too long or the angle is too great as shown in FIG. 5C, the anchor may pass entirely through the bone and exit into the joint itself, here the acetabular socket A, potentially damaging the cartilage and interfering with joint motion. Thus, when repairing a torn labrum in an acetabular or glenoid rim, the anchor has a diameter usually less than 5 mm, preferably less than 4 mm, and more preferably 3.5 mm or less. The length must be long enough to gain adequate purchase in the bone while also being short enough to avoid penetration into the articular surface, preferably being at least about 5 mm and less than or equal to about 14 mm in length.

Figure 6A:
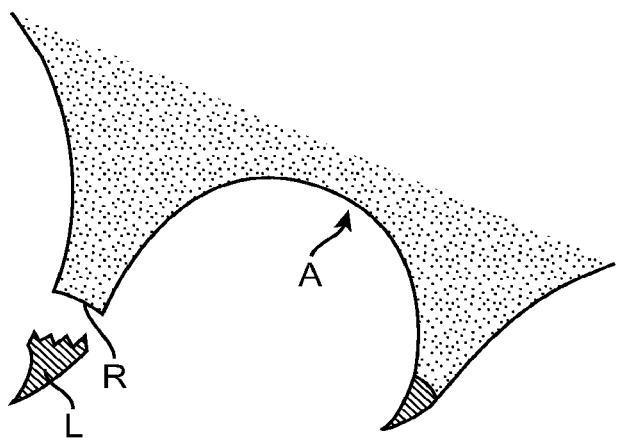
FIGS. 6A-6D are partial side cross-sections illustrating an exemplary method of reattaching torn tissue to a substrate.
Figure 6B:
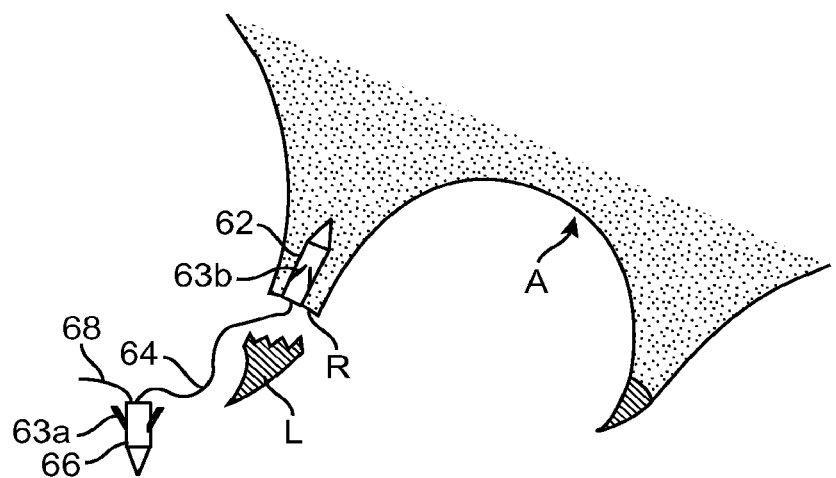
Figure 6C:
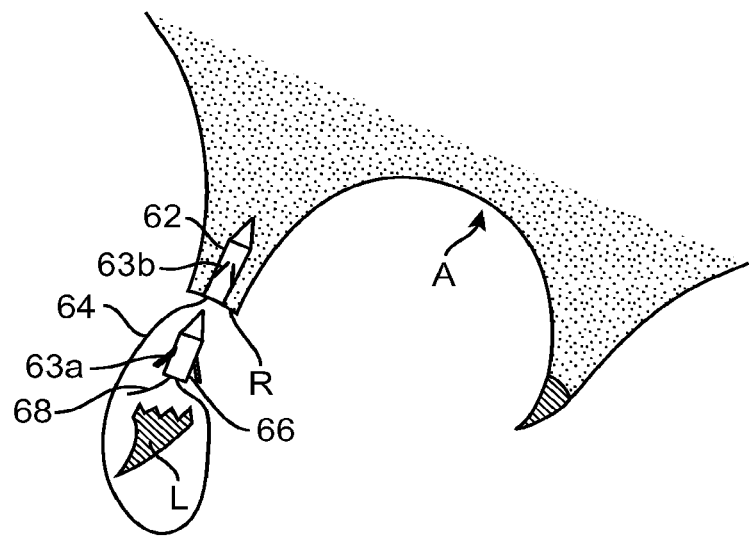
Figure 6D:
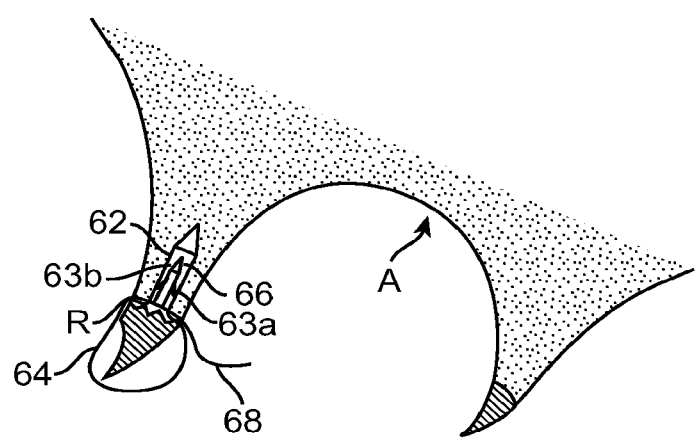

FIGS. 6A-6D illustrate an exemplary system and method for reattaching a torn labrum to the acetabular rim. The suture anchor system includes an outer anchor 62 and an inner anchor 66. A length of suture 64 having a free end 68 is coupled to both of the anchors 62, 66. Preferably suture 64 is pre-threaded in both anchors 62, 66 such that no threading of the suture through the anchors is required during the procedure, before or after placement of either anchor. The pair of anchors 62, 66 include a coupling mechanism 63a, 63b that allow the two anchors to interlock with one another when the inner anchor 66 is inserted into the outer anchor 62. In this embodiment, the inner anchor 66 is inserted concentrically into an inner cavity in the outer anchor 62, while in other embodiments described below, the anchors may be coupled together axially in a stacked relationship. In FIG. 6A, the torn labrum L is shown separated from the acetabular rim R of a hip joint having an acetabulum A. The outer anchor 62 is inserted into the acetabular rim R in FIG. 6B, either by placing the anchor into a pre-drilled hole or by directly driving the anchor into the bone. The suture 64 is then looped around the torn labrum L as shown in FIG. 6C and then the inner anchor 66 is inserted into the outer anchor 62 where the coupling mechanism 63a, 63b lock the two anchors together as shown in FIG. 6D. The suture 68 may then be tightened by pulling the free end which advances the suture through a cinching mechanism (not illustrated) in either the inner or outer anchor to tension the suture and draw the torn labrum into apposition with the acetabular rim R. The cinching mechanism allows the suture to be tensioned when pulled in one direction and constrains movement of the suture in the opposite direction. Once the appropriate tension has been achieved, the free end of the suture and any excess suture may be severed and removed from the treatment site. Additional details related to this method, the suture anchors and cinching mechanism may be found in U.S. patent application Ser. No. 12/605,065 and other U.S. Provisional patent applications previously incorporated herein by reference.

Figure 7A:
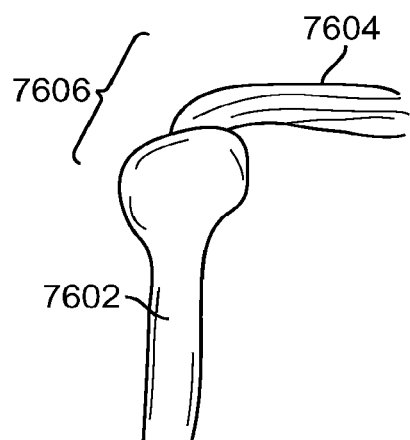
FIGS. 7A-7C are side-views illustrating repair of a torn rotator cuff.
Figure 7B:
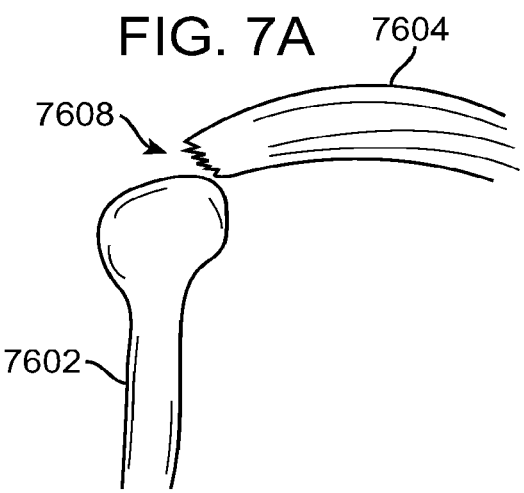
Figure 7C:
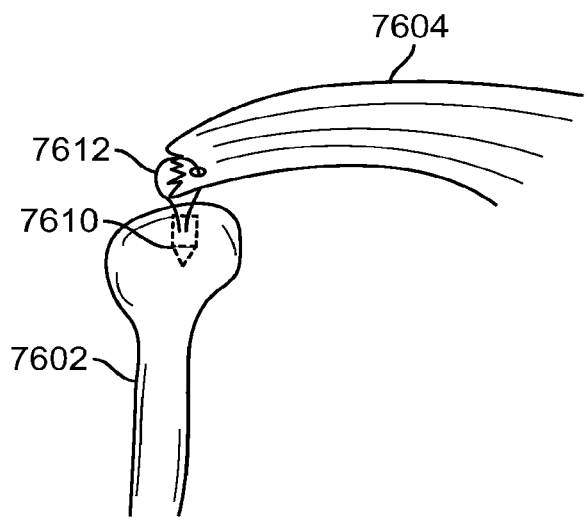
Figure 7D:
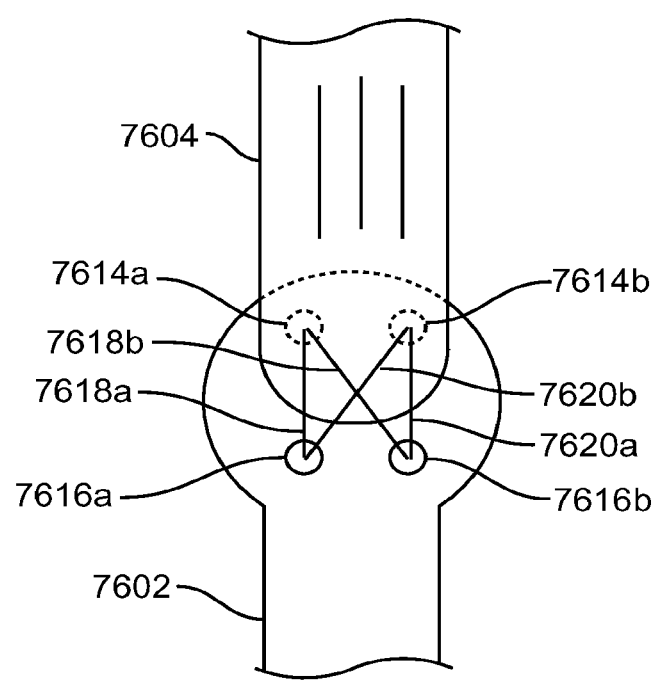
FIG. 7D is a top-view of a repaired rotator cuff.

The devices, systems and methods of the present invention may also be used for repair of a torn rotator cuff. FIG. 7A illustrates the basic anatomy of a rotator cuff 7606 which forms a covering around the top of the upper arm bone, i.e. the humerus. The cuff 7604 includes a group of four tendons and the related muscles (supraspinatus, infraspinatus, subscapularis, and teres minor) that are attached to the humerus 7602. The rotator cuff 7606 stabilizes the shoulder joint by holding the humerus in place in the shoulder joint and enables the arm to be raised, lowered and rotated. Rotator cuff tear is a common cause of pain and disability in adults. Most tears occur in the supraspinatus muscle, but other parts of the cuff may be involved. FIG. 7B shows separation 7608 of the cuff 7604 from the humerus 7602. Surgery is often used to repair the torn cuff and often involves debridement, subacromial smoothing (removing bone so that tendons or other tissue are not pinched or irritated), followed by sewing the torn edges of the supraspinatus tendon together and to the top of the humerus. FIG. 7C illustrates a basic method of repair where a suture anchor 7610 is positioned in the humerus 7602 and a suture 7612 is then used to attach the cuff 7604 to the anchor 7610. Recent methods for repairing a torn rotator cuff now include the use of a double row suture bridge, as illustrated in FIG. 7D. A pair of medial suture anchors 7614a, 7614b are positioned in the humerus 7602 along with a pair of lateral suture anchors 7616a, 7616b. Extending from each medial suture anchor 7614a, 7614b are two strands of suture, 7618a, 7618b, 7620a, 7620b. One strand of suture extends from a medial suture anchor to the lateral suture anchor directly opposite thereof and the other strand of suture extents from the medial suture anchor diagonally across the cuff tissue 7604 to an opposite lateral suture anchor. Thus, a first strand of suture 7618a extends from a first medial anchor 7614a to the first lateral anchor 7616a directly opposite thereof, and a second strand of suture 7618b extends from the first medial anchor 7614a diagonally to the second lateral anchor 7616b. Similarly, a first strand of suture 7620a extends from the second medial anchor 7614b to the second lateral anchor 7616b directly opposite thereof, and a second strand of suture 7620b extends diagonally from the second medial anchor 7614b to the first lateral anchor 7616a. The suture may be fixed, tied or otherwise attached to the suture anchors and either placed in pre-drilled holes in the bone, or driven directly into the bone. The double row suture bridge more evenly distributes loading and therefore is a more robust repair method than other repair methods, such as the one illustrated in FIG. 7C.

Other procedures for reattaching torn tissue to a substrate such as bone include the SLAP repair for a SLAP tear (superior labral tear from anterior to posterior) of a glenoid labrum, as well as the Bankart repair of a shoulder lesion. Any of the suture anchor systems described herein may be used in any of these procedures and in a variety of other procedures where the anchoring of sutures, wires, or other filaments to bone or other tissue is desired. The anchor systems may also be configured for placement in soft tissues and useful in any of various surgical procedures, wherever securing a suture or other filament to tissue may be desired.

Suture Anchor Architectures:

Any of the suture anchors described herein may be fabricated from metals such as stainless steel, nitinol, titanium, etc., ceramics, and other biocompatible materials. However, in preferred embodiments, the anchors are made from MRI (magnetic resonance imaging) compatible polymers such as PEEK (polyetherether ketone) or carbon reinforced PEEK. Dense, hard polymers are preferred so that the anchors will be non-resilient and do not deform when implanted. Preferred embodiments of anchors displace the bone or other substrate tissue when implanted and rely in significant part on the recoil of the substrate tissue against the anchor as well as other mechanical interference mechanisms between the anchor and the tissue to retain the anchor therein. Knotless anchors can also be manufactured by a variety of implantable biodegradable, bioabsorbable or bioresorbable polymers. These polymers are absorbed into the body through biological processes after implantation. Examples of these polymers include polylactide, lactide/glycolide copolymers and lactide/caprolactone copolymers. Each of the above bioabsorbable polymers could also be compounded with bone minerals such as hydroxyapatite or tri-calcium phosphate to create a biocomposite material. Anchors manufactured with these minerals introduce chemicals into the anchor hole which promote the formation of bone as well as a strong bond between the anchor and the bone surface.

Figure 8:
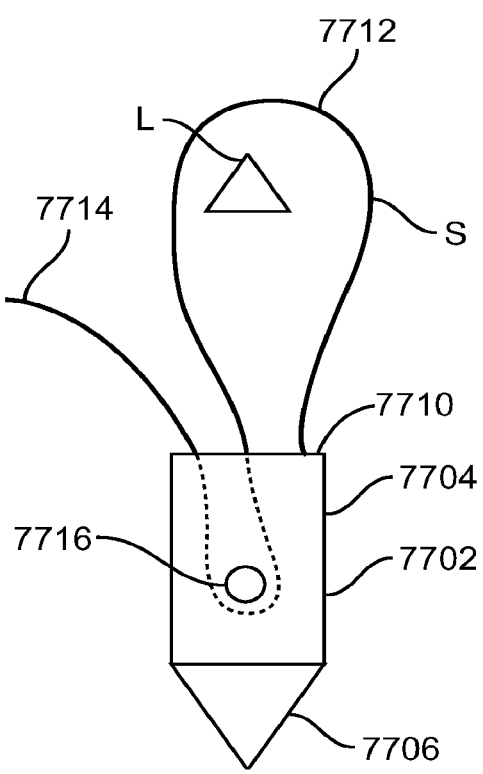
FIG. 8 is a side-view illustrating an exemplary embodiment of a single suture anchor.

In some embodiments, a single suture anchor may be used to reattach torn tissue to a substrate such as bone. For example, FIG. 8 shows a suture anchor 7702 having a generally cylindrical shaped body 7704 and a tapered distal tip 7706 for penetrating the bone. One end of a length of suture S is pre-attached or attached during a surgical procedure to a coupling 7710 on the anchor body 7704. The suture S is then either looped 7712 over the damaged tissue, here a torn labrum L, or advanced through the damaged tissue, and the other free end of the suture 7714 is passed through a cinching mechanism 7716. The cinching mechanism allows the physician to adjust length or tension in the suture S and preferably allows the suture to be tightened by pulling in one direction and the cinching mechanism prevents loosening of the suture in the opposite direction. This eliminates the need for the surgeon to tie knots in the suture in order to secure the tissue as is required with most conventional anchors. One of skill in the art will appreciate that any of the cinching mechanisms disclosed herein may be used in this embodiment, as well as a number of other mechanisms disclosed in patent applications previously incorporated by reference, or known in the art. Thus, in this embodiment, the free end 7714 of the suture S may be pulled to adjust suture length or tension. In alternative embodiments, the suture may be pre-loaded through the cinching mechanism and thus the looped portion 7712 of the suture S only needs to capture the damaged tissue before suture length and tension are adjusted. In such embodiments both ends of the suture S may be initially unattached from anchor body 7704, which will include a coupling element for capturing or securing one of the free ends after it has been passed around or through the tissue to be repaired.

Figure 9:
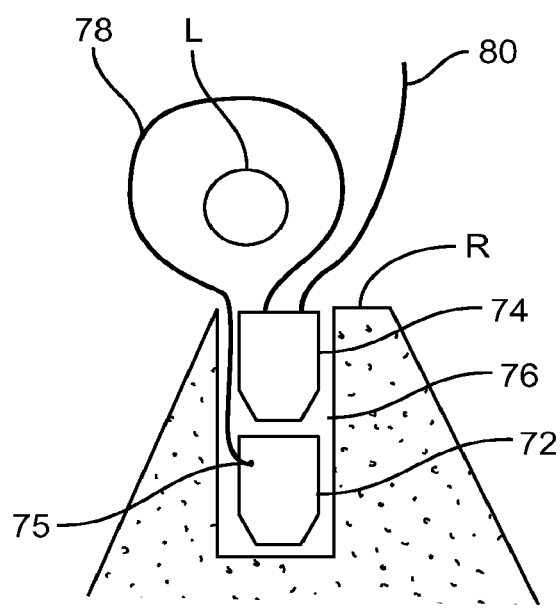
FIG. 9 is a partial side cross-section of a suture anchor disposed in a substrate tissue.

In other embodiments of suture systems, the anchor may include more than one suture anchor positioned in a single hole. For example, an approach for the deployment of suture anchors in an axially stacked arrangement in the same hole is illustrated in FIG. 9. A pair of suture anchors 72, 74 and a length of suture 78 having a free end 80 are used to reattach a torn labrum L to the acetabular rim R. In this exemplary embodiment, both anchors 72, 74 are placed end-to-end in a single pre-drilled hole 76 or they may be directly driven into the acetabular rim R. Suture 78 is coupled to the distal-most anchor 72 with a knot 75 or using another fastening method (e.g. crimping, bonding, etc.) and the length of suture encircles the labrum L and passes through the proximal-most anchor 74. The proximal-most anchor includes a cinching mechanism (not shown) that allows the free end 80 of the suture 78 to be pulled and tensioned in one direction while constraining movement of the suture in the opposite direction. By placing the two anchors end-to-end, both anchors may have maximum diameter within the constraints of the target anatomical location which allows the cinching mechanism size to also be maximized. Moreover, this configuration also minimizes the number of holes that must be drilled into the bone during the procedure. Another advantage of this configuration is that a portion of the suture 78 is pinched between an outer surface of the proximal-most anchor 74 and the inner wall of the hole 76 to secure the suture in position. Additional details on cinching mechanisms which may be used in these anchors are described below, as well as in Provisional and Non-Provisional patent applications previously incorporated herein by reference. The suture anchors may also be placed in separate holes in the bone if desired.

Figure 10:
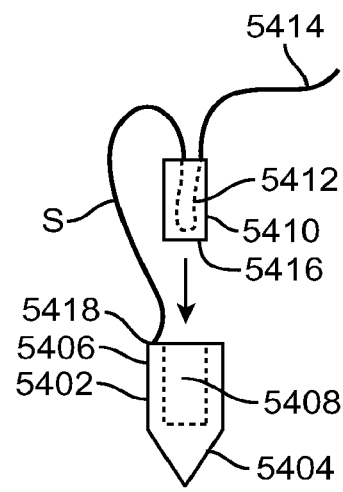
FIGS. 10-12 are side-views illustrating exemplary embodiments of suture anchor systems.

The various suture anchor systems described in detail herein may be configured in a variety of different architectures. These include both one-piece and multi-piece architectures, some of which are illustrated schematically in FIGS. 10-18. Any of the elements and features of the various embodiments described herein may be incorporated into any of these architectures. For example, FIG. 10 schematically illustrates a two-part suture anchor system having an anchor 5402 and an insert 5410 coupled together with a suture S. The anchor 5402 generally has a cylindrical shaped body 5406 and a pointed tip 5404 that is adapted to penetrate into bone. A central channel 5408 is substantially parallel to the longitudinal axis of the cylindrical body 5406. The insert 5410 also is generally cylindrically shaped and is concentrically positionable in the central channel 5408 such that the distal end 5416 of the insert 5410 bottoms out in the central channel 5408. The insert 5410 may be sized such that it is press fit into the central channel 5408 or it may have a locking mechanism, such as a detent mechanism, snap fit, threads, or other mechanical locking mechanism to lock the insert 5410 with the anchor 5402. The insert 5410 also has a cinching mechanism 5412 that allows the suture to be pulled in one direction for adjustment and tightening, while constraining movement of the suture in the opposite direction. The cinching mechanism may be any of the cinching mechanisms disclosed herein. The suture S has one end attached to the anchor with a knot 5418 or by other techniques known to those skilled in the art and the suture also passes through the cinching mechanism 5412 and a free end 5414 extends from the insert. The free end 5414 may be pulled to tighten the suture.

Figure 11:
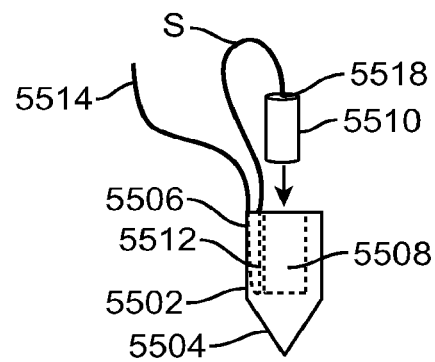

FIG. 11 schematically illustrates another anchor system configuration similar to that of FIG. 10, with the major difference being that the cinching mechanism is a part of the anchor instead of the insert. In FIG. 11, the anchor 5502 generally has a cylindrical shaped body 5506 and a pointed tip 5504 that can penetrate into bone. The anchor 5502 also has a central channel 5508 and a cinching mechanism 5512. The cinching mechanism may take the form of any of the cinching mechanisms described herein. The insert 5510 is also generally cylindrically shaped and is positionable in the central channel 5508 where it may be locked in place using any of the features described herein. A suture S is coupled to both the anchor 5502 and the insert 5510. One end of the suture S is tied in a knot 5518 or otherwise secured to the insert 5510 and the suture passes through the cinching mechanism 5512 of the anchor 5502. A free end 5514 extends from the anchor 5502 and may be pulled in one direction to tighten the suture.

Figure 12:
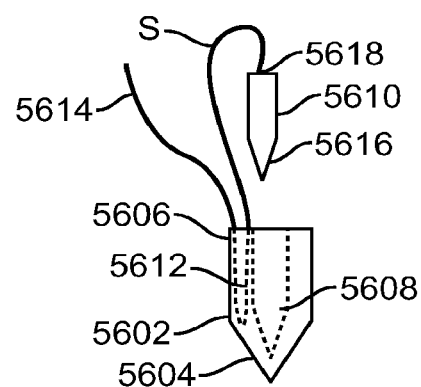

FIG. 12 schematically illustrates still another anchor system having an anchor 5602, a suture S, and a needle insert 5610. The anchor 5602 has a generally cylindrical shaped body 5606 with a central channel 5608 and a pointed tip 5604 adapted to penetrate into bone. A cinching mechanism 5612 that generally takes the form of any of the cinching mechanisms disclosed herein is included in the anchor 5602. The needle insert 5610 also has a cylindrically shaped body and a distal tissue penetrating tip 5616 for passing through tissue. A suture S is coupled to both the needle insert 5610 and the anchor 5602. One end of the suture S is fixed to the needle insert 5610 with a knot 5618 or other technique and the suture S passes through the cinching mechanism 5612. A free end 5614 extends from the cinching mechanism 5602 and may be pulled through the cinching mechanism in one direction to tighten the suture S. The cinching mechanism constrains movement of the suture therethrough in the opposite direction.

Figure 13:
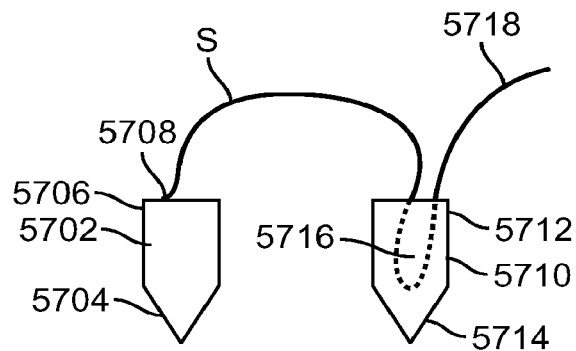
FIGS. 13-15 are side-views illustrating exemplary embodiments of suture anchor systems.

FIG. 13 schematically illustrates yet another anchor system having two anchors 5702, 5710. The first anchor 5702 has a generally cylindrical shaped body 5706 and a pointed tip 5704 for penetrating into bone. The second anchor 5710 similarly has a cylindrically shaped body 5712 and a pointed tip 5714 for penetrating into bone. The second anchor may be positioned in the same or a different location than the first anchor. The second anchor 5710 also includes a cinching mechanism 5716 that allows the suture S to be advanced in one direction and constrained in the opposite direction. A suture S is coupled to both anchors 5702, 5710. One end of the suture S is fixed to the first anchor 5702 with a knot 5708 or with other techniques known to those skilled in art, and the suture S passes through the cinching mechanism 5716 in the second anchor 5710. A free end 5718 of the suture S extends from the cinching mechanism and may be pulled to adjust suture length extending between the anchors 5702, 5710.

Figure 14:
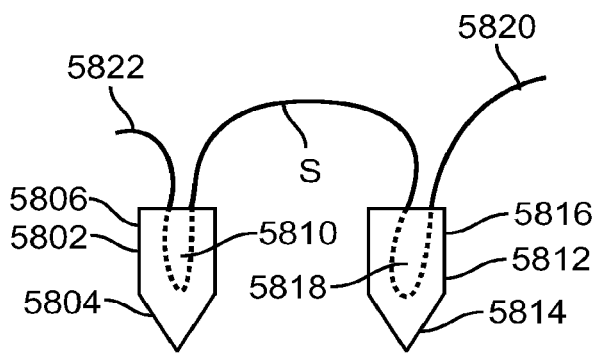

FIG. 14 illustrates another anchor system having two anchors 5802, 5812. In this embodiment, both anchors 5802, 5812 include cinching mechanisms 5810, 5818. The first anchor 5802 has a generally cylindrical shaped body 5806, a pointed distal tip 5804 for penetrating tissue such as bone and a cinching mechanism 5810. The second anchor 5812 similarly has a cylindrically shaped body 5816, a pointed tip 5814 for penetrating bone or other tissue, and a cinching mechanism 5818. The second anchor may be positioned in the same location or a different location than the first anchor. A length of suture S is coupled to both anchors 5802, 5812. The suture passes through both cinching mechanisms 5810, 5818, and has a first free end 5822 that extends from the first anchor 5802, and a second free end 5820 that extends from the second anchor 5812. Thus, in this exemplary embodiment, either or both free ends 5820, 5822 may be pulled in order to adjust the length of the suture extending between the anchors.

Figure 15:
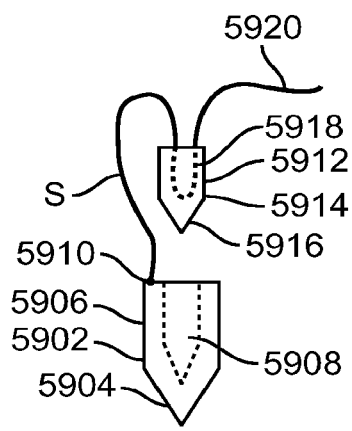

FIG. 15 schematically illustrates another anchor system having two anchors 5902, 5912. The first anchor 5902 includes a generally cylindrically shaped housing 5906, a pointed distal tip 5904 for penetrating into bone and a central channel 5908. The second anchor 5912 also includes a generally cylindrically shaped body 5914, a pointed distal tip 5916 for penetrating bone, and a cinching mechanism 5918. The second anchor 5912 may be positioned directly into bone or it may be positioned concentrically in the central channel 5908 of the first anchor 5902 and locked in place using any of the locking mechanisms described herein or known in the art. A length of suture S is coupled to both anchors 5902, 5912. One end of the suture S is fixed to the first anchor 5902 with a knot 5910 or by other methods known in the art. The suture S passes through the cinching mechanism 5918 in the second anchor 5912 and a free end 5920 extends from the second anchor 5912 and may be pulled in one direction to adjust the suture length between the two anchors. The cinching mechanism prevents the suture from moving in the opposite direction.

Figure 16:
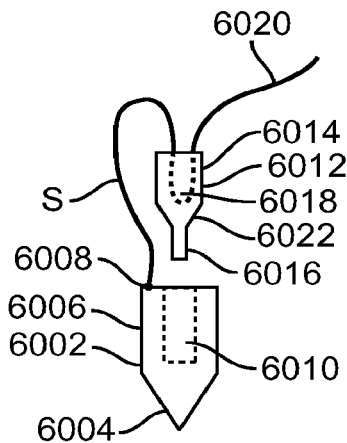
FIGS. 16-18 are side-views illustrating exemplary embodiments of suture anchor systems.

FIG. 16 schematically illustrates another anchor system having two stacked anchors 6002, 6012. The first anchor 6002 has a generally cylindrically shaped body 6006, a pointed tip 6004 for penetrating bone and a central channel 6010 that is generally parallel with the longitudinal axis of the first anchor 6002. The second anchor 6012 also includes a generally cylindrically shaped body 6014 and a cinching mechanism 6018. The cylindrical body 6014 has a tapered shoulder 6022 near the distal end of the anchor 6012 and a reduced diameter distal region 6016 that is positionable and lockable in the central channel 6010 of anchor 6002. A suture S is coupled to both anchors 6002, 6012. One end of the suture S is fixed to the first anchor 6002 with a knot 6008 or by other techniques. The suture passes through the cinching mechanism 6018 and a free end 6020 extends therefrom.

Figure 17:
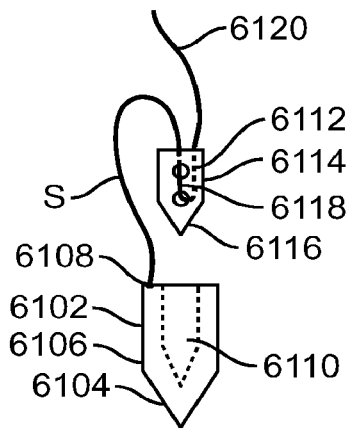

FIG. 17 schematically illustrates another anchor system having an anchor 6102 and a needle insert 6112. The anchor 6102 generally takes the same form as other anchors disclosed herein and includes a cylindrically shaped body 6106, a pointed distal tip 6104 for penetrating tissue such as bone, and a central channel 6110 that is substantially parallel to the longitudinal axis of the anchor 6102. The needle insert 6112 includes a cylindrically shaped body 6114, a cinching mechanism 6118, and a pointed distal tip 6116 that can penetrate tissue or bone. The needle insert 6112 is positionable and lockable in the central channel of the anchor 6102. A suture S is coupled to both the anchor 6102 and the needle insert 6112. One end of the suture S is attached to the anchor 6102 with a knot 6108 or by other attachment means known in the art. The suture also passes through the cinching mechanism 6118 and a free end 6120 of the suture S extends from the needle insert 6112 and may be pulled through the cinching mechanism to tighten the suture, while movement of the suture in the opposite direction is constrained. In this exemplary embodiment, the cinching mechanism may take the form of any of the embodiment disclosed herein.

Figure 18:
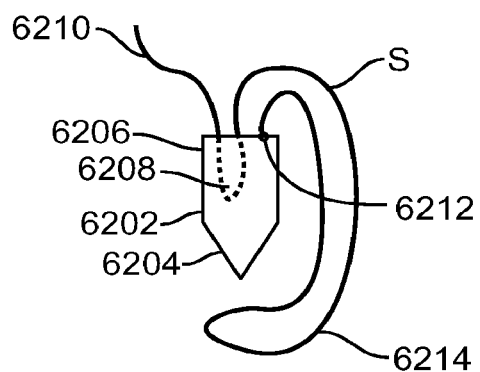

FIG. 18 schematically illustrates still another anchor system, this time with a single anchor 6202. The anchor 6202 includes a generally cylindrically shaped body 6206, a cinching mechanism 6208, and a pointed distal tip 6204 for penetrating tissue such as bone. One end of a suture S is fixed to the anchor 6202 with a knot 6212 or by other means and forms a loop region 6214 before passing through the cinching mechanism 6208. A free end 6210 of the suture S extends from the anchor 6202 and may be pulled to adjust the suture. In use, the suture at least partially encircles tissue to be captured and then the anchor 6202 passes through the loop 6214 and is then anchored into bone or other tissue. The suture can then be adjusted by pulling the free end 6210.

In anchoring systems having two or more suture anchors, it may be advantageous to attach the two anchors directly together. This minimizes the possibility that the anchors will become dislodged. For example, in FIG. 19, two anchors are stacked together in the same hole and joined with one another. A pair of anchors 82, 84 are coupled together with a suture 86 having a free end 86*a*. A coupling element 83 extends from the proximal end of the distal anchor 82 and allows the two anchors to be joined together. One end of the suture 86 is fixed to one anchor 82 with a knot 88 or other fastening methods may be used, and this anchor 82 may be placed into the bone before the other anchor 84. Once the anchor 82 is positioned into a pre-drilled hole in the bone or driven directly into the bone, the target tissue is captured by wrapping the second anchor around it or placing the second anchor through a penetration through the target tissue. Second anchor 84 is preferably placed into the same hole as first anchor 82, but may be configured for placement in a separate hole if desired. The second anchor 84 is advanced in the hole until its distal end butts up against the proximal end of the first anchor 82 and the coupling element 83 joins the two anchors together. The coupling element 83 may be a threaded rod that allows the two anchors to be screwed together, or the coupling element 83 may be a compression coupling with ribs or other features to enhance friction that is press fit into a corresponding bore (not shown) in the second anchor 84. Coupling element 83 may also have a relief feature 83*a* which allows two opposing halves of the relief feature to flex radially inward toward each other to facilitate insertion in the bore in the distal end of proximal anchor 84. One of skill in the art will appreciate that other coupling mechanisms, such as a ratchet, detent, snap fit or other mechanism may be used to join the two anchors together. Once the two anchors are coupled together, the free end 86*a* of the suture may be pulled to advance the suture 86 through a cinching mechanism (not shown) in the second anchor 84 thereby allowing adjustment of suture length and tension. The second anchor 84 may have any of the cinching mechanisms disclosed in this specification.

Figure 19:
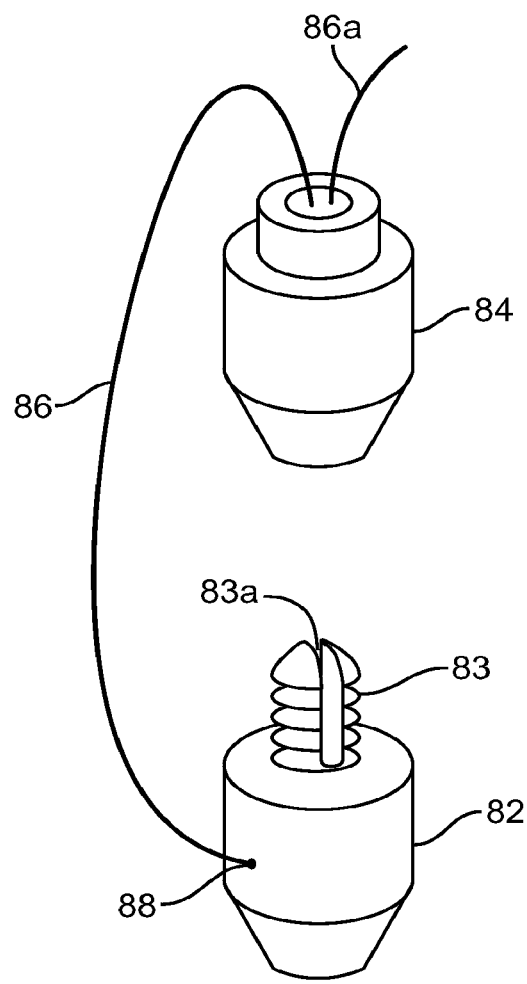
FIG. 19 is a perspective view of a two-part suture anchor system.
Figure 20:
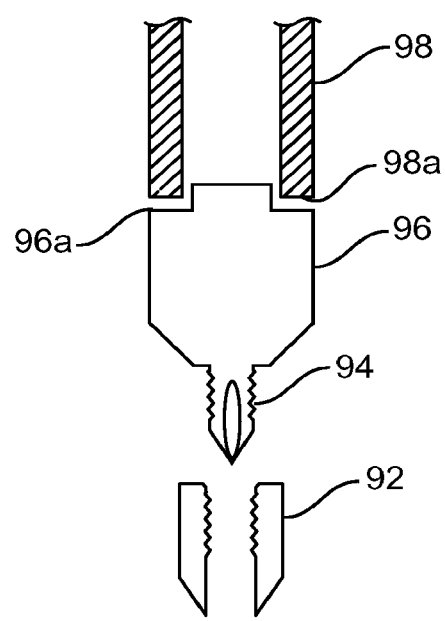
FIG. 20 is a partial side cross-section of an exemplary suture anchor system and delivery instrument.

FIG. 20 illustrates a variation of the embodiment in FIG. 19. In this exemplary embodiment, two anchors 92, 96 are placed end-to-end into engagement with one another. This variation is similar to that of FIG. 19, with the major difference being that the coupling element 94 is fixed to the top or proximal-most anchor 96 instead of on the bottom or distal-most anchor 92. The coupling element 94 may take any of forms previously described with respect to coupling element 83 in FIG. 19. Additionally, in this embodiment, a pusher tube 98 may be used to help drive anchor 96 into the bone or to help drive the two anchors into engagement with one another. A distal end 98*a* of the pusher tube 98 may be placed against a shoulder 96*a* of the upper anchor 96 and used to press the two anchors together. Alternatively, the proximal end of the pusher tube 98 may also be impacted with a hammer or similar object to help drive the two anchors into the bone and into engagement with one another. It will be understood that the distal and proximal anchors 92, 94 will be coupled to a length of suture and will include a knotless cinching mechanism in one or both anchors as described elsewhere herein.

Figure 21:
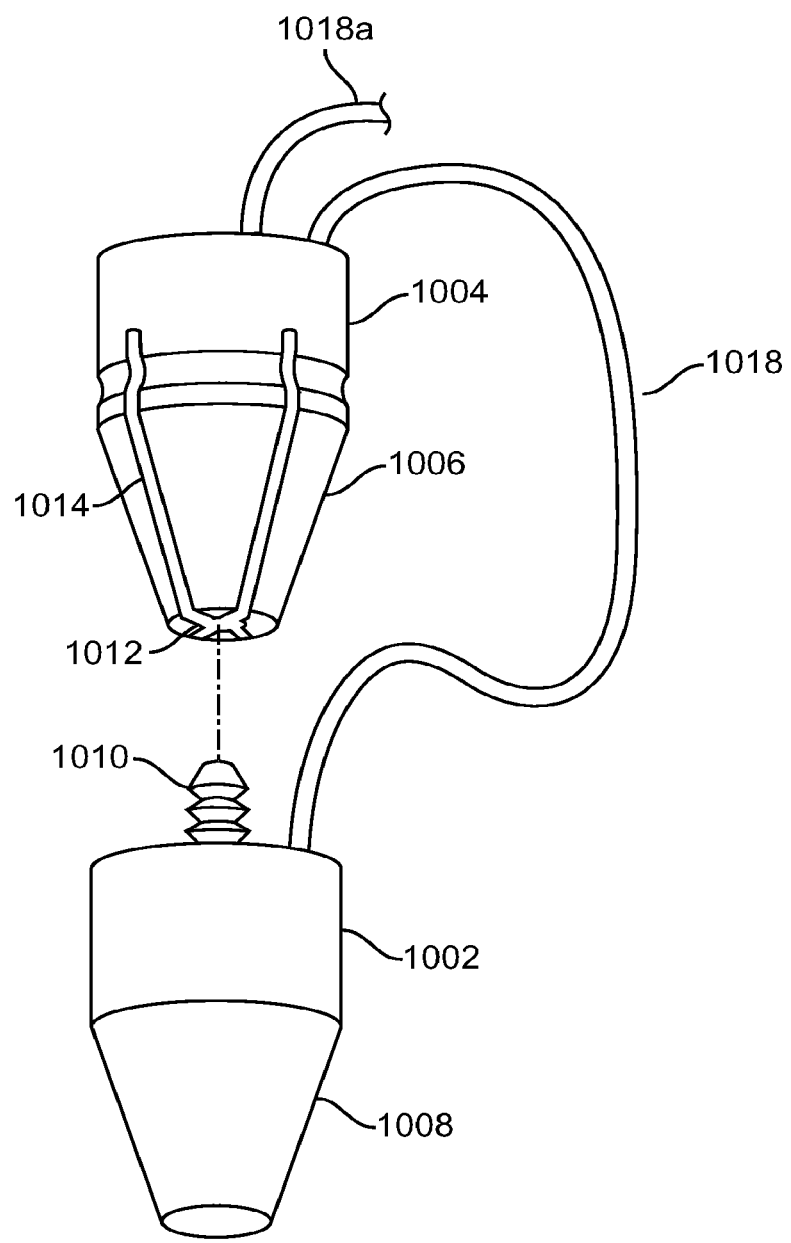
FIG. 21 is a side-view of an exemplary two-part suture anchor system.

FIG. 21 illustrates another exemplary embodiment of a pair of anchors that couple together in an end-to-end configuration. The anchors 1002, 1004 are coupled together with a length of suture 1018 having a free end 1018*a*. Each anchor 1002, 1004 has a tapered distal end 1006, 1008 that helps align the anchor into a hole drilled into the bone or provides a penetrating tip that may be driven directly into bone. A coupling element 1010 is attached to anchor 1002 and may be a threaded rod or a compression coupling that engages with the corresponding engagement feature (e.g. a threaded female receptacle or a channel) 1012 on anchor 1004. Additionally, anchor 1004 includes a series of relief slots 1014 that allow the distal extremity of the anchor to radially expand and contract as the coupling element 1010 is advanced into engagement with anchor 1004. Thus, as the coupling element is initially advanced into aperture 1012, the relief slots allow the anchor 1004 to expand and receive the coupling element 1010. Once the coupling element has been inserted into anchor 1004, the anchor collapses back to its natural shape, locking the coupling element 1010 in place and providing an end-to-end or stacked pair of suture anchors. While this embodiment illustrates the male coupling element 1010 on anchor 1004, one will of course appreciate that it could easily be placed on anchor 1004. In use, once the anchors have been placed into the bone, the free end of the suture 1018*a* may be pulled, pulling the suture 1018 through a cinching mechanism (not shown) in anchor 1004. The cinching mechanism may be any of the mechanisms disclosed in this specification or incorporated by reference.

Figure 22:
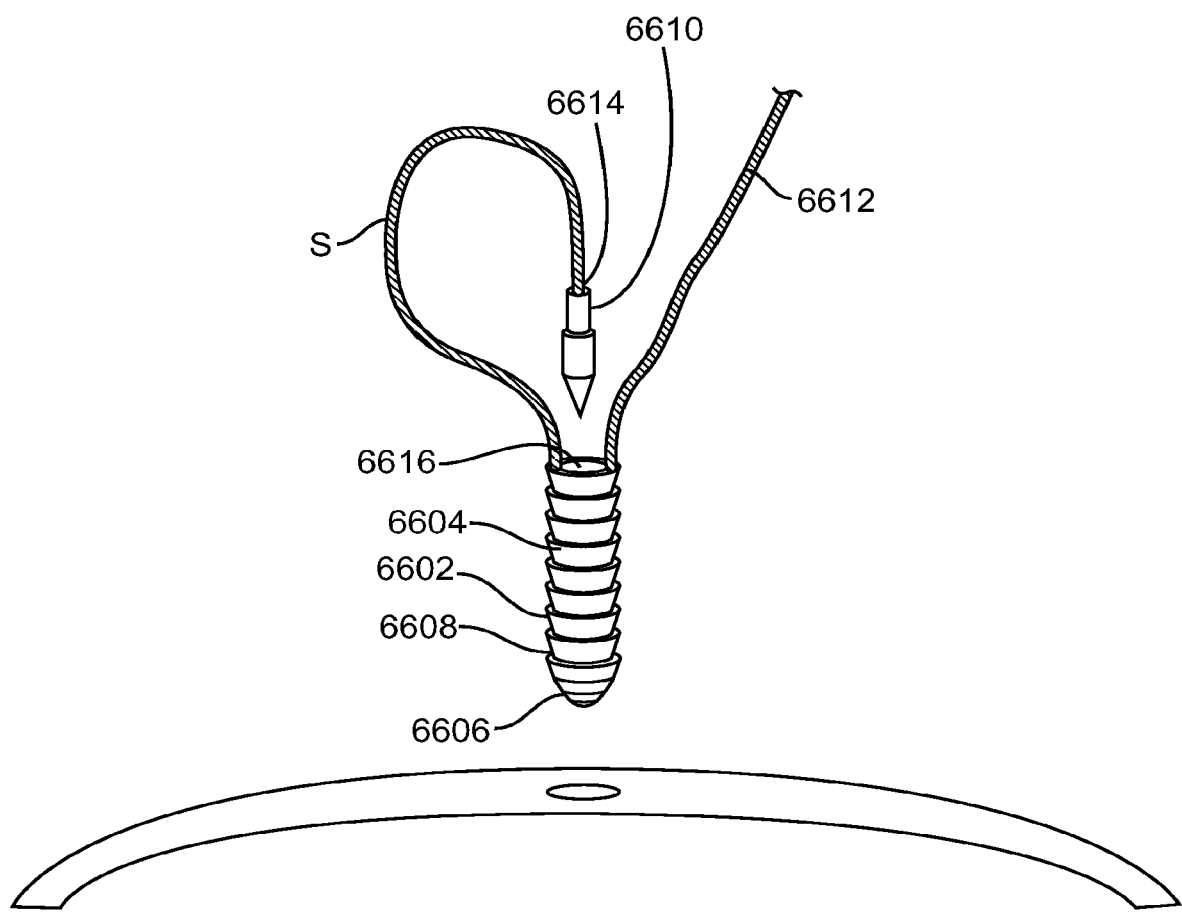
FIG. 22 is a perspective view of an exemplary two-part suture anchor system.

In some embodiments, a portion of the anchoring system includes a piercing needle for capturing the damaged tissue by passing the suture therethrough. FIG. 22 illustrates another embodiment of an anchor system and needle. The anchor 6602 has a generally cylindrical shaped body 6604 with barbs 6608 along the outer surface and a tissue piercing tip 6606. The anchor 6602 includes any of the cinching mechanisms described herein and has a central passage 6616 for receiving the tissue piercing needle 6610. A length of suture S having a free end 6612 is fixed to the needle with a knot 6614 or by crimping, bonding, or by other methods. The suture passes into the cinching mechanism (not illustrated) in the anchor 6602 and the free end 6612 exits the anchor. In use, the anchor 6602 is positioned in bone and the suture S at least partially captures the tissue to be repaired. The needle 6610 is then pierced through the tissue and the suture is also passed through the tissue. The needle is then inserted concentrically into the central channel 6616 of the anchor 6602 and locked into position. The suture S is then adjusted by pulling on the free end 6612 of the suture. In preferred embodiments, the needle diameter ranges from about 1.0 mm to about 2.2 mm. Needle length may range from about 2 mm to about 13 mm. The needle may have a straight tip or the tip may be curved or angled. An angled needle may range from 20 to 60 degrees. Using a needle to pass through the tissue may help retain the natural shape of the tissue thereby helping it to reattach and heal more quickly than if the tissue were deformed by tightening the suture around the tissue.

In addition to the multi-piece architectures described above, the anchor systems of the invention may have various single-piece and other architectures, several embodiments of which are described below.

One-Way Cinching Mechanisms:

In the following detailed description, it will be understood that the term "suture" may include any of various materials used in surgical procedures to repair tissue or to fasten tissues to other tissues or prosthetic structures. These may include not only conventional suture material, but wire, cord, ribbon, tape, fabrics or other flexible filament-like materials. In addition, a suture may be described as entering or exiting an anchor or other structure. It will be appreciated that the terms "enter" and "exit" are relative and therefore a suture that enters an aperture may also be considered to be exiting the aperture. Similarly, a suture that is described as exiting an aperture may be considered to be entering the aperture. The foregoing applies throughout this specification unless indicated to the contrary.

Figure 23B:
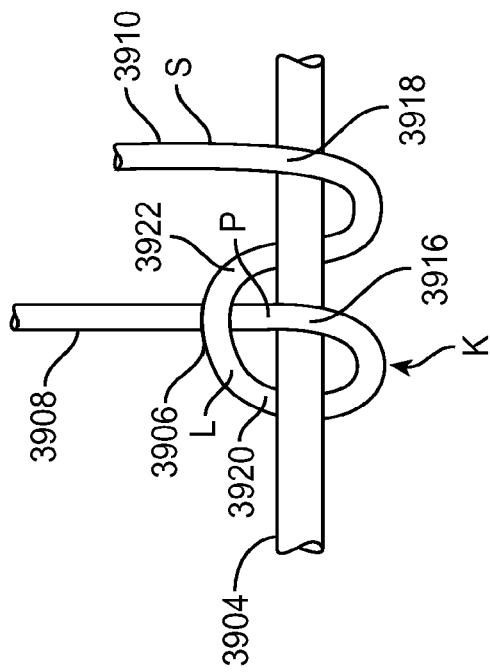
FIG. 23B is a side-view of a cinching mechanism.
Figure 23A:
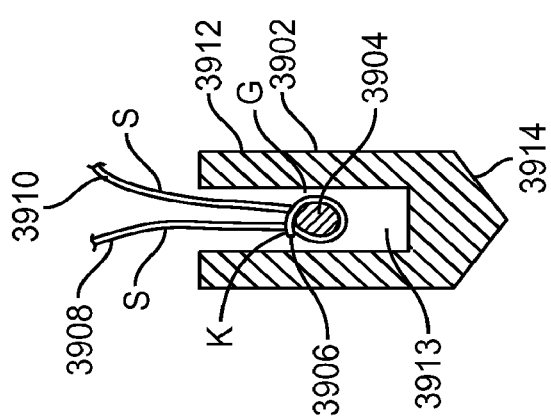
FIG. 23A is a side cross-section of a cinching mechanism.

As discussed above, the suture anchor systems described herein preferably include one or more mechanisms for adjusting suture length and tension without requiring the surgeon to tie a knot in the suture. FIG. 23A is a schematic illustration of an exemplary embodiment of a suture anchor in cross-section having a one-way cinching mechanism. The anchor 3902 includes a housing 3912 having an inner cavity 3913, a tissue penetrating distal tip 3914, and a bar 3904 (also referred to as a pin) disposed within cavity 3913 generally transverse to the longitudinal axis of the anchor. Inner cavity 3913 is closed at its distal end but open proximally. The suture is wrapped around the bar to form a knot K that allows the suture to move around bar 3904 in one direction while locking it in the opposite direction. Knot K may be any of various one-way sliding knots, but in a preferred embodiment the knot is a munter hitch. As shown in FIG. 23B, to form the knot K, a first extremity 3908 of suture S forms a pole P oriented transversely to the axis of bar 3904. From pole P suture S loops around the bar 3904 to form a front segment 3916 in front of bar 3904 and a rear segment 3920 behind bar 3904. Similarly, second extremity 3910 of suture S enters the anchor and loops around the bar 3904 to form a front segment 3918 in front of bar 3904 and a rear segment 3922 behind bar 3904. An intermediate segment 3906 of suture S forms a U-loop L which loops around pole P and connects the rear segment 3920 of first extremity 3908 to the rear segment 3922 of second extremity 3910. When the first extremity 3908 of the suture is pulled away from the anchor (generally parallel to the longitudinal axis), the suture is allowed to slide about the bar and thus suture tension or length may be adjusted. When the second extremity 3910 of the suture S is pulled away from the anchor (generally parallel to the longitudinal axis), the U-loop L will cinch down on pole P, pulling transversely on pole P and generally tangentially to the outer surface of bar 3904. This increases friction between the U-loop L and pole P, as well as friction between suture S and bar 3904, inhibiting suture S from sliding. In addition, as tension on second extremity 3910 is increased, U-loop L may pull pole P into the gap G between the bar 3904 and the wall of cavity 3913, compressing rear segments 3920, 3922 and intermediate segment 3906 therebetween, further preventing suture S from moving relative to anchor 3902. Thus, suture S is allowed to move freely when first extremity 3908 is tensioned, but is inhibited or prevented from moving when second extremity 3910 is tensioned. Preferably, the cinching mechanism will resist movement of suture S when a force of up to at least about 10 lbs, more preferably at least about 20 lbs, is exerted on second extremity 3910. Optionally, features such as bumps, ridges, scales, surface roughening, or sticky coatings may be provided on bar 3904 or along the inner wall of cavity 3913 to enhance friction with the suture.

It will be understood that the term "bar" encompasses a variety of possible structures suitable for wrapping the suture and tying one-way sliding knots according to the invention. The bar may be described as having an axial axis about which the suture is wrapped, and a transverse axis generally perpendicular to the axial axis. The bar may have a cylindrical, oval, race-track, D-shaped or other rounded cross-section, with a curvature or partially rounded surfaces formed around the bar's axial axis to allow the suture to slide easily. The bar may be elongated like a pin, beam or post, with an axial length larger than its transverse width, but may also be short in axial length, just needing sufficient length to accommodate the width of the suture for the desired number of wraps around the bar. The bar may also constitute a portion of material lying between two parallel channels or passages through which the suture may be threaded to form a one-way sliding knot. The bar may be a polymer, metal or other biocompatible material of suitable strength to withstand tensile forces on the suture, and may be molded as an integral part of the anchor, or a separate part that is fixed to the anchor by bonding, welding, press-fit, threads or other suitable connection. The bar may be coupled to the anchor in various orientations, with its axial axis perpendicular, parallel, or at another angle relative to the longitudinal axis of the anchor. As described elsewhere herein, the bar may be mounted to the anchor in various positions, including recessed in a cavity within the anchor, or extending from an exterior surface of the anchor in an elevated configuration.

Figure 23C:
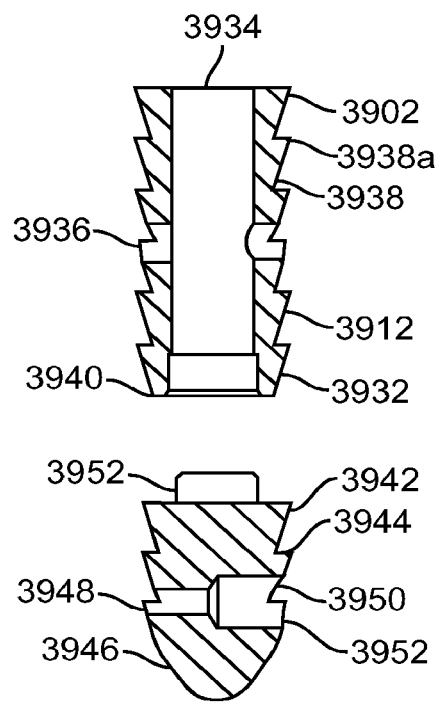
FIG. 23C is a side cross-section of a suture anchor system.
Figure 23D:
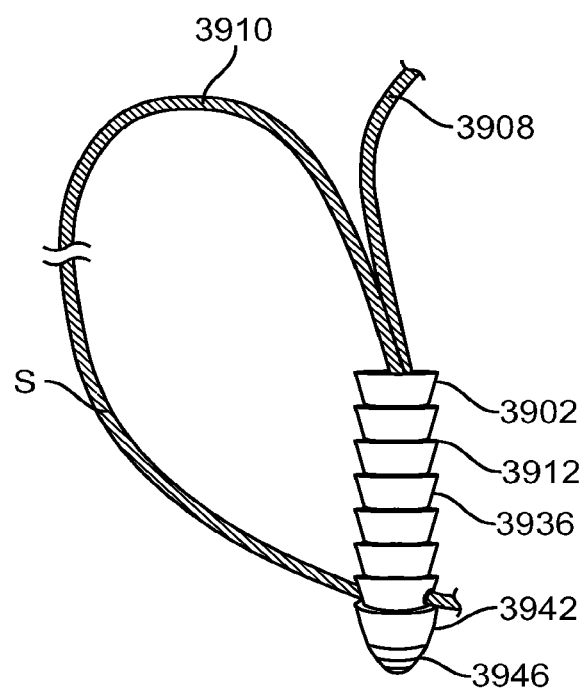
FIG. 23D is a side-view of a suture anchor system.

The cinching mechanism of FIGS. 23A-23B may be used in any of various anchor housings or configurations. For example, FIGS. 23C and 23D illustrate an exemplary embodiment of an anchor system that may utilize this type of cinching mechanism. The anchor system includes an upper anchor component 3932 having a housing 3912 that is cylindrically shaped. The outer surface 3938 of the housing 3912 includes a number of circumferential scalloped or barbed regions 3938a that help with insertion of the housing into a bone while also helping to prevent the housing from sliding out of the bone. The housing 3912 has a central longitudinal channel 3934 (also referred to as a cavity) and a transverse channel 3936 (also referred to as a passage or a suture retaining structure or element) in which bar 3904 (not shown in FIG. 23C) like that shown in FIGS. 23A-23B is positioned. The bar 3904 may be press fit, bonded, welded or otherwise secured in channel 3936. Bar 3904 may also be molded as a unitary structure with housing 3912. A distal portion 3940 of the channel 3934 is tapered, flanged or otherwise formed to interlock with the proximal end 3952 of the distal-most portion of the anchor 3942. The second portion of the anchor system, a distal anchor 3942 also has a cylindrically shaped housing with a pointed tip 3946 for penetrating into bone or other tissue. The outside surface also includes a scalloped region or a barbed region 3944 for helping to advance the anchor into bone and prevent dislodgement of the anchor from the bone. A passage 3950 transverse to the longitudinal axis of the anchor 3942 has one side with a smaller passage 3948 and the other side with a larger passage 3952. This allows suture to be threaded through the passage as shown in FIG. 23D and knotted in the larger passage 3952. The knot cannot pass through the smaller passage 3948, thus one end of the suture will be secured to the distal-most portion 3942 of the anchor. In this or any of the embodiments disclosed herein having a transverse channel for attaching the free end of the suture, the distal end of the anchor body may alternatively have an open channel or a forked configuration that allows the suture to be captured by placement therein rather than having to be threaded through the passage. Eyelets, suture loops, hooks and other suture capturing structures at the distal end of the anchor are also possible.

FIG. 23D illustrates the two anchor portions coupled together with one end of a suture S fixed to the lower anchor portion 3942 forming a repair loop for capturing damaged tissue, and the other end of the suture S passing through the cinching mechanism of FIG. 23A-23B (not visible in FIG. 23D) with a free end 3908 of suture exiting the anchor system. By pulling on free end 3908 the size of repair loop may be reduced to apply the desired degree of tension on the tissue captured therein. The one-way mechanism within the anchor allows suture S to move in the direction required to shorten the repair loop, but substantially prevents the suture from moving in the opposite direction even as tension is increased in the repair loop, effectively locking the suture without the need to tie a knot.

Figure 23E:
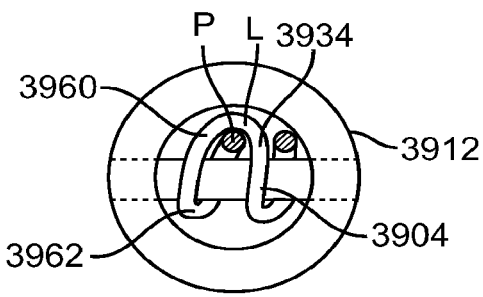
FIGS. 23E-23G are top-views of a suture anchor.
Figure 23F:
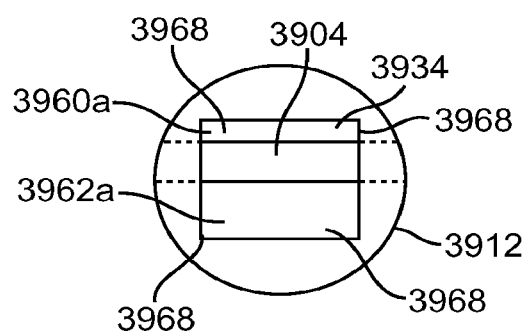
Figure 23G:
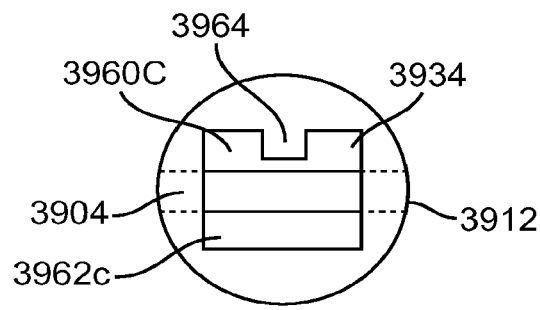

Referring to FIGS. 23E-23G, in certain situations, if the spacing between the inner wall of central channel 3934 and bar 3904 is large enough, when suture extremity 3910 is tensioned, the U-loop L along with pole P may rotate relative to bar 3904, "flipping" to the opposite side of bar 3904. In order to address this, the central channel 3934 may be configured with a blocking structure to prevent the knot from rotating about the bar. In one embodiment, the blocking structure comprises the inner wall of central channel 3934. Preferably, bar 3904 is asymmetrically positioned in central channel 3934 such that the gap 3960 on one side of bar 3904 is larger than the gap 3962 on the opposite side of bar 3904. Larger gap 3960 will be large enough to easily accommodate the uncompressed cross-sectional size of at least one and preferably two strands of suture and allow them to slide easily through it. The smaller gap 3962 will be substantially smaller than gap 3960, preferably small enough that three strands of suture (two comprising U-loop L and one pole P) when compressed cannot pass through it. In this way pole P may extend through the larger gap 3960 with U-loop L wrapped around it so as to pull pole P toward the smaller gap 3960 when U-loop L is tensioned, preventing them from flipping around bar 3904.

In the embodiment of FIG. 23F, the central channel 3934 is of rectangular cross-section with bar 3904 asymmetrically positioned to divide central channel 3934 into a first larger passage 3962a and a second smaller passage 3960a. The use of rectangular passages provides corners 3968 to provide more space for the sliding of the suture strands when contracting the repair loop. Because the space between the bar 3904 and the wall of smaller channel 3960a is not large enough to accommodate the combined cross-section of the U-loop L and pole P, the knot is prevented from flipping.

FIG. 23G illustrates yet another embodiment which prevents the knot from flipping. In this embodiment a tooth 3964 extends from an inner wall of the channel in the first passage 3960c. The knot (that is, U-loop L and pole P) cannot move past the tooth 3964, thereby preventing flipping. However, the spaces alongside tooth 3964 are large enough to allow suture S to slide in the desired direction when tensioning the suture. In an alternative configuration (not shown), a tooth like tooth 3964 may extend laterally outward from bar 3904 to prevent knot flipping in a similar manner.

Figure 23H:
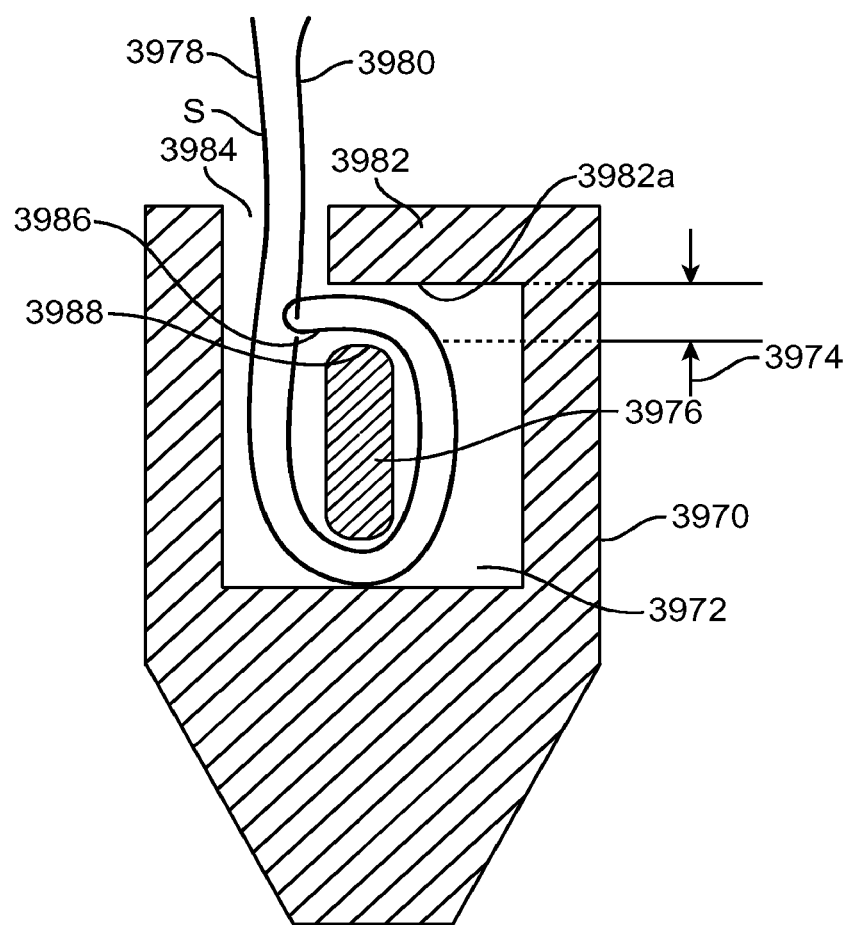
FIG. 23H is a side cross-section of a suture anchor.

FIG. 23H illustrates a variation of the cinching mechanism illustrated in FIG. 23B with the major difference being the orientation of the hitch-type knot and the blocking feature of the anchor. The anchor body or housing 3970 may have any of the geometries disclosed herein, but preferably is cylindrical with a tapered tip. An aperture 3984 at the proximal end of the anchor housing 3970 allows the suture S to enter and exit a central channel 3972. The suture S is wrapped around a transverse bar 3976 passing through the central channel 3972. The transverse bar 3976 is oval shaped, with its longer transverse axis generally aligned with the longitudinal axis of anchor body 3970. Additionally, the transverse bar 3976 is disposed under a shoulder 3982 which forms a locking gap 3974 between a bottom surface 3982a of the shoulder 3982 and a top surface 3988 of the transverse bar 3976. Suture S forms a U-loop 3986 around extremity 3980. When suture extremity 3978 is pulled, U-loop 3986 pulls extremity 3980 in a direction tangential to the outer surface of bar 3976, pulling it into the locking gap 3974 and compressing it between the top surface 3988 of the transverse bar 3976 and the bottom surface 3982a of the shoulder 3982. This locks the suture from moving longitudinally and prevents the U-loop from rotating ("flipping") around bar 3976. The locking gap 3974 may be adjusted in order to prevent flipping of the suture as previously discussed, or to vary the locking force on suture S. Advantageously, by positioning the locking gap 3974 at the top, rather than the side, of bar 3976, the forces are redistributed to act along the longer transverse axis of the bar along which the bar is more rigid, thereby reducing the chance of bar deformation.

Figure 24A:
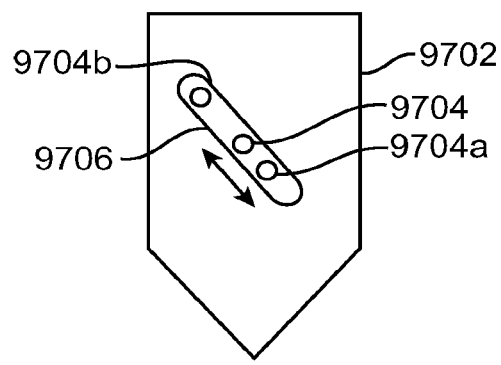
FIGS. 24A-24B are side-views of suture anchors.
Figure 24B:
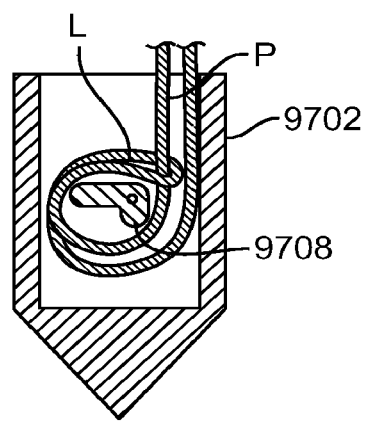
Figure 24C:
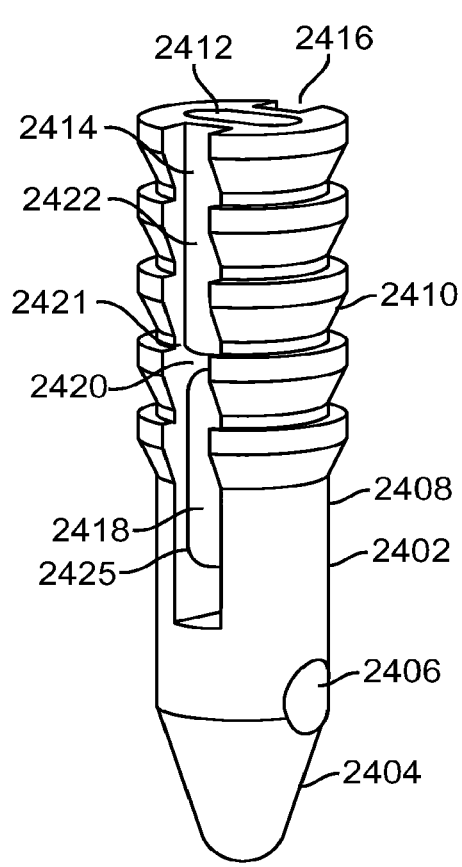
FIG. 24C is a perspective view of a suture anchor.

FIGS. 24A-24B illustrate two other embodiments that prevent the knot from flipping. In FIG. 24A, the anchor 9702 includes a transverse bar 9704 that floats along an angled slot 9706. The bar can move from a distal end 9704a of the slot 9706 to a proximal end 9704b of the slot 9706. The suture (not illustrated) is wrapped around the transverse bar 9704 using any of the configurations described herein, and preferably using the hitch-type knot described in FIG. 23B. When one end of the suture is tensioned, the bar will move toward the proximal position 9704b and will reach the end of the slot which is closer to an inner side wall of the anchor. Because the bar cannot travel any further and because the gap between the bar and the sidewall is small enough, the suture will lock and the suture knot will be prevented from flipping around the bar. When the opposite end of the suture is tensioned, the bar moves closer to the distal position 9704a such that the spacing between the bar and the wall increases, allowing the suture to move more freely. FIG. 24B illustrates a variation where instead of a sliding transverse bar, the suture is looped around a rotatable cam 9708 that is shaped such that when U-loop L is tightened, the cam will rotate to a position which forms a narrower gap between the cam and an inner sidewall of the anchor, preventing the knot flipping. The cam is shaped so that the suture may pass freely over the cam without being pinched or otherwise constrained when the suture is pulled in the opposite direction.

FIGS. 24C-24F illustrate another exemplary embodiment of a suture anchor with a cinching mechanism. In this embodiment, suture anchor 2402 is preferably molded as a single unitary body to eliminate any need to assemble multiple parts. The suture anchor 2402 has a generally cylindrically shaped body 2408 and a tapered distal tip 2404. A transverse channel 2406 extends through the anchor body and may be used help attach a suture to the anchor or to pass a suture therethrough, as described elsewhere in this specification. The body 2408 also includes circumferential barbs or scallops 2410 to help advance the anchor into bone and retain it in place. Two longitudinally oriented channels 2414, 2416 extend from the proximal end of the anchor distally, but the channels do not extend all the way to the distal end of the anchor. The suture extremities reside in the channels as seen in FIG. 24F so that the suture will not be pinched between an outer surface of the anchor and an inner surface of the bone when implanted.

Figure 24D:
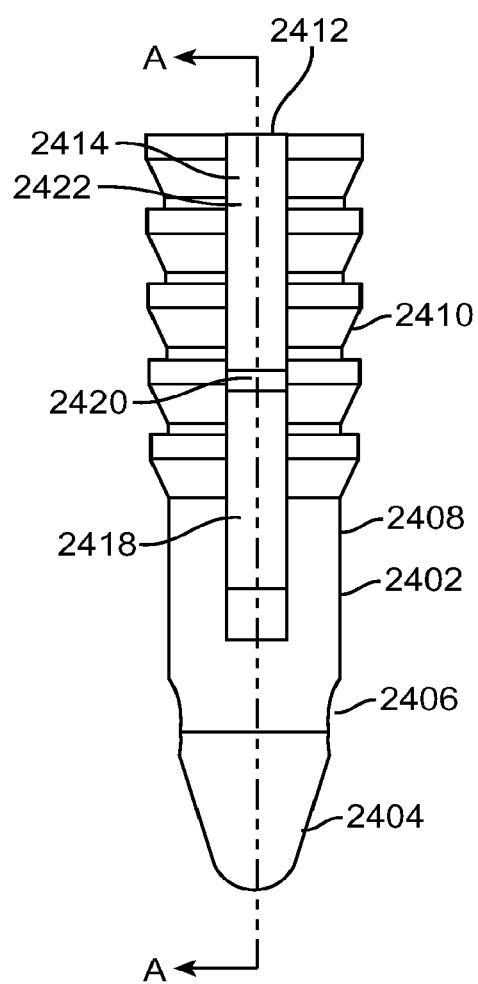
FIG. 24D is a side-view of the suture anchor in FIG. 24C.

FIG. 24E is a cross-section taken along line A-A in FIG. 24D and FIG. 24F is the same view as FIG. 24E, except this time illustrating how the suture S passes through the anchor to form a hitch-type cinching mechanism 2426 that generally take the same form as in FIG. 23B above. As seen in FIGS. 24E-24F, anchor 2402 has a proximal shank 2422 having a blind central channel 2412 extending axially from the proximal end partially through the shank for coupling to an insertion tool. A cavity 2425 extends transversely through a mid-portion of anchor body 2408 distally of shank 2422. A bar 2418 is disposed transversely across cavity 2425 and has a cross-sectional shape suitable for forming a one-way sliding knot therearound. Bar 2418 may be press fit into the anchor, molded as an integral part of the anchor body, or formed by other techniques known in the art. An upper gap 2424*a* is disposed between the proximal side of the bar 2418 and the upper wall of cavity 2425, and a lower gap 2424*b* is disposed between the distal side of the bar 2418 and the lower wall of cavity 2425 to allow suture to pass therethrough. Both upper gap 2424*a* and lower gap 2424*b* extend between and communicate with the longitudinal channels 2414, 2416. The upper gap preferably has a width substantially smaller than the lower gap to prevent the hitch type knot from flipping around lower bar 2418, as previously described. The distal end of shank 2422 has a rounded tip with a larger radius 2423*a* on one edge and a smaller radius of curvature 2423*b* on the opposite edge. Similarly, the bar 2418 has a proximal side with a larger radius 2419*a* and a smaller radius of curvature 2419*b*. The proximal end of the bar is positioned adjacent the distal end of the shank such that the regions with the larger radius are adjacent one another and the regions with the smaller radius are also adjacent one another. This forms a tapered lead in or funnel section 2420 communicating with upper gap 2424*a* on one side of the bar, and a less tapered region on the opposite side. As shown in FIG. 24F, the suture S extends downward along channel 2414, passes through gap 2424*b* under the bar 2418, upward through channel 2416, and then enters the tapered funnel 2420 and through upper gap 2424*a* above bar 2418. The suture then is looped around itself forming a U-loop and is then passed back through upper gap 2424*a* and ultimately exits the anchor along channel 2416. The wider funnel section allows suture to be slide more easily through upper gap 2424*a* when suture end 2428 is tensioned, and the narrower section constricts and traps the U-loop formed around suture end 2428 when suture end 2430 is tensioned. Thus, pulling suture extremity 2428 allows the suture to slide to adjust of suture length and tension, while pulling suture extremity 2430 locks the suture. As an alternative to the longitudinal channels 2414, 2416, anchor 2402 may have an internal channel (not shown) that extends axially through shank 2422 from the proximal end of the anchor distally into communication with the cavity 2425, allowing suture ends 2428, 2430 to extend from bar 2418 through this internal channel rather than through the external longitudinal channels.

Figure 25A:
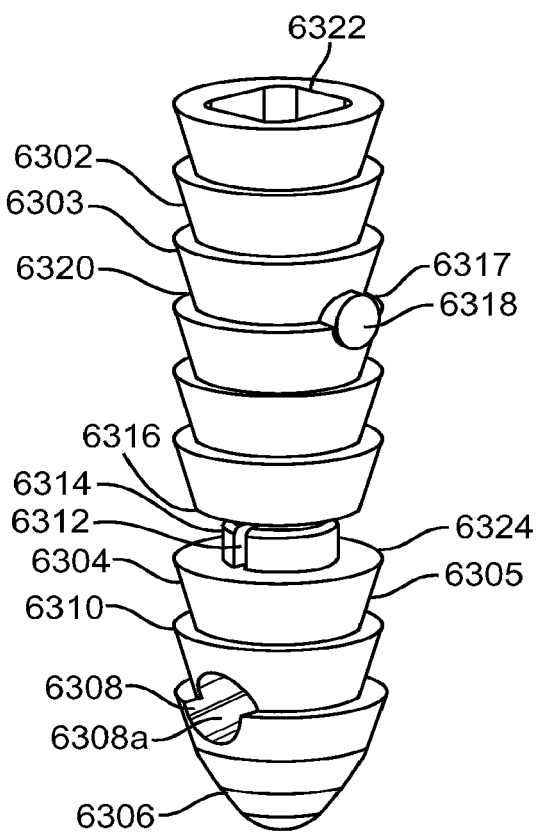
FIGS. 25A-25C are perspective, side, and top-views of a suture anchor.
Figure 25B:
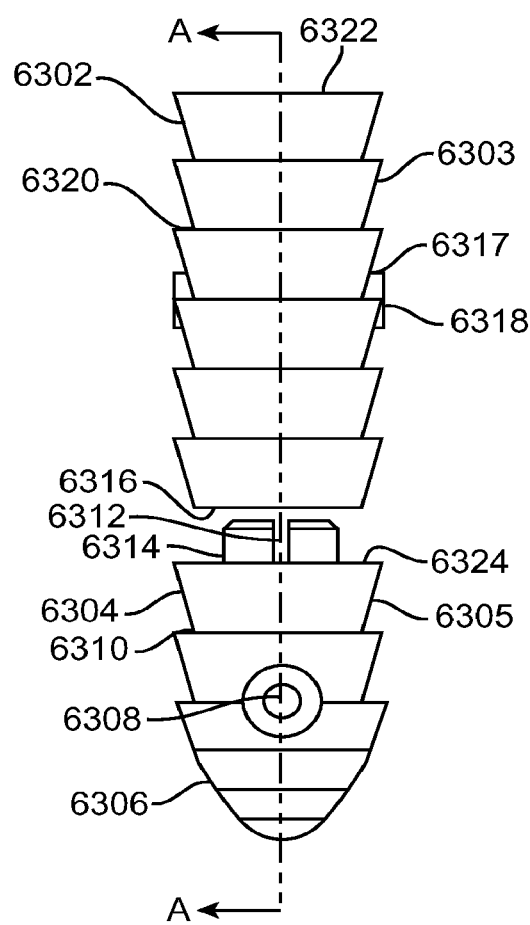
Figure 25C:
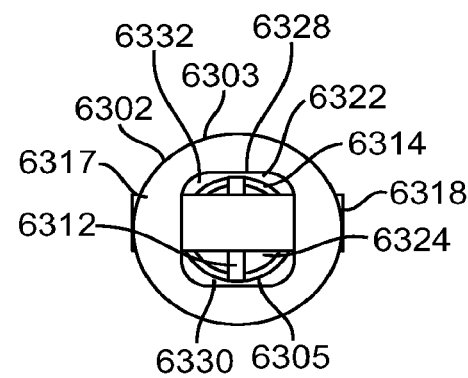

FIGS. 25A-25F illustrate an exemplary embodiment of a two part suture anchor system using the hitch-style knot of FIGS. 23A-23B and an offset bar to prevent the knot from flipping. FIG. 25A is a perspective assembly view of the system, FIG. 25B is a side view of the system and FIG. 25C is a top view. FIG. 25D is a cross-sectional view taken along the line A-A in FIG. 25B. The two part anchor system includes an upper anchor 6302 which has generally cylindrically shaped body 6303 and a square shape central channel 6322 that extends parallel with the longitudinal axis of the upper anchor 6302. A cylindrical bar 6318, preferably a polymer, is molded into the upper anchor body 6303 or press fit, bonded, welded, or otherwise inserted into a cylindrical channel 6317 transverse to the longitudinal axis of the anchor and is used to form the suture hitch therearound. The outer surface of the housing includes a plurality of circumferential scalloped regions or barbed edges 6320 that help the anchor insert into bone and also help to prevent the anchor from slipping out of the bone. The distal end 6316 of the upper anchor has a flat, blunt face so that it can butt up against and sit flat against the lower anchor 6304. The central channel 6322 may extend all the way through the anchor 6302 and has an aperture 6326 on its distal end (best seen in FIG. 25D) that may be coupled to the lower anchor 6304. The lower anchor 6304 also has a generally cylindrically shaped body 6305 with scalloped or barbed regions 6310 similar to those on the upper anchor 6302 and a pointed distal tip 6306 for piercing tissue such as bone, or for directing and centering the lower anchor 6306 into a predrilled hole in bone. The lower anchor 6304 also includes a passage 6308 that is transverse to the longitudinal axis of the lower anchor 6304. The transverse passage 6308 includes a small diameter region 6308*b* and a larger diameter region 6308*a* (best seen in FIG. 25D). This allows a suture (not illustrated) to be secured to the lower anchor by threading the suture through the passage 6308 and knotting one end of the suture in the larger diameter region 6308*a*. The knot (not illustrated) is too large to pass through the small diameter region 6308*b* and thus the suture will remain attached to the lower anchor 6304. The proximal end of the lower anchor 6304 includes a coupling member 6314 that may be received by aperture 6326 into channel 6322 of the upper anchor 6302. The coupling member 6314 includes a slotted region 6312 that allows the coupling member to compress inward as it is press fit or otherwise engaged with the upper anchor. Once engaged, the coupling member expands to its unbiased shape and the upper and lower anchors are attached to one another. The coupling member may join the two anchors together with a press fit, a snap fit, threads, or other fastening techniques known to those skilled in the art. A flat shoulder 6324 on the proximal end of the lower anchor allows the upper and lower anchors 6302, 6304 to sit flush against one another when coupled together and stacked on top of one another.

FIG. 25C illustrates a top view of the anchor system. Bar 6318 is asymmetrically positioned in the central channel 6322 in the upper anchor housing 6303, i.e. bar 6318 is closer to one sidewall 6328 of central channel 6322 than the opposite sidewall 6330. This creates a wider region 6330 and a narrower region 6332 through which the suture can pass. Preferably, the wider region 6330 has a width at least as large as the uncompressed transverse dimension (diameter, if round) of the suture, allowing the suture to slide freely when the adjustment end of the suture is pulled. The narrower regions 6332 is preferably substantially smaller than the uncompressed transverse dimension of the suture, preferably being no more than about 0.6-0.9 times the uncompressed suture diameter. As described above, the narrower region 6332 is sized to prevent flipping of the hitch-style knot around the bar 6318, thereby preventing slippage of the suture. In an exemplary embodiment, the width of the wider region is at least about 1.2 times the width of the narrow region, or at least about 0.8-1.1 times the uncompressed suture diameter. In a particular embodiment for use with No. 2 "Force Fiber" ultrahigh molecular weight polyethylene suture having an uncompressed diameter of 0.0197"-0.0248", the wider region has a width of about 0.020"-0.022" and the narrower region has a width of about 0.015"-0.017".

FIG. 25E illustrates a perspective view of the lower anchor 6304 in FIGS. 25A-25D showing the coupling member 6314. FIG. 25F illustrates a perspective view of a variation of the lower anchor 6304a. The exemplary embodiment is substantially similar to that in FIG. 25E with the major difference being that the coupling member 6314a is a square shaped peg that engages with the distal end of the upper anchor 6302. One of skill in the art will appreciate that a number of other configurations may be used for the coupling member.

FIGS. 26A-26E illustrate another exemplary embodiment of an anchor system using a hitch-style knot in the cinching mechanism. This embodiment preferably uses a polymer bar that is molded into the upper anchor as a unitary construct. The anchor shown may be part of a two-part anchor system with a separate distal anchor (not illustrated here), which may be similar to any of the distal anchors disclosed herein.

The anchor 6402 has a cylindrically shaped body 6404 with a plurality of scalloped or barbed edges 6406 similar to others previously described. An oval or racetrack shaped central channel 6410 extends longitudinally through the anchor 6402 and an oval shaped bar 6412 extends transversely across the central channel 6410. The distal end 6408 of the upper anchor 6402 is illustrated as having a flat face, but may alternatively have a tapered or pointed distal tip. The top view in FIG. 26D shows bar 6412 extending transversely across central channel 6410. Bar 6412 is asymmetrically positioned in the central channel 6410 such that the bar is closer to one wall of the central channel than the other. This creates a smaller space 6414 between the central channel wall and one side of bar 6412 slightly smaller than the suture diameter, but just large enough to allow one width of suture to pass through. The asymmetric positioning of the bar also creates a larger space 6416 between the opposite central channel wall and the opposite side of the bar 6412 that more easily allows suture to pass through. This configuration enhances locking forces and prevents the knot from flipping past the smaller space 6414 as previously described above. FIG. 26B highlights the asymmetrical positioning of bar 6412 in the central channel and also illustrates how the bar 6412 is integrated into the anchor body 6404 to form a single piece.

The side cross-section view in FIG. 26E more clearly illustrates how the suture is knotted around the bar 6412. The bar 6412 in this embodiment is a polymer that is molded into the upper anchor, and in preferred embodiments is molded with the same material as the upper anchor, preferably polyetheretherketone (PEEK). Being a molded polymer rather than a metal, the strength of bar 6412 is preferably enhanced by configuring the bar in an oval or racetrack cross-section, having a transverse height substantially larger than the transverse width. The upper and lower edges 6420, 6418 are preferably rounded to allow the suture S to move more easily. Thus, the combination of the racetrack profile of the bar and its asymmetric positioning in the central channel results in increased locking force and reduced tensioning force for the suture.

The suture S has a first extremity 6422 that enters a top portion of the central channel 6410 and extends downward into the central channel 6410. The suture S extends partially over top surface 6420 of bar 6412 and downward alongside bar 6412 through the larger space 6416 between the bar 6412 and the inner wall of the central channel 6410. The suture then passes underneath bar 6412 and around lower surface 6418, extending upward alongside bar 6412 through the smaller space 6414. The suture then forms a loop 6426 around the first extremity 6422 and passes back downward through smaller space 6414, looping under bar 6412. A second extremity 6428 then extends upward through the larger space 6416 of central channel 6410 and out of the central channel away from the anchor. As previously described, when the first extremity 6422 of suture is pulled, the suture will move freely and thus can be adjusted. However, when the second extremity is pulled, the looped portion 6426 of suture S will cinch down on the first extremity 6422 creating friction between the two strands of suture and between the suture and the bar, inhibiting suture movement. Further tension may draw loop 6426 and first extremity 6422 into the narrower gap between the bar and the inner sidewall of central channel 6410, thereby preventing the suture from moving. The free end of the second extremity will be wrapped around or passed through the tissue to be repaired, and then coupled to the anchor by means of a second anchor component as described above or by means of a suture retention structure on anchor body 6404 itself. Alternatively the second extremity may be placed into the bone hole prior to anchor placement and trapped between the anchor and the surrounding bone. Advantageously, with the anchor fully inserted into the bone and the second extremity secured, the degree of tension around the tissue may be finely adjusted by pulling on first extremity 6422. The one-way cinching mechanism of the anchor prevents the suture from loosening without the need for the surgeon to tie knots.

FIGS. 27A-27C illustrate still another variation of a suture anchor using a hitch-type cinching mechanism in a single piece construct. In FIG. 27A, the anchor 6902 includes a generally cylindrical shaped body 6904 with an upper portion 6906, a lower portion 6912 and a central portion 6910 therebetween. The upper portion 6906 and lower portion 6912 include circumferential scalloped or barbed regions 6908 and 6914. These scalloped or barbed regions help the anchor advance into bone and resist its removal therefrom, enhancing retention of the anchor in the bone. The central portion 6910 has a generally smooth outer surface although it may also include barbs or scallops like the upper and lower portions 6906, 6912. The lower portion 6912 also includes a pointed or tapered tip 6916 which facilitates advancement of the anchor into bone or other tissue. The tip 6916 also includes a channel 6918 that is generally transverse to the longitudinal axis of the anchor 6902 used for retaining a free end of suture S, as described below. It will be understood that various other structures for retaining a free end of suture S on the anchor may also be used. The upper portion 6906 includes a top surface 6920 that has a square aperture 6924 leading to a central channel 6938 (best seen in FIG. 27C). Central channel 6938 may be blind as shown (extending only partially through the length of anchor body 6904) or it may extend through the entire length of the anchor body. FIG. 27B is a top view of anchor 6902 showing a pin or bar 6922 that is transverse to the longitudinal axis of the anchor 6902. The pin or bar 6922 is preferably integrally molded into the anchor body 6904, or alternatively may be press fit, molded, bonded or otherwise secured to the anchor. The bar 6922 has a rectangular cross-section 6942 with rounded top and bottom edges 6940a, 6940b as best seen in FIG. 27C and is configured to allow suture S to be wrapped therearound. The bar 6922 is offset from the central longitudinal axis 6928 of the central channel, thus bar 6922 creates two regions of different width in the central channel. A wide region 6934 is disposed between one side of the bar 6922 and a wall 6936 of the central channel 6938, and a narrow region 6930 is disposed between an opposite side of bar 6922 and a wall 6932 of the central channel 6938. The wide region 6934 is spacious enough to allow the suture S to pass easily therethrough while narrow region 6930 is sized to prevent the loop 6946 of the suture from flipping or passing through it as discussed above with respect to FIG. 23F. In this exemplary embodiment, the centerline of the bar 6922 is offset from the central longitudinal axis of the central channel 6938 by 0.010" to 0.015", and more preferably by 0.005" to 0.010", however one of skill in the art will appreciate that other offset dimensions (greater or less) may be used as required to accommodate different suture sizes and materials.

FIG. 27C shows a cross-section of the anchor 6902 taken along line A-A in FIG. 27A and illustrates how a suture S is coupled with the anchor. A first extremity 6944 of suture S passes through aperture 6924 and extends downward into central channel 6938 adjacent wall 6932. The suture passes over a top edge 6940a of bar 6922 and extends downward through the wider space between bar 6922 and wall 6936. The suture crosses under bottom edge 6940b of bar 6922 and then extends upward through the narrower space between bar 6922 and wall 6932. The suture forms a U-loop 6946 that crosses over a portion of the first extremity 6944 of the suture that extends downward and that is disposed over the top edge 6940a of the bar 6922. The suture then extends downward along bar 6922 through the narrower space between bar 6922 and wall 6932. The suture then wraps under bottom edge 6940b of bar 6922 and the suture then extends upward through the wider space between bar 6922 and wall 6936. The suture then extends upward through the central channel and exits the anchor 6902. The suture then forms a repair loop RL around the target tissue, here a torn labrum, L and passes through transverse channel 6918 such that a free end 6952 projects from the transverse channel 6918. When the anchor is inserted into a bone hole, second extremity 6950 is pinched or captured between an outer surface of the anchor and the inner surface of the hole in the bone, thereby securing the suture in position. In use, the size of repair loop RL, and the degree of tension applied around labrum L, may be first grossly adjusted by sliding second extremity 6950 through transverse channel 6918. Anchor 6902 may then be inserted into the bone hole, thereby trapping the free end 6952 of second extremity 6950 between anchor 6902 and the surrounding bone to secure it in position. After the anchor is fully inserted and in its final position in the bone, the size of and tension in repair loop RL may then be more finely adjusted by pulling the first extremity 6944, wherein the suture will pass freely through the one-way cinching mechanism of the anchor. Tension exerted on the second extremity 6950 causes loop 6946 to tighten down on the first extremity 6944, increasing friction on the suture so as to maintain the desired tension in repair loop RL without having to tie a knot in the suture. The step of tensioning of repair loop RL is thus performed independently of anchor insertion, and may be adjusted to its final tension with the anchor in its final implanted position without further manipulations of the anchor to lock the suture in place.

Figure 28A:
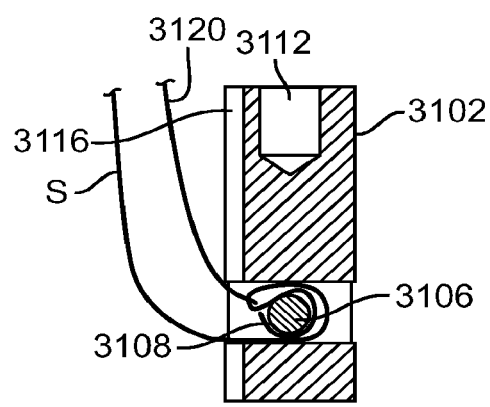
FIGS. 28A-28B and 29A-29B are perspective views of a suture anchor system.
Figure 28B:
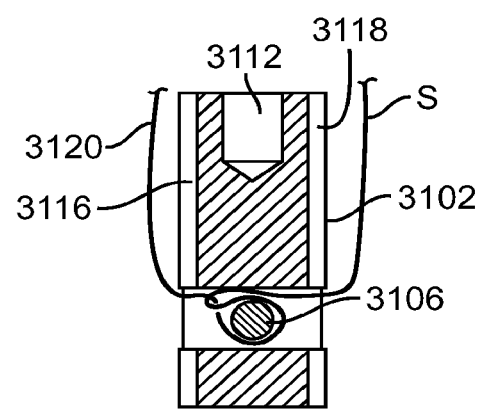

FIGS. 28A-28AA, 28B-28BB, 29A-29AA, and 29B-29BB illustrate other anchor system configurations that may use the cinching mechanism of FIGS. 23A-23B. For example, in FIG. 28A, a two part stackable anchor system includes an upper anchor housing 3102 and a lower anchor housing 3104 having a tapered tip 3110. FIG. 28AA illustrates a partial cross-section of FIG. 28A highlighting the path of the suture S through the anchor. The upper anchor housing 3102 has a transverse channel 3108 in which bar 3106 is disposed. Bar 3106 is oriented transversely relative to the longitudinal axis of anchor housing 3102. An opening 3112 may be used for engaging a delivery tool during deployment. The opening 3112 may optionally be threaded. The housing 3102 also has an open-topped concave channel 3116 extending longitudinally along its outer wall extending from the proximal end of the housing 3102 to the transverse channel 3108 in which the suture S may lie. This prevents the suture S from binding between the outer surface of the housing 3102 and the bone or tissue when inserted therein, allowing the suture to slide so as to be tightened. One end of the suture S is attached with a knot 3114 to the lower anchor housing 3104 while the other end is passed through the cinching mechanism in upper anchor housing 3102, forming a loop to be passed around the tissue to be repaired then the suture courses through the concave channel 3116 into the cinching mechanism and then the free end 3120 exits the cinching mechanism along the concave channel 3116, extending away from the upper anchor housing 3102. FIG. 28B illustrates an embodiment similar to that in FIG. 28A, with the major exception being that the upper anchor housing includes two longitudinal concave channels 3116 and 3118 for the suture. FIG. 28BB illustrates a partial cross-section of FIG. 28B highlighting the path of the suture S through the anchor. Thus, as the suture enters the anchor and cinching mechanism, it follows the first longitudinal concave channel 3116. As the suture exits the cinching mechanism and extends away from the anchor, it follows the second concave channel 3116. Both channels prevent the suture from getting pinched between the outer anchor surface and the bone or tissue when the anchor is inserted therein.

Figure 29A:
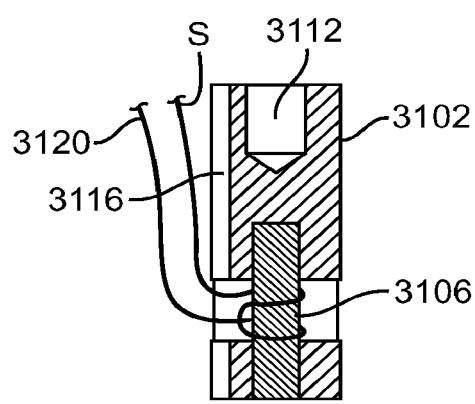
Figure 29B:
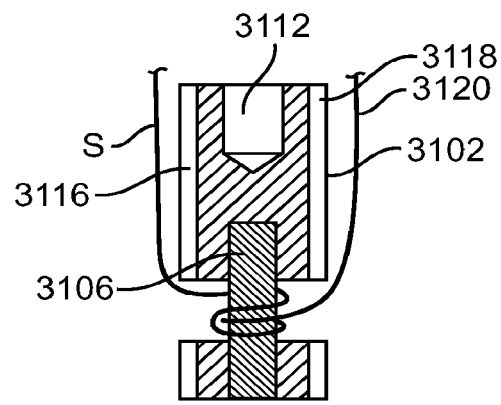

FIGS. 29A-29AA illustrate another variation of a hitch-type cinching mechanism. In this embodiment, the bar 3106 is inserted substantially parallel to the longitudinal axis of the anchor body, rather than in the transverse direction. FIG. 29AA illustrates a partial cross-section of FIG. 29A highlighting the path of the suture S through the anchor. The other features generally take the same form as those described in FIG. 28A. FIG. 29B illustrates a variation of the embodiment in FIG. 29A, again having a bar 3106 that is substantially parallel to the longitudinal axis of the anchor body and also having two concave channels 3116, 3118 similar to that in FIG. 28B. FIG. 29BB illustrates a partial cross-section of FIG. 29B highlighting the path of the suture S through the anchor. The other features of FIG. 29B generally take the same form as those described in FIGS. 29A and 28B.

Figure 30:
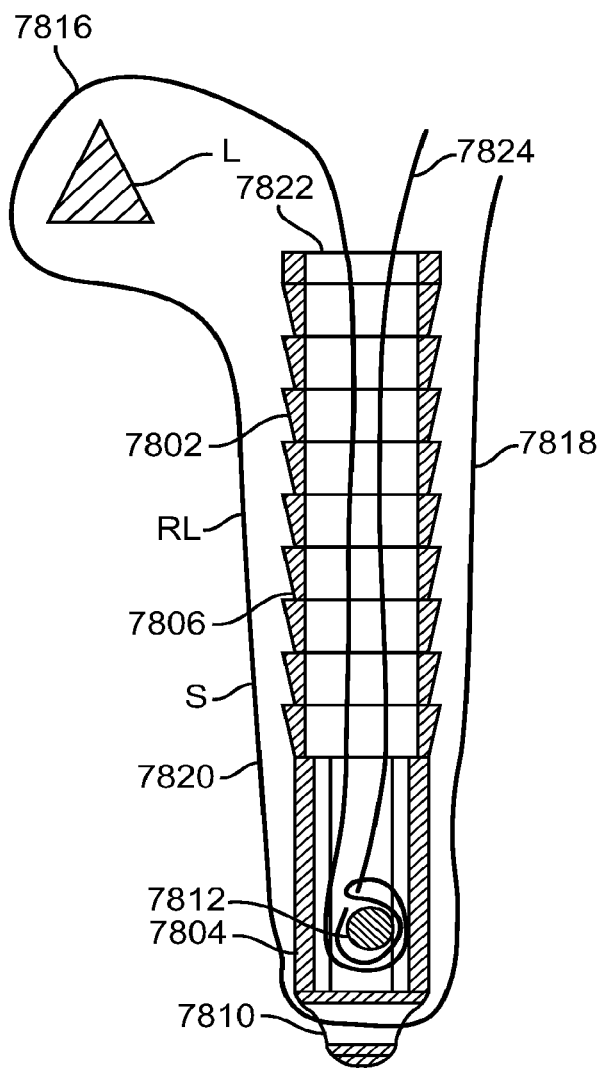
FIG. 30 is a side-view of a suture anchor.

FIG. 30 illustrates an alternative embodiment of a suture anchor system having an upper anchor 7802 and a lower anchor 7804. Both the upper and lower anchors 7802, 7804 have generally cylindrical shaped bodies that stack together in a hole in the substrate tissue. The two anchors are positionable end-to-end with one another, and may have any of the coupling mechanisms described herein in order to attach the two anchors together. The upper anchor 7802 has a series of circumferential barbs or scallops 7806 along its outer surface to help keep the anchor lodged in the substrate tissue, such as bone. This embodiment is similar to other two-part anchor systems described above, with the major difference being that the one-way cinching mechanism is disposed in the lower anchor 7804 rather than in the upper anchor component. Additionally, instead of an extremity of the suture being secured directly to one of the anchors, in this embodiment one end of the suture is passed through a transverse channel 7810 in lower anchor 7804 and secured by pinching it in between an outer surface of the anchor and the surrounding bone. A first extremity 7824 of suture S extends into a central channel 7822 of the anchor system and then loops around transverse bar 7812 in a first direction. The suture is then looped around itself and then loops around bar 7812 in a second direction opposite the first direction. The suture then extends out of the central channel 7822 and is looped 7816 around the target tissue, here a torn labrum L. The repair portion 7820 of the suture S extends downward along an outer surface of the anchor and through transverse channel 7810 in the lower anchor 7804, forming a repair loop RL around the tissue to be repaired, e.g. labrum L. A free end 7818 of the repair portion 7820 then extends upward along an outer surface of the anchor. Thus, when the upper 7802 and lower 7804 anchors are positioned in the bone or other substrate tissue, the two portions 7818, 7820 are pinched between the outer anchor surface and the bone. The suture S length or tension is adjusted grossly by pulling on the free end 7818 as the anchor is inserted into bone, whereby the suture slides relative to the anchor to pull the labrum L toward the anchor and the bone surface. Upon anchor insertion into the bone the suture is clamped in position by compression between the outer surface of the anchor and the bone. Suture tension may then be adjusted more finely by pulling on the free end 7824 to reach the final desired tissue position and tension. The cinching mechanism in the anchor allows only one-way movement of the suture to reach the final tension, permanently preventing the suture from loosening without any knot-tying by the operator.

Figure 31A:
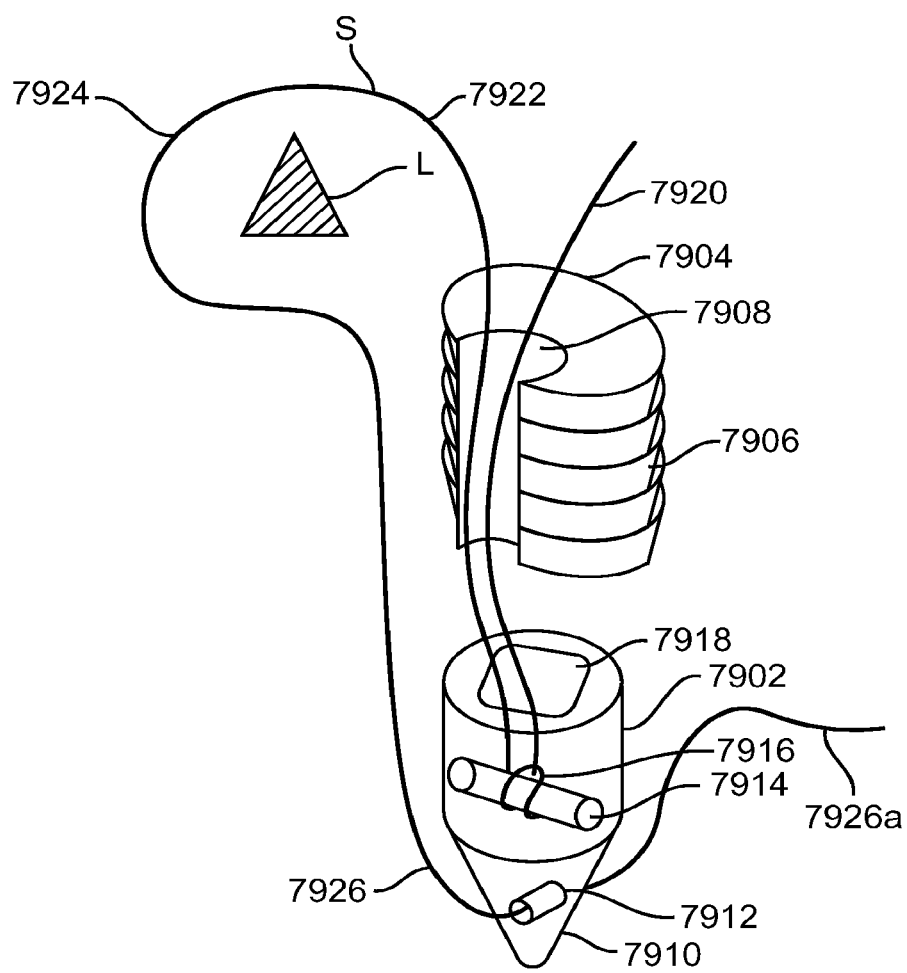
FIGS. 31A-31B are perspective views of suture anchor systems.

FIG. 31A illustrates another embodiment of an anchor system having an upper portion 7904 which engages the bone, and a lower portion 7902 having a square central channel 7918 through which the suture S passes, and an optionally pointed tip 7910 for penetrating tissue such as bone. A one-way cinching mechanism, which may be configured similarly to any of the various embodiments described herein, is disposed in the lower portion 7902. The cinching mechanism may comprise a transverse bar 7914 for forming the hitch-style cinching mechanism 7916 therearound. The lower portion is configured to be placed in the bone hole without screwing or hammering, and it remains removable from the bone hole until upper portion is engaged with the bone. The upper anchor 7902 has barbs or threads 7906 to secure it in the bone and to lock the lower anchor 7902 in position. Additionally, the upper anchor 7904 has a longitudinal concave channel 7908, here hemi-cylindrically shaped, extending from its proximal end to its distal end that allows the suture to pass therethrough and into the central channel 7918 of the lower portion 7902 so that the suture is not pinched between the outer surface of the upper anchor 7904 and the bone, thus allowing suture length and tension to be easily adjusted after both anchors have been inserted into the substrate tissue. A free end 7920 passes through this channel and may be pulled to adjust suture length and tension. Another portion 7922 of the suture passes through this channel and may be looped 7924 around the tissue, here a torn labrum L to be reattached. The lower anchor 7902 includes a transverse channel 7912 that allows one end 7926 of the suture to be threaded through it and either secured with a knot or clamped between the exterior of the anchor and the surrounding bone. In some embodiments, the suture may have a free end 7926a extending from the channel 7910.

Figure 31B:
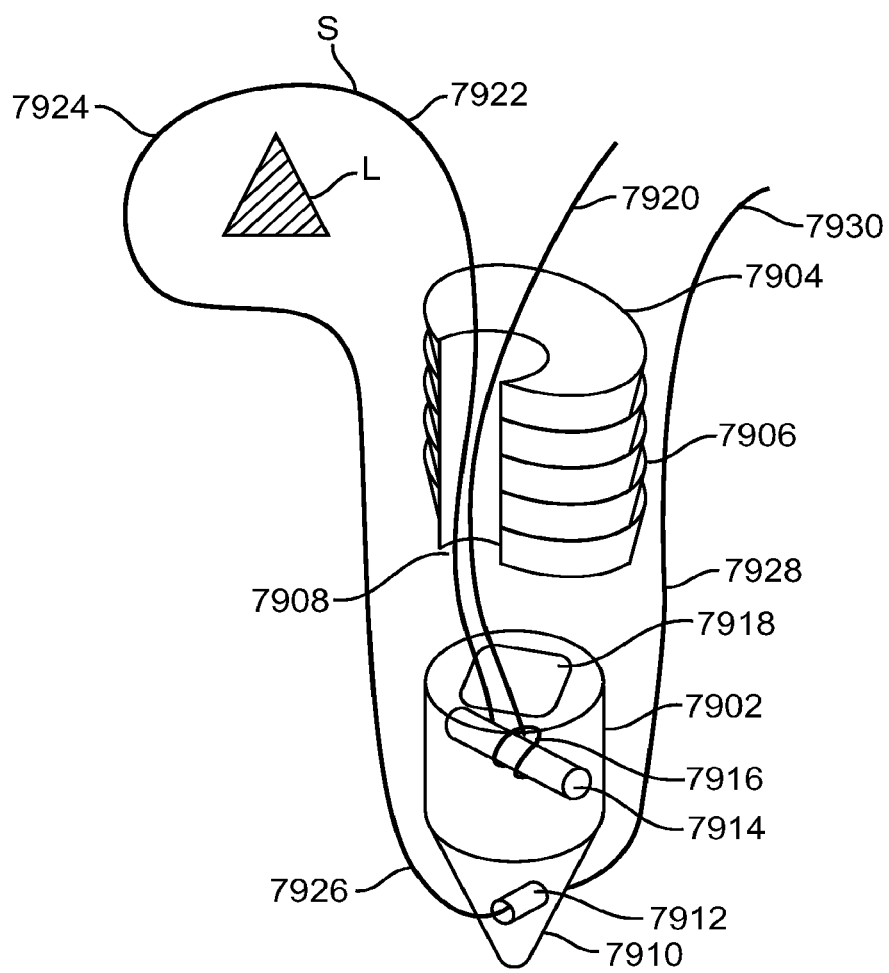

FIG. 31B illustrates a variation of the embodiment in FIG. 31A. The major difference in this embodiment is that instead of end 7926 being secured to the lower anchor 7902 in transverse channel 7912, the suture passes through the transverse channel 7912 and an extremity 7928 of the suture S extends upward along an outer surface of the upper and lower anchors 7902, 7904 such that a free end 7930 extends away from the anchoring system. In use, free end 7930 may be used to grossly adjust the suture length and tension prior to positioning of the upper and lower anchors 7902, 7904 into the substrate tissue, here bone. Once both anchors are positioned into the bone, the suture will be pinched between the outer anchor surface and the bone, thereby locking the suture in position. Fine adjustment of suture length and tension is then accomplished by pulling on free end 7920. Optionally, the distal end of the upper anchor portion 7904 may have a lead-in funnel (not illustrated) in order to facilitate engagement of the upper anchor portion 7904 and the lower anchor portion 7902.

Figure 32A:
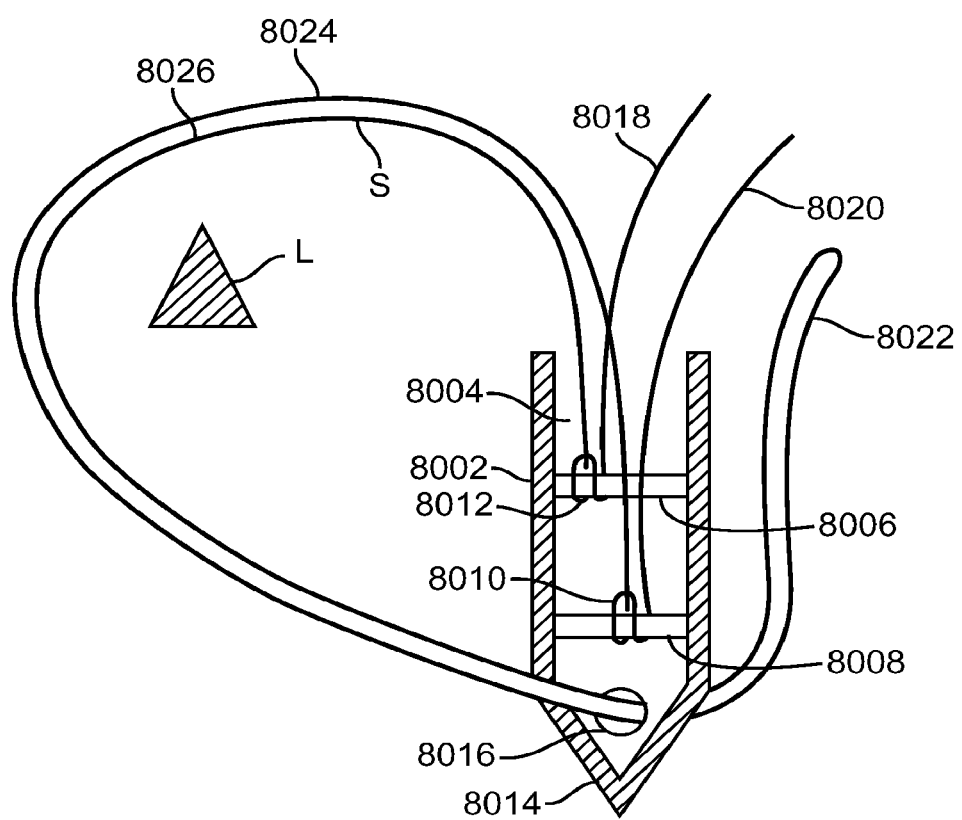
FIGS. 32A-32B are side cross-sectional views of suture anchor systems.

In some cases it may be advantageous for the suture anchor to include two or more one-way cinching mechanisms. These may be threaded with two or more separate sutures so that more than one suture may be attached to the same anchor. Alternatively, a pair of one-way cinching mechanisms on the anchor may be threaded with opposing ends of the same length of suture so as to be able to adjust suture tension by pulling either or both of the two ends of the suture. FIG. 32A illustrates a suture anchor 8002 with two hitch-type cinching mechanisms 8010, 8012 that allow both free ends of the suture to be adjusted, thereby allowing more even length and tension adjustment in the suture. The suture anchor 8002 has a generally cylindrical body with a central channel 8004 extending at least partially therethrough, and a pointed tip 8014 for helping the anchor pass through substrate tissue such as bone. The anchor has an upper transverse bar 8006 and a lower transverse bar 8008. A length of suture S is coupled to the anchor such that each of the ends of the suture S is wrapped around a transverse bar 8006, 8008 to form a hitch-type cinching mechanism 8010, 8012 that generally takes the same form as described in FIG. 23B with free ends 8018, 8020 of the suture extending away from the anchor for later adjustment. Both ends 8024, 8026 of the suture S exiting away from the hitch-style cinching mechanism then are looped around the damaged tissue, here a torn labrum L and then passed through a transverse channel 8016 in the anchor 8002 and terminate in a looped portion 8022, or optionally in two free ends (not illustrated). The looped portion 8022 may be pulled by a physician to grossly adjust suture length and tension prior to positioning the anchor into the substrate tissue, after which the suture will be locked in place because it is pinched between an outer surface of the anchor and the bone. Alternatively, the anchor 8002 may be passed through the loop 8022 to secure tissue to the anchor as will be described in greater detail below. In still other embodiments, one or both free ends 8018, 8020 may be passed through the loop 8022 to secure tissue to the anchor as will be described in greater detail below. A further advantage of this embodiment is that it provides two strands of suture extending around the target tissue, doubling the strength of the repair.

Figure 32B:
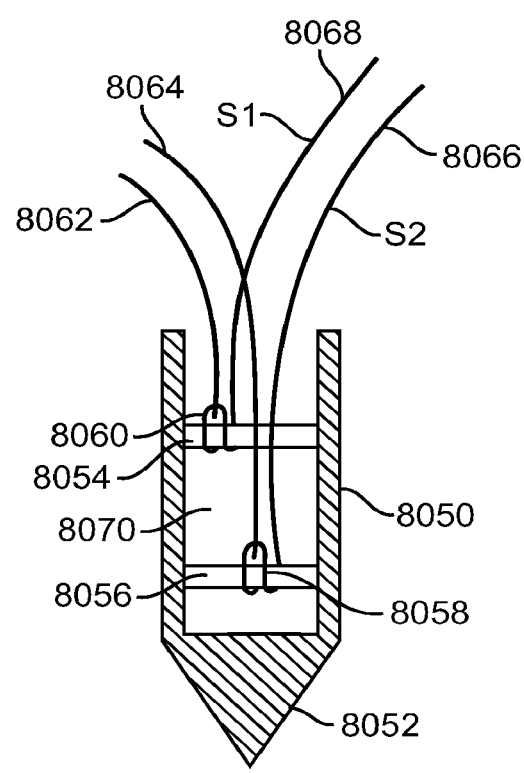

FIG. 32B illustrates a variation of the previous embodiment wherein two separate lengths of suture are coupled to separate one-way cinching mechanisms in the same anchor. The suture anchor 8050 has a generally cylindrically shaped body, a tapered distal tip 8052 and two transverse bars 8054, 8056 in the central channel 8070. A first strand of suture S1 is wrapped around upper bar 8054 and a second suture S2 is wrapped around lower bar 8056, each forming a hitch-type knot similar to that of FIG. 23B, thereby forming two one-way cinching mechanisms 8058, 8060. Unlike the previous embodiment where opposing ends of a single length of suture are passed through the two cinching mechanisms, in this embodiment, the suture strands S1, S2 may be separately connected to tissue and independently tensioned through its own dedicated cinching mechanism. Optionally, anchor 8050 may further include one or more suture retention structures (not shown), such as transverse channels through the anchor body, to allow a free end of each suture to be retained by the anchor when it is inserted, forming two or more independently-tensionable repair loops for capturing tissue. One or more of the suture ends may be attached to other anchors or other tissues, such as in the formation of a double row suture bridge used in rotator cuff repair (FIG. 7D). Pulling on one or both of ends 8062, 8064 adjusts suture length or tension, whereas if the opposite ends 8066, 8068 are pulled the sutures are prevented from moving through the anchor.

FIGS. 32C-32E illustrate a further embodiment of a suture anchor having multiple one-way cinching mechanisms. In this embodiment, anchor 8080 comprises a cylindrical body 8081 having a plurality of external circumferential ribs 8082 or other retention features similar to other embodiments described elsewhere herein. A cavity 8083 extends transversely through a middle region of the body 8081. An upper bar 8084 and a lower bar 8085 are disposed transversely within cavity 8083 dividing the cavity up into an upper channel 8086, middle channel 8087, and lower channel 8088. A transverse channel 8089 extends through a distal portion of body 8081 in a direction transverse to cavity 8083 and is configured to slidably receive one or more sutures therethrough in order to retain the free ends of the sutures when the anchor is inserted in the base tissue. Longitudinal channels 8090, 8091 extend from the proximal end of body 8081 axially on opposing sides thereof until they intersect with cavity 8083. A first suture S1 is tied to upper bar 8084 and a second suture S2 tied to lower bar 8085, each tied to form a sliding knot, preferably a munter hitch as described elsewhere herein. The extremities S1A, S1B and S2A, S2B of each suture extend from cavity 8083 through longitudinal channels 8090, 8091 which keep the sutures from being pinched between the anchor body and the surrounding bone when the anchor is implanted, thus allowing the sutures to be slidably adjusted. It should be noted that while both upper bar 8084 and lower bar 8085 are illustrated as being within a single cavity 8083, anchor 8080 may alternatively have multiple independent cavities separated from each other by interior walls or septa, with each bar being disposed in a separate cavity.

Each of sutures S1, S2 has a first extremity S1A, S2A which can be pulled to slide the suture around the respective upper and lower bars 8084, 8085, allowing adjustment of suture tension. The other extremities S1B, S2B may be passed around or through the tissue to be repaired and then placed through the transverse channel 8089 to form two repair loops RL1, RL2. The free ends of extremities S1B, S2B may be pulled to adjust the size of and tension in the repair loops prior to anchor insertion. The anchor may then be inserted into the base tissue, trapping extremities S1B, S2B between the bone and the anchor to lock them in place. Following anchor insertion, extremities S1A, S2A may be tensioned to adjust repair loops RL1, RL2 to their final size and tension. In this manner, multiple sutures may be coupled to a single anchor and independently adjusted. It should be noted that while anchor 8080 is illustrated with two bars 8084, 8085 to accommodate two sutures, anchor 8080 may include three, four or more such bars to allow three, four or more independently adjustable sutures to be coupled to a single anchor. With a simple, unitary, moldable construction without moving parts, the one-way cinching mechanism in the anchors of the invention can be manufactured at very small scale to facilitate this multi-suture capability.

FIG. 33 illustrates exemplary use of a suture anchor having a hitch-type cinching mechanism. The anchor 7002 is schematically illustrated and is similar to the embodiment described in FIGS. 26A-26E. One end of the suture S is attached at a point 7004 to the anchor 7002 using techniques described elsewhere in this specification. The suture is wound around a transverse bar 7016 using a hitch-type knot 7006 as described previously in FIGS. 23A-23B above and the free end 7012 of the suture S exits the anchor 7002 and may be pulled to adjust the suture tension or length. This forms a loop 7008 which can be looped around the tissue to be repaired, here a torn labrum L. Anchor 7002 may then be placed through the loop 7008 so that both the free end 7012 and the repair portion 7018 of the suture S extend through loop 7008. Anchor 7002 is then inserted into the base tissue, and following placement, the tension in the repair loop may be adjusted by pulling free end 7012.

FIG. 34 illustrates an alternative embodiment of a suture anchor that allows the suture to be tensioned more evenly by adjustment of both ends of the suture. The suture anchor 7002 has a substantially cylindrical body but may take the form of any of the anchor housings described herein. The anchor has a first upper transverse bar 7006 and a second lower transverse bar 7004 for wrapping the suture S therearound. In this embodiment, the suture S has a first extremity 7016 that enters the anchor 7002 and extends downward and is then wrapped around the second lower bar 7004 in a hitch-type knot 7010 that generally takes the same form as described in FIGS. 23A-23B. The suture S then exits the anchor as a first free end 7012. A second extremity 7018 of the suture S enters the anchor 7002 and extends downward and is wrapped around the first upper bar 7006 in a hitch-type knot 7008 that generally takes the same form as described in FIGS. 23A-23B. The suture then exits the anchor as a second free end 7014. Both first and second extremities 7016, 7018 are connected together to form a loop 7020 and in use, the loop 7020 is at least partially wrapped around the tissue to be repaired, here a torn labrum L and then the anchor 7002 is passed through the loop 7020 into the bone. After placing the anchor in the base tissue, the suture S is then adjusted by pulling on first and second free ends 7012, 7014 in order to adjust length or tension in the suture S. FIG. 34 illustrates both transverse pins 7004, 7006 in a horizontal position 7022, 7024 as shown in FIG. 34A, however one of skill in the art will appreciate that other positions are possible. For example, the lower bar may be disposed at an angle 7026 as shown in FIG. 34B relative to the longitudinal axis of the anchor or it may be vertical 7028 as shown in FIG. 34C. Varying the bar angles changes the force required to pull the suture through the hitch-type cinching mechanism. In the exemplary embodiment of FIG. 34 with both pins 7004, 7008 in the horizontal position results in a force of approximately 3 pounds to pull the second free end 7014 and a force about approximately 4 pounds to pull the first free end 7012. Of course pull force is a function of many factors, including, but not limited to suture material, suture size, bar angle, bar material, etc., therefore these pull forces are not intended to be limiting.

Figure 35A:
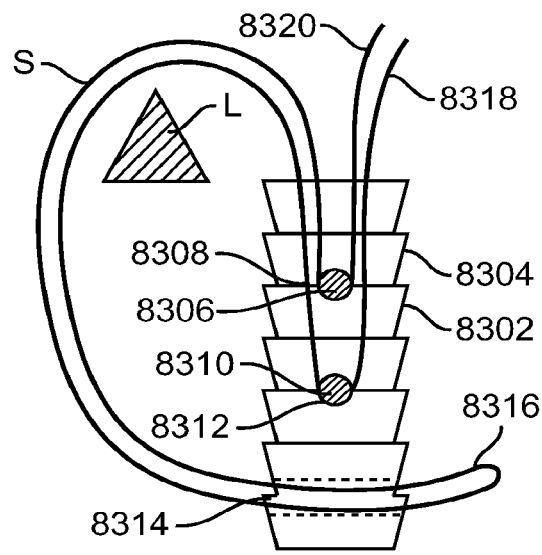
FIG. 35A-35B are side, and partial side cross-sectional views of a suture anchor system.
Figure 35B:
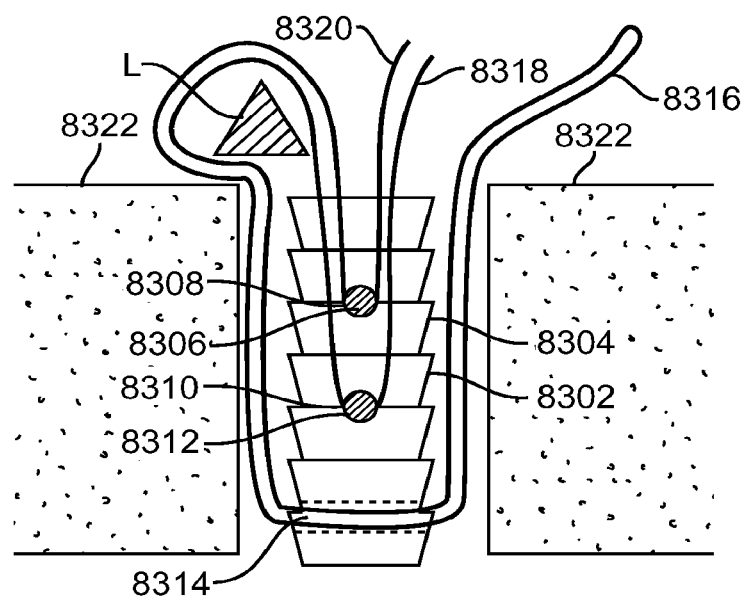

In addition to facilitating more even adjustment of suture length and tension, a double hitch-type cinching mechanism allows increases in the strength of the repair resulting from the anchoring system. In the embodiment illustrated in FIGS. 35A-35B, anchor 8302 includes barbs 8304 on the outer surface that help the anchor lodge into bone and two transverse pins 8306, 8310 for forming upper and lower hitch-type cinching mechanisms 8308, 8312 that are similar to that in FIG. 23B. The anchor 8302 also includes a transverse channel 8314 for receiving the loop formed in suture S. In this embodiment, the suture S has each end passing through one of cinching mechanisms 8308, 8312. Free ends 8318 and 8320 may be pulled to adjust the suture length and tension. Additionally, the suture has a loop forming a bight 8316 that passes through the transverse channel 8314. In use, the double stranded suture bight 8316 is looped around the damaged tissue, here a torn labrum L, and then fed into the transverse channel 8314. The bight 8316 may be pulled to initially grossly adjust suture length and tension. Then, once anchor 8302 is positioned in the bone 8322, the bight 8316 is pinched between the bone and the anchor, thereby fixing it in position. The excess suture in the bight may be severed. Fine adjustment of suture length and tension may be achieved by pulling on either of the free ends 8318, 8320. Because a double strand of suture is used to a capture the labrum, the force required to displace the labrum will be higher as compared to a single suture. Also, because both free ends of the suture may be adjusted, adjustment forces will be lower since only part, and not the entire suture is adjusted.

Figure 36A:
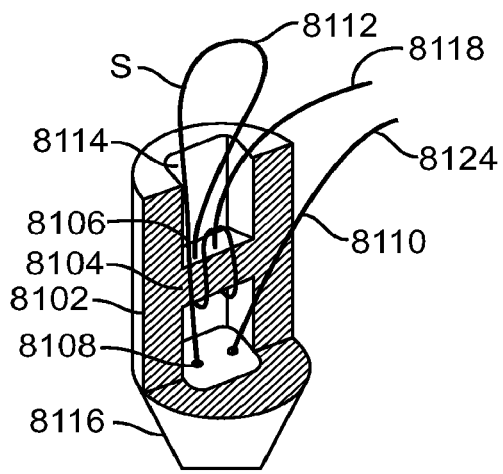
FIGS. 36A-36E are partial side cross-sectional views of a suture anchor system.
Figure 36B:
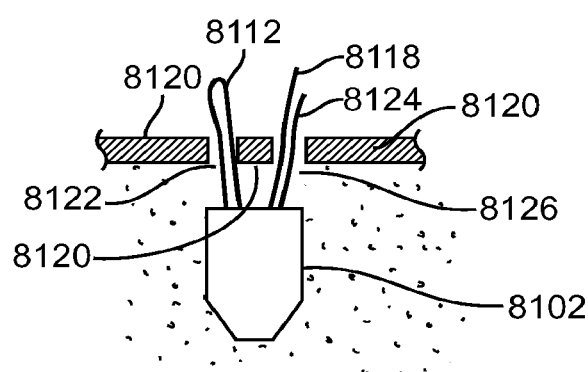
Figure 36C:
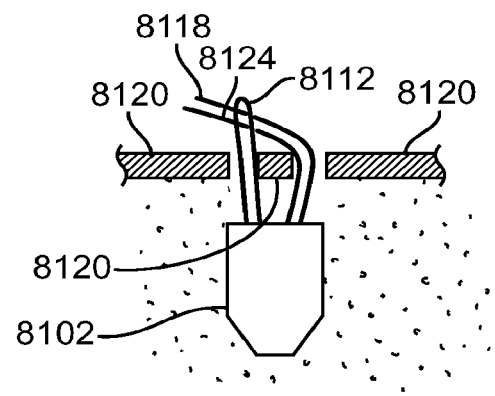

The hitch-type cinching mechanism may also be used to form the double row bridge suture used to repair torn rotator cuffs and illustrated in FIG. 7D. For example, FIG. 36A illustrates a partial cross-section of a suture anchor 8102 having a cylindrically shaped body with a transverse bar 8104 and a tapered distal tip 8116. A central channel 8114 in the body accommodates the suture S. In this embodiment a first length of suture has one end 8108 secured to the anchor. The rest of the suture S extends through the central channel 8114 and forms a loop or bight 8112 outside of the anchor. The suture S then is looped around the transverse bar 8104 forming a hitch-type cinching mechanism similar to that described in FIG. 23B above. An extremity 8118 then extends away from the anchor leaving a free end that may be pulled to adjust the size of the bight 8112. A second suture 8110 has one end also attached to the anchor and a free end 8124 extending away from the anchor. In use, the anchor 8102 is positioned in the tissue/bone substrate underneath the damaged tissue 8120. The bight 8112 is passed through the damaged tissue 8120, here the torn rotator cuff through a first hole 8122, and the two free ends 8118, 8124 pass through a second hole 8126. In FIG. 36C, the two free ends 8118, 8124 are passed through the bight 8112. Free end 8118 may then be pulled in order to tighten the bight 8112 thereby securing the tissue in contact with the underlying bone without requiring a knot to be formed. This contact helps provide a point of apposition between the torn tissue and the bone. The two free ends 8118, 8124 can then extend over the damaged tissue and be directed to two separate suture anchors positioned laterally away from anchor 8102. This allows the double row suture bridge to be formed.

Figure 36D:
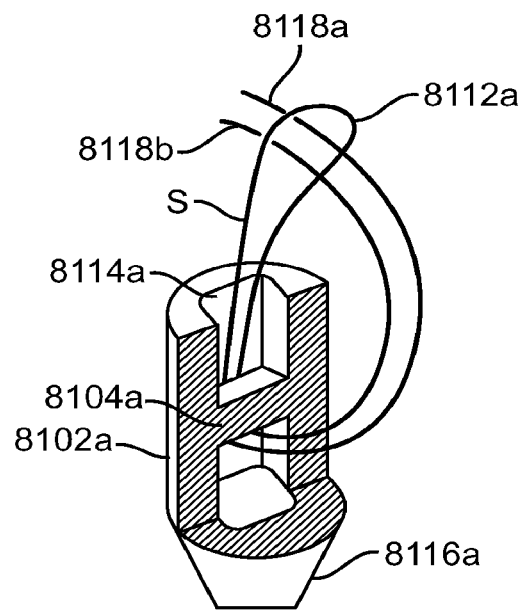
Figure 36E:
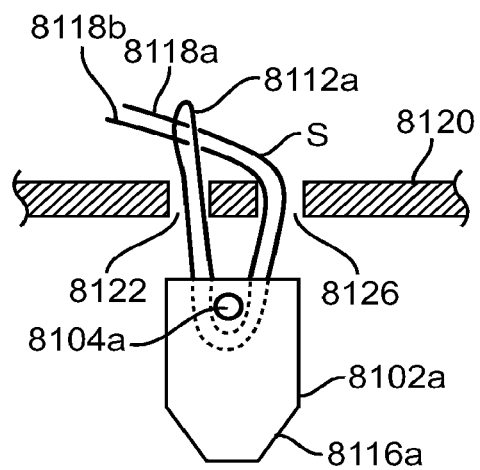

FIG. 36D illustrates an alternative embodiment of a suture anchor system that provides two free ends of suture for forming a double row bridge or other repairs. The anchor 8102a includes a central channel 8114a, a transverse bar 8104a and a tapered tip 8116a. The suture S is doubled over on itself to form a loop or bight 8112a that extends from the anchor 8102a. The suture then extends downward into the central channel 8114a and is looped around the transverse bar 8104a. Both free ends 8118a, 8118b pass through the bight 8112a. Pulling the free ends 8118a, 8118b tighten the bight 8112a and secure the suture S to the transverse bar 8104. In use, anchor 8102a is implanted in the bone underlying the target tissue 8120 to be repaired. The bight may be passed through a first hole 8122 in the tissue 8120, and the free ends 8118a, 8118b may be passed through a second hole 8126 in the tissue 8120 so that when tightened, the suture will provide a point of contact between the tissue and the substrate, as illustrated in FIG. 36E. The free ends 8118a, 8118b may then be extended to one or more separate anchors spaced apart from anchor 8102a and secured thereto so as to form a double row suture bridge or other repair.

Figure 37B:
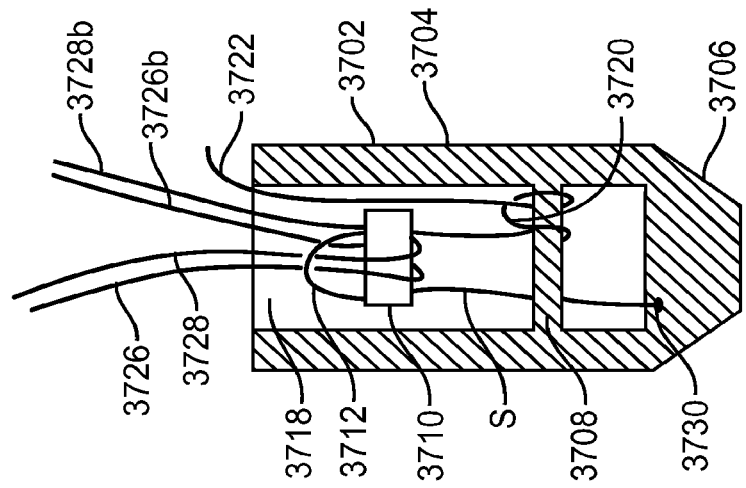
FIGS. 37A-37B are side cross-sectional views of a suture anchor system.
Figure 37A:
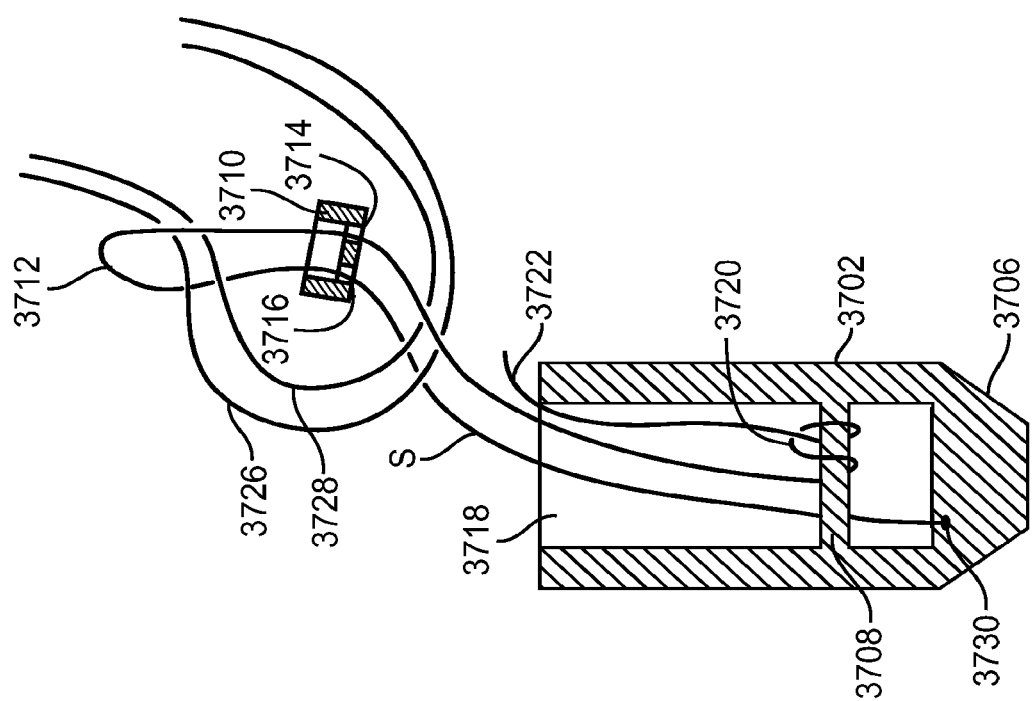

FIGS. 37A-37B illustrate another embodiment where the hitch-type cinching mechanism may be used to secure additional sutures to the anchor, allowing the anchor to be placed in the base tissue before being coupled to the tissue to be repaired. Suture anchor 3702 includes a substantially cylindrical housing with a central channel 3718 and a tapered tip 3706 that generally takes the same form as other anchor bodies or housings described herein. The anchor 3702 also includes a transverse bar 3708 within central channel 3718 for forming the hitch-type cinching knot 3720 therearound. The system also includes a locking suture S, a strangling element 3710 and one or more repair sutures 3726, 3728. Strangling element 3710 has a cylindrical cap-like shape with one closed end to form an internal concavity, with two parallel axial channels 3714, 3716 extending through the closed end. Strangling element 3710 is configured to slide axially within central channel 3718 in anchor 3702. A locking suture S has one of its ends 3730 secured to the anchor within central channel 3718. The locking suture S then extends upward through the central channel 3718 and out of the anchor and is threaded into a first axial channel 3716 in strangling element 3710 and then into a second axial channel 3714 in the strangling element 3710, thereby forming a looped region or bight 3712. The suture then re-enters the anchor via channel 3718 and is looped around the transverse bar 3708 forming a hitch-type knot 3720 previously described in FIG. 23B. An extremity 3722 of the suture S then exits the anchor through central channel 3718. Strangling element 3710 is configured to provide sufficient clearance within central channel 3718 to allow free end 3722 to slide for purposes of tightening the locking suture when the strangling element is positioned in the central channel. Alternatively, anchor 3702 may have a side passage extending through its sidewall from central channel 3718 which intersects a longitudinal channel on the exterior of the anchor body similar to those shown in FIGS. 28-29. Instead of extending proximally through central channel 3718, free end 3722 may extend through the side passage in the anchor body and proximally through the longitudinal channel which permits the locking suture S to slide after the anchor is placed in bone, thus allowing locking suture S to be tightened by pulling on free end 3722.

Repair sutures 3726, 3728 (which may comprise separate lengths of suture or a single continuous length of suture for passing through or around tissue to be repaired) are received under the strangling element 3710, in between the bight 3712 and then looped over the strangling element 3710 and back through the bight 3712 in the opposite direction. The repair sutures 3726, 3728 may be sutures received from one or more adjacent suture anchors, or the sutures may be secured to anchor 3702 and then extend to other suture anchors, to form, for example, a double row bridge for repairing a torn rotator cuff. Alternatively, repair sutures 3726, 3728 may comprise the two ends of a single continuous length of suture which is passed through or around tissue to be repaired, or is coupled to another anchor or other structure. Anchor 3702 may first be driven into the bone or other base tissue before repair sutures 3726, 3728 are coupled to the anchor or the locking suture S. The repair sutures 3726, 3728 may then be passed through the bight 3712 and pulled to grossly adjust the position of the tissue being repaired and the tension of the repair sutures. The free end 3722 of suture S may then be pulled, thereby drawing the strangling element 3710 and the bight 3712 into the central channel 3718 of the anchor 3702. Length and tension of the locking suture S is further adjusted until the bight 3712 is pulled tight against strangling element 3710, thereby clamping the repair sutures 3726, 3728 therein. The strangling element 3710 is free to slide along the length of suture S, which may be tightened to pull the strangling element to the desired depth within the central channel 3718 to finely adjust the tension in repair sutures 3726, 3728. The hitch-type knot around bar 3708 prevents the suture from moving in the reverse direction so that bight 3712 remains tight. This embodiment thus has the advantage of allowing the repair suture to be coupled to the target tissue while the suture is unattached to the anchor, and of allowing the anchor to be inserted without being attached to the repair suture, giving the operator maximum flexibility and ease of use. Further this anchor system allows the repair suture to be coupled to the anchor by the operator in situ with the anchor in its final implanted position. This contrasts conventional knotless anchors which require the repair suture to be pre-threaded through the anchor outside the body cavity and require the repair suture to be fastened to the target tissue while the suture is coupled to the anchor.

Figure 37C:
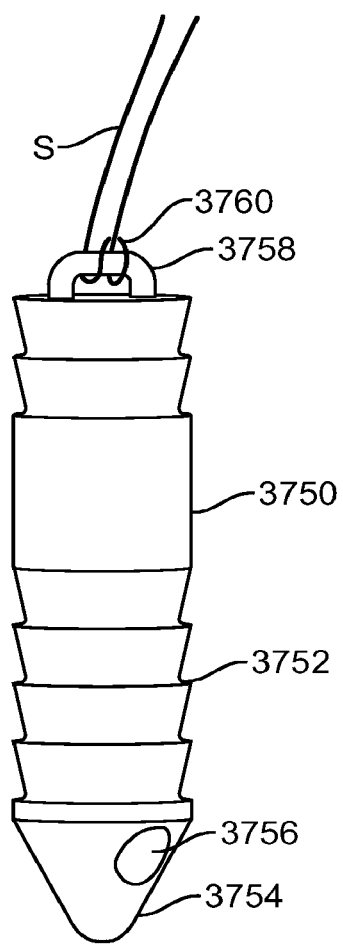
FIGS. 37C-37D are side-views of suture anchor systems.
Figure 37D:
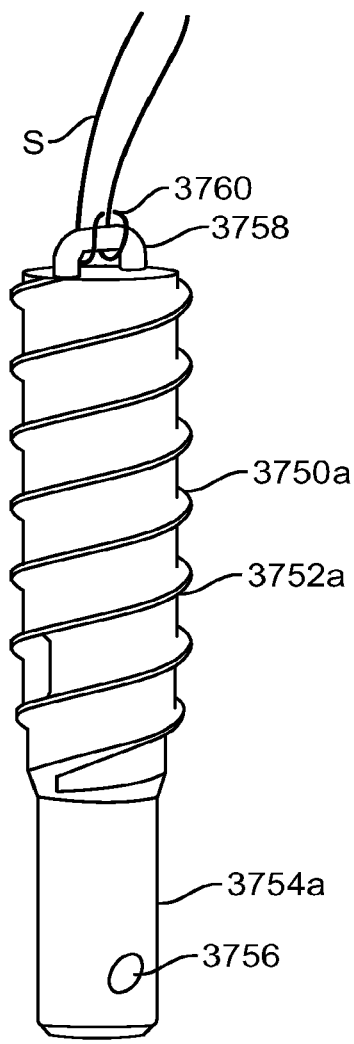

FIGS. 37C-37D illustrate other exemplary embodiments of suture anchor systems having a cinching mechanism that is disposed on a proximal surface of the anchor, unlike other embodiments where the cinching mechanism is disposed in a central channel of the anchor. In FIG. 37C the suture anchor 3750 has a generally cylindrically shaped body with a plurality of barbs 3752 disposed on the outer anchor surface to facilitate with fixation of the anchor in bone or other substrate tissue when the anchor is pushed or impacted therein. The anchor has a tapered distal tip 3754 to help with insertion into the bone and a transverse channel 3756 near the distal end through which a free end of the suture may be threaded after passing it through or around the target tissue to be repaired. The free end may be pulled as the anchor is inserted into the bone to draw the tissue into approximation with the bone, and the free end is then clamped in place by compression of the suture between the bone and the exterior of the anchor. A handle-like upper bar 3758 is disposed on the proximal end of the anchor and allows the suture S to be wrapped therearound with the hitch-type knot of FIG. 23B thereby forming a cinching mechanism 3760. The bar 3758 is similar to a bucket handle and allows the hitch-type knot to be more easily formed since it is free of obstructions, as compared with embodiments where the cinching knot is disposed in a central channel of the anchor body. After the anchor is implanted the remaining free end of the suture may be tensioned in order to fully approximate the tissue to the bone and impart the desired degree of tension in suture S. In an alternative configuration, in place of the handle-like bar 3758 extending proximally from the anchor, a slot or eyelet may be formed in the body of the anchor itself near its proximal end through which the hitch-type knot may be formed. FIG. 37D illustrates a variation of the embodiment in FIG. 37C with the major difference being that instead of barbs on the outer surface of the anchor body 3750a, this embodiment has helical threads 3752a which allow the anchor to be threadably engaged with the bone or other substrate tissue so as to be implanted by rotation rather than by pounding. This embodiment also has an unthreaded, elongate distal shaft 3754a. Other features of the anchor are generally the same as those in FIG. 37C.

In preferred embodiments, the hitch-type knots used to form the one-way cinching mechanisms of the invention will be pre-tied within the anchor so that the physician need not tie any further knots during the procedure in order to repair the target tissue. However, in some cases physicians may desire to perform a procedure with the suture initially decoupled from the anchor and to later tie the suture to the anchor during the procedure. FIGS. 37E-37G illustrate an exemplary method of forming the hitch-type knots discussed herein which can be performed by a physician during a procedure, either before or after the anchor is implanted. In FIG. 37E, the anchor 3770 has a transverse bar 3772 for forming the hitch therearound. A pre-threaded snare 3774 having a looped end 3776 is wrapped partially under the bar 3772 such that the loop can capture a suture 3778. Snare 3774 may comprise a wire, suture, or similar flexible filament-like structure. The suture 3778 is folded back on itself so as to form a loop 3778a and has two free ends 3778b, 3778c. Both free ends 3778b, 3778c are passed through the loop 3776 of the snare 3774. The snare 3774 is retracted such that the suture 3778 is drawn into the central channel of anchor 3770 and wrapped under bar 3772, with both free ends 3778b, 3778c on one side of bar 3772, and looped end 3778a on the opposite side of bar 3773 extending proximally away from the anchor as seen in FIG. 37F. The snare 3774 may then be discarded. In FIG. 37G, one of the free suture ends 3778c is passed through the loop 3778a and pulled until the hitch-type knot forms the cinching mechanism 3780 in FIG. 37H.

Figure 38A:
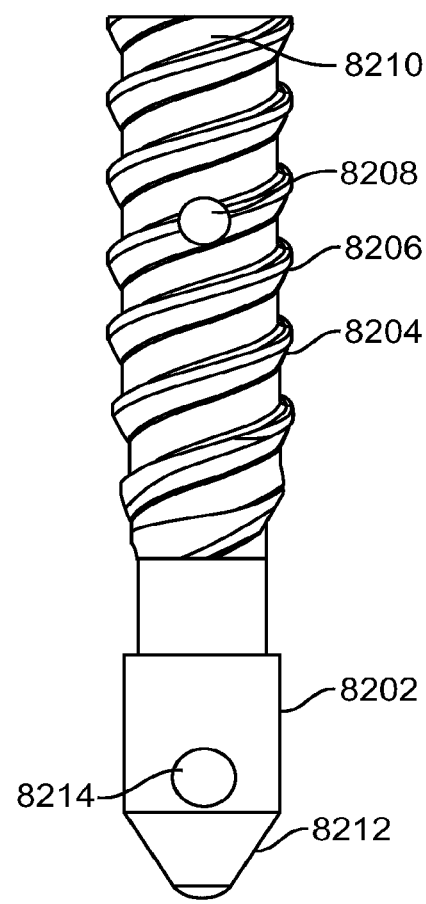
FIG. 38A-38C are side-views of suture anchor systems.
Figure 38B:
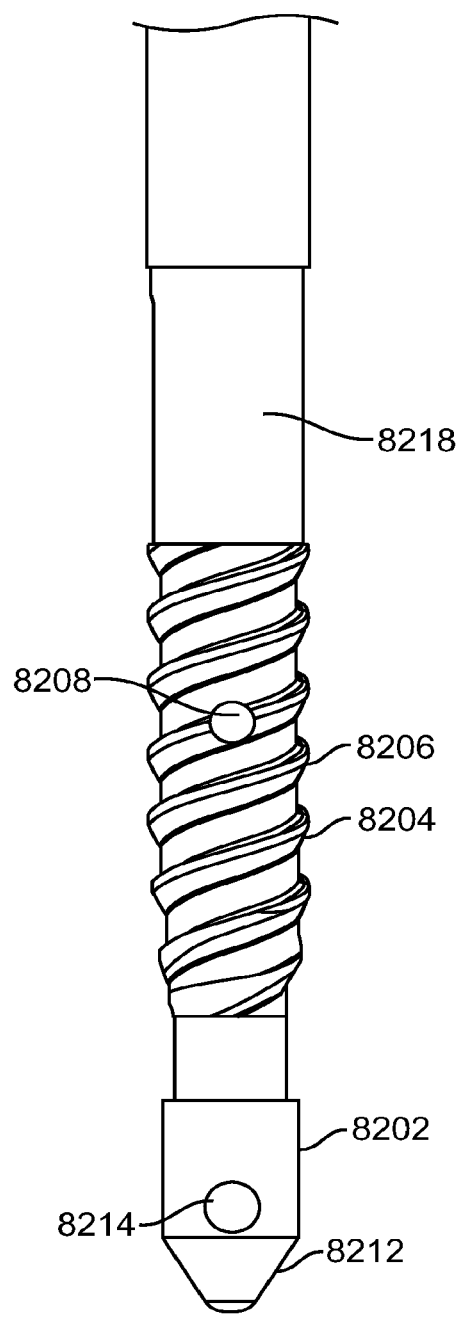
Figure 38C:
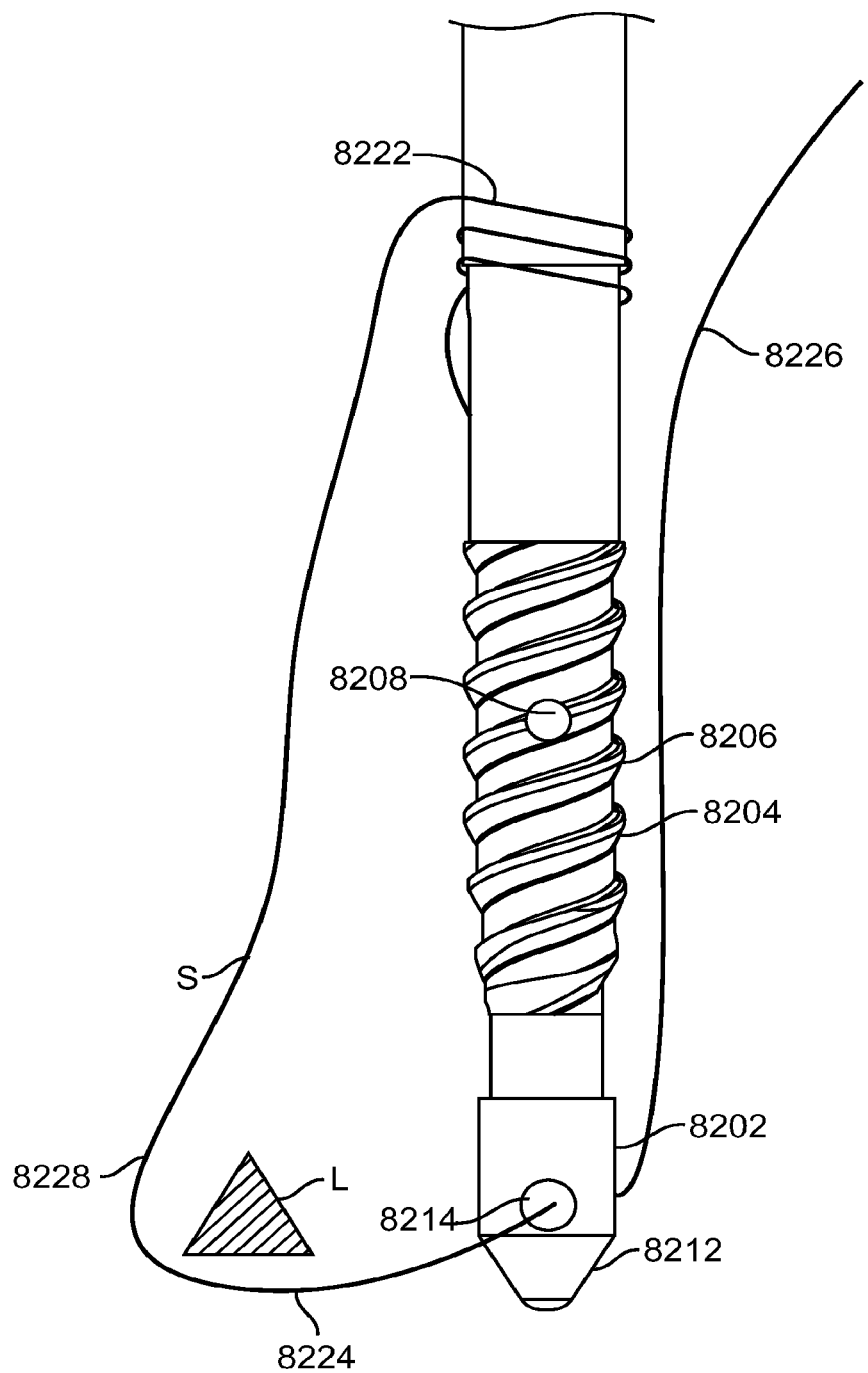
Figure 38D:
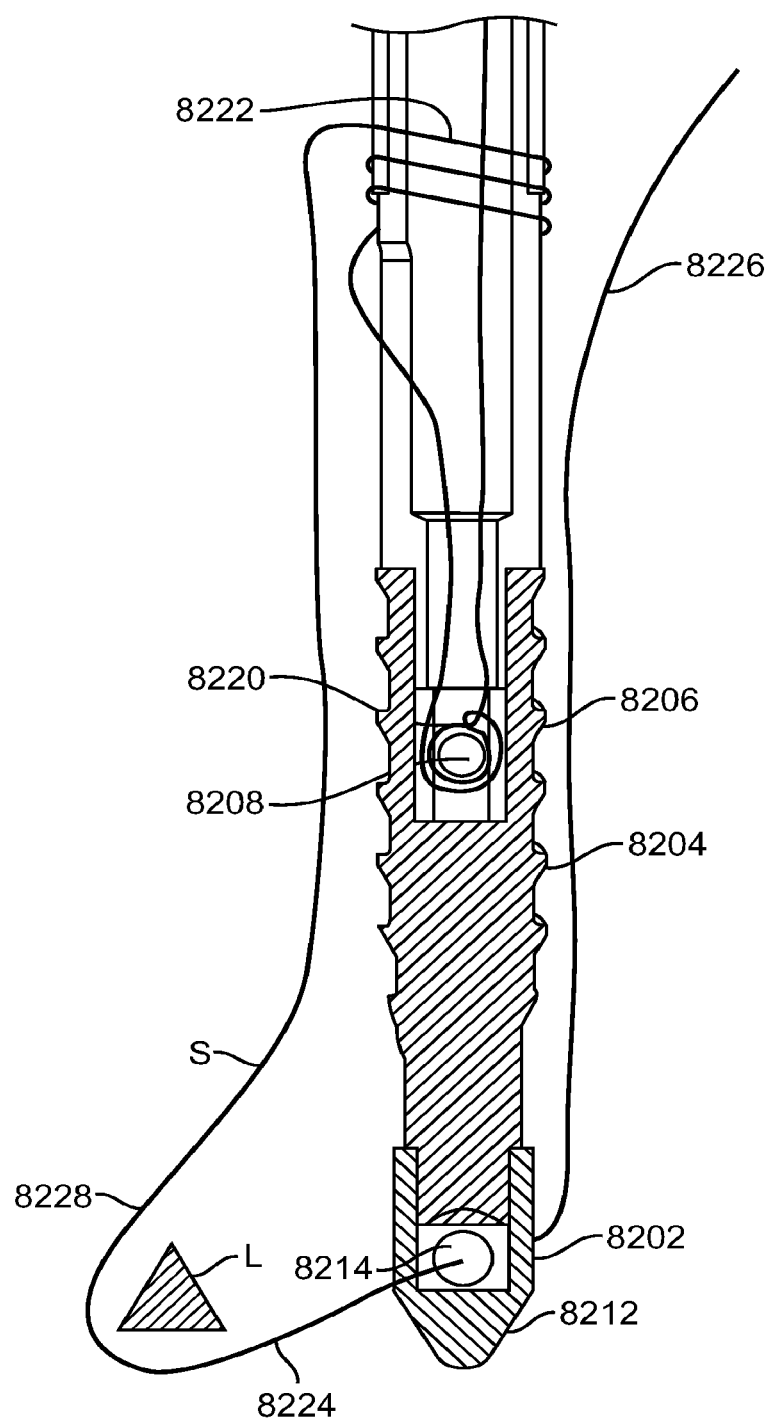
FIG. 38D is a partial side cross-section of a suture anchor system.

FIG. 38A-38D illustrate still another embodiment of a suture anchor that has threads for securing the anchor into bone. The anchor has a lower anchor tip 8202 generally cylindrically shaped and having a tapered end 8212 and a transverse channel 8214 through which a free end of suture S may be threaded. Lower anchor tip 8202 is rotatably coupled to a distal end of an upper anchor body 8204. The upper anchor body 8204 has a generally cylindrically shaped body with a central channel 8210 and a transverse pin or bar 8208 for forming the hitch-type cinching mechanism around. Threads 8206 on the upper anchor help secure the upper anchor into the bone or other substrate tissue. The threaded portion of the body may optionally be tapered in the distal direction to facilitate screwing the anchor into bone. The upper anchor body 8204 and the lower anchor 8202 maybe joined together with threads or any other rotatable couplings as described below in connection with FIGS. 38E-38F, allowing the lower tip 8202 to remain stationary relative to the bone while allowing upper anchor body 8204 to rotate relative to lower tip 8202 as the anchor is inserted. This prevents a suture coupled to the lower tip 8202 from tangling or wrapping around the anchor as the upper anchor is rotated. As shown in FIG. 38D, suture S is wrapped around a transverse bar 8208 in upper anchor body 8204 to form a hitch-type cinching mechanism 8220 that generally takes the same form as described above in FIG. 23B.

FIG. 38B-38D illustrate an optional driver shaft 8218 that may be coupled to the upper anchor body for rotating the anchor so as to screw the upper anchor into the bone or other substrate. In order to prevent the suture from being wrapped around driver shaft 8218 as the anchor is screwed in, the suture S is pre-wrapped around the driver shaft 8218 to form a pre-determined number of wraps 8222 in the opposite direction to the rotation of the driver shaft. The number of wraps 8222 is selected such that the suture will be completely unwound from the shaft when the anchor has been rotated sufficiently to be fully implanted in the bone. Typically, the number of wraps 8222 will correspond approximately to the number of threads on upper anchor body 8204 which pass from outside the bone hole to inside the bone hole as the anchor is screwed in. Thus, as driver shaft 8222 is rotated to thread upper anchor body 8204 into the bone, the suture will unwind from the shaft without twisting or tangling. The remainder of the suture 8228 is used to form a loop 8224 and capture the torn tissue, here a torn labrum, L, and then the suture passes through the transverse channel 8214 in the lower anchor 8202. The free end 8226 of the suture S can be pulled relative to the anchor to grossly adjust suture length or tension. Pulling the other free end of the suture through the cinching mechanism allows fine adjustments to be made. Upon full implantation the free end of the suture 8226 will also be pinched between the anchor and the bone, securing the suture in position. Any excess suture may then be severed.

In alternative embodiments, a double helical thread may be used in order to facilitate threading into bone. In still other embodiments, the diameter of the double start screw may be tapered from the proximal to the distal end. This allows the screw to be advanced halfway into a hole in bone without pressure or rotation, and can therefore be screwed completely into the hole with half as many turns.

Figure 38E:
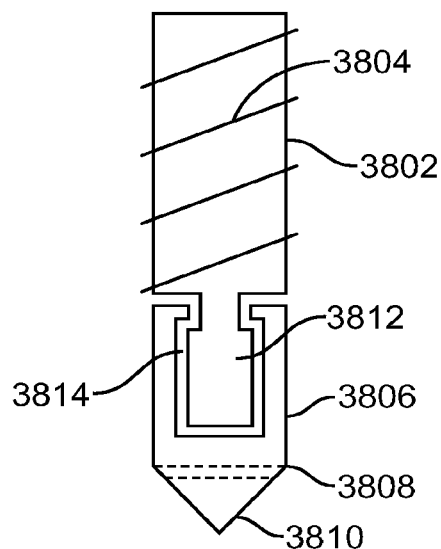
FIGS. 38E-38F are side-views of suture anchor systems.
Figure 38F:
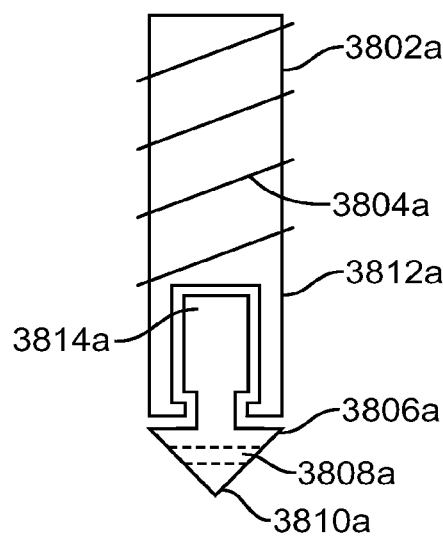

Suture Free End Coupling Mechanisms:

FIGS. 38E-38F illustrate exemplary embodiments of rotatable couplings between the lower anchor tip and the upper anchor body which may be utilized in the anchor of FIGS. 38A-38D. In FIG. 38E the suture anchor includes an upper anchor 3802 having threads 3804 for screwing into bone and a lower anchor 3806 having a pointed distal tip 3810 and a transverse channel 3808 for attaching a suture thereto. The upper anchor 3802 has an enlarged distal head 3812 that is received in a cooperating socket 3814 in the lower anchor 3806 so as to be rotatable therein.

Socket 3814 has an inwardly extending flange around its proximal end to retain the head 3812 therein. Thus, as the upper anchor is threadably engaged with bone or other tissue, the lower anchor will remain stationary, preventing the suture coupled thereto from tangling. FIG. 38F illustrates a similar embodiment, except in this version, the upper anchor has a socket 3812*a* configured to received a head 3814*a* extending from the proximal end of the lower anchor. Socket 3812*a* has an inwardly extending flange at its distal end to retain head 3814*a* therein. The upper anchor 3802*a* includes threads 3804*a* for screwing into bone and the lower anchor 3806*a* has a tapered tip 3810*a* and a transverse channel 3808*a* for securing suture thereto. This allows the upper anchor to be threaded into bone or other tissue while the lower anchor remains stationary, again preventing suture entanglement.

FIGS. 38F1-38F5 illustrate still another embodiment of a suture anchor having a one-way cinching mechanism and threads for securing the anchor into tissue. FIG. 38F1 illustrates a distal region of the anchor 4802 having a generally cylindrically shaped body 4804 and threads 4806 for securing the anchor into bone or other substrate tissue. A transverse pin or bar 4808 extends through the anchor and is used to form the one-way cinching mechanism therearound. The distal portion of the anchor includes a tapered tip 4810 rotatably coupled to the anchor body 4804 via neck region 4814. A transverse channel 4812 extends through the tapered tip and allows suture to be secured to the anchor or to be passed therethrough. FIG. 38F3 illustrates anchor 4802 rotated approximately 90 degrees. FIG. 38F2 illustrates a cross section taken along line B-B in FIG. 38F3 and illustrates the square shaped central channel 4818 that extends through the anchor body. FIG. 38F4 illustrates a cross section taken along line C-C in FIG. 38F3 and illustrates the triangular drive hole 4820 on the proximal end of the anchor that cooperates with a similarly shaped driver tool for threading the anchor into the bone. FIG. 38F5 is a cross section taken along line A-A in FIG. 38F3 and illustrates how the suture S passes through the anchor forming a hitch-style cinching mechanism 4816 similar to those previously discussed above. Additionally, FIG. 38F5 shows how the tapered tip 4810 is coupled to neck 4814 which extends into the central channel 4818 of the anchor. This allows the tapered tip 4810 to remain stationary relative to the bone while the anchor body 4804 is screwed into the bone, preventing the free end of the suture S (not shown) placed through channel 4812 from becoming wrapped around the body of the anchor.

It should be noted that the rotatable tips disclosed in FIGS. 38D-38F may be used with pound-in anchors as well as screw-in anchors. In fact, any of the rotatable tip configurations disclosed herein may be utilized on any of the various anchor embodiments described in this specification. Even in pound-in anchors, the use of a rotatable tip having a bore or other means for coupling to a free end of the suture may be advantageous to keep the suture from wrapping around the anchor body as it is manipulated by the surgeon.

Figure 38G:
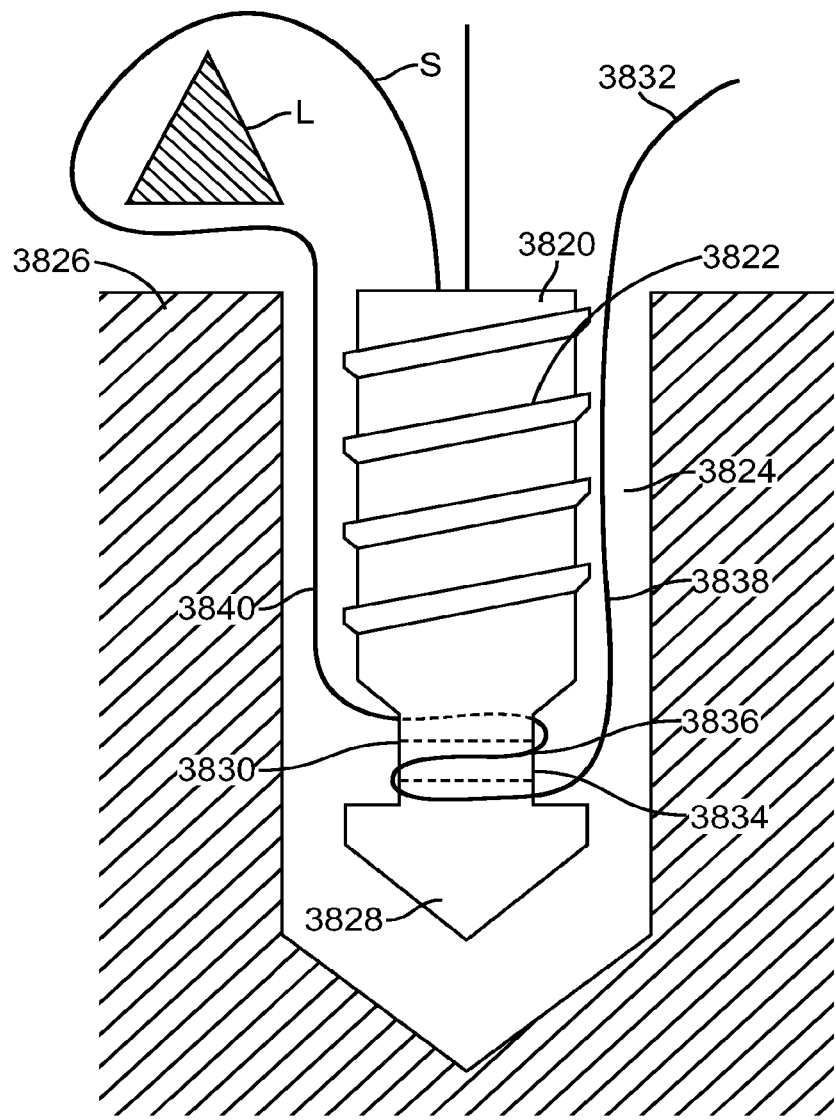
FIG. 38G is a partial side cross-sectional view of suture anchor disposed in a substrate tissue.

In some embodiments, the suture may be wrapped around or spooled on a part of the anchor as the anchor is threaded into the bone. For example, FIG. 38G illustrates an anchor 3820 with threads 3822 that allow the anchor to be secured in a hole 3824 in bone 3826 by rotating the anchor. The anchor includes a tapered distal tip 3828 and a narrow neck region 3834 (also referred to as a spool or hub) disposed between distal tip 3828 and threads 3822. A transverse channel 3830 extends through neck region 3834. The anchor includes a one-way cinching mechanism (not shown) in its interior, which may take the form of any of the cinching mechanisms described elsewhere herein. After capturing the target tissue, here a labrum L, a free end 3822 of suture S may be threaded through transverse channel 3830. As the anchor is screwed into the bone, suture S is wrapped or spooled into a plurality of wraps 3836 about neck region 3834 thereby taking up the excess suture S and drawing the labrum L toward the bone 3826. Also in this embodiment, the suture S is clamped in two places 3840, 3838 between the bone and the anchor, securing the suture and holding the damaged tissue, here a torn labrum L. Once the anchor is fully inserted, the other free end of the suture may be pulled through the one-way cinching mechanism of the anchor to further approximate the labrum L to the bone with the desired degree of tension.

FIGS. 38H1-38H2, 38I1-38I2, 38J1-38J2, 38K1-38K2, and 38L1-38L2 illustrate further embodiments of rotatable couplings between the lower anchor tip and the proximal anchor body and structures for securing a free end of the suture, any of which may be used in the anchor of FIGS. 38A-38D. In FIGS. 38H1-38H2, the anchor includes a lower anchor portion 3850 having a tapered distal tip 3852, a central channel 3856 having internal threads 3854 and a transverse channel 3862 through the sidewall of the anchor. An upper anchor portion 3858 includes a distal threaded region 3860 for threadably engaging with the central channel 3856 and a transverse channel 3864. The suture S is loaded through both transverse channels 3862, 3864. Thus, as the upper anchor portion 3858 is threaded into the lower anchor portion 3850, the suture S will spool around the distal threaded region 3860 of the upper anchor portion 3858, as seen in FIG. 38H2, thereby forming a plurality of windings 3866. This takes up slack in the suture S and draws the target tissue toward the bone. Further, the multiple winding 3866 are clamped between the lower anchor portion 3850 and upper anchor portion 3858 to securely hold the suture relative to the anchor. FIGS. 38I1-38I2 illustrate a similar embodiment, except that only the upper anchor portion has a transverse channel therethrough. The lower anchor 3850a has a tapered distal tip 3852a and a central channel 3856a with threads 3854a. The upper anchor 3858a includes a distal threaded region 3860a and a transverse channel 3864a for passing the suture S therethrough. In this embodiment suture S is allowed to rotate with the upper anchor as it is threaded into the lower anchor. The suture is clamped between an outer surface of the upper anchor and an inner surface of the lower anchor to secure it in place.

FIGS. 38J1-38J2 illustrate the lower anchor portion 3850b includes a tapered distal tip 3852b and a central channel 3856b having threads 3854b and a transverse channel 3862b through the sidewall of the anchor. The upper anchor portion 3858b has a lower distal threaded portion 3860b that threads into central channel 3856b. The suture S is threaded through the transverse channel 3862b so that when the upper anchor portion 3858b is threaded into the central channel 3856b, the suture S will be compressed between the inner and outer anchors along the sides of the distal threaded portion 3860b and, optionally at the bottom of the central channel, as illustrated in FIG. 38J2.

In another variation, FIGS. 38K1-38K2 illustrate another embodiment where the suture is pinched between the upper and lower anchors. The lower anchor 3850c includes a tapered distal tip 3852c, a central channel 3856c which is partially threaded 3854c and has a transverse channel 3862c extending through the sidewalls of the anchor below the threaded portion of the central channel. The upper anchor portion 3858c has a distal threaded portion 3860c. The suture S is threaded through the transverse channel 3862c and thus when the upper anchor portion 3858c is threaded into the central channel 3856c, the suture will be pressed downward until it is pinched between the distal tip of the threaded portion 3860c and the bottom of the central channel 3856c, as shown in FIG. 38K2.

FIGS. 38L1-38L2 show another variation where the suture is pinched between the upper and lower anchor portions. The lower anchor 3850d includes a tapered distal tip 3852d and a proximal threaded portion 3851 having a transverse channel 3862d therethrough. The upper anchor 3858d includes a central channel 3859 at its distal end having threads 3860d for engaging the proximal threaded portion 3851 of the lower anchor 3850d. In use, the suture S is threaded through the transverse channel 3862d and the upper and lower anchors 3858d, 3850d are threadably engaged together. This forces the suture up into the central channel 3859 where it becomes compressed between the upper and lower anchors along the sidewalls of proximal threaded portion 3851, as seen in FIG. 38L2.

FIGS. 38M1-38M2 illustrate an alternative mechanism for attaching the free end of the repair suture to the anchor. FIGS. 38M3-38M5 illustrate side, cross-sectional and oblique views of the device of FIG. 38M1 mounted on an anchor insertion tool, highlighting the suture passer loop. The anchor system includes a tubular upper anchor portion 3870 slidably or threadably coupled to a lower anchor portion 3876 having a one-way cinching mechanism as elsewhere described herein, and a transverse channel 3874 near a distal end thereof. A suture passer loop 3872 is pre-threaded through the upper anchor 3870 and through the transverse channel 3874 in lower anchor 3876. The loop 3878 is then fed back through the upper anchor 3870. Initially, the upper anchor portion is retracted proximally relative to the lower anchor portion, allowing suture passer loop 3872 to slide between the two. After capturing the target tissue with the repair suture, the free end of the repair suture 3880 is fed through the loop 3878 so that when the passer loop 3872 is pulled back the free end of the repair suture will be pulled through the upper anchor, through the transverse channel and back up through the upper anchor. FIG. 38M2A shows the repair suture 3880 coupled with the anchor once the suture passer loop 3872 has been removed, and FIG. 38M2B is a cross-section of FIG. 38M2A showing an internal view of the suture threaded through the anchor. When the desired length and tension have been imparted to the repair suture loop, the upper anchor portion is advanced distally relative to the lower anchor portion by sliding or screwing them together, compressing the free end of the repair suture between the upper and lower anchor portions, locking the suture in position. The free end may then be trimmed or be coupled to another suture anchor. The other free end of the suture may then be pulled for additional tensioning of the repair loop via the one-way cinching mechanism.

Figure 39C:
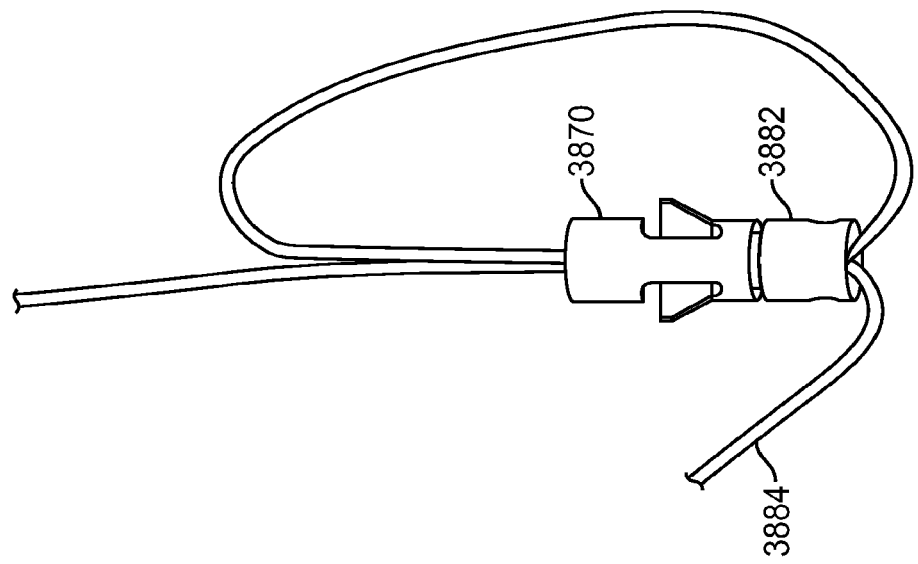
FIGS. 39A-39D are side-views illustrating another method of securing the free end of a repair suture to a suture anchor.
Figure 39B:
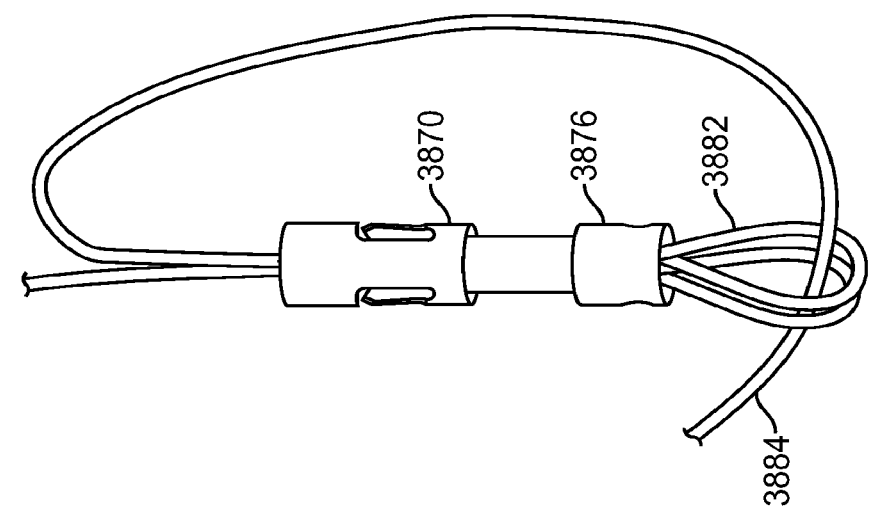
Figure 39A:
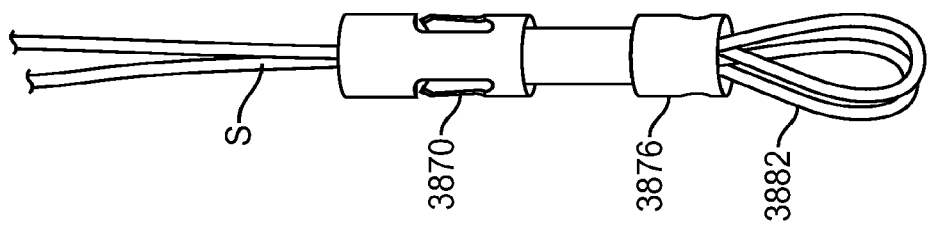
Figure 39D:
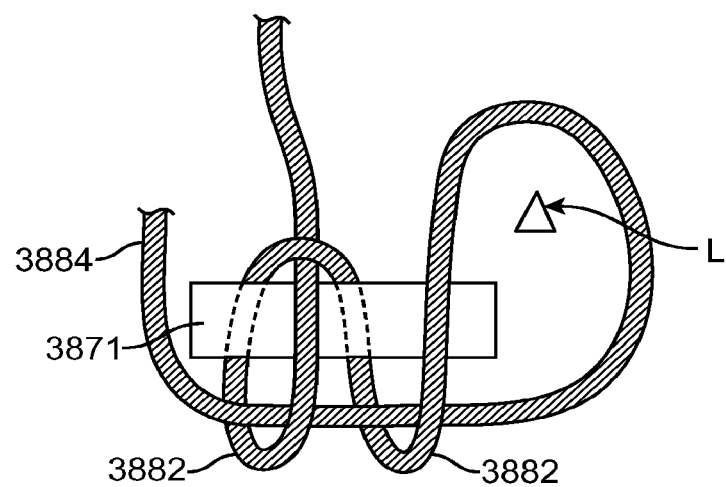

Another mechanism for securing the free end of a repair suture to the suture anchor is illustrated in FIGS. 39A-39D. The suture anchor has an upper anchor portion 3870 and a lower anchor portion 3876. The upper or lower anchor has a cinching mechanism similar to that seen in FIG. 23B. Suture S is therefore looped twice around a transverse bar 3871 (best seen in FIG. 39D) within a longitudinal channel extending through the anchor. One or both loops forming the hitch-type knot around the bar are loosened and pulled out of the bottom of the bottom anchor 3876 leaving one or two exposed loops 3882. In FIG. 39B after the target tissue has been captured with the repair suture S the free end 3884 of the repair suture S is then passed through one or both loops 3882. The adjustment suture is then tensioned so as to shorten the loops and tighten them around the transverse bar within the anchor. One or both loops 3882 pull the free end of the suture 3884 within the lower anchor portion 3876, deforming it into a tortuous path and pinching it between one or both loops 3882 and the inner wall of lower anchor portion 3876 and/or the transverse bar 3871 in the anchor. This locks the repair suture relative to the anchor. The free end 3884 may then be trimmed or used to attach to another suture anchor.

It should be understood that any of the one-way cinching mechanisms or the mechanisms for securing the free end of the repair suture described in the context of any particular embodiment herein may also be used in any other of the anchor embodiments disclosed.

Figure 40A:
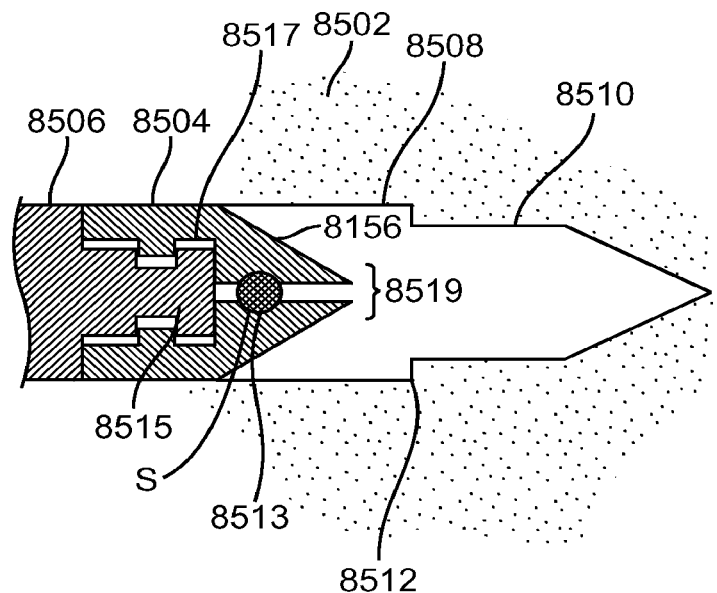
FIGS. 40A-40B are cross-sectional side views illustrating a method of placing suture anchors into bone.
Figure 40B:
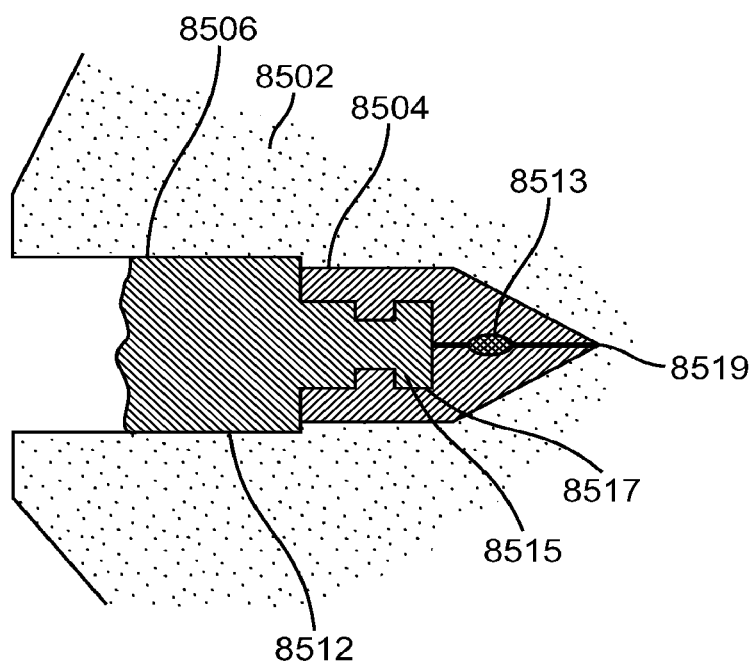

FIGS. 40A-40B illustrate another embodiment of a mechanism for coupling and locking a suture relative to a suture anchor, which may be used for securing the free end of the repair loop in any of the anchor embodiments disclosed herein. A hole 8512 having a large diameter section 8508 and a small diameter section 8510 is pre-drilled into the bone 8502. Upper anchor 8506 has a flanged extension 8515 which is secured within a socket 8517 in lower anchor 8504. Optionally lower anchor 8504 is rotatable relative to the upper anchor 8506. The lower anchor 8504 may be longitudinally fully or partially split forming a pair of opposing jaws 8519 between which suture S may be positioned. Optionally a transverse channel 8513 may be formed in jaws 8519 for receiving the suture S. In FIG. 40B, both anchors 8504, 8506 are driven into the hole 8512. As the distal tip 8516 of the lower anchor 8504 enters the smaller diameter region 8510 of the hole 8512, a press fit is created and the slotted region clamps down around suture S locking it in position.

Anchoring Features:

The suture anchors disclosed herein may be anchored to substrate tissue such as bone by a number of means. As described above, the anchor may be threaded or press fit into a hole in the substrate tissue. Surface features such as barbs, ribs, or threads may be disposed on the anchor's exterior to help to secure the anchor into the tissue. Alternatively, the anchors of the invention may have separate bone-engaging mechanisms which are operable independently of the insertion of the anchor into the bone such that the anchor may be first inserted, then secured in a separate step. In anchor systems having two or more anchor components, the anchor components may interact with one another in order to help lodge them in the bone. For example, in FIGS. 41A-41E, a suture anchoring system includes an inner anchor 8602 having barbs or threads 8606 and a transverse channel 8604 for securing a suture to the inner anchor 8602. The system also includes an outer anchor 8608 with barbs or threads 8612 as well as upper slits 8610 and lower slits 8614. Thus, as shown, as inner anchor 8602 is inserted into the outer anchor 8608, the outer anchor is forced to radially expand slightly outward due to the difference between the outer diameter of the inner anchor 8602 and the inner diameter of outer anchor 8608. The slits 8610, 8614 allow the outer anchor to expand and contract. When the anchors 8602, 8608 are positioned in a hole in bone, the resulting increase in diameter of outer anchor 8608 helps lodge the anchor in the hole. A suture will be coupled to one or both of the inner and outer anchors, and either the inner anchor or the outer anchor will preferably contain a one-way cinching mechanism for the suture as elsewhere described herein. A free end of the suture (not illustrated) may be passed through transverse channel 8604 and upon insertion of the inner anchor into the outer anchor, the free end will be pinched between the inner and outer anchors to lock it in place. Because the transverse channel 8604 is disposed close to a proximal end of the inner anchor 8602, the suture will not be pinched until the inner anchor is almost entirely inserted into the outer anchor. This allows the gross adjustment of suture length or tension prior to full insertion of the inner anchor, followed by fine adjustment of the suture length and tension with the cinching mechanism.

Figure 42:
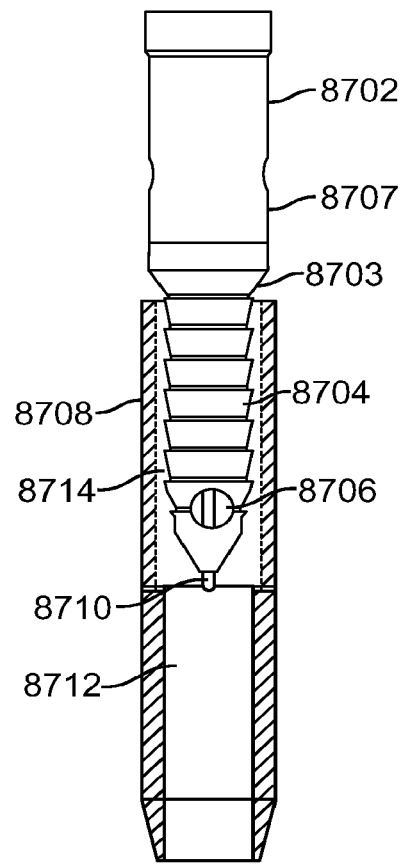
FIG. 42 is a side-view illustrating another suture anchor system having features for lodging the anchor in tissue.

FIG. 42 shows an alternative embodiment where the transverse channel 8706 is disposed closer to the distal end of the inner anchor 8702. The anchor system includes an upper anchor 8702 having a smaller diameter barbed or threaded distal portion 8704 with a transverse channel 8706 near the distal end, a tapered mid section 8703, and large diameter proximal portion 8707. The upper anchor 8702 is positionable inside an outer anchor 8708 having upper slits 8710 and a central channel with a larger diameter section 8714 and a smaller diameter section 8712. As the larger diameter portion 8707 of inner anchor 8702 enters the larger diameter section 8714, the upper region of the outer anchor will again radially expand outward against the bone, locking the anchor into position. As the inner anchor 8702 is inserted deeper into the outer anchor 8708, the inner anchor 8702 will eventually enter the smaller diameter region 8712, where the threads or barbs on the smaller diameter portion 8704 engage the side walls of outer anchor 8712 to prevent the inner anchor from moving proximally. Optionally the inner wall of the smaller diameter region 8712 may have surface features which mate with the barbs or threads on the inner anchor to enhance retention. A suture (not illustrated) may be advanced through the transverse channel 8706 so that the suture will be pinched between the inner anchor 8702 and the outer anchor 8708 when the inner anchor is fully inserted therein. The position of the transverse channel 8706 may be selected so that the pinching occurs later in the process of inserting the inner anchor than the embodiment seen in FIGS. 41A-41E, therefore a physician can still grossly adjust the suture length or tension until just before the two anchors are fully coupled together.

Figure 43A:
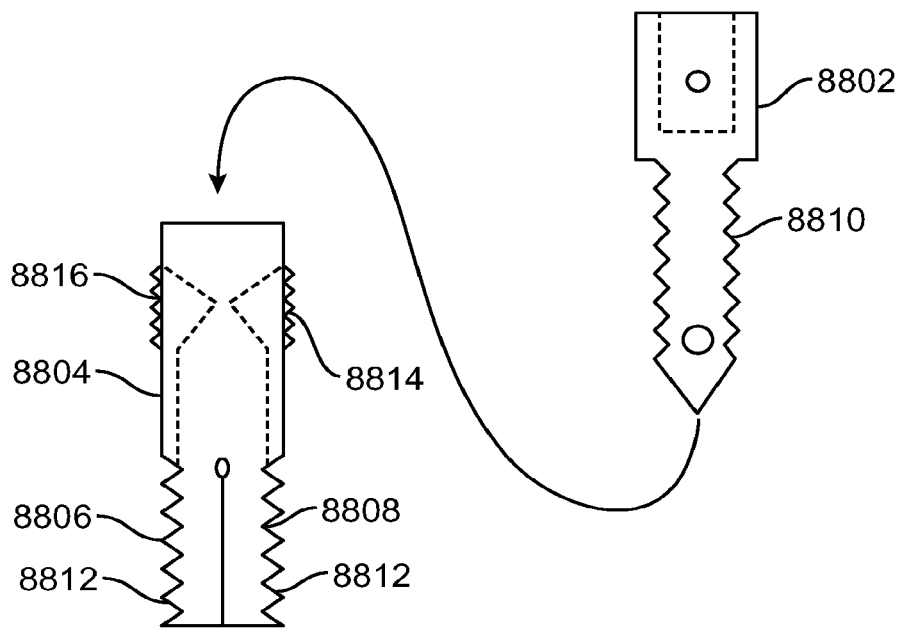
FIGS. 43A-43B are side-views illustrating other anchor lodging features.
Figure 43B:
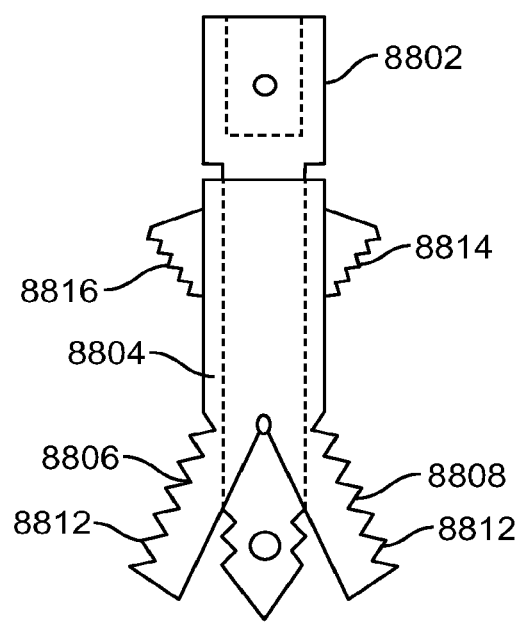

FIGS. 43A-43B illustrate another exemplary embodiment where an upper anchor 8802 is positioned into a lower anchor 8804 causing wings (also referred to as tissue retention structures or elements) to radially expand outward to lock the anchoring system in position. A camming element may force the wings outward. The upper anchor 8802 may include threads 8810 to engage the lower anchor 8804. The lower anchor includes a pair of wings 8806, 8808 near the distal end and optionally include barbs or other surface features 8812. Additionally, the lower anchor 8804 may also include a pair of upper wings 8814, 8816 near the proximal end. As shown in FIG. 43B, when the upper anchor 8802 is inserted or threaded into the lower anchor 8804, this causes the distal wings 8806, 8808 to expand radially outward. Also, the proximal wings 8814, 8816 expand radially outward. Thus, the two pairs of wings help secure the anchor system into the bone. The surface features help to engage the wings with the bone.

Figure 44A:
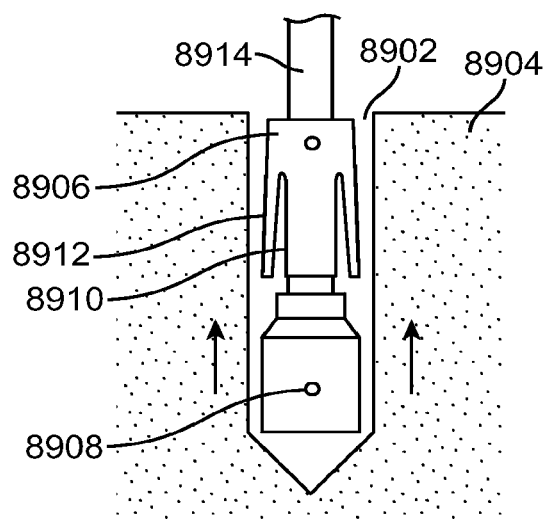
FIGS. 44A-44B are partial side cross-sectional views illustrating still other anchor lodging features.
Figure 44B:
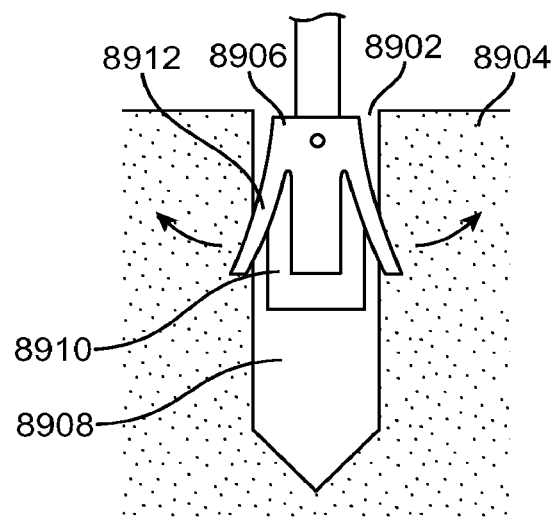

FIGS. 44A-44B illustrate a further embodiment in which one anchor component may be used to expand wings on a second anchor component to help lodge the anchor system in position. Upper 8906 and lower 8908 suture anchors are disposed in a hole 8902 in bone 8904. The upper anchor 8906 includes several axially oriented slits 8910 that form wings or fingers 8912 in the upper anchor 8906. As the lower anchor 8908 is drawn upward and received into the upper anchor 8906, the lower anchor 8908 forces the wings 8912 to deflect radially outward into apposition with the bone 8904. A puller tool 8914 may be coupled to the lower anchor 8908 and may be used to draw the lower anchor 8908 into the upper anchor 8906. In alternative embodiments, a suture, wire or tether may also be coupled to the lower anchor and used to draw the lower anchor into the upper anchor.

Figure 45A:
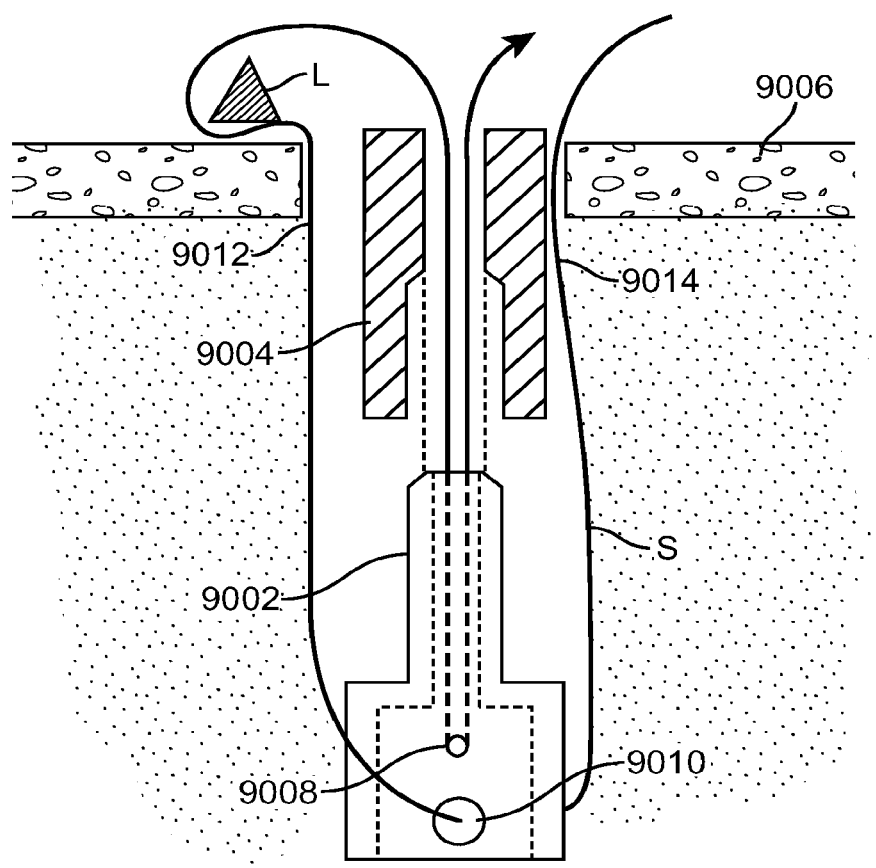
FIGS. 45A-45B are partial side cross-sectional views illustrating other anchor lodging features.
Figure 45B:
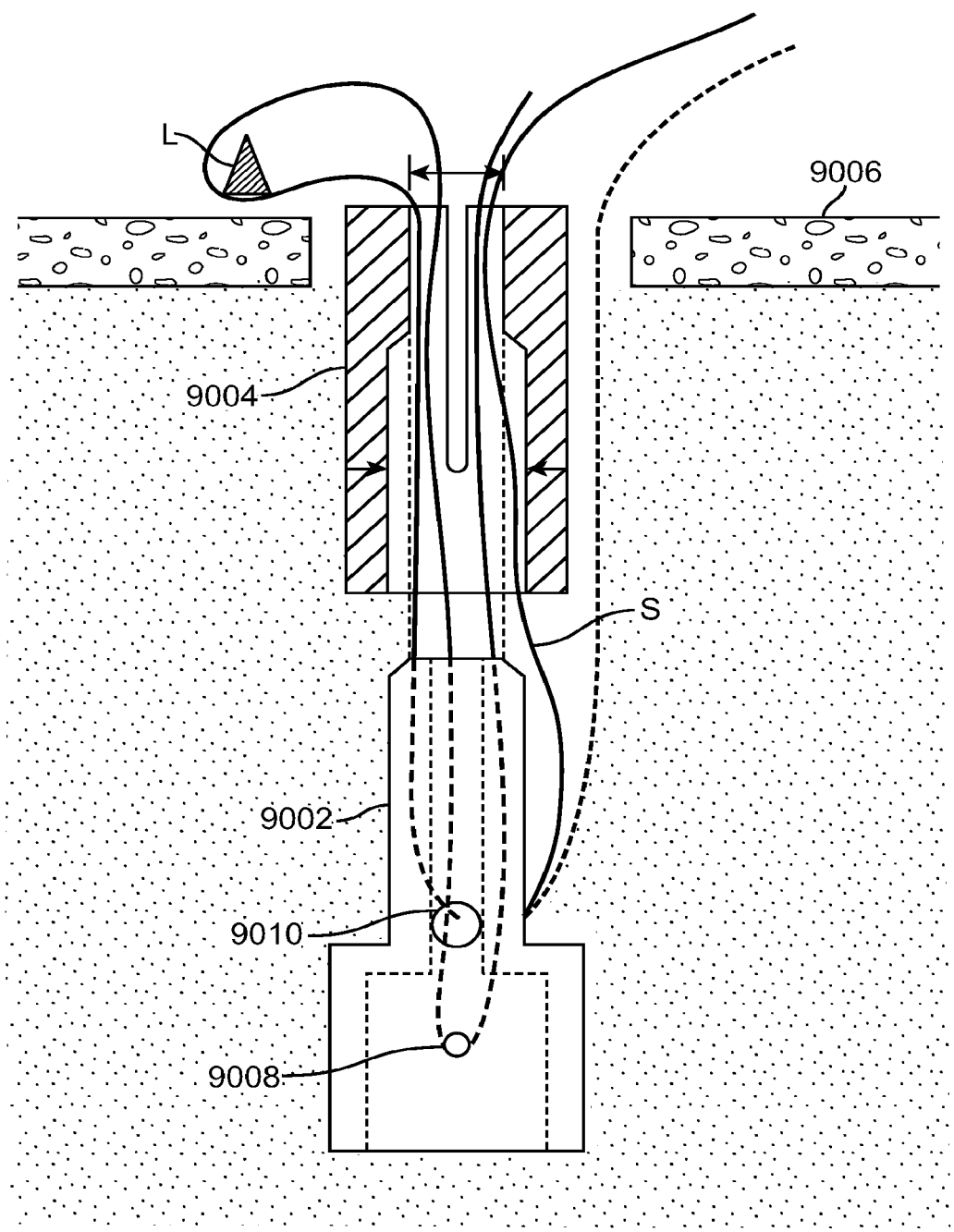

FIGS. 45A-45B illustrate further embodiments of a suture anchor system which includes an upper anchor 9004 and a lower anchor 9002. Drawing the lower anchor 9002 into the upper anchor 9004 radially expands the upper anchor 9004 against the cortical bone 9006. Upper anchor 9004 has a tapered inner passage which receives the proximal end of inner anchor 9002. When retracted proximally relative to the upper anchor 9004, inner anchor 9002 engages and radially expands upper anchor 9004. Suture S passes through a one-way cinching mechanism 9008 in lower anchor 9002, which may comprise any of the cinching mechanisms disclosed herein, and has two free ends which extend proximally through the central passage in upper anchor 9004. One of the free ends may be passed around labrum L and inserted through a transverse channel 9010 in lower anchor 9002. When the anchor is inserted in the bone hole, the suture 9004, 9014 is trapped between the outer surface of the upper anchor 9004 and the surrounding bone compressing the suture to hold it in place. FIG. 45B illustrates a variation of the embodiment in FIG. 45A. In this embodiment, the relative positions of the transverse channel 9010 and the cinching mechanism 9008 have been transposed, and the free end of the suture S extends from the transverse channel between the upper and lower anchors. Thus, the suture S will be pinched between the inner and outer suture anchors 9002, 9004 when coupled together. Optionally the free end of the suture may run alongside an outer surface of the upper anchor as illustrated by the dotted line in FIG. 45B, and therefore it may be pinched between the bone and the upper anchor. In either embodiment, once the two-part anchor has been inserted in the bone hole and the first free end of the suture locked in place, the opposing free end may be pulled to shorten the loop around the labrum to the desired length and degree of tension.

Figure 46A:
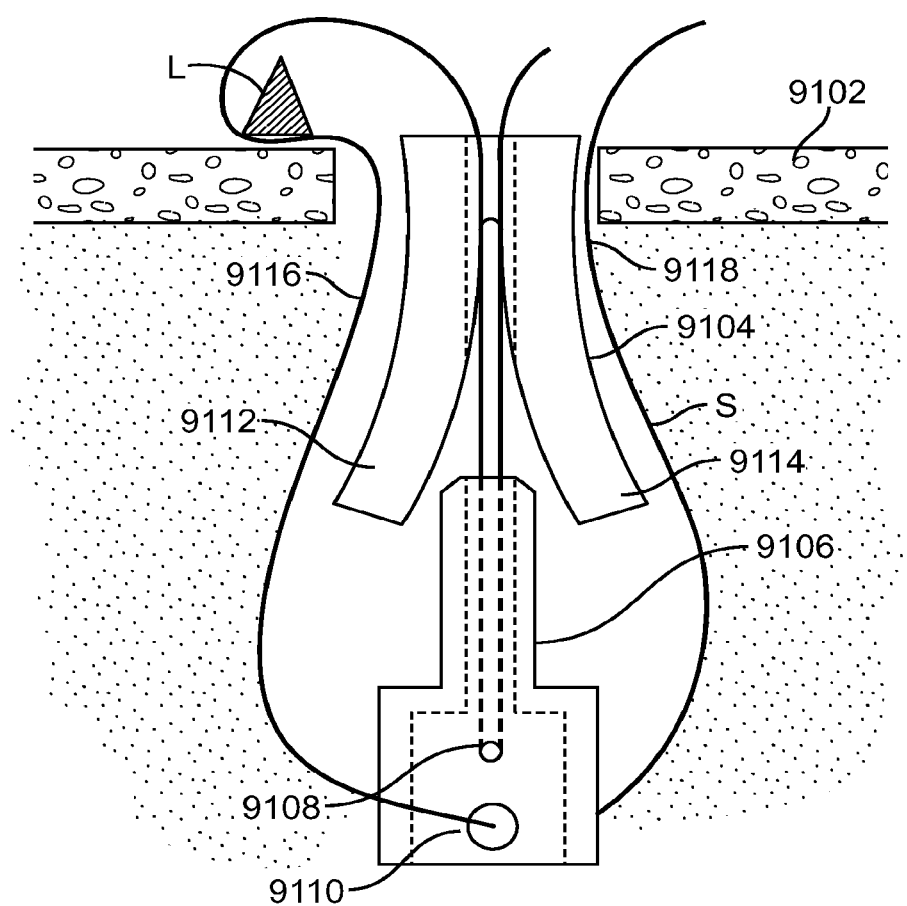
FIGS. 46A-46B are partial side cross-sectional views illustrating additional anchor lodging features.
Figure 46B:
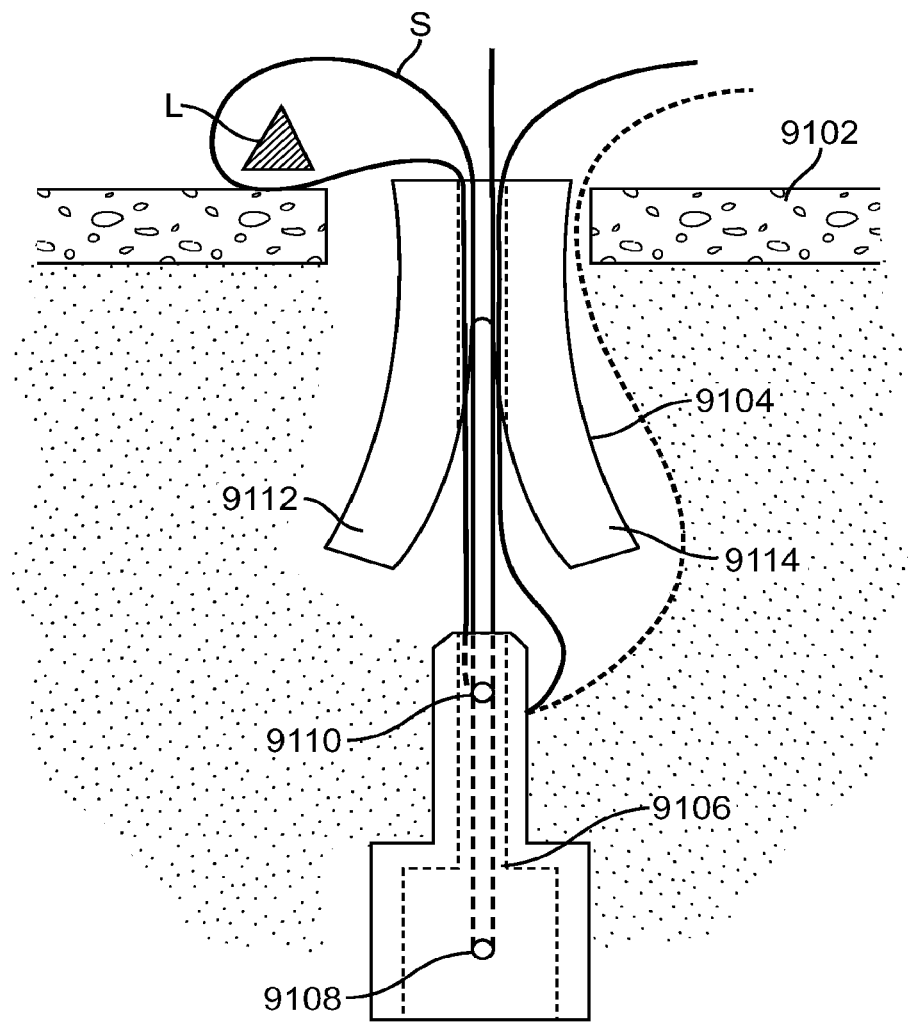

FIGS. 46A-46B illustrate embodiments of a suture anchoring system where wings flare outward to secure the anchor to the bone below the layer of cortical bone 9102. The system includes an upper anchor 9104 having wings 9112, 9114 that point downwardly (distally) and flare outward when lower anchor 9106 is drawn into the upper anchor 9104. In this embodiment, the wings flare radially outward just below the layer of cortical bone to compress the surrounding cancellous bone and engage the lower surface of the cortical layer. Suture S passes through a one-way cinching mechanism 9108 in lower anchor 9106, which may be any of the cinching mechanisms disclosed herein. A free end of the suture S may be passed through a transverse channel 9110 in lower anchor 9106, which lies distally of the cinching mechanism 9108. Thus, the suture portions 9116, 9118 run around the outside of the upper anchor 9104 and therefore will be pinched between the upper anchor 9104 and the cortical bone 9102 to retain the free end of the suture in place. FIG. 46B illustrates a variation on the embodiment of FIG. 46A, where the position of the transverse channel 9110 and the cinching mechanism 9108 have been transposed. Thus, the suture S will be pinched between the inner and outer anchors 9104, 9106 when the two are coupled together. Optionally, the free end of the repair portion of the suture may extend from the lower anchor 9106 between the outer anchor 9104 and the bone to lock it in place, as shown in phantom. Additionally, in this embodiment, the tension-adjusting end of the suture extends proximally from the one-way cinching mechanism through a central channel of the upper anchor 9104, so that the suture will not be pinched between the upper anchor and the bone, allowing it to be pulled to adjust suture length and tension after anchor placement.

Figure 47D:
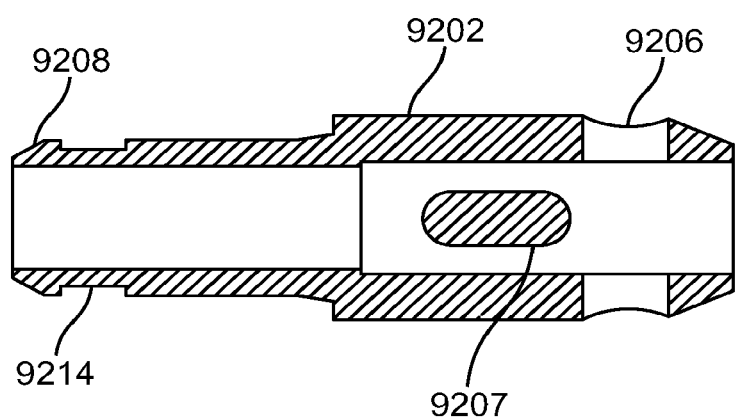
FIG. 47D is a side cross-sectional view of the anchor in FIG. 47A.
Figure 47E:
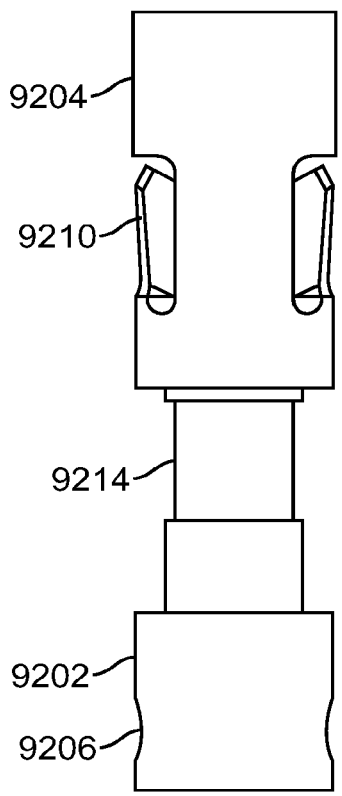
FIGS. 47E-47F are side-views of the anchor in FIG. 47A.
Figure 47F:
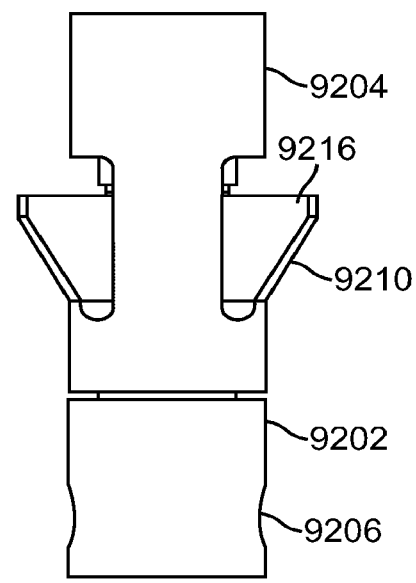
Figure 48A:
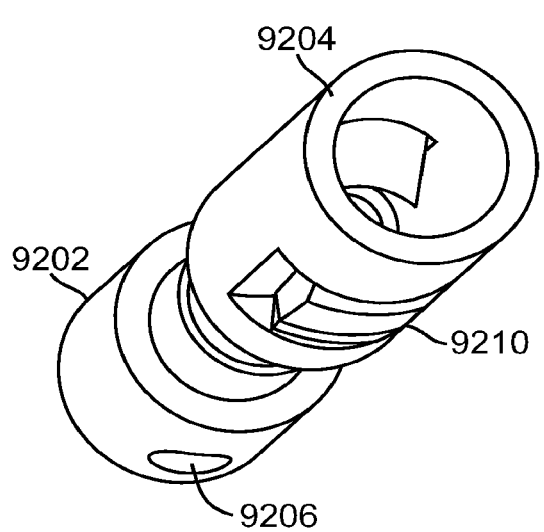
FIGS. 48A-48B are perspective views of a anchor lodging features.
Figure 48B:
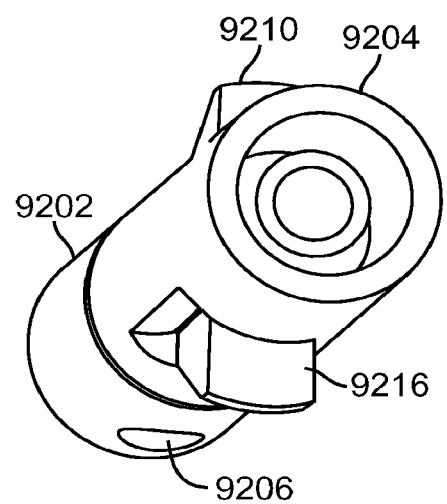

FIGS. 47A-47F illustrate an exemplary embodiment of a suture anchoring system having anchor components and locking wings. An inner cylindrical anchor 9202 includes a tapered proximal end 9208, a reduced diameter middle section 9214 and a transverse channel 9206 through which a free end of a suture (not illustrated) may be inserted where it is locked in place by compression between the inner anchor and the surrounding bone. The outer cylindrical anchor 9204 includes a pair of resiliently deflectable wings 9210 having inwardly angled inner surfaces to form a proximally tapered inner channel 9212. Preferably wings 9210 are integrally formed into outer anchor 9204, e.g. being cut-way from the walls of the cylindrical body thereof, and are deployed by deflecting outwardly when engaged by proximal end 9208 of inner anchor 9202. Alternatively, wings 9210 may comprise separate components which are coupled to the body of outer anchor 9204 by hinges or other suitable couplings allowing the wings to deflect. In use, the inner anchor is positioned into a hole in the substrate tissue such as bone. The outer anchor is positioned into the hole on top of the inner anchor, either at the same time or in a subsequent step. Using an inserter tool (not shown) coupled to inner anchor 9202, inner anchor 9202 is drawn upward into the outer anchor 9204 such that the tapered tip 9208 engages the angled inner channel 9212 forcing the wings 9210 to deflect radially outward as seen in FIG. 47B. The inner anchor is drawn into the outer anchor until wings 9210 recoil into the reduced diameter section 9214 thereby locking the inner anchor relative to the outer anchor to maintain wings 9210 in the deployed position. A flat shoulder region 9216 extends laterally from the anchor to engage the underside of the cortical layer of bone, thereby providing a stopping surface for preventing the anchor system from sliding out of the hole in the bone. FIG. 47C illustrates a perspective view of the upper anchor 9204 with the wings 9210 deployed. It will be understood that either the inner or outer anchor will contain a one-way cinching mechanism as described elsewhere herein to allow one-way tensioning of the suture after the anchor has been implanted. FIG. 47D illustrates an embodiment similar to that of the inner anchor 9202 in FIG. 47A, yet in this cross section, the transverse pin or bar 9207 is illustrated. The bar 9207 is used to form the hitch-type knot therearound and may be coupled with the outer anchor 9204 in FIG. 47A. FIGS. 47E-47F show the anchor before and after the wings 9210 have been deployed and FIGS. 48A-48B illustrate perspective views of the anchor before and after the wings have been deployed.

Figure 49A:
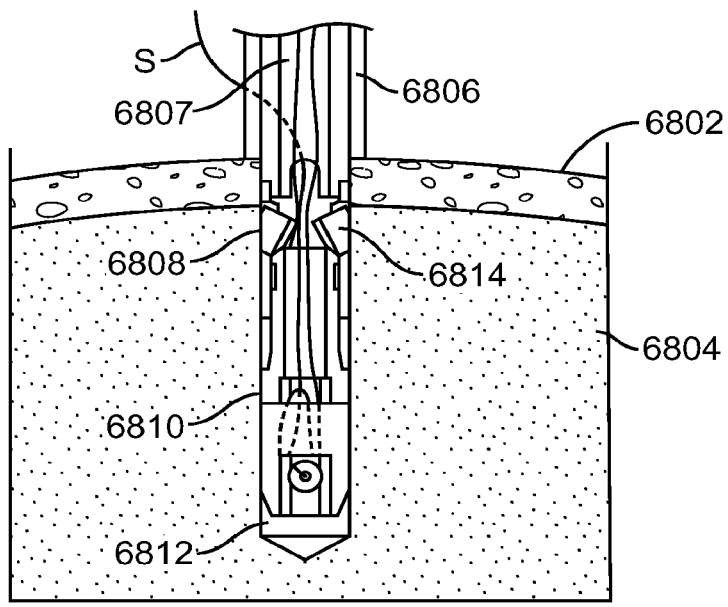
FIGS. 49A-49C are partial side cross-sectional views illustrating anchor lodgement.
Figure 49B:
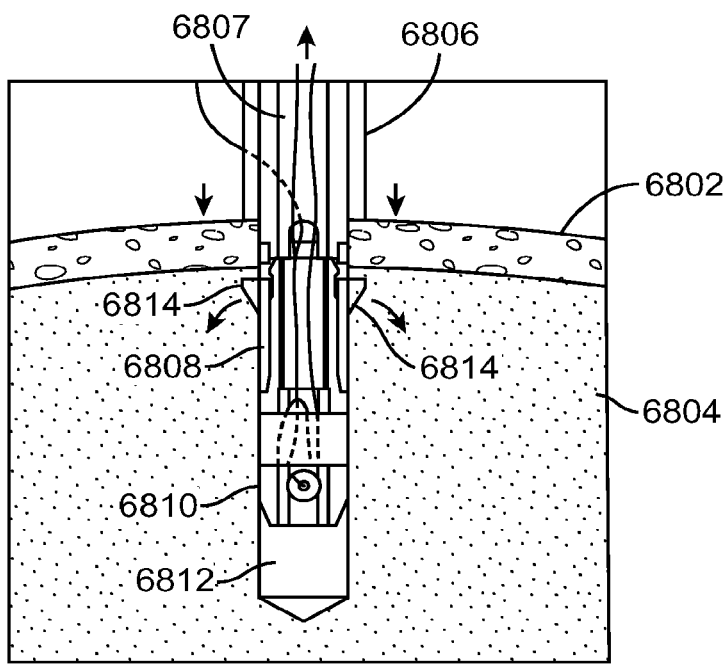
Figure 49C:
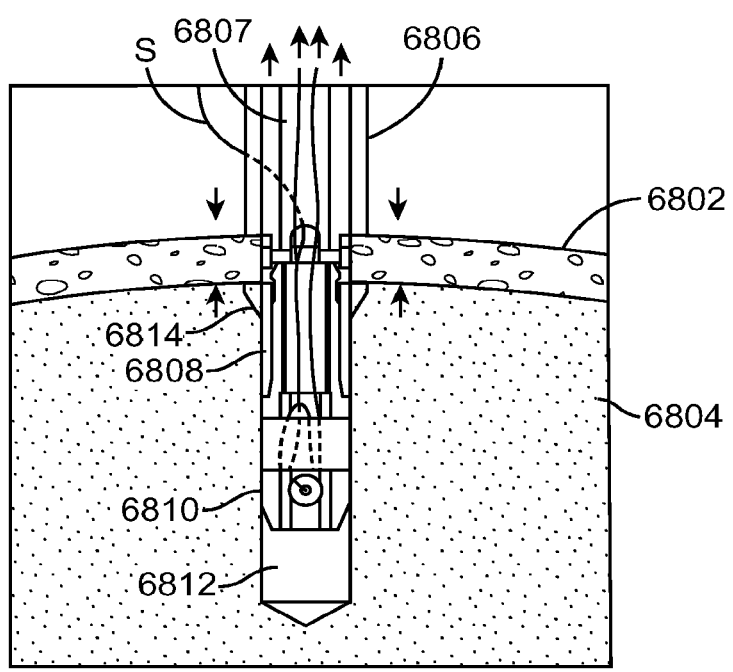
Figure 50E:
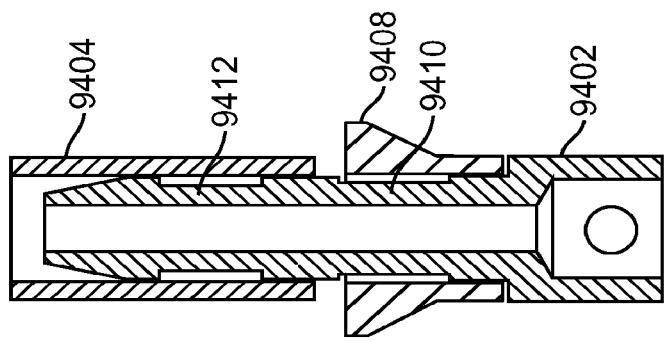
FIGS. 50D-50E are side cross-sectional views of the anchor lodging features in FIG. 50A.
Figure 50D:
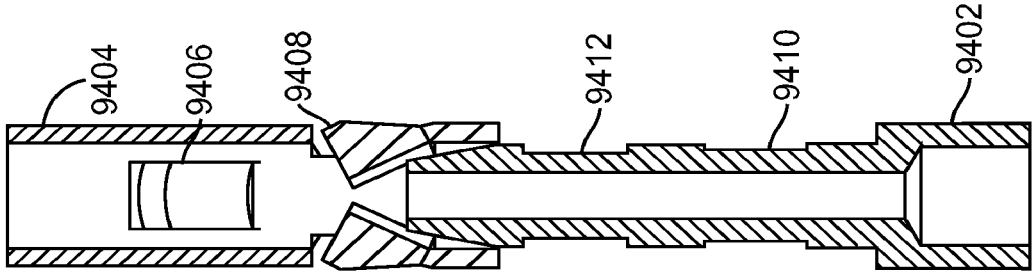
Figure 50C:
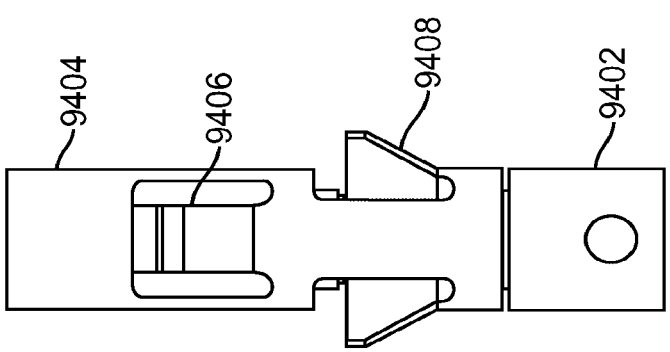
FIGS. 50B-50C are side-views of the anchor lodging features in FIG. 50A.
Figure 50B:
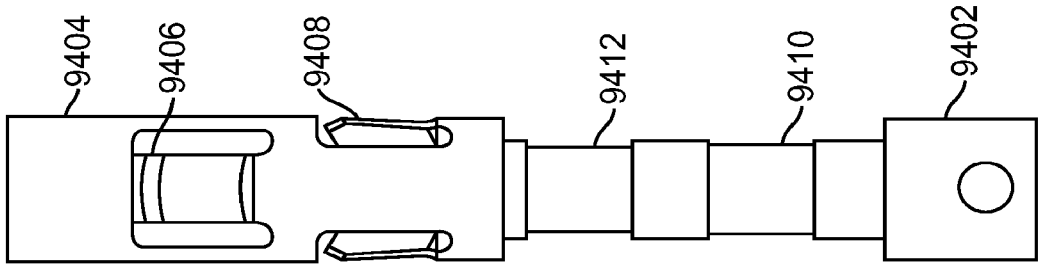
Figure 50A:
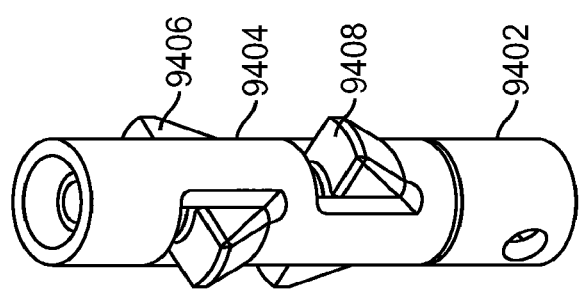
FIG. 50A is a perspective view of an anchor with lodging features.

FIGS. 49A-49C illustrate an exemplary method of lodging a suture anchor like that of FIGS. 47-48 into bone. In FIG. 49A, an insertion tool having a shaft 6806 carries the suture anchor. The suture anchor includes an upper anchor portion 6808 and a lower anchor portion 6810 and a repair suture S. A hole 6812 is pre-drilled through the cortical layer 6802 of bone and into the cancellous layer of bone 6804 to a desired depth approximately the same as the length of the suture anchor system. The insertion tool is advanced such that the distal end of the shaft 6806 is in apposition with the outer layer of the cortical bone 6802 and over the hole 6812. Inner shaft 6807 is advanced distally, pushing the upper and lower anchors 6808, 6810 out of the shaft 6806 into the hole 6812. Retraction of shaft 6807 causes the lower anchor 6810 to be drawn toward the upper anchor 6808 such that the two anchor portions lock together and a proximal portion of the lower anchor forces a pair of wings 6814 to deploy radially outward, as seen in FIG. 49B. In FIG. 49C, the shaft 6807 is drawn proximally, drawing the upper and lower anchor portions proximally such that the wings 6814 engage an underside of the cortical layer 6802 of bone, thereby lodging the anchor in position. A portion of the wings 6814 are also anchored in the softer cancellous layer 6804 of bone. Once the anchor has been fully lodged in bone, it may be released from the insertion tool (not illustrated).

FIGS. 50A-50E illustrate a suture anchor system having a pair of upper wings and a pair of lower wings for anchoring into bone. The suture anchor system includes an inner anchor 9402 and an outer anchor 9404. The outer anchor 9404 has two lower wings 9408 spaced 180 degrees apart, and two upper wings 9406 spaced 180 degrees apart, with the upper and lower wing pairs being axially spaced apart along the anchor body and circumferentially offset 90 degrees relative to one another. The wings thereby engage the bone on four rather than two sides of the anchor, increasing retention force. Deployment of the wings works in generally the same manner as described above with respect to FIGS. 47A-47C, except in this embodiment, the inner anchor has two reduced diameter sections 9410, 9412 for locking the wings in the deployed configuration.

FIGS. 51A-51E illustrate an embodiment of a suture anchor system having modular wings. The anchor system includes a lower anchor 9502 and an upper anchor 9504. The upper anchor 9504 includes two modules 9508, 9510 with each module having a pair of wings 9506, 9512 spaced 180 degrees apart. While this embodiment has two modules, any number of modules may be used. The modules are simply stacked together and offset from one another by 90 degrees such that a wing extends from the anchor every 90 degrees. Thus, when inner anchor 9502 is drawn into each of the modules 9508, 9510, the wings 9506, 9512 extend radially outward. This allows one pair of wings 9512 to engage the cortical bone while the other pair of wings 9506 engage the cancellous bone. Inner anchor 9502 includes two reduced diameter sections 9514, 9516 for locking the inner anchor with the outer anchor and with the wings in the deployed configuration. In an alternative embodiment, the two wing modules may be formed of a unitary construction. FIG. 51F illustrates a perspective view of a suture anchor 9518 that is similar to that of FIG. 51A, yet instead of having modular wings, the anchor is of unitary construction. The anchor has a pair of lower wings 9520 and a pair of upper wings 9522 deployed.

Although not illustrated, it will be understood that any of the embodiments of the suture anchors of the invention described herein may include features on the exterior thereof to enhance retention of the anchor in bone or other tissue, or to promote tissue ingrowth into the anchor. Such features may comprise bumps, divots, barbs, ridges, axial or circumferential ribs, threads, scales, flaring wings, projections, concave regions, or other structures to enhance friction or to mechanically engage the surrounding bone or tissue and resist proximal movement of the anchor after it has been fully inserted. Such features are well-known in the art, with examples illustrated in U.S. Pat. Nos. 6,554,852, 6,986,781, and 6,007,566, which are incorporated herein by reference.

Figure 52A:
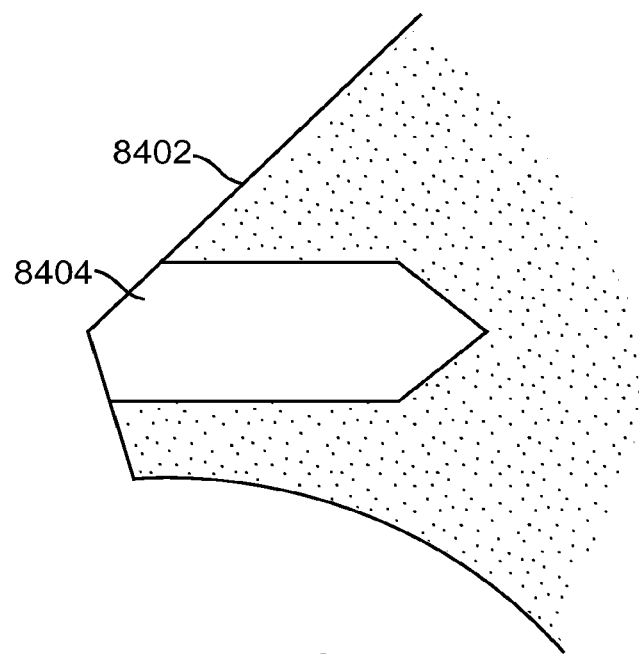
FIGS. 52A-52C are side cross-sectional views illustrating anchor delivery into a substrate tissue.
Figure 52B:
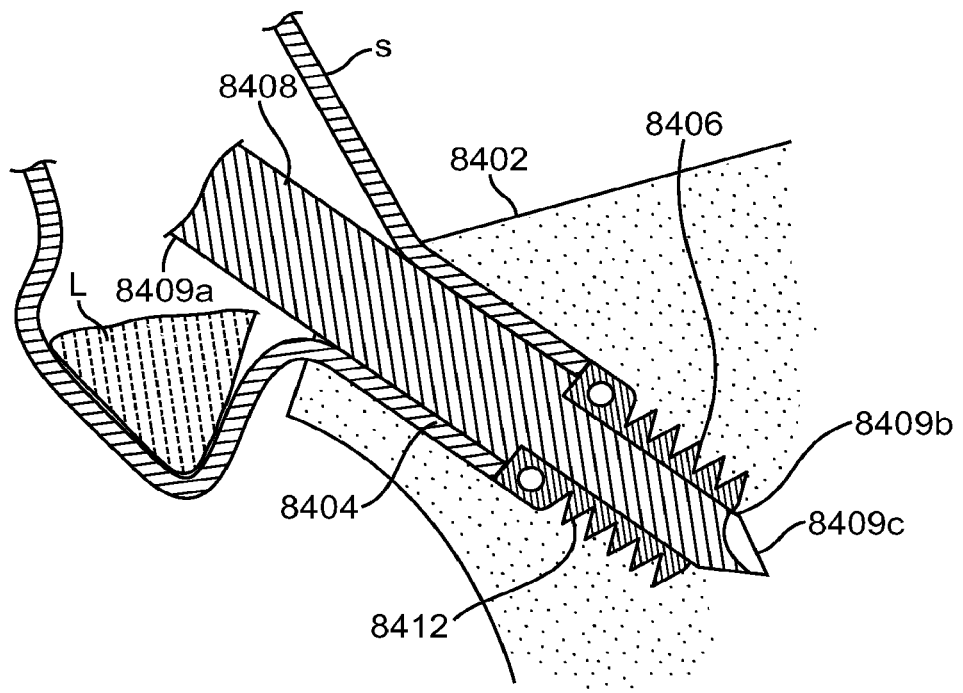
Figure 52C:
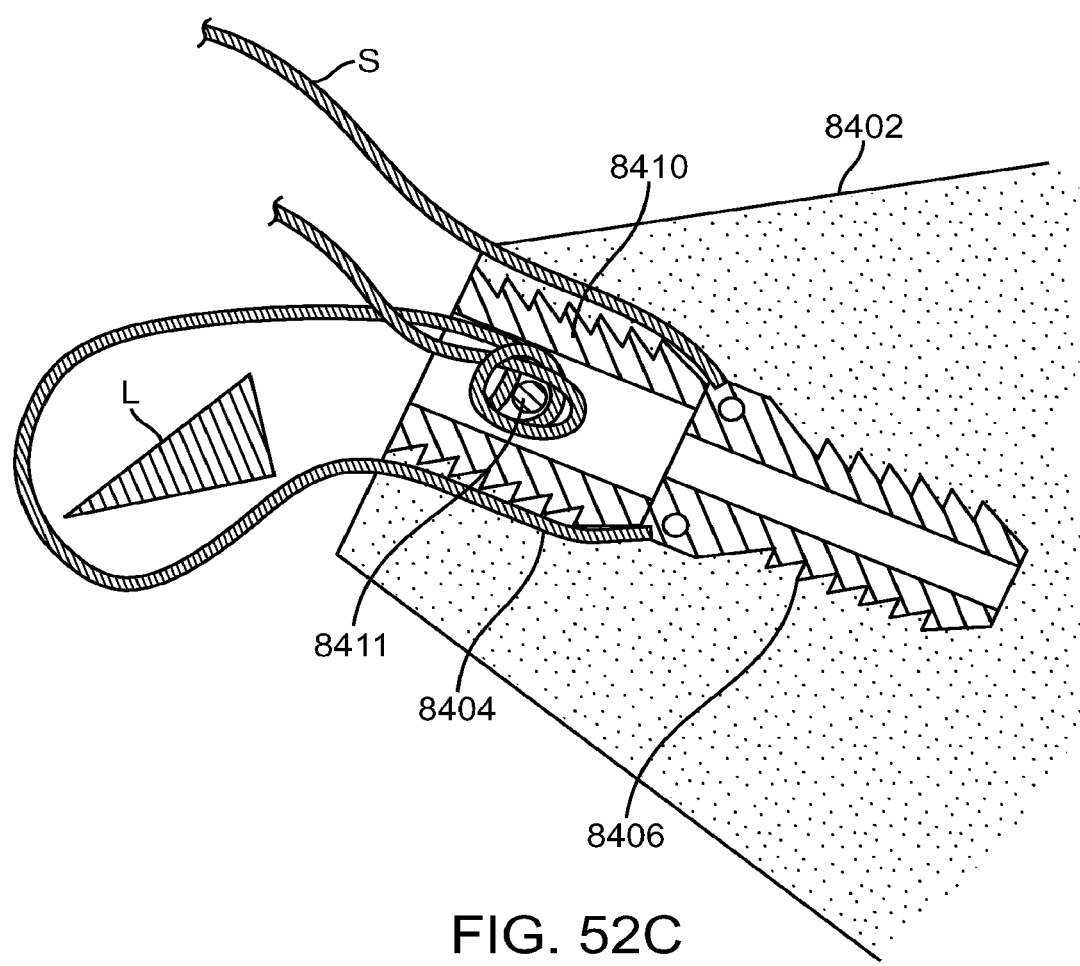

Delivery Instruments:

FIGS. 52A-52C illustrate a further exemplary embodiment in which a portion of the anchor is implanted in conjunction with drilling a hole in the bone. In FIG. 52A, a relatively shallow hole 8404 is first pre-drilled into the cortical bone 8402. A driver tool 8408 is used to drive a first anchor 8406 into the cancellous bone underlying the hole 8404 without need for drilling a separate hole. Driver tool 8408 has a proximal shaft portion 8409*a* sized to fit within predrilled hole 8404 and a distal portion 8409*b* sized to extend through first anchor 8406 and having a distal cutting tip 8409*c* that extends beyond the distal end of first anchor 8406. Driver tool 8408 with first anchor 8406 mounted thereon is inserted into predrilled hole 8404 and the shaft 8409*a* is rotated so that distal tip 8409*c* drills a hole into the bone of suitable size that first anchor 8406 may be inserted therein. First anchor 8406 may be configured to be press fit into the hole created by distal tip 8409*c*, wherein the first anchor 8406 remains stationary as shaft 8409*a* spins. Alternatively, first anchor 8406 may have external threads 8412 and may be fixed to shaft 8409*a*, whereby the anchor is screwed into the bone as shaft 8409*a* turns. One or more sutures S are attached to first anchor 8406. Preferably the free end of at least one of sutures S is coupled to a one-way cinching mechanism on a second anchor 8410, shown in FIG. 52C. The one way cinching mechanism may be as described elsewhere herein, preferably including a transverse pin or bar 8411 about which the suture is wrapped in a hitch-like configuration. Once first anchor 8406 is in place, second anchor 8410 may be passed around the target tissue and inserted into the first predrilled hole 8404 over the first anchor 8406. Second anchor 8406 may have threads or barbs so it may be press fit or screwed in to hole 8404, or it may be configured to couple to the first anchor 8406 for retention in the hole. Suture length and tension is then adjusted by tensioning the free end of suture S in order to bring the torn labrum L into apposition with the bone 8402.

Figure 53A:
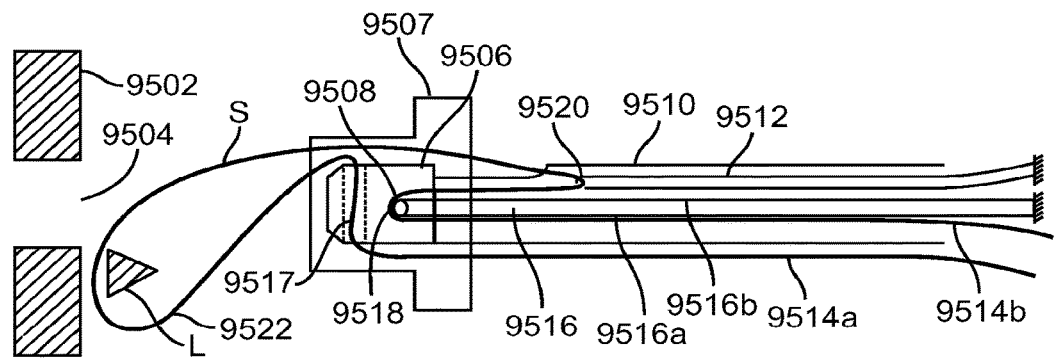
FIGS. 53A-53B are side views of suture anchor deliver tools.

FIG. 53A schematically illustrates another exemplary embodiment of a suture anchor delivery instrument for delivering a suture anchor 9506 through a portal or trocar sleeve 9507 into a pre-drilled hole 9504 in bone 9502 or other tissue. The suture anchor 9506, which may be any of the suture anchor embodiments described elsewhere herein, includes a transverse bar 9508 for looping the suture S around in order to form a hitch-type cinching mechanism similar to that of FIG. 23B. The delivery instrument includes an outer shaft 9510 having a proximal and distal end. The suture anchor 9506 is coupled to the distal end of the outer shaft 9510 and held in place with an anchor retention suture 9516 looped around the transverse bar 9508 in the suture anchor 9506 and having two free ends 9516*a*, 9516*b* that are releasably attached to a proximal end of the shaft 9510. An operator may release the ends of the anchor retention suture 9516*a*, 9516*b* from the proximal end of the shaft or a handle when ready to separate the anchor from the delivery instrument. The suture S is loaded into the delivery shaft 9510 such that the suture is looped around the transverse bar 9508 forming the hitch-type cinching mechanism 9518 described above in FIG. 23B. One free end of the suture S forms a repair suture 9514*a* which is passed around the target tissue (labrum L), through the transverse channel 9517 in anchor 9506, and proximally along the exterior of outer shaft 9510. The other free end of suture S forms an adjustment suture 9514*b* which extends proximally from transverse bar 9508 through the interior of shaft 9510 and is used to adjust length or tension in the suture after the anchor has been positioned in the hole 9504. An additional management suture 9512 extends through shaft 9510 and is looped 9520 around the repair suture 9514*a* in order to provide a factory pre-set amount of slack in the suture. The free ends of the management suture 9512 are releasably attached to a proximal end of the shaft 9510 or a handle. Gross suture adjustment may be performed by releasing management suture 9512 and pulling free end 9514*a* as the anchor is advanced into the hole 9504 in order to take up excess slack in the loop around labrum L. Once the anchor is implanted in the bone hole, repair suture 9514*a* is locked in place by compression between the exterior of anchor 9506 and the surrounding bone. Once the anchor 9506 has been positioned into the hole 9504, adjustment suture 9514*b* may be tensioned to adjust the loop 9522 around the labrum to its desired final tension. Then both the management suture 9512 and the retention suture 9516*a*, 9516*b* may be released from the proximal end of the shaft 9510 to release anchor 9506 from shaft 9510.

Figure 53B:
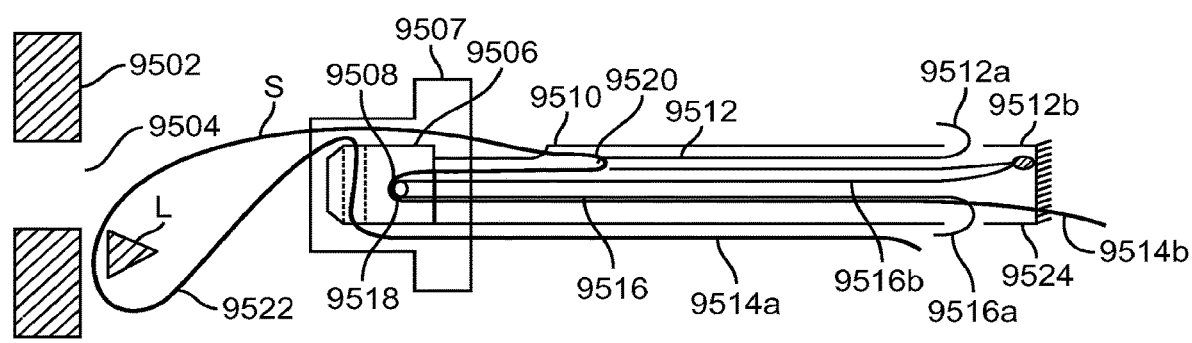

FIG. 53B illustrates a variation of the embodiment in FIG. 53A, with the major difference being in how the management suture 9512 and the retention suture 9516 are actuated. In the previous embodiment, both ends of the management and retention sutures are attached to a proximal end of the delivery shaft 9510 or to a handle. In this embodiment, one end 9512*a*, 9516*a* of each of the management and retention sutures 9512, 9516 are draped over a proximal end of the delivery shaft 9510 or passed through a hole in the sidewall of the shaft 9510. A retention cap 9524 is then press fit, snapped or threaded over a proximal portion of the shaft 9510 such that the draped ends 9512*a*, 9516*a* are captured between the outer shaft wall and the retention cap 9524. The other ends 9512*b*, 9516*b* of the retention and management sutures are fixed to the retention cap 9524. Thus, after the suture has captured the labrum L, and the anchor is properly positioned in the hole 9502, the retention cap 9524 may be separated from the shaft 9510. As the cap 9524 is pulled away from the shaft, the retention suture 9516 and the management suture 9521 will also be free to be released from the suture S and the anchor 9506.

Figure 53C:
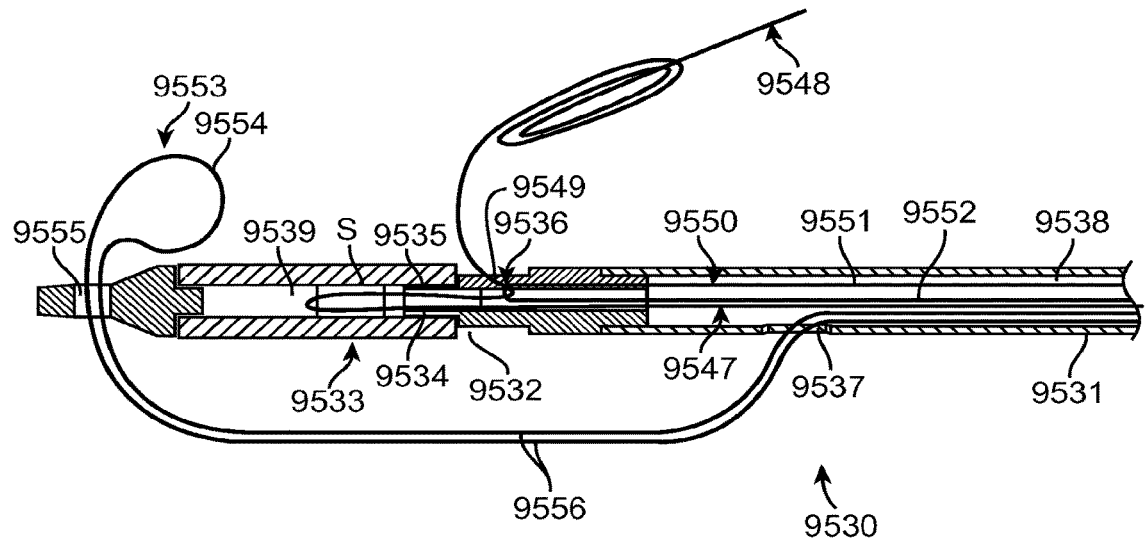
FIGS. 53C-53D are side cross-sectional views of distal and proximal portions, respectively, of a delivery instrument and anchor according to the invention.
Figure 53D:
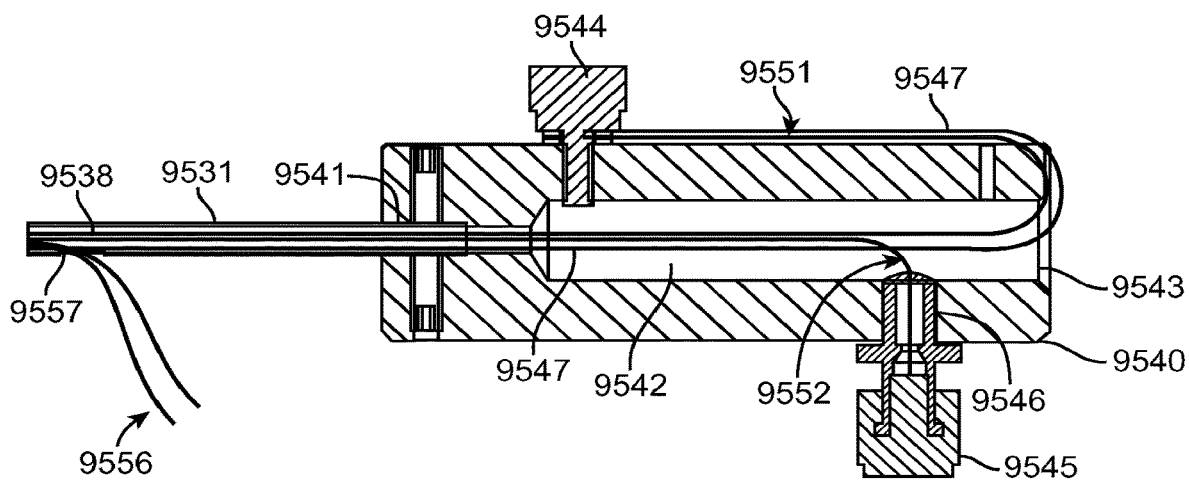

FIGS. 53C-53D illustrate in greater detail the distal and proximal ends respectively of a delivery instrument for use with the anchor systems of the invention. Referring first to FIG. 53C, delivery instrument 9530 has a tubular shaft 9531 with a distal end 9532 adapted for coupling to an anchor 9533, which may be in the form of any of the embodiments described herein. Distal end 9532 has a tip 9534 configured to fit within a socket 9535 in the proximal end of anchor 9533 and maintain a friction fit therewith. A first side port 9536 is disposed in shaft 9531 near the distal end 9532 and a second side port 9537 is disposed in shaft 9531a short distance proximally of first side port 9536, each of the side ports being in communication with an inner lumen 9538 of shaft 9531. Anchor 9533 has an internal cavity 9539 which communicates with socket 9535 and a bar (not shown) mounted within cavity 9539 about which a suture S may be tied in the form of a one-way sliding knot, described elsewhere herein.

Referring to FIG. 53D, a handle 9540 is mounted to a proximal end 9541 of shaft 9531. Handle 9540 has an inner passage 9542 communicating with inner lumen 9538 of shaft 9531 and extending to a port 9543 at the handle's proximal end. A thumbscrew 9544 is threadably coupled to handle 9540, and a pull tab 9545 is frictionally fit within a hole 9546 in handle 9540 which communicates with passage 9542. An adjustment end 9547 of suture S extends proximally from anchor 9533 through inner lumen 9538 of shaft 9531 and through passage 9542 in handle 9540, exiting through port 9543 and being retained by thumbscrew 9544 against handle 9540. As shown in FIG. 53C, a repair end 9548 of suture S extends from anchor 9533 into shaft 9531, forms a slack loop 9549 within lumen 9538 and exits through first side port 9536. A slack retention suture 9550 is looped through slack loop 9549, having first and second ends 9551, 9552 extending proximally through inner lumen 9538 into handle 9540 and exiting port 9543. First end 9551 is retained by thumbscrew 9544, while second end 9552 extends through hole 9546 and is fixed to pull tab 9545. A suture snare 9553, which may comprise a suture, wire, or other flexible filament, forms a loop 9554 adjacent anchor 9533 and then passes through a transverse channel 9555 in anchor 9533, as shown in FIG. 53C. The ends 9556 of suture snare 9553 extend into second side port 9537 in shaft 9531 and through inner lumen 9538, exiting the shaft through a third side port 9557 near handle 9540.

In use, repair end 9548 of suture S is first passed around or through the tissue to be repaired and then through loop 9554 in suture snare 9553. The ends 9556 of suture snare 9553 may then be pulled by the operator to draw the repair end 9548 through transverse channel 9555 in anchor 9533. By continuing to pull the suture snare, the repair end 9548 may be drawn into shaft 9531 and the repair loop formed by repair end 9548 through the target tissue may be shortened to an initial size and degree of tension. Advantageously, the slack retention suture 9550 maintains slack loop 9549 to ensure that the repair loop is not excessively shortened prior to anchor placement. Delivery instrument 9530 is then manipulated to insert anchor 9533 into the bone or other base tissue, trapping the free end of repair end 9548 between the bone and the anchor to lock its position relative to the anchor. After insertion of the anchor to its final implanted position, thumbscrew 9544 may be loosened, releasing adjustment end 9547 of suture S and first end 9551 of slack retention suture 9550. Pull tab 9545 is then withdrawn from hole 9546 and retracted to pull slack retention suture 9550 out of delivery instrument 9530, thus releasing slack loop 9549. Adjustment end 9547 of suture S may then be pulled to further shorten the repair loop through the target tissue and to apply the desired degree of final tension. Shaft 9531 is then decoupled from anchor 9533 and withdrawn from the surgical site, and the adjustment and repair ends of suture S trimmed as needed, completing the repair.

Figure 54D:
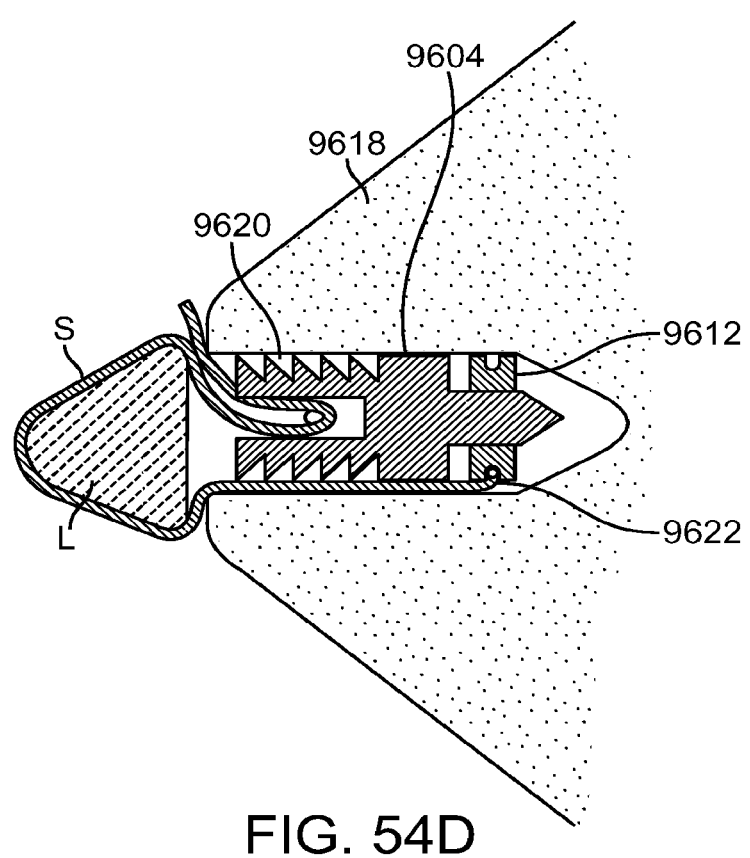

FIGS. 54A-54D illustrate another exemplary embodiment of a method for delivering a suture anchor and reattaching tissue to bone. An anchor delivery system includes an outer shaft 9602 that houses a proximal suture anchor 9604. The proximal anchor 9604 includes barbs 9606, threads or other surface features for facilitating lodging of the anchor into the bone 9618. Also, the proximal anchor 9604 includes a hitch-type cinching mechanism 9606, which may take the form of any of the cinching mechanisms described elsewhere herein, for one-way adjustment of the suture S. A deployment arm 9610 extends from the distal end of the outer shaft 9602 and is releasably coupled to the distal anchor 9612 which includes a central channel 9614 sized to receive the distal tip of the proximal anchor 9604. A free end of the suture S is also attached 9622 to the distal anchor 9612. Suture management clips 9616 along the deployment arm 9610 are releasably coupled to the suture S in order to keep the suture S from tangling. FIG. 54A shows the deployment arm advanced distally from the outer shaft 9602 and FIG. 54B is a plan view of the distal anchor. The deployment arm 9610 is pre-shaped with a bend to facilitate introduction of the suture S and the distal anchor 9612 around a torn labrum L or other damaged tissue and also is shaped so that the central channel 9614 is axially aligned with the distal tip of the proximal anchor, as seen in FIG. 54C. The proximal anchor 9604 is then advanced distally out of the shaft 9602 through engagement with a pusher tube (not illustrated) slidably disposed within outer shaft 9602, or by retraction of the outer shaft 9602 relative to the proximal anchor 9604 thereby forming a loop around the torn labrum L. The proximal anchor 9604 is advanced until its distal tip is received by the central channel of the distal anchor 9612. The deployment arm 9610 may be released from the suture S and the distal anchor 9612 and the proximal anchor 9604 together with the distal anchor 9612 are then advanced into the hole 9620 in the bone 9618 as seen in FIG. 54D. Once the proximal and distal anchors 9604, 9612 are secured in the hole 9620, suture tension and length may be adjusted by pulled the suture through the cinching mechanism thereby bringing the torn labrum L back into apposition with the bone 9618 as seen in FIG. 54D.

The anchor systems of the invention may further include a suture threading device to allow the suture to be threaded through the one-way cinching mechanism of the anchor during a surgical procedure. In this way the anchor and suture may be supplied initially separated from each other, and the physician may place the suture through the target tissue to be repaired before it is coupled to the anchor, giving him/her maximum flexibility in the type and location of stitches used. Once these stitches are placed, the physician may use the suture threading device to thread the suture through the one-way mechanism of the anchor, and the anchor may then be placed in the substrate tissue.

Figure 55A:
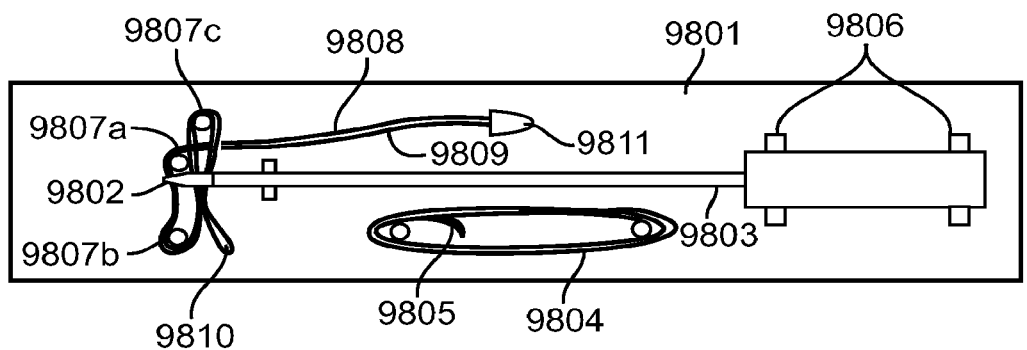
FIG. 55A is an elevational side-view of a suture anchor and insertion tool kit with a suture threading device according to the invention.
Figure 55B:
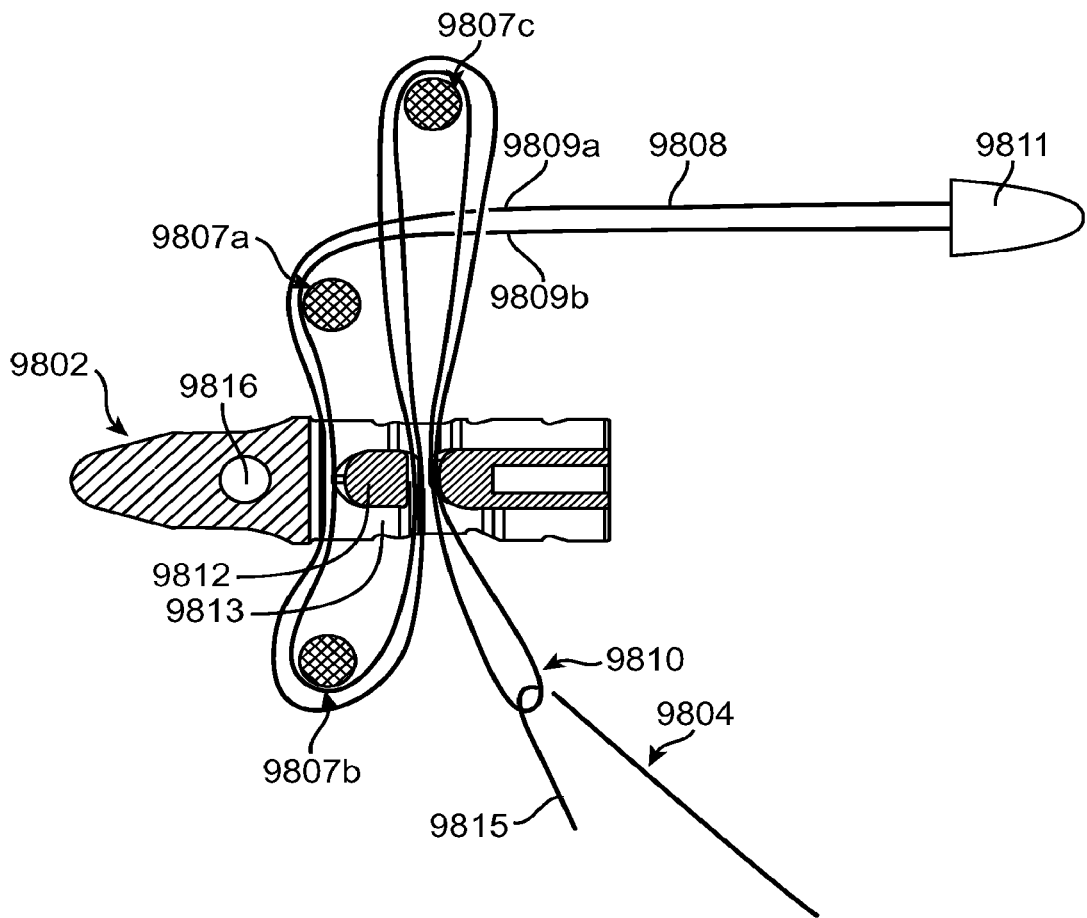
FIG. 55B is a side cross-sectional view of the anchor and suture threading device of FIG. 55A.

As shown in FIGS. 55A-55B, the anchor system may be supplied in a sterile package 9801 which contains an anchor 9802 coupled to the tip of a delivery instrument 9803. A suture 9804, with or without attached needles 9805, is also contained in package 9801, decoupled from anchor 9802. Delivery instrument 9803 and anchor 9802 are held in a fixed position within package 9801 by retainers 9806. Fixed with respect to the delivery instrument 9801 and anchor 9802 are a plurality of routing pins 9807a, 9807b, 9807c. A suture threading device 9808 comprises a loop of suture thread or wire 9809 which is routed around the routing pins 9807a, 9807b, 9807c and passes through the one-way cinching mechanism of anchor 9802 so that a bight 9810 extends from one side of the anchor and a finger grip 9811 is fixed to the opposite end, as shown in FIG. 55B.

Anchor 9802 may be any of the embodiments described above, preferably being an embodiment in which one or more bars are contained within a cavity which opens on a sidewall of the anchor, like that shown in FIGS. 32C-32E. In this embodiment, anchor 9802 has a single bar 9812 within a cavity 9813 in a middle portion of anchor 9802. Suture threading device 9808 is routed so as to extend from finger grip 9811 around first routing pin 9807a, through anchor 9802 via inner cavity 9813 distally of bar 9812, and around second routing pin 9807b Threading device 9808 then extends back through cavity 9813 proximally of bar 9812, underneath the two threads 9809a, 9809b leading to finger grip 9811, around third routing pin 9807c, then over the top of the same two threads 9809a, 9809b. The threading device then extends back through cavity 9813 such that bight 9810 extends laterally away from the anchor on the side opposite finger grip 9811. It will be appreciated that anchor 9802 may have multiple bars to accommodate multiple sutures, and may have separate threading devices to allow threading of each suture around each respective bar.

It will also be understood that while the routing pins 9807a, 9807b, 9807c are illustrated as being fixed to the package 9801 for the anchor system of the invention, the routing pins could alternatively be part of a structure detachably coupled to the distal end of delivery instrument 9803 or to anchor 9802. As a further alternative, structures like these routing pins could be integrated into anchor 9802 itself, either being implanted with the anchor, or decoupled therefrom once the suture has been threaded.

In use, suture 9804 is first passed into the body cavity and placed around or through the target tissue to be repaired. The ends of suture 9804 are then drawn back out of the body cavity and the end 9815 which is to become the tensioning end is passed through bight 9810 as shown in FIG. 55B. Finger grip 9811 is then pulled to withdraw suture threading device 9808 from anchor 9802 and drawing suture 9804 around bar 9812 to form a one-way sliding knot therearound. Suture end 9815 is then removed from bight 9810 and threading device 9808 may be discarded. Delivery instrument 9803, with anchor 9802 coupled thereto, may then be removed from package 9801. The opposite free end of suture 9804 (not shown) may then be passed through transverse channel 9816 in anchor 9802, forming a repair loop in suture 9804 that contains the target tissue to be repaired. Instrument 9803 may then be manipulated to insert anchor 9802 with attached suture 9804 into the substrate tissue, optionally into a pre-drilled hole in the tissue. This secures the repair end of the suture which passes through channel 9816 in place in the substrate tissue. The tensioning end 9815 may then be pulled to draw the target tissue to its final repaired position with the desired degree of tension in suture 9802.

Figures 55C, 55D:
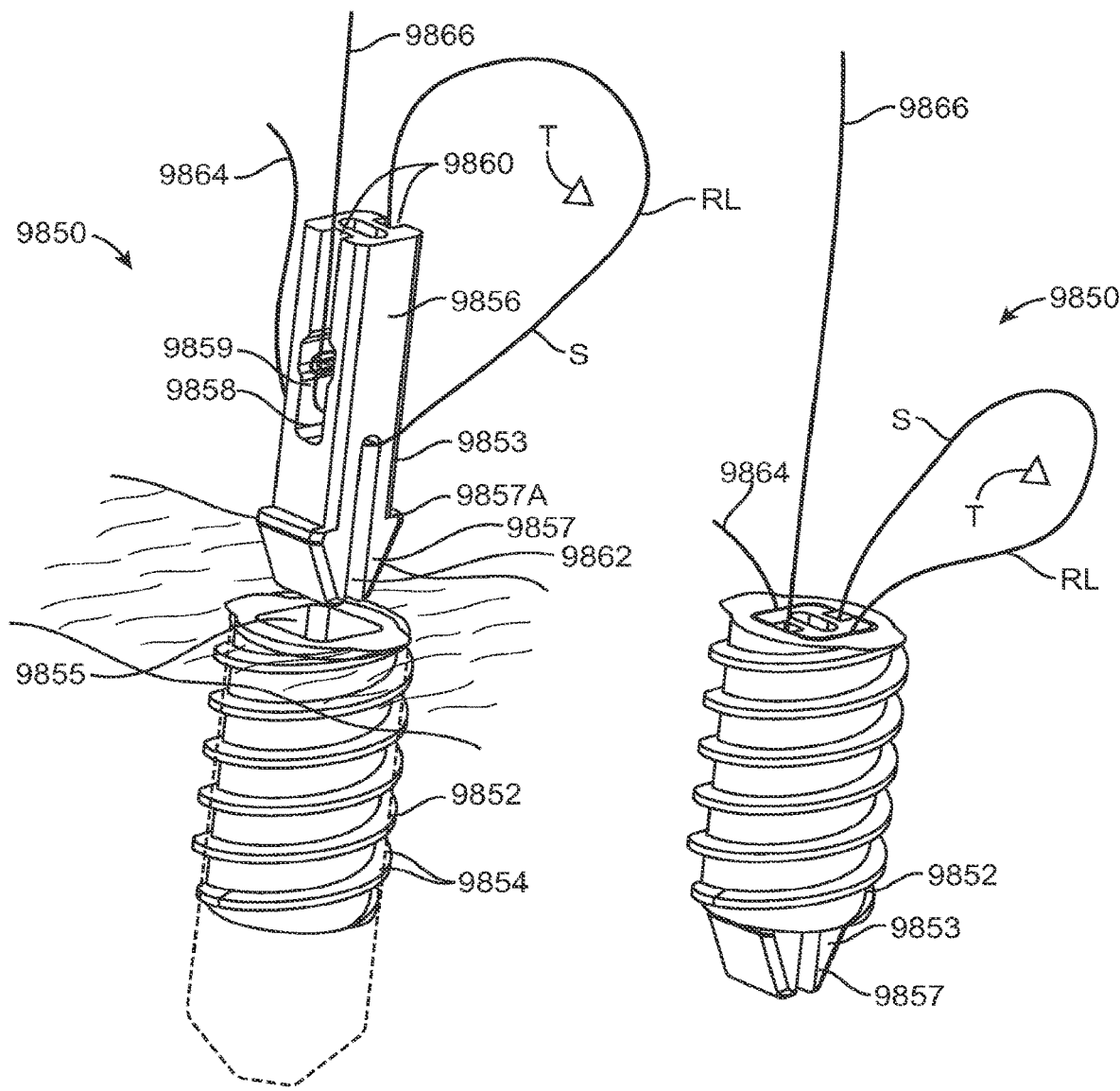
FIGS. 55C-55D are oblique views of a further embodiment of a suture anchor system according to the invention, in separated and coupled configurations, respectively.

A further embodiment of an anchor system which can be threaded intraoperatively is illustrated in FIGS. 55C-55D. In this embodiment, anchor system 9850 includes an outer anchoring component 9852 and an inner suture retention component 9853. Outer anchoring component 9852 may have external threads 9854 suitable for being screwed into bone or other tissue. Alternatively, it may have circumferential ribs or other features suited for being pounded or pressed into bone as in other embodiments described above. Advantageously, in applications where a threaded anchor is desired, this embodiment eliminates challenges with suture management, e.g. twisting and wrapping of the sutures, since the outer anchoring component 9852 may be inserted into the bone while decoupled from the inner suture retention component 9853, as shown in FIG. 55C. Outer anchoring component 9852 has a longitudinal channel 9855 extending from its proximal end through its entire length. Longitudinal channel 9855 may have various cross-sectional shapes cooperative with the external shape of inner suture retention component 9853, including round or rectangular, but in an exemplary embodiment is square. Using a non-circular geometry allows the rotational position of the anchor, including its one-way cinching mechanism, to be selected and maintained relative to the anatomy such that the position and direction of forces applied by suture S can be optimized.

Inner suture retention component 9853 has an axial shank 9856 with a bifurcated arrowhead-shaped tip 9857. The opposing halves of arrowhead tip 9857 are resiliently deflectable inwards toward each other. The proximal edge 9857A of the arrowhead tip has a transverse dimension larger than the width of longitudinal channel 9855 such that upon insertion into channel 9855, the opposing halves of arrowhead tip 9857 deflect inwardly until they pass beyond the distal tip of outer anchoring component 9852, whereupon they spring back to their original configuration. The proximal edge 9857A of arrowhead tip 9857 engages the distal end of anchoring component 9852, locking the inner suture retention component 9853 to the outer anchoring component 9852.

Shank 9856 has a transverse channel 9858 extending through a mid-portion thereof. A bar 9859 is mounted within channel 9858 to as to have gaps along its proximal and distal sides through which a suture may be threaded. In this way a suture S may be tied around the bar to form a one-way sliding knot as described elsewhere herein. A pair of longitudinal channels 9860 extend on opposite sides of shank 9856 from its proximal end distally until they intersect with transverse channel 9858. These channels are configured to slidably receive the two extremities of suture S extending from bar 9859 when the inner suture retention member 9853 is locked within the outer anchoring component 9852. A transverse slot 9862 which opens at the distal tip of inner suture retention member 9853 bifurcates arrowhead tip 9857 and further serves as a means to retain a free end of suture S when the inner suture retention member is inserted in the outer anchoring component, as shown in FIG. 55C.

In use, the outer anchoring component 9852 is driven into the base tissue, either by screwing, pounding or pressing. In some cases a hole will first be pre-drilled into the bone, although outer anchoring component 9852 may be self tapping to avoid the need for pre-drilling. The suture is initially decoupled from the inner suture retention component, and may be passed through or around the target tissue independently of the anchor. Suture S is then threaded through inner suture retention component 9853 to form the one-way sliding knot described above, using a threading device like that described above in connection with FIGS. 55A-B. The repair end 9864 of suture S which forms repair loop RL around the target tissue T is passed through transverse slot 9862 in inner suture retention component 9853 and is tensioned to grossly adjust the size of repair loop RL. Inner suture retention component 9853 is then inserted into outer anchoring component 9852 by pressing or pounding until arrowhead tip 9857 extends beyond the distal end of the outer anchoring component to lock the components together, as shown in FIG. 55D. It should be noted that the arrowhead tip may penetrate into the softer trabecular bone beyond the outer anchoring component; in harder bone, a pre-drilled hole may optionally be drilled to a sufficient depth to accommodate this added length. Repair end 9864 of suture S is trapped between the exterior of shank 9856 and the wall of channel 9855, locking it in place. The adjustment end 9866 of suture S may then be pulled to adjust repair loop RL to its final size and tension. The one-way knot around bar 9859 allows suture S to slide as adjustment end 9866 is pulled, but prevents the suture from moving in the opposite direction, thereby maintaining the desired tension.

Figure 56:
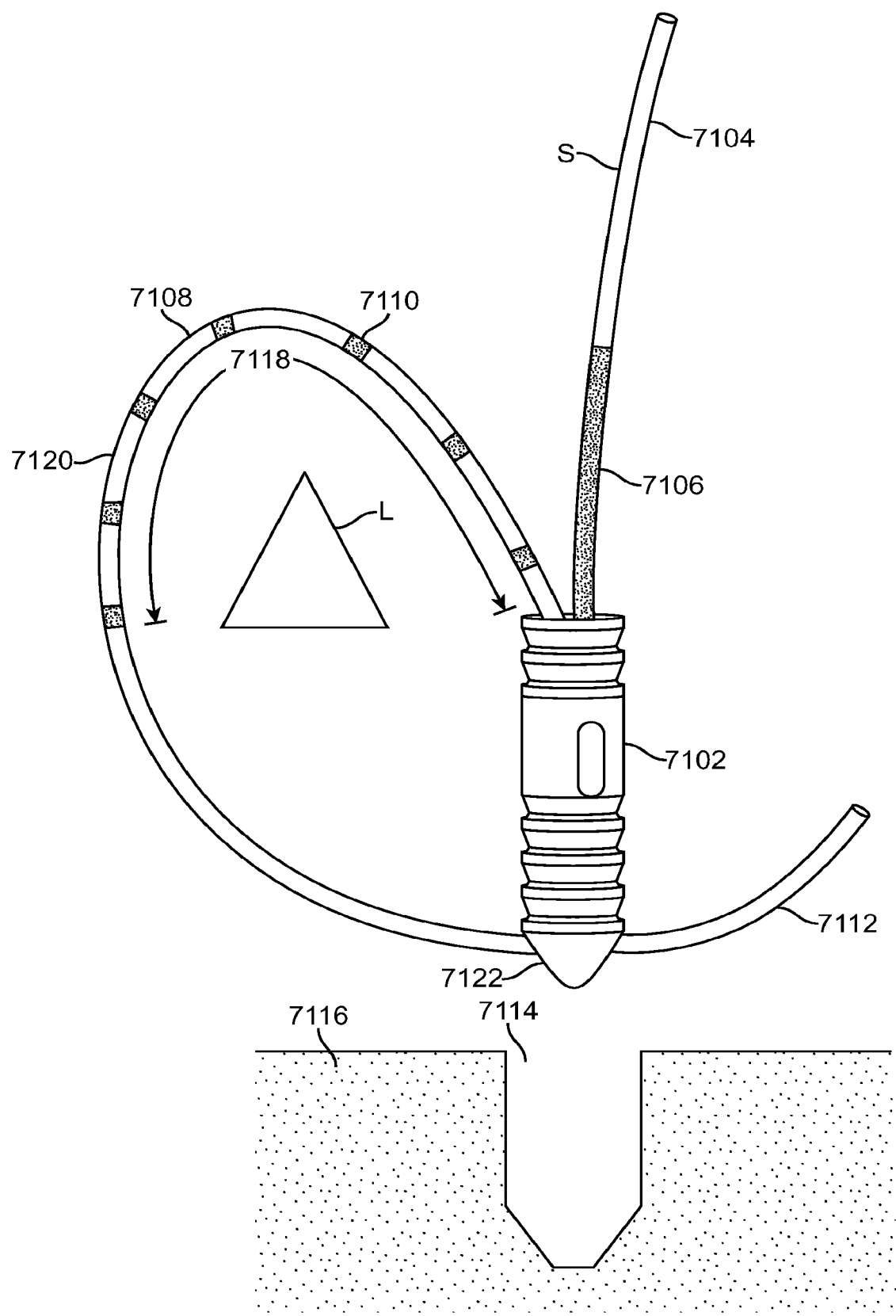
FIG. 56 illustrates a side view of an exemplary embodiment of suture marking.

Suture Marking Features:

In some situations, it may be advantageous to identify different portions of the repair suture in order to facilitate suture manipulation during a repair procedure such as when positioning the anchor 7102 into a hole 7114 in bone 7116. For example, in minimally invasive procedures where the surgical field is small, or in procedures where blood obstructs viewing the suture, it may be difficult to identify which end of the suture can be adjusted. FIG. 56 illustrates an exemplary embodiment of suture that has been marked in several places in order to facilitate identification of the various portions of the repair suture. The repair suture S has a first extremity 7104 that enters suture anchor 7102 having a one-way cinching mechanism (not illustrated) such as those previously described above. A second extremity 7108 of the suture S exits the anchor 7102 and forms a repair loop 7120 which is used to capture the damaged tissue, here a torn labrum L. The free end of the repair loop 7112 is then passed through a transverse channel 7122 in a distal portion of anchor 7102 leaving a second free end 7112 extending therefrom. The suture may include visual markings or indicators in the form of coloration, marker bands, flags, or other means to help the surgeon identify the different extremities of the suture. For example, free end 7104 may have a solid colored band 7106 around a portion of the suture to indicate that this section may be pulled in order to adjust length or tension of the suture. The colored band may be any length, but in preferred embodiments ranges from about 0.50" to about 0.80". Similarly, the repair loop portion 7108 may have colored dashed markings 7110 to indicate that this portion of the suture forms the repair loop used to capture the damaged tissue. The marked region of the repair loop portion 7108 may be any length, but in preferred embodiments the length 7118 ranges from about 0.50" to about 0.80" Also, the second free end 7112 may be left unmarked, or it may be marked with another pattern, to indicate that it passes through the transverse channel. The marking may be made using pad printing or other techniques known in the art.

While the above detailed description and figures are a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

What is claimed is:

1. A method of securing target tissue to base tissue comprising:

providing a first anchor having a bar and a suture tied around the bar to form a hitch which allows the suture to slide around the bar in a first direction and substantially prevents the suture from sliding around the bar in a second opposite direction, the suture having first and second extremities extending from the hitch, wherein the hitch comprises a pole portion and a loop portion wrapped around the pole portion, and wherein the loop portion comprises first and second sections extending from opposite sides of the pole portion along a same side of the bar, the first section leading to the first extremity and the second section leading to the second extremity, the second extremity comprising a free end portion configured to be passed through or around the target tissue;

coupling the second extremity to the target tissue;

inserting the first anchor into the base tissue; and tensioning the first extremity to slide the suture relative to the bar in the first direction whereby the target tissue is drawn toward the base tissue by the second extremity.

2. The method of claim 1 whereby tension on the loop portion pulls the pole portion in a direction transverse to the pole portion, increasing friction between the pole portion and the bar.

3. The method of claim 2 wherein tension on the loop portion pulls the pole portion in a direction tangential to an outer surface of the bar.

4. The method of claim 2 wherein the loop portion pulls the pole portion into a gap disposed between the bar and a wall of the first anchor whereby the pole and loop portions are wedged between the bar and the wall.

5. The method of claim 1 wherein the suture is wrapped around the bar so that the second extremity is looped around the first extremity and wrapped back around the bar so that both the first and second extremities extend proximally from the same lateral side of the bar.

6. The method of claim 1 wherein the first anchor comprises a cavity having a sidewall, the bar being disposed within the cavity.

7. The method of claim 6 wherein a first gap lies between the bar and the sidewall, the loop portion pulling the pole portion toward the first gap when the second extremity is tensioned.

8. The method of claim 7 wherein the first gap has a first width which is less than the combined thickness of the first and second extremities.

9. The method of claim 8 wherein a second gap lies between the bar and a second wall of the cavity, the second gap having a second width substantially larger than the first width.

10. The method of claim 1 wherein inserting comprises screwing the first anchor into the base tissue.

11. The method of claim 10 wherein inserting comprises coupling an insertion tool to the first anchor, and rotating the insertion tool to screw in the anchor, further comprising preventing the second extremity from wrapping around the insertion tool as it is rotated.

12. The method of claim 11 wherein the second extremity is pre-wound around the insertion tool a predetermined number of winds, and the preventing step comprises unwrapping the predetermined number of winds from the insertion tool as it is rotated.

13. The method of claim 10 wherein the step of coupling comprises passing the second extremity a round or through the target tissue; and then retaining the free end portion of the second extremity in the first anchor as the first anchor is inserted in the base tissue.

14. The method of claim 13 wherein the free end portion is retained in the suture anchor such that the free end portion remains in a stationary position relative to the base tissue as the anchor is screwed into the base tissue.

15. The method of claim 14 wherein the free end portion is retained by a retaining structure rotatably coupled to the first anchor.

16. The method of claim 1 further comprising deploying a retention element from the first anchor after the step of inserting.

17. The method of claim 16 further wherein the first anchor has an actuation element coupled thereto, wherein deploying comprises moving the actuation element relative to the retention structure.

18. The method of claim 1 wherein coupling the second extremity to the target tissue comprises creating a loop with the second extremity, passing at least a portion of the loop around or through the target tissue, and coupling the loop to the first anchor.

19. The method of claim 18 wherein the loop is coupled to the first anchor by retaining the free end portion of the second extremity on the first anchor.

20. The method of claim 19 wherein the free end portion is retained by passing it through a transverse passage in the first anchor.

21. The method of claim 19 wherein retaining the free end portion comprises clamping the free end portion between two opposing surfaces of the first anchor.

22. The method of claim 19 wherein retaining the free end portion comprises passing the free end portion through a loop formed by the second extremity a round the bar.

23. The method of claim 22 wherein the second extremity forms two loops around the bar, and the free end portion is passed through both loops.

24. The method of claim 19 wherein the free end portion is retained on the first anchor without tying a knot in the second extremity.

25. The method of claim 1 wherein the first and second extremities comprise free end portions extending away from the first anchor.

26. The method of claim 1 wherein the loop portion comprises a u-loop.

27. The method of claim 1, wherein the hitch substantially prevents the suture from sliding around the bar in the second direction when the second extremity is tensioned.

28. The method of claim 1 wherein providing the anchor having the bar and the suture tied around the bar to form the hitch occurs before coupling the free end portion of the second extremity to the anchor to form the repair loop.

29. A method of securing target tissue to base tissue comprising:
providing an anchor having a one-way cinching mechanism and a suture pre-threaded through the one-way cinching mechanism, the suture having first and second extremities extending from the anchor, wherein the one-way cinching mechanism comprises a bar coupled to the anchor, the suture being tied around the bar to form a hitch with first and second extremities extending away from the bar in the same direction, wherein the first extremity extends from a pole portion and the second extremity extends from a loop portion wrapped around the pole portion, and wherein the first and second extremities terminate in free end portions, the free end portion of the second extremity being configured to pass through or around the target tissue; and
after providing the anchor:
passing the second extremity through or around the target tissue;
coupling the free end portion of the second extremity to the anchor to form a repair loop coupled to the target tissue;
inserting the anchor into the base tissue; and
tensioning the first extremity to shorten the repair loop to a final size without moving the anchor relative to the base tissue, wherein the one-way cinching mechanism allows the suture to move through the anchor in a first direction when the first extremity is tensioned and substantially prevents movement of the suture in an opposite direction so as to maintain tension in the repair loop.

30. The method of claim 29 wherein the step of tensioning the first extremity is performed after the anchor is fully inserted in the base tissue.

31. The method of claim 29 wherein tension in the repair loop causes the loop portion to pull transversely on the pole portion to inhibit movement of the suture.

32. The method of claim 29 wherein the anchor is inserted using an insertion tool to which the anchor is releasably coupled, further comprising releasing the anchor from the insertion tool after the step of inserting.

33. The method of claim 32 wherein the first extremity may be tensioned to increase tension in the repair loop after the step of releasing.

34. The method of claim 29 further comprising after coupling the free end portion of the second extremity to the anchor: tensioning the second extremity to shorten the repair loop to an initial size; and locking the second extremity in position relative to the anchor.

35. The method of claim 34 wherein the second extremity is locked without forming a knot in the second extremity.

36. The method of claim 34 wherein the step of tensioning the first extremity is performed after the step of locking the second extremity.

37. The method of claim 34 wherein the final size is smaller than the initial size, the method further comprising holding a predetermined portion of the repair loop as the second extremity is tensioned such that the repair loop may not be shortened beyond the initial size.

38. The method of claim 29 wherein coupling the free end portion of the second extremity comprises passing the free end portion through a passage in the anchor.

39. The method of claim 31 wherein locking the second extremity comprises trapping a portion of the second extremity between the anchor and the base tissue.

40. The method of claim 31 wherein locking the second extremity comprises clamping a portion of the second extremity between two surfaces in the anchor.

41. The method of claim 40 wherein clamping comprises moving at least one of the two surfaces relative to another of the two surfaces.

42. The method of claim 29 wherein coupling the free end portion of the second extremity to the anchor occurs after passing the second extremitythrough or around the target tissue.

43. The method of claim 29 wherein the loop portion comprises a u-loop.

44. A method of securing target tissue to base tissue comprising:
providing a first anchor having a bar and a suture tied around the bar to form a hitch which allows the suture to slide around the bar in a first direction and substantially prevents the suture from sliding around the bar in a second opposite direction, the suture having first and second extremities extending from the hitch, wherein the hitch comprises a pole portion and a loop portion wrapped around the pole portion, wherein the suture extends from the first section, wraps entirely around the bar in a first direction, forms a u-loop around the first extremity, and returns back around the bar in a second opposite direction to lead to the second extremity, the second extremity comprising a free end configured to be passed through or around the target tissue, whereby tension on the loop portion pulls the pole portion in a direction transverse to the pole portion, increasing friction between the pole portion and the bar;

coupling the second extremity to the target tissue;

inserting the first anchor into the base tissue; and tensioning the first extremity to slide the suture relative to the bar in the first direction whereby the target tissue is drawn toward the base tissue by the second extremity.

45. The method of claim 44 wherein tension on the loop portion pulls the pole portion in a direction tangential to an outer surface of the bar.

46. The method of claim 44 wherein the loop portion pulls the pole portion into a gap disposed between the bar and a wall of the first anchor whereby the pole and loop portions are wedged between the bar and the wall.

47. The method of claim 44 wherein the first anchor comprises a cavity having a sidewall, the bar being disposed within the cavity.

48. The method of claim 47 wherein a first gap lies between the bar and the sidewall, the loop portion pulling the pole portion toward the first gap when the second extremity is tensioned.

49. The method of claim 48 wherein the first gap has a first width which is less than the combined thickness of the first and second extremities.

50. The method of claim 49 wherein a second gap lies between the bar and a second wall of the cavity, the second gap having a second width substantially larger than the first width.

* * * * *